US012648964B2

(12) United States Patent
Corey et al.

(10) Patent No.: US 12,648,964 B2
(45) Date of Patent: *Jun. 9, 2026

(54) CHIMERIC TIM RECEPTORS AND USES THEREOF

(71) Applicant: CERO THERAPEUTICS HOLDINGS, INC., South San Francisco, CA (US)

(72) Inventors: Daniel Mark Corey, Menlo Park, CA (US); Nathan Kipniss, San Francisco, CA (US)

(73) Assignee: CERO THERAPEUTICS HOLDINGS, INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/019,111

(22) Filed: Jan. 13, 2025

(65) Prior Publication Data

US 2025/0195575 A1 Jun. 19, 2025

Related U.S. Application Data

(63) Continuation of application No. 18/041,195, filed as application No. PCT/US2021/046014 on Aug. 13, 2021.

(60) Provisional application No. 63/226,643, filed on Jul. 28, 2021, provisional application No. 63/066,085, filed on Aug. 14, 2020.

(51) Int. Cl.

| | |
|---|---|
| *A61K 35/17* | (2025.01) |
| *A61K 31/519* | (2006.01) |
| *A61K 40/11* | (2025.01) |
| *A61K 40/42* | (2025.01) |
| *A61P 35/00* | (2006.01) |
| *C07K 14/47* | (2006.01) |
| *C07K 14/705* | (2006.01) |

(52) U.S. Cl.
CPC ............ *A61K 35/17* (2013.01); *A61K 31/519* (2013.01); *A61K 40/11* (2025.01); *A61K 40/421* (2025.01); *A61P 35/00* (2018.01); *C07K 14/4727* (2013.01); *C07K 14/70503* (2013.01); *C07K 2319/03* (2013.01)

(58) Field of Classification Search
None
See application file for complete search history.

(56) References Cited

U.S. PATENT DOCUMENTS

| | | | |
|---|---|---|---|
| 5,019,368 A | 5/1991 | Epstein et al. | |
| 5,283,173 A | 2/1994 | Fields et al. | |
| 5,468,614 A | 11/1995 | Fields et al. | |
| 5,641,863 A | 6/1997 | Schreiber et al. | |
| 5,641,875 A | 6/1997 | Schreiber et al. | |
| 5,747,498 A | 5/1998 | Schnur et al. | |
| 5,776,910 A | 7/1998 | Schreiber et al. | |
| 5,821,071 A | 10/1998 | Schreiber et al. | |
| 6,068,983 A | 5/2000 | Schreiber et al. | |
| 6,475,997 B1 | 11/2002 | Schreiber et al. | |
| 6,630,313 B2 | 10/2003 | Fadok et al. | |
| 7,195,761 B2 | 3/2007 | Holtzman et al. | |
| 7,247,303 B2 | 7/2007 | Thorpe et al. | |
| 7,892,544 B2 | 2/2011 | Pfeifer et al. | |
| 7,910,333 B2 | 3/2011 | Chilcote et al. | |
| 8,025,878 B2 | 9/2011 | Gellerfors et al. | |
| 8,119,772 B2 | 2/2012 | Yang et al. | |
| 8,496,938 B2 | 7/2013 | Smith et al. | |
| 8,940,276 B2 | 1/2015 | Weihofen et al. | |
| 8,956,616 B2 | 2/2015 | Thorpe et al. | |
| 10,093,717 B2 | 10/2018 | Li et al. | |
| 10,125,193 B2 | 11/2018 | Cooper et al. | |
| 10,793,641 B2 | 10/2020 | Wang et al. | |
| 10,934,331 B2 | 3/2021 | Corey et al. | |
| 10,980,836 B1 | 4/2021 | Getts et al. | |
| 11,655,282 B2 | 5/2023 | Corey | |
| 11,708,423 B2 * | 7/2023 | Corey | C07K 14/70596 424/130.1 |
| 12,291,557 B2 * | 5/2025 | Corey | |
| 2003/0072743 A1 | 4/2003 | Albert et al. | |
| 2003/0095962 A1 | 5/2003 | Ueda et al. | |
| 2003/0124114 A1 | 7/2003 | McIntire et al. | |
| 2003/0130218 A1 | 7/2003 | Schreiber et al. | |
| 2006/0002940 A1 | 1/2006 | Stevenson | |
| 2006/0257359 A1 | 11/2006 | Francois et al. | |
| 2007/0258897 A1 | 11/2007 | Devitt et al. | |
| 2008/0213216 A1 | 9/2008 | Schreiber et al. | |
| 2011/0165649 A1 | 7/2011 | Tyler et al. | |
| 2013/0071414 A1 | 3/2013 | Dotti et al. | |
| 2014/0162290 A1 | 6/2014 | Watanabe et al. | |

(Continued)

FOREIGN PATENT DOCUMENTS

| | | |
|---|---|---|
| CN | 106749675 A | 5/2017 |
| EP | 0566226 B1 | 11/1995 |

(Continued)

OTHER PUBLICATIONS

Aderem, "Phagocytosis and the Inflammatory Response," *JID* 187(Suppl 2):S340-S345, 2003.

Agaugue et al., "224. Development of Safer & Optimized CAR-T Cells Using Lentiviral Vectors," *Mol. Ther.* 23(Suppl. 1):S88, May 2015.

Aggen et al., "Single-chain V(alpha)V(beta) T-cell receptors function without mispairing with endogenous TCR chains," *Gene Therapy* 19:365-374, 2012.

Albert et al., "αvβ5 integrin recruits the CrkII-Dock180-Rac1 complex for phagocytosis of apoptotic cells," *Nature Cell Biology* 2:899-905, Dec. 2000.

Alder et al., "Antibody responses of variable lymphocyte receptors in the lamprey," *Nature Immunology* 9(3):319-327, Mar. 2008.

(Continued)

*Primary Examiner* — Daniel E Kolker
*Assistant Examiner* — Maureen Varina Driscoll
(74) *Attorney, Agent, or Firm* — Fox Rothschild LLP

(57) ABSTRACT

The present disclosure relates to chimeric Tim receptors, host cells modified to include chimeric Tim receptor molecules, and methods of making and using such receptor molecules and modified cells.

22 Claims, 16 Drawing Sheets

Specification includes a Sequence Listing.

(56) References Cited

U.S. PATENT DOCUMENTS

| 2015/0023986 A1 | 1/2015 | Jones et al. |
| 2017/0058024 A1 | 3/2017 | West et al. |
| 2017/0151281 A1 | 6/2017 | Wagner et al. |
| 2017/0166622 A1 | 6/2017 | Baeuerle et al. |
| 2017/0166657 A1 | 6/2017 | O'Neill et al. |
| 2017/0209492 A1 | 7/2017 | June et al. |
| 2018/0186855 A1 | 7/2018 | Rosenthal |
| 2018/0186878 A1 | 7/2018 | Rosenthal |
| 2018/0244748 A1 | 8/2018 | Gill et al. |
| 2018/0291089 A1 | 10/2018 | Epstein et al. |
| 2018/0319862 A1 | 11/2018 | Thompson et al. |
| 2018/0334653 A1 | 11/2018 | O'Neill |
| 2019/0350972 A1 | 11/2019 | Mason et al. |
| 2020/0002402 A1 | 1/2020 | Emtage et al. |
| 2020/0055917 A1 | 2/2020 | Corey |
| 2020/0239592 A1 | 7/2020 | Vale et al. |
| 2020/0308305 A1 | 10/2020 | Corey |
| 2021/0015865 A1 | 1/2021 | Corey |
| 2021/0023135 A1 | 1/2021 | Corey |
| 2021/0024607 A1 | 1/2021 | Corey et al. |
| 2021/0087251 A1 | 3/2021 | Corey |
| 2021/0253696 A1 | 8/2021 | Corey et al. |
| 2022/0098273 A1 | 3/2022 | Corey |
| 2024/0285684 A1 | 8/2024 | Corey et al. |

FOREIGN PATENT DOCUMENTS

| EP | 0520722 B1 | 12/1996 |
| EP | 0787722 A1 | 8/1997 |
| EP | 0837063 A1 | 4/1998 |
| WO | WO 9633980 A1 | 10/1996 |
| WO | WO 9702266 A1 | 1/1997 |
| WO | WO 9709433 A1 | 3/1997 |
| WO | WO 9730034 A1 | 8/1997 |
| WO | WO 9738983 A1 | 10/1997 |
| WO | WO 9749688 A1 | 12/1997 |
| WO | WO 9810767 A2 | 3/1998 |
| WO | WO 9903854 A1 | 1/1999 |
| WO | WO 0168709 A1 | 9/2001 |
| WO | WO 0185207 A2 | 11/2001 |
| WO | WO 02066470 A1 | 8/2002 |
| WO | WO 03064383 A2 | 8/2003 |
| WO | WO 2004067569 A1 | 8/2004 |
| WO | WO 2005019429 A2 | 3/2005 |
| WO | WO 2005090573 A2 | 9/2005 |
| WO | WO 2005097211 A2 | 10/2005 |
| WO | WO 2006122806 A2 | 11/2006 |
| WO | WO 2007084786 A1 | 7/2007 |
| WO | WO 2009036082 A2 | 3/2009 |
| WO | WO 2009055730 A1 | 4/2009 |
| WO | WO 2013074916 A1 | 5/2013 |
| WO | WO 2013192294 A1 | 12/2013 |
| WO | WO 2014031687 A1 | 2/2014 |
| WO | WO 2014059173 A2 | 4/2014 |
| WO | WO 2014153114 A1 | 9/2014 |
| WO | WO 2015066262 A1 | 5/2015 |
| WO | WO 2015123642 A1 | 8/2015 |
| WO | WO 2015184228 A1 | 12/2015 |
| WO | WO 2016019300 A1 | 2/2016 |
| WO | WO 2016044605 A1 | 3/2016 |
| WO | WO 2016126608 A1 | 8/2016 |
| WO | WO 2017019848 A1 | 2/2017 |
| WO | WO 2017025944 A2 | 2/2017 |
| WO | WO 2017083700 A1 | 5/2017 |
| WO | WO 2017205747 A1 | 11/2017 |
| WO | WO 2017219916 A1 | 12/2017 |
| WO | WO 2018031419 A1 | 2/2018 |
| WO | WO 2018064076 A1 | 4/2018 |
| WO | WO 2018132695 A1 | 7/2018 |
| WO | WO 2018212770 A1 | 11/2018 |
| WO | WO 2018220224 A1 | 12/2018 |
| WO | WO 2019067328 A1 | 4/2019 |
| WO | WO 2019079529 A1 | 4/2019 |
| WO | WO 2019086512 A1 | 5/2019 |
| WO | WO 2019091478 A1 | 5/2019 |
| WO | WO 2019157440 A1 | 8/2019 |
| WO | WO 2019191332 A1 | 10/2019 |
| WO | WO 2019191334 A1 | 10/2019 |
| WO | WO 2019191339 A1 | 10/2019 |
| WO | WO-2019191340 A1 * | 10/2019 | ............ C07K 16/28 |
| WO | WO 2020114518 A1 | 6/2020 |
| WO | WO 2020223550 A1 | 11/2020 |
| WO | WO 2021003428 A1 | 1/2021 |
| WO | WO 2021067875 A1 | 4/2021 |
| WO | WO 2022036285 A1 | 2/2022 |
| WO | WO 2022036287 A1 | 2/2022 |
| WO | WO 2023010097 A1 | 2/2023 |

OTHER PUBLICATIONS

Altman et al., "Phenotypic Analysis of Antigen-Specific T Lymphocytes," *Science* 274:94-96, 1996.

Arandjelovic et al., "Phagocytosis of apoptotic cells in homeostasis," *Nat. Immunol.* 16(9):907-917, Sep. 2015.

Baral et al., "Experimental therapy of African trypanosomiasis with a nanobody-conjugated human trypanolytic factor," *Nature Medicine* 12(5):580-584, May 2006.

Barthelemy et al., "Comprehensive Analysis of the Factors Contributing to the Stability and Solubility of Autonomous Human VH Domains," *J. Biol. Chem.* 283(6):3639-3654, Feb. 8, 2008.

Belzile et al., "Antibody targeting of phosphatidylserine for the detection and immunotherapy of cancer," *ImmunoTargets and Therapy*, (7) pp. 1-14, 2018.

Blackburn et al., "Coregulation of CD8+ T cell exhaustion by multiple inhibitory receptors during chronic viral infection," *Nature Immunology* 10(1):29-37, Jan. 2009.

Blasius et al., "Intracellular Toll-like Receptors," *Immunity* 32:305-315, Mar. 26, 2010. (11 pages).

Burns et al., "A high molecular weight-melanoma associated antigen-specific chimeric antigen receptor redirects lymphocytes to target human melanomas," *Cancer Res.* 70(8):3027-3033, Apr. 15, 2010.

Castellano et al., "Membrane recruitment of Rac1 triggers phagocytosis," *Journal of Cell Science* 113:2955-2961, 2000.

Chen et al., "Fusion Protein Linkers: Property, Design and Functionality," *Adv. Drug Deliv. Rev.* 65(10): 1357-1369, Oct. 15, 2013.

Chen et al., "TIM-2 is expressed on B cells and in liver and kidney and is a receptor for H-ferritin endocytosis," *JEM* 202(7):955-965, Oct. 2005. (11 pages).

Clackson et al., "Making antibody fragments using phage display libraries," *Nature* 352:624-628, Aug. 1991.

Colman, "Effects of amino acid sequence changes on antibody-antigen interactions," *Research in Immunology* 145(1):33-36, 1994.

Cordoba et al., "The large ectodomains of CD45 and CD148 regulate their segregation from and inhibition of ligated T-cell receptor," *Blood* 121(21):4295-4302, 2013.

Corey et al., "Novel engineered chimeric engulfment receptors trigger T cell effector functions against SIV-infected CD4+ T cells," Mol Ther Methods Clin Dev. 28:1-10, Nov. 2022.

Cortez-Retamozo et al., "Efficient Cancer Therapy with a Nanobody-Based Conjugate," *Cancer Research* 64:2853-2857, Apr. 2004.

Delgado Tascón et al., "The granulocyte orphan receptor CEACAM4 is able to trigger phagocytosis of bacteria," *Journal of Leukocyte Biology* 97:521-531, Mar. 2015.

Dillon et al., "Annexin V Binds to Viable B Cells and Colocalizes with a Marker of Lipid Rafts upon B Cell Receptor Activation," *The Journal of Immunology* 164:1322-1332, 2000.

Dolezal et al., "ScFv multimers of the anti-neuraminidase antibody NC10: shortening of the linker in single-chain Fv fragment assembled in V(L) to V(H) orientation drives the formation of dimers, trimers, tetramers and higher molecular mass multimers," *Protein Engineering* 13(8):565-574, 2000.

Duclos et al., "Rab5 regulates the kiss and run fusion between phagosomes and endosomes and the acquisition of phagosome leishmanicidal properties in RAW 264.7 macrophages," *Journal of Cell Science* 113:3531-3541, 2000.

Engels et al., "Retroviral Vectors for High-Level Transgene Expression in T Lymphocytes," *Human Gene Therapy* 14:1155-1168, Aug. 2003.

(56) References Cited

OTHER PUBLICATIONS

Feng et al., "Interleukin-6 increases prostate cancer cells resistance to bicalutamide via TIF2," *Mol. Cancer Ther.* 8(3): 665-671, Mar. 2009.

Fesnak et al., "Engineered T Cells: The Promise and Challenges of Cancer Immunotherapy," *Nature Reviews Cancer* 16(9):566-581, Sep. 2016.

Frecha et al., "Advances in the Field of Lentivector-based Transduction of T and B Lymphocytes for Gene Therapy," *Molecular Therapy* 18(10):1748-1757, Oct. 2010.

Genbank Accession No. NP_612388 (2006).

Genbank Accession No. NP_848874 (2009).

Gerber et al., "Tumor-specific targeting by Bavituximab, a phosphatidylserine-targeting monoclonal antibody with vascular targeting and immune modulating properties, in lung cancer xenografts," *Am. J. Nucl. Med. Mol. Imaging* 5(5):493-503, 2015.

Ghahroudi et al., "Selection and identification of single domain antibody fragments from camel heavy-chain antibodies," *FEBS Letters* 414:521-526, 1997.

Green et al., "Mitochondria and Apoptosis," *Science* 281(5381):1309-1312, Aug. 1998.

Greenberg et al., "Clustered syk tyrosine kinase domains trigger phagocytosis," *Proc. Natl. Acad. Sci. USA* 93:1103-1107, Feb. 1996.

Greenberg, "Programmed cell death: A way of life for plants," *Proc. Natl. Acad. Sci. USA* 93:12094-12097, Oct. 1996.

Guest et al., "The Role of Extracellular Spacer Regions in the Optimal Design of Chimeric Immune Receptors: Evaluation of Four Different scFvs and Antigens," *Journal of Immunotherapy* 28(3):203-211, May/Jun. 2005.

Hamers-Casterman et al., "Naturally occurring antibodies devoid of light chains," *Nature* 363:446-448, Jun. 1993.

Hanayama et al., "Identification of a factor that links apoptotic cells to phagocytes," *Nature* 417:182-187, May 2002.

Hartt Meyers et al., "TIM-4 is the ligand for TIM-1, and the TIM-1-TIM-4 interaction regulates T cell proliferation," *Nat. Immunol.* 6(5):455-464, May 2005.

Hayashi et al., "The innate immune response to bacterial flagellin is mediated by Toll-like receptor 5," Nature, 410(6832), Apr. 2001, pp. 1099-1103.

Herrin et al., "Structure and specificity of lamprey monoclonal antibodies," *PNAS* 105(6):2040-2045, Feb. 2008.

Hochreiter-Hufford et al., "Clearing the Dead: Apoptotic Cell Sensing, Recognition, Engulfment, and Digestion," *Cold Spring Harb Perspect Biol* 5:a008748, 2013. (21 pages).

Hudecek et al., "Receptor Affinity and Extracellular Domain Modifications Affect Tumor Recognition by ROR1-Specific Chimeric Antigen Receptor T Cells," *Clin. Cancer Res.* 19(12):3153-31564, 2013.

Hudecek et al., "The Nonsignaling Extracellular Spacer Domain of Chimeric Antigen Receptors Is Decisive for In Vivo Antitumor Activity," *Cancer Immunol. Res.* 3(2):125-135, Feb. 2015.

Hull et al., "The Mononuclear Phagocyte System in Homeostasis and Disease: A Role for Heme Oxygenase-1," *Antioxidants & Redox Signaling* 20(11):1770-1788, 2014.

International Search Report and Written Opinion, mailed Aug. 19, 2019, for International Application No. PCT/US2019/024441, 13 pages.

International Search Report and Written Opinion, mailed Feb. 6, 2018, for International Application No. PCT/US2017/053553, 13 pages.

International Search Report and Written Opinion, mailed Jun. 28, 2019, for International Application No. PCT/US2019/024442, 12 pages.

International Search Report and Written Opinion, mailed Jun. 7, 2019, for International Application No. PCT/US2019/024433, 13 pages.

International Search Report and Written Opinion, mailed Mar. 25, 2019, for International Application No. PCT/US2018/052297, 11 pages.

International Search Report and Written Opinion, mailed May 29, 2019, for International Application No. PCT/US2019/024435, 14 pages.

International Search Report and Written Opinion, mailed Jan. 25, 2022, for International Application No. PCT/US2021/046043, 17 pages.

International Search Report and Written Opinion, mailed Dec. 14, 2021, for International Application No. PCT/US2021/046041, 17 pages.

International Search Report and Written Opinion, mailed Feb. 4, 2022, for International Application No. PCT/US2021/046014, 21 pages.

Jespers et al., "Aggregation-resistant domain antibodies selected on phage by heat denaturation," *Nature Biotechnology* 22(9):1161-1165, Sep. 2004.

Jolly, "9: Emerging Viral Vectors," *Cold Spring Harbor Monograph Archive* 36:209-240, 1999.

Jones et al., "Lentiviral Vector Design for Optimal T Cell Receptor Gene Expression in the Transduction of Peripheral Blood Lymphocytes and Tumor-Infiltrating Lymphocytes," *Human Gene Therapy* 20:630-640, Jun. 2009.

June, "Adoptive T cell therapy for cancer in the clinic," *The Journal of Clinical Investigation* 117(6):1466-1476, Jun. 2007.

Kao et al., "Systematic Comparison of the EF-1 Alpha Short (EFS) and Viral Promoters for Gene Modification of Human Primary Cells for Clinical Applications," *Blood* 124(21):3497, Dec. 6, 2014. (3 pages).

Khogeer et al., "Antiphosphatidylserine antibodies as diagnostic indicators of antiphospholipid syndrome," *Lupus* 24:186-190, 2015.

Kitchen et al., "Engineering Antigen-Specific T Cells from Genetically Modified Human Hematopoietic Stem Cells in Immunodeficient Mice," *PLoS One* 4(12):e8208, Dec. 2009.

Kobayashi et al., "TIM-1 and TIM-4 Glycoproteins Bind Phosphatidylserine and Mediate Uptake of Apoptotic Cells," *Immunity* 27:927-940, Dec. 2007.

Kochenderfer et al., "Construction and Pre-clinical Evaluation of an Anti-CD19 Chimeric Antigen Receptor," *J. Immunother.* 32(7):689-702, 2009.

Krisky et al., "Development of herpes simplex virus replication-defective multigene vectors for combination gene therapy applications," *Gene Therapy* 5:1517-1530, 1998.

Kruskal et al., "Phagocytic Chimeric Receptors Require Both Transmembrane and Cytoplasmic Domains from the Mannose Receptor," *J. Exp. Med.* 176:1673-1680, Dec. 1992.

Luo et al., "Development of genetically engineered CD4$^+$ and CD8$^+$ T cells expressing TCRs specific for a M. tuberculosis 38-kDa antigen," *Journal of Molecular Medicine* 89:903-913, 2011.

Maeda et al., "Engineering of Functional Chimeric Protein G-Vargula Luciferase," *Analytical Biochemistry* 249:147-152, 1997.

Miksa et al., "A novel method to determine the engulfment of apoptotic cells by macrophages using pHrodo succinimidyl ester," *J Immunol Methods* 342:71-77, 2009.

Misyurin, "Structure and Functions of Main Apoptosis Receptors and Ligands," Russian Journal of Biotherapy 14(2):23-30, 2015.

Miyanishi et al., "Identification of Tim4 as a phosphatidylserine receptor," *Nature* 450:435-439, Nov. 2007.

Moller-Tank et al., "Characterizing Functional Domains for TIM-Mediated Enveloped Virus Entry", J. Virology, Jun. 2014, 88(12):6702-6713).

Moller-Tank et al., "Phosphatidylserine receptors: enhancers of enveloped virus entry and infection," Virology 468-470:565-580, Nov. 2014.

Morgan et al., "Cancer Regression in Patients After Transfer of Genetically Engineered Lymphocytes," *Science* 314(5796):126-129, Oct. 2006.

Morrissey et al., "Chimeric antigen receptors that trigger phagocytosis," eLife, 2018. (21 pages).

Muller et al., "Spliceosomal Peptide P140 for Immunotherapy of Systemic Lupus Erythematosus: Results of an Early Phase II Clinical Trial," *Arthritis & Rheumatism* 58(12):3873-3883, Dec. 2008.

(56) References Cited

OTHER PUBLICATIONS

Nakaya, "Research on Molecular Mechanisms of Engulfment of Apoptotic Cells", *The Pharmaceutical Society of Japan* 135(8):949-954, 2015.

Nguyen et al., "Heavy-chain antibodies in *Camelidae*; a case of evolutionary innovation," *Immunogenetics* 54:39-47, 2002.

Nguyen et al., "The Specific Variable Domain of Camel Heavy-chain Antibodies is Encoded in the Germline," *J. Mol. Biol.* 275:413-418, 1998.

Nishi et al., "Systematic characterization of deubiquitylating enzymes for roles in maintaining genome integrity," *Nat Cell Biol.* 16(10):1016-8, Oct. 2014. (27 pages).

Nishi et al., "Tim4- and MerTK-Mediated Engulfment of Apoptotic Cells by Mouse Resident Peritoneal Macrophages," *Molecular and Cellular Biology* 34(8):1512-1520, Apr. 2014.

Nix et al., "In Vitro-Selected Nanobody-Based Cellular Therapy Targeting CD72 for Treatement of Refractory B-Cell Malignancies", Blood, American Society of Hematology, vol. 134, Nov. 2019, 4 pages.

Ortiz et al., "The evolutionary history of the CD209 (DC-SIGN) family in humans and non-human primates," Genes and Immunity, Jun. 2008, 2008(9), pp. 483-492.

Park et al., "The Phosphatidylserine Receptor TIM-4 Does Not Mediate Direct Signaling," *Current Biology* 19:346-351, Feb. 2009. (6 pages).

Parmar et al., "The CHK1 Inhibitor Prexasertib Exhibits Monotherapy Activity in High-Grade Serous Ovarian Cancer Models and Sensitizes to PARP Inhibition", Translational Cancer Mechanisms and Therapy, Clinical Cancer Research, Aug. 2019, 25(20): 6127-6140.

Penberthy et al., "Apoptotic cell recognition receptors and scavenger receptors," *Immunological Reviews* 269:44-59, 2016.

Pfeifer et al., "Gene Therapy: Promises and Problems," *Annu. Rev. Genomics Hum. Genet.* 2:177-211, 2001.

Portolano et al., "Lack of Promiscuity in Autoantigen-Specific H and L Chain Combinations as Revealed by Human H and L Chain "Roulette"," *J. Immunol.* 150(3):880-887, Feb. 1993.

Qin et al., "Prelinical Development of Bivalent Chimeric Antigen Receptors Targeting Both CD19 and CD22," Molecular Therapy: Oncolytics, vol. 11, Dec. 2018, pp. 127-137.

Ravichandran "Find-me and eat-me signals in apoptotic cell clearance: progress and conundrums," *J. Exp. Med.* 207(9):1807-1817, 2017.

Rossi et al., "Genetic therapies against HIV," *Nat. Biotechnol.* 25(12):1444-1454, Dec. 2007.

Roux et al., "Structural analysis of the nurse shark (new) antigen receptor (NAR): Molecular convergence of NAR and unusual mammalian immunoglobulins," *PNAS* 95:11804-11809, Sep. 1998.

Safdari et al., "Antibody humanization methods—a review and update," *Biotechnology and Genetic Engineering Reviews* 29(2):175-186, 2013.

Sandberg et al., "Human T-cell lines with well-defined T-cell receptor gene rearrangements as controls for the BIOMED-2 multiplex polymerase chain reaction tubes," *Leukemia* 21:230-237, 2007.

Sato et al., "Enhancement of Fcγ Receptor-Mediated Phagocytosis by Transforming Mutants of Cbl1," *The Journal of Immunology* 163(11):6123-6131, 1999.

Scatchard et al., "The Attractions of Proteins for Small Molecules and Ions," *Ann. N.Y. Acad. Sci.* 51:660-672, 1949.

Schmitt et al., "T Cell Receptor Gene Therapy for Cancer," *Human Gene Therapy* 20:1240-1248, 2009.

Scholten et al., "Codon modification of T cell receptors allows enhanced functional expression in transgenic human T cells," *Clin. Immunol.* 119:135-145, 2006.

Schutters et al., "Phosphatidylserine targeting for diagnosis and treatment of human diseases," *Apoptosis* 15:1072-1082, 2010.

Segawa et al., "An Apoptotic 'Eat Me' Signal: Phosphatidylserine Exposure," Trends Cell Biol. 25(11):639-650, Nov. 2015.

Sommermeyer, "Chimeric antigen receptor-modified T cells derived from defined CDS+ and CD4+ subsets confer superior antitumor reactivity in vivo," Leukemia 30(2):492-500, Feb. 2016.

Srivastava et al., "Engineering CAR-T Cells: Design Concepts," *Trends Immunol.* 36(8):494-502, 2015.

Stone et al., "A novel T cell receptor single-chain signaling complex mediates antigen-specific T cell activity and tumor control," *Cancer Immunol. Immunother.* 63(11):1163-1176, Nov. 2014. (NIH Public Access, Author Manuscript, available in PMC Nov. 1, 2015) (23 pages).

Teplyakov et al., "Antibody modeling assessment II. Structures and models," *Proteins* 82(8):1563-1582, 2014. (20 pages).

Vallabhapurapu et al., "Variation in human cancer cell external phosphatidylserine isregulated by flippase activity and intracellular calcium," *Oncotarget* 6(33):34375-34388, 2015.

Verhoeyen et al., "Chapter 8: Lentiviral Vector Gene Transfer into Human T Cells," *Methods Mol. Biol.* 506:97-114, 2009.

Vincke et al., "General Strategy to Humanize a Camelid Single-domain Antibody and Identification of a Universal Humanized Nanobody Scaffold," *J. Biol. Chem.* 284(5):3273-3284, Jan. 2009.

Walseng et al., "A TCR-based Chimeric Antigen Receptor," *Scientific Reports* 7: 10713, 2017. (10 pages).

Wang et al., "A transgene-encoded cell surface polypeptide for selection, in vivo tracking, and ablation of engineered cells," *Blood* 118(5):1255-1263, Aug. 2011.

Williamson et al., "Abstract A165: Engineering approaches to uncover the mechanism of apoptotic cell clearance by a conserved signaling system," *CRI-CIMT-EATI-AACR Inaugural International Cancer Immunotherapy Conference: Translating Science into Survival*, New York, New York, Sep. 16-19, 2015. (6 pages).

Williamson et al., "Abstract PR15: Engineering phagocytic signaling," CRI-CIMT-EATI-AACR International Cancer Immunotherapy Conference: Translating Science into Survival, New York, New York, Sep. 25-28, 2016. (4 pages).

Williamson et al., "Cellular reconstitution of apoptotic cell clearance reveals a multi-step phosphorylation mechanism for Draper receptor triggering," bioRxiv: 1-48, 2017. (58 pages).

Williamson et al., "Spatial control of Draper receptor signaling initiates apoptotic cell engulfment," *J. Cell Biol.* 217(11):3977-3992, 2018.

Wilson, "Analyzing Biomolecular Interactions," *Science* 295(5562):2103-2105, 2002.

Wolff et al., "Monoclonal Antibody Homodimers: Enhanced Antitumor Activity in Nude Mice," *Cancer Res.* 53:2560-2565, Jun. 1993.

Wong K et al., "Phosphatidylserine receptor Tim-4 is essential for the maintenance of the homeostatic state of resident peritoneal macrophages," Proc Natl Acad Sci USA 107(19) 8712-7, May 2010.

Wälchli et al., "A Practical Approach to T-Cell Receptor Cloning and Expression," *PLoS One* 6(11):e27930, 2011. (11 pages).

Yang et al., "Development of optimal bicistronic lentiviral vectors facilitates high-level TCR gene expression and robust tumor cell recognition," *Gene Therapy* 15:1411-1423, May 22, 2008. (13 pages).

Zaritskaya et al., "New flow cytometric assays for monitoring cell-mediated cytotoxicity," *Expert Review of Vaccines* 9(6):601-616, Jun. 2010. (26 pages).

Zhang et al., "Transduction of Human T Cells with a Novel T-Cell Receptor Confers Anti-HCV Reactivity," *PLoS Pathogens* 6(7):e1001018, Jul. 2010. (13 pages).

Zhao et al., "Primary Human Lymphocytes Transduced with NY-ESO-1 Antigen-Specific TCR Genes Recognize and Kill Diverse Human Tumor Cell Lines," *J. Immunol.* 174:(7):4415-4423, Apr. 2005. (25 pages).

George et al., "Third-generation anti-CD19 chimeric antigen receptor Tcells incorporating a TLR2 domain for relapsed or refractory B-cell lymphoma: a phase I clinical trial protocol (ENABLE)", BMJ Open, Feb. 9, 2020, vol. 10 No 2, e034629.

Shakhov et al., "SMUCKLER/TIM4 is a distinct member of TIM family expressed by stromal cells of secondary lymphoid tissues and associated with lymphotoxin signaling", European Journal of Immunology, Feb. 2004, vol. 34 No 2, 494-503.

(56) References Cited

OTHER PUBLICATIONS

Heo et al. "Niraparib: A Review in Ovarian Cancer." Targeted Oncol. Aug. 2018, 13:533-539.

Lai et al. "Toll-like receptor 2 costimulation potentiates the antitumor efficacy of CAR T Cells." Leukemia. Mar. 2018, 32, 801-808.

Drew et al. "Phase II study of olaparib + durvalumab (MEDIOLA): Updated results in germline BRCA-mutated platinum-sensitive relapsed (PSR) ovarian cancer (OC)." Ann. Oncol. Oct. 2019, 30(5), v485-v486).

Bobbin et al. "TIM-4-CER T Cells Elicit PS-Dependent Cytotoxic and Innate-Like Function and Synergize with Approved PARP Inhibitors in an Ovarian Cancer Model." Poster M195 presented at the American Society of Gene and Cell Therapy 25th Annual Meeting, May 16-20, 2022.

Gura, "Systems for identifying new drugs are often faulty," Science 278, No. 5340 (Nov. 7, 1997): 1041-42.

Kaiser, "First Pass at Cancer Genome Reveals Complex Landscape," Science 313, No. 5792 (Sep. 7, 2006): 1370.

Jena et al., "Redirecting T-cell Specificity by Introducing a Tumor-specific Chimeric Antigen Receptor," Blood 116, No. 7 (May 4, 2010): 1035-44.

Tosello-Trampont et al. "Evidence for a Conserved Role for CrkII and Rac in Engulfment of Apoptotic Cells," J. Biol. Chem. (Apr. 2001) 276:13797-13802.

Barth et al., "Mediastinal (thymic) large B-cell lymphoma: where do we stand?" The Lancet Oncology (Apr. 2002), 3:229-234.

"2022 ASGCT Annual Meeting Abstracts." Molecular Therapy 30, No. 4 (May 2, 2022): 151 (Abstract #314). DOI: 10.1016/j.ymthe.2022.04.017.

* cited by examiner

SEQUENCE LISTING

```
Sequence total quantity: 158
SEQ ID NO: 1              moltype = AA  length = 378
FEATURE                   Location/Qualifiers
source                    1..378
                          mol_type = protein
                          organism = Homo sapiens
SEQUENCE: 1
MSKEPLILWL MIEFWWLYLT PVTSETVVTE VLGHRVTLPC LYSSWSHNSN SMCWGKDQCP  60
YSGCKEALIR TDGMRVTSRK SAKYRLQGTI PRGDVSLTIL NPSESDSGVY CCRIEVPGWF  120
NDVKINVRLN LQRASTTTHR TATTTTRRTT TTSPTTTRQM TTTPAALPTT VVTTPDLTTG  180
TPLQMTTIAV FTTANTCLSL TPSTLPEEAT GLLTPEPSKE GPILTAESET VLPSDSWSSV  240
ESTSADTVLL TSKESKVWDL PSTSHVSMWK TSDSVSSPQP GASDTAVPEQ NKTTKTGQMD  300
GIPMSMKNEM PISQLLMIIA PSLGFVLFAL FVAFLLRGKL METYCSQKHT RLDYIGDSKN  360
VLNDVQHGRE DEDGLFTL                                                378

SEQ ID NO: 2              moltype = AA  length = 314
FEATURE                   Location/Qualifiers
```

```
source                     1..314
                           mol_type = protein
                           organism = Homo sapiens
SIGNAL                     1..24
SEQUENCE: 2
MSKEPLILWL MIEFWWLYLT PVTSETVVTE VLGHRVTLPC LYSSWSHNSN SMCWGKDQCP    60
YSGCKEALIR TDGMRVTSRK SAKYRLQGTI PRGDVSLTIL NPSESDSGVY CCRIEVPGWF   120
NDVKINVRLN LQRASTTTHR TATTTTRRTT TTSPTTTRQM TTTPAALPTT VVTTPDLTTG   180
TPLQMTTIAV FTTANTCLSL TPSTLPEEAT GLLTPEPSKE GPILTAESET VLPSDSWSSV   240
ESTSADTVLL TSKESKVWDL PSTSHVSMWK TSDSVSSPQP GASDTAVPEQ NKTTKTGQMD   300
GIPMSMKNEM PISQ                                                     314

SEQ ID NO: 3               moltype = AA  length = 12
FEATURE                    Location/Qualifiers
REGION                     1..12
                           note = modified IgG4 hinge
source                     1..12
                           mol_type = protein
                           organism = synthetic construct
SEQUENCE: 3
ESKYGPPCPP CP                                                        12

SEQ ID NO: 4               moltype = AA  length = 41
FEATURE                    Location/Qualifiers
source                     1..41
                           mol_type = protein
                           organism = Homo sapiens
SEQUENCE: 4
RSKRSRLLHS DYMNMTPRRP GPTRKHYQPY APPRDFAAYR S                        41

SEQ ID NO: 5               moltype = AA  length = 112
FEATURE                    Location/Qualifiers
REGION                     1..112
                           note = mutated human CD3z ITAM-containing activating domain
source                     1..112
                           mol_type = protein
                           organism = synthetic construct
SEQUENCE: 5
RVKFSRSADA PAYQQGQNQL YNELNLGRRE EYDVLDKRRG RDPEMGGKPR RKNPQEGLYN    60
ELQKDKMAEA YSEIGMKGER RRGKGHDGLY QGLSTATKDT YDALHMQALP PR           112

SEQ ID NO: 6               moltype = AA  length = 21
FEATURE                    Location/Qualifiers
source                     1..21
                           mol_type = protein
                           organism = Homo sapiens
SEQUENCE: 6
LLMIIAPSLG FVLFALFVAF L                                              21

SEQ ID NO: 7               moltype = AA  length = 27
FEATURE                    Location/Qualifiers
source                     1..27
                           mol_type = protein
                           organism = Homo sapiens
SEQUENCE: 7
FWVLVVVGGV LACYSLLVTV AFIIFWV                                        27

SEQ ID NO: 8               moltype = AA  length = 21
FEATURE                    Location/Qualifiers
source                     1..21
                           mol_type = protein
                           organism = Homo sapiens
SEQUENCE: 8
IYAGVCISVL VLLALLGVII A                                              21

SEQ ID NO: 9               moltype = AA  length = 52
FEATURE                    Location/Qualifiers
source                     1..52
                           mol_type = protein
                           organism = Homo sapiens
SEQUENCE: 9
YFLGRLVPRG RGAAEAATRK QRITETESPY QELQGQRSDV YSDLNTQRPY YK            52

SEQ ID NO: 10              moltype = AA  length = 22
FEATURE                    Location/Qualifiers
source                     1..22
                           mol_type = protein
                           organism = Homo sapiens
SEQUENCE: 10
```

-continued

```
MLLLVTSLLL CELPHPAFLL IP                                            22

SEQ ID NO: 11          moltype = AA   length = 24
FEATURE                Location/Qualifiers
source                 1..24
                       mol_type = protein
                       organism = Homo sapiens
SEQUENCE: 11
MSKEPLILWL MIEFWWLYLT PVTS                                          24

SEQ ID NO: 12          moltype = AA   length = 18
FEATURE                Location/Qualifiers
REGION                 1..18
                       note = T2A self-cleaving peptide
source                 1..18
                       mol_type = protein
                       organism = synthetic construct
SEQUENCE: 12
EGRGSLLTCG DVEENPGP                                                 18

SEQ ID NO: 13          moltype = AA   length = 19
FEATURE                Location/Qualifiers
REGION                 1..19
                       note = P2A self-cleaving peptide
source                 1..19
                       mol_type = protein
                       organism = synthetic construct
SEQUENCE: 13
ATNFSLLKQA GDVEENPGP                                                19

SEQ ID NO: 14          moltype = AA   length = 20
FEATURE                Location/Qualifiers
REGION                 1..20
                       note = E2A self-cleaving peptide
source                 1..20
                       mol_type = protein
                       organism = synthetic construct
SEQUENCE: 14
QCTNYALLKL AGDVESNPGP                                               20

SEQ ID NO: 15          moltype = AA   length = 22
FEATURE                Location/Qualifiers
REGION                 1..22
                       note = F2A self-cleaving peptide
source                 1..22
                       mol_type = protein
                       organism = synthetic construct
SEQUENCE: 15
VKQTLNFDLL KLAGDVESNP GP                                            22

SEQ ID NO: 16          moltype = AA   length = 285
FEATURE                Location/Qualifiers
source                 1..285
                       mol_type = protein
                       organism = Homo sapiens
SEQUENCE: 16
RKVCNGIGIG EFKDSLSINA TNIKHFKNCT SISGDLHILP VAFRGDSFTH TPPLDPQELD   60
ILKTVKEITG FLLIQAWPEN RTDLHAFENL EIIRGRTKQH GQFSLAVVSL NITSLGLRSL   120
KEISDGDVII SGNKNLCYAN TINWKKLFGT SGQKTKIISN RGENSCKATG QVCHALCSPE   180
GCWGPEPRDC VSCRNVSRGR ECVDKCNLLE GEPREFVENS ECIQCHPECL PQAMNITCTG   240
RGPDNCIQCA HYIDGPHCVK TCPAGVMGEN NTLVWKYADA GHVCH                   285

SEQ ID NO: 17          moltype = AA   length = 192
FEATURE                Location/Qualifiers
source                 1..192
                       mol_type = protein
                       organism = Homo sapiens
SEQUENCE: 17
MQAIKCVVVG DGAVGKTCLL ISYTTNAFPG EYIPTVFDNY SANVMVDGKP VNLGLWDTAG   60
QEDYDRLRPL SYPQTDVFLI CFSLVSPASF ENVRAKWYPE VRHHCPNTPI ILVGTKLDLR   120
DDKDTIEKLK EKKLTPITYP QGLAMAKEIG AVKYLECSAL TQRGLKTVFD EAIRAVLCPP   180
PVKKRKRKCL LL                                                      192

SEQ ID NO: 18          moltype = AA   length = 215
FEATURE                Location/Qualifiers
source                 1..215
                       mol_type = protein
                       organism = Homo sapiens
SEQUENCE: 18
```

-continued

```
MASRGATRPN GPNTGNKICQ FKLVLLGESA VGKSSLVLRF VKGQFHEFQE STIGAAFLTQ    60
TVCLDDTTVK FEIWDTAGQE RYHSLAPMYY RGAQAAIVVY DITNEESFAR AKNWVKELQR   120
QASPNIVIAL SGNKADLANK RAVDFQEAQS YADDNSLLFM ETSAKTSMNV NEIFMAIAKK   180
LPKNEPQNPG ANSARGRGVD LTEPTQPTRN QCCSN                              215

SEQ ID NO: 19              moltype = AA  length = 207
FEATURE                    Location/Qualifiers
source                     1..207
                           mol_type = protein
                           organism = Homo sapiens
SEQUENCE: 19
MTSRKKVLLK VIILGDSGVG KTSLMNQYVN KKFSNQYKAT IGADFLTKEV MVDDRLVTMQ    60
IWDTAGQERF QSLGVAFYRG ADCCVLFDV TAPNTFKTLD SWRDEFLIQA SPRDPENFPF   120
VVLGNKIDLE NRQVATKRAQ AWCYSKNNIP YFETSAKEAI NVEQAFQTIA RNALKQETEV   180
ELYNEFPEPI KLDKNDRAKA SAESCSC                                      207

SEQ ID NO: 20              moltype = AA  length = 184
FEATURE                    Location/Qualifiers
source                     1..184
                           mol_type = protein
                           organism = Homo sapiens
SEQUENCE: 20
MREYKLVVLG SGGVGKSALT VQFVQGIFVE KYDPTIEDSY RKQVEVDCQQ CMLEILDTAG    60
TEQFTAMRDL YMKNGQGFAL VYSITAQSTF NDLQDLREQI LRVKDTEDVP MILVGNKCDL   120
EDERVVGKEQ GQNLARQWCN CAFLESSAKS KINVNEIFYD LVRQINRKTP VEKKKPKKKS   180
CLLL                                                               184

SEQ ID NO: 21              moltype = AA  length = 193
FEATURE                    Location/Qualifiers
source                     1..193
                           mol_type = protein
                           organism = Homo sapiens
SEQUENCE: 21
MAAIRKKLVI VGDGACGKTC LLIVFSKDQF PEVYVPTVFE NYVADIEVDG KQVELALWDT    60
AGQEDYDRLR PLSYPDTDVI LMCFSIDSPD SLENIPEKWT PEVKHFCPNV PIILVGNKKD   120
LRNDEHTRRE LAKMKQEPVK PEEGRDMANR IGAFGYMECS AKTKDGVREV FEMATRAALQ   180
ARRGKKKSGC LVL                                                     193

SEQ ID NO: 22              moltype = AA  length = 191
FEATURE                    Location/Qualifiers
source                     1..191
                           mol_type = protein
                           organism = Homo sapiens
SEQUENCE: 22
MQTIKCVVVG DGAVGKTCLL ISYTTNKFPS EYVPTVFDNY AVTVMIGGEP YTLGLFDTAG    60
QEDYDRLRPL SYPQTDVFLV CFSVVSPSSF ENVKEKWVPE ITHHCPKTPF LLVGTQIDLR   120
DDPSTIEKLA KNKQKPITPE TAEKLARDLK AVKYVECSAL TQKGLKNVFD EAILAALEPP   180
EPKKSRRCVL L                                                       191

SEQ ID NO: 23              moltype = AA  length = 21
FEATURE                    Location/Qualifiers
source                     1..21
                           mol_type = protein
                           organism = Mus musculus
SEQUENCE: 23
ILIIACCVGF VLMVLLFLAF L                                             21

SEQ ID NO: 24              moltype = AA  length = 279
FEATURE                    Location/Qualifiers
SIGNAL                     1..22
source                     1..279
                           mol_type = protein
                           organism = Mus musculus
SEQUENCE: 24
MSKGLLLLWL VTELWWLYLT PAASEDTIIG FLGQPVTLPC HYLSWSQSRN SMCWGKGSCP    60
NSKCNAELLR TDGTRIISRK STKYTLLGKV QFGEVSLTIS NTNRGDSGVY CCRIEVPGWF   120
NDVKKNVRLE LRRATTTKKP TTTTRPTTTP YVTTTTPELL PTTVMTTSVL PTTTPPQTLA   180
TTAFSTAVTT CPSTTPGSFS QETTKGSAFT TESETLPASN HSQRSMMTIS TDIAVLRPTG   240
SNPGILPSTS QLTTQKTTLT TSESLQKTTK SHQINSRQT                          279

SEQ ID NO: 25              moltype = AA  length = 22
FEATURE                    Location/Qualifiers
source                     1..22
                           mol_type = protein
                           organism = Mus musculus
SEQUENCE: 25
MSKGLLLLWL VTELWWLYLT PA                                            22

SEQ ID NO: 26              moltype = AA  length = 41
```

-continued

```
FEATURE                 Location/Qualifiers
REGION                  1..41
                        note = human CD28 costimulatory signaling domain with
                         L186G/L187G substitutions - positions reference to full
                         length protein
source                  1..41
                        mol_type = protein
                        organism = synthetic construct
SEQUENCE: 26
RSKRSRGGHS DYMNMTPRRP GPTRKHYQPY APPRDFAAYR S                   41

SEQ ID NO: 27           moltype = AA  length = 113
FEATURE                 Location/Qualifiers
source                  1..113
                        mol_type = protein
                        organism = Homo sapiens
SEQUENCE: 27
RVKFSRSADA PAYQQGQNQL YNELNLGRRE EYDVLDKRRG RDPEMGGKPQ RRKNPQEGLY  60
NELQKDKMAE AYSEIGMKGE RRRGKGHDGL YQGLSTATKD TYDALHMQAL PPR        113

SEQ ID NO: 28           moltype = AA  length = 23
FEATURE                 Location/Qualifiers
REGION                  1..23
                        note = T2A self-cleaving peptide variant
source                  1..23
                        mol_type = protein
                        organism = synthetic construct
SEQUENCE: 28
LEGGGEGRGS LLTCGDVEEN PGP                                       23

SEQ ID NO: 29           moltype = AA  length = 19
FEATURE                 Location/Qualifiers
REGION                  1..19
                        note = T2A self-cleaving peptide variant
source                  1..19
                        mol_type = protein
                        organism = synthetic construct
SEQUENCE: 29
EGRGSLLTCG DVEENPGPR                                            19

SEQ ID NO: 30           moltype = AA  length = 24
FEATURE                 Location/Qualifiers
REGION                  1..24
                        note = T2A self-cleaving peptide variant
source                  1..24
                        mol_type = protein
                        organism = synthetic construct
SEQUENCE: 30
LEGGGEGRGS LLTCGDVEEN PGPR                                      24

SEQ ID NO: 31           moltype = AA  length = 27
FEATURE                 Location/Qualifiers
REGION                  1..27
                        note = P2A self-cleaving peptide variant
source                  1..27
                        mol_type = protein
                        organism = synthetic construct
SEQUENCE: 31
RAKRSGSGAT NFSLLKQAGD VEENPGP                                   27

SEQ ID NO: 32           moltype = AA  length = 39
FEATURE                 Location/Qualifiers
REGION                  1..39
                        note = CD28 hinge region
source                  1..39
                        mol_type = protein
                        organism = synthetic construct
SEQUENCE: 32
IEVMYPPPYL DNEKSNGTII HVKGKHLCPS PLFPGPSKP                      39

SEQ ID NO: 33           moltype = AA  length = 24
FEATURE                 Location/Qualifiers
REGION                  1..24
                        note = CD8a transmembrane domain
source                  1..24
                        mol_type = protein
                        organism = synthetic construct
SEQUENCE: 33
IYIWAPLAGT CGVLLLSLVI TLYC                                      24
```

-continued

```
SEQ ID NO: 34            moltype = AA  length = 111
FEATURE                  Location/Qualifiers
source                   1..111
                         mol_type = protein
                         organism = Homo sapiens
SEQUENCE: 34
ETVVTEVLGH RVTLPCLYSS WSHNSNSMCW GKDQCPYSGC KEALIRTDGM RVTSRKSAKY  60
RLQGTIPRGD VSLTILNPSE SDSGVYCCRI EVPGWFNDVK INVRLNLQRA S           111

SEQ ID NO: 35            moltype = AA  length = 179
FEATURE                  Location/Qualifiers
source                   1..179
                         mol_type = protein
                         organism = Homo sapiens
SEQUENCE: 35
TTTHRTATTT TRRTTTTSPT TTRQMTTTPA ALPTTVVTTP DLTTGTPLQM TTIAVFTTAN  60
TCLSLTPSTL PEEATGLLTP EPSKEGPILT AESETVLPSD SWSSVESTSA DTVLLTSKES  120
KVWDLPSTSH VSMWKTSDSV SSPQPGASDT AVPEQNKTTK TGQMDGIPMS MKNEMPISQ   179

SEQ ID NO: 36            moltype = AA  length = 364
FEATURE                  Location/Qualifiers
source                   1..364
                         mol_type = protein
                         organism = Homo sapiens
SEQUENCE: 36
MHPQVVILSL ILHLADSVAG SVKVGGEAGP SVTLPCHYSG AVTSMCWNRG SCSLFTCQNG  60
IVWTNGTHVT YRKDTRYKLL GDLSRRDVSL TIENTAVSDS GVYCCRVEHR GWFNDMKITV  120
SLEIVPPKVT TTPIVTTVPT VTTVRTSTTV PTTTTVPMTT VPTTTVPTTM SIPTTTTVLT  180
TMTVSTTTSV PTTTSIPTTT SVPVTTTVST FVPPMPLPRQ NHEPVATSPS SPQPAETHPT  240
TLQGAIRREP TSSPLYSYTT DGNDTVTESS DGLWNNNQTQ LFLEHSLLTA NTTKGIYAGV  300
CISVLVLLAL LGVIIAKKYF FKKEVQQLSV SFSSLQIKAL QNAVEKEVQA EDNIYIENSL  360
YATD                                                              364

SEQ ID NO: 37            moltype = AA  length = 295
FEATURE                  Location/Qualifiers
SIGNAL                   1..20
source                   1..295
                         mol_type = protein
                         organism = Homo sapiens
SEQUENCE: 37
MHPQVVILSL ILHLADSVAG SVKVGGEAGP SVTLPCHYSG AVTSMCWNRG SCSLFTCQNG  60
IVWTNGTHVT YRKDTRYKLL GDLSRRDVSL TIENTAVSDS GVYCCRVEHR GWFNDMKITV  120
SLEIVPPKVT TTPIVTTVPT VTTVRTSTTV PTTTTVPMTT VPTTTVPTTM SIPTTTTVLT  180
TMTVSTTTSV PTTTSIPTTT SVPVTTTVST FVPPMPLPRQ NHEPVATSPS SPQPAETHPT  240
TLQGAIRREP TSSPLYSYTT DGNDTVTESS DGLWNNNQTQ LFLEHSLLTA NTTKG       295

SEQ ID NO: 38            moltype = AA  length = 108
FEATURE                  Location/Qualifiers
source                   1..108
                         mol_type = protein
                         organism = Homo sapiens
SEQUENCE: 38
SVKVGGEAGP SVTLPCHYSG AVTSMCWNRG SCSLFTCQNG IVWTNGTHVT YRKDTRYKLL  60
GDLSRRDVSL TIENTAVSDS GVYCCRVEHR GWFNDMKITV SLEIVPPK               108

SEQ ID NO: 39            moltype = AA  length = 167
FEATURE                  Location/Qualifiers
source                   1..167
                         mol_type = protein
                         organism = Homo sapiens
SEQUENCE: 39
VTTTPIVTTV PTVTTVRTST TVPTTTTVPM TTVPTTTVPT TMSIPTTTTV LTTMTVSTTT  60
SVPTTTSIPT TTSVPVTTTV STFVPPMPLP RQNHEPVATS PSSPQPAETH PTTLQGAIRR  120
EPTSSPLYSY TTDGNDTVTE SSDGLWNNNQ TQLFLEHSLL TANTTKG                167

SEQ ID NO: 40            moltype = AA  length = 20
FEATURE                  Location/Qualifiers
source                   1..20
                         mol_type = protein
                         organism = Homo sapiens
SEQUENCE: 40
MHPQVVILSL ILHLADSVAG                                              20

SEQ ID NO: 41            moltype = AA  length = 108
FEATURE                  Location/Qualifiers
REGION                   1..108
                         note = modified Tim1 IgV domain
source                   1..108
```

-continued

```
                              mol_type = protein
                              organism = synthetic construct
SEQUENCE: 41
SVKVGGEAGP SVTLPCHYSG AVTSMCWNRG SCSLFTCQNG IVWTNGTHVT YRKDTRYKLL   60
GDLSRGDVSL TIENTAVSDS GVYCCRVEHR GWFNDMKITV SLEIVPPK               108

SEQ ID NO: 42              moltype = AA   length = 290
FEATURE                    Location/Qualifiers
source                     1..290
                           mol_type = protein
                           organism = Homo sapiens
SEQUENCE: 42
ETVVTEVLGH RVTLPCLYSS WSHNSNSMCW GKDQCPYSGC KEALIRTDGM RVTSRKSAKY   60
RLQGTIPRGD VSLTILNPSE SDSGVYCCRI EVPGWFNDVK INVRLNLQRA STTTHRTATT  120
TTRRTTTTSP TTTRQMTTTP AALPTTVVTT PDLTTGTPLQ MTTIAVFTTA NTCLSLTPST  180
LPEEATGLLT PEPSKEGPIL TAESETVLPS DSWSSVESTS ADTVLLTSKE SKVWDLPSTS  240
HVSMWKTSDS VSSPQPGASD TAVPEQNKTT KTGQMDGIPM SMKNEMPISQ             290

SEQ ID NO: 43              moltype = AA   length = 275
FEATURE                    Location/Qualifiers
source                     1..275
                           mol_type = protein
                           organism = Homo sapiens
SEQUENCE: 43
SVKVGGEAGP SVTLPCHYSG AVTSMCWNRG SCSLFTCQNG IVWTNGTHVT YRKDTRYKLL   60
GDLSRGDVSL TIENTAVSDS GVYCCRVEHR GWFNDMKITV SLEIVPPKVT TTPIVTTVPT  120
VTTVRTSTTV PTTTTVPMTT VPTTTVPTTM SIPTTTTVLT TMTVSTTTSV PTTTSIPTTT  180
SVPVTTTVST FVPPMPLPRQ NHEPVATSPS SPQPAETHPT TLQGAIRREP TSSPLYSYTT  240
DGNDTVTESS DGLWNNNQTQ LFLEHSLLTA NTTKG                            275

SEQ ID NO: 44              moltype = AA   length = 48
FEATURE                    Location/Qualifiers
source                     1..48
                           mol_type = protein
                           organism = Homo sapiens
SEQUENCE: 44
KKYFFKKEVQ QLSVSFSSLQ IKALQNAVEK EVQAEDNIYI ENSLYATD               48

SEQ ID NO: 45              moltype = AA   length = 43
FEATURE                    Location/Qualifiers
source                     1..43
                           mol_type = protein
                           organism = Homo sapiens
SEQUENCE: 45
LRGKLMETYC SQKHTRLDYI GDSKNVLNDV QHGREDEDGL FTL                    43

SEQ ID NO: 46              moltype = AA   length = 274
FEATURE                    Location/Qualifiers
REGION                     1..274
                           note = TRAF6 signaling domain
source                     1..274
                           mol_type = protein
                           organism = synthetic construct
SEQUENCE: 46
MSLLNCENSC GSSQSESDCC VAMASSCSAV TKDDSVGGTA STGNLSSSFM EEIQGYDVEF   60
DPPLESKYEC PICLMALREA VQTPCGHRFC KACIIKSIRD AGHKCPVDNE ILLENQLFPD  120
NFAKREILSL MVKCPNEGCL HKMELRHLED HQAHCEFALM DCPQCQRPFQ KFHINIHILK  180
DCPRRQVSCD NCAASMAFED KEIHDQNCPL ANVICEYCNT ILIREQMPNH YDLDCPTAPI  240
PCTFSTFGCH EKMQRNHLAR HLQENTQSHM RMLA                             274

SEQ ID NO: 47              moltype = AA   length = 193
FEATURE                    Location/Qualifiers
REGION                     1..193
                           note = TLR8 signaling domain
source                     1..193
                           mol_type = protein
                           organism = synthetic construct
SEQUENCE: 47
HHLFYWDVWF IYNVCLAKVK GYRSLSTSQT FYDAYISYDT KDASVTDWVI NELRYHLEES   60
RDKNVLLCLE ERDWDPGLAI IDNLMQSINQ SKKTVFVLTK KYAKSWNFKT AFYLALQRLM  120
DENMDVIIFI LLEPVLQHSQ YLRLRQRICK SSILQWPDNP KAEGLFWQTL RNVVLTENDS  180
RYNNMYVDSI KQY                                                    193

SEQ ID NO: 48              moltype = AA   length = 303
FEATURE                    Location/Qualifiers
REGION                     1..303
                           note = TRAF2 signaling domain
source                     1..303
                           mol_type = protein
```

```
                     organism = synthetic construct
SEQUENCE: 48
MAAASVTPPG SLELLQPGFS KTLLGTKLEA KYLCSACRNV LRRPFQAQCG HRYCSFCLAS   60
ILSSGPQNCA ACVHEGIYEE GISILESSSA FPDNAARREV ESLPAVCPSD GCTWKGTLKE  120
YESCHEGRCP LMLTECPACK GLVRLGEKER HLEHECPERS LSCRHCRAPC CGADVKAHHE  180
VCPKFPLTCD GCGKKKIPRE KFQDHVKTCG KCRVPCRFHA IGCLETVEGE KQQEHEVQWL  240
REHLAMLLSS VLEAKPLLGD QSHAGSELLQ RCESLEKKTA TFENIVCVLN REVERVAMTA  300
EAC                                                               303

SEQ ID NO: 49            moltype = AA  length = 476
FEATURE                  Location/Qualifiers
REGION                   1..476
                         note = Chimeric Tim - Tim1IgV - Tim1Mucin - Tim1TM - Tim1SD
                          - CD3zSD
source                   1..476
                         mol_type = protein
                         organism = synthetic construct
SEQUENCE: 49
MHPQVVILSL ILHLADSVAG SVKVGGEAGP SVTLPCHYSG AVTSMCWNRG SCSLFTCQNG   60
IWTNGTHVT YRKDTRYKLL GDLSRRDVSL TIENTAVSDS GVYCCRVEHR GWFNDMKITV  120
SLEIVPPKVT TTPIVTTVPT VTTVRTSTTV PTTTTVPMTT VPTTTVPTTM SIPTTTTVLT  180
TMTVSTTTSV PTTTSIPTTT SVPVTTTVST FVPPMPLPRQ NHEPVATSPS SPQPAETHPT  240
TLQGAIRREP TSSPLYSYTT DGNDTVTESS DGLWNNNQTQ LFLEHSLLTA NTTKGIYAGV  300
CISVLVLLAL LGVIIAKKYF FKKEVQQLSV SFSSLQIKAL QNAVEKEVQA EDNIYIENSL  360
YATDRVKFSR SADAPAYQQG QNQLYNELNL GRREEYDVLD KRRGRDPEMG GKPRRKNPQE  420
GLYNELQKDK MAEAYSEIGM KGERRRGKGH DGLYQGLSTA TKDTYDALHM QALPPR      476

SEQ ID NO: 50            moltype = AA  length = 471
FEATURE                  Location/Qualifiers
REGION                   1..471
                         note = Chimeric Tim - Tim1IgV - Tim1Mucin - Tim1TM - Tim4SD
                          - CD3zSD
source                   1..471
                         mol_type = protein
                         organism = synthetic construct
SEQUENCE: 50
MHPQVVILSL ILHLADSVAG SVKVGGEAGP SVTLPCHYSG AVTSMCWNRG SCSLFTCQNG   60
IWTNGTHVT YRKDTRYKLL GDLSRRDVSL TIENTAVSDS GVYCCRVEHR GWFNDMKITV  120
SLEIVPPKVT TTPIVTTVPT VTTVRTSTTV PTTTTVPMTT VPTTTVPTTM SIPTTTTVLT  180
TMTVSTTTSV PTTTSIPTTT SVPVTTTVST FVPPMPLPRQ NHEPVATSPS SPQPAETHPT  240
TLQGAIRREP TSSPLYSYTT DGNDTVTESS DGLWNNNQTQ LFLEHSLLTA NTTKGIYAGV  300
CISVLVLLAL LGVIIALRGK LMETYCSQKH TRLDYIGDSK NVLNDVQHGR EDEDGLFTLR  360
VKFSRSADAP AYQQGQNQLY NELNLGRREE YDVLDKRRGR DPEMGGKPRR KNPQEGLYNE  420
LQKDKMAEAY SEIGMKGERR RGKGHDGLYQ GLSTATKDTY DALHMQALPP R          471

SEQ ID NO: 51            moltype = AA  length = 363
FEATURE                  Location/Qualifiers
REGION                   1..363
                         note = Chimeric Tim - Tim1IgV - Tim1Mucin - CD28TM - CD28SD
source                   1..363
                         mol_type = protein
                         organism = synthetic construct
SEQUENCE: 51
MHPQVVILSL ILHLADSVAG SVKVGGEAGP SVTLPCHYSG AVTSMCWNRG SCSLFTCQNG   60
IWTNGTHVT YRKDTRYKLL GDLSRRDVSL TIENTAVSDS GVYCCRVEHR GWFNDMKITV  120
SLEIVPPKVT TTPIVTTVPT VTTVRTSTTV PTTTTVPMTT VPTTTVPTTM SIPTTTTVLT  180
TMTVSTTTSV PTTTSIPTTT SVPVTTTVST FVPPMPLPRQ NHEPVATSPS SPQPAETHPT  240
TLQGAIRREP TSSPLYSYTT DGNDTVTESS DGLWNNNQTQ LFLEHSLLTA NTTKGFWVLV  300
VVGGVLACYS LLVTVAFIIF WVRSKRSRLL HSDYMNMTPR RPGPTRKHYQ PYAPPRDFAA  360
YRS                                                               363

SEQ ID NO: 52            moltype = AA  length = 590
FEATURE                  Location/Qualifiers
REGION                   1..590
                         note = Chimeric Tim - Tim1IgV - Tim1Mucin -Tim1TM - TRAF6SD
source                   1..590
                         mol_type = protein
                         organism = synthetic construct
SEQUENCE: 52
MHPQVVILSL ILHLADSVAG SVKVGGEAGP SVTLPCHYSG AVTSMCWNRG SCSLFTCQNG   60
IWTNGTHVT YRKDTRYKLL GDLSRRDVSL TIENTAVSDS GVYCCRVEHR GWFNDMKITV  120
SLEIVPPKVT TTPIVTTVPT VTTVRTSTTV PTTTTVPMTT VPTTTVPTTM SIPTTTTVLT  180
TMTVSTTTSV PTTTSIPTTT SVPVTTTVST FVPPMPLPRQ NHEPVATSPS SPQPAETHPT  240
TLQGAIRREP TSSPLYSYTT DGNDTVTESS DGLWNNNQTQ LFLEHSLLTA NTTKGIYAGV  300
CISVLVLLAL LGVIIAMSLL NCENSCGSSQ SESDCCVAMA SSCSAVTKDD SVGGTASTGN  360
LSSSFMEEIQ GYDVEFDPPL ESKYECPICL MALREAVQTP CGHRFCKACI IKSIRDAGHK  420
CPVDNEILLE NQLFPDNFAK REILSLMVKC PNEGCLHKME LRHLEDHQAH CEFALMDCPQ  480
CQRPFQKFHI NIHILKDCPR RQVSCDNCAA SMAFEDKEIH DQNCPLANVI CEYCNTILIR  540
EQMPNHYDLD CPTAPIPCTF STFGCHEKMQ RNHLARHLQE NTQSHMRMLA            590
```

```
SEQ ID NO: 53              moltype = AA  length = 596
FEATURE                   Location/Qualifiers
REGION                    1..596
                          note = Chimeric Tim - Tim1IgV - Tim1Mucin -CD28TM - TRAF6SD
source                    1..596
                          mol_type = protein
                          organism = synthetic construct
SEQUENCE: 53
MHPQVVILSL ILHLADSVAG SVKVGGEAGP SVTLPCHYSG AVTSMCWNRG SCSLFTCQNG    60
IVWTNGTHVT YRKDTRYKLL GDLSRRDVSL TIENTAVSDS GVYCCRVEHR GWFNDMKITV   120
SLEIVPPKVT TTPIVTTVPT VTTVRTSTTV PTTTTVPMTT VPTTTVPTTM SIPTTTTVLT   180
TMTVSTTTSV PTTTSIPTTT SVPVTTTVST FVPPMPLPRQ NHEPVATSPS SPQPAETHPT   240
TLQGAIRREP TSSPLYSYTT DGNDTVTESS DGLWNNNQTQ LFLEHSLLTA NTTKGFWVLV   300
VVGGVLACYS LLVTVAFIIF WVMSLLNCEN SCGSSQSESD CCVAMASSCS AVTKDDSVGG   360
TASTGNLSSS FMEEIQGYDV EFDPPLESKY ECPICLMALR EAVQTPCGHR FCKACIIKSI   420
RDAGHKCPVD NEILLENQLF PDNFAKREIL SLMVKCPNEG CLHKMELRHL EDHQAHCEFA   480
LMDCPQCQRP FQKFHINIHI LKDCPRRQVS CDNCAASMAF EDKEIHDQNC PLANVICEYC   540
NTILIREQMP NHYDLDCPTA PIPCTFSTFG CHEKMQRNHL ARHLQENTQS HMRMLA       596

SEQ ID NO: 54              moltype = AA  length = 619
FEATURE                   Location/Qualifiers
REGION                    1..619
                          note = Chimeric Tim - Tim1IgV - Tim1Mucin - Tim1TM - TRAF2SD
source                    1..619
                          mol_type = protein
                          organism = synthetic construct
SEQUENCE: 54
MHPQVVILSL ILHLADSVAG SVKVGGEAGP SVTLPCHYSG AVTSMCWNRG SCSLFTCQNG    60
IVWTNGTHVT YRKDTRYKLL GDLSRRDVSL TIENTAVSDS GVYCCRVEHR GWFNDMKITV   120
SLEIVPPKVT TTPIVTTVPT VTTVRTSTTV PTTTTVPMTT VPTTTVPTTM SIPTTTTVLT   180
TMTVSTTTSV PTTTSIPTTT SVPVTTTVST FVPPMPLPRQ NHEPVATSPS SPQPAETHPT   240
TLQGAIRREP TSSPLYSYTT DGNDTVTESS DGLWNNNQTQ LFLEHSLLTA NTTKGIYAGV   300
CISVLVLLAL LGVIIAMAAA SVTPPGSLEL LQPGFSKTLL GTKLEAKYLC SACRNVLRRP   360
FQAQCGHRYC SFCLASILSS GPQNCAACVH EGIYEEGISI LESSSAFPDN AARREVESLP   420
AVCPSDGCTW KGTLKEYESC HEGRCPLMLT ECPACKGLVR LGEKERHLEH ECPERSLSCR   480
HCRAPCCGAD VKAHHEVCPK FPLTCDGCGK KKIPREKFQD HVKTCGKCRV PCRFHAIGCL   540
ETVEGEKQQE HEVQWLREHL AMLLSSVLEA KPLLGDQSHA GSELLQRCES LEKKTATFEN   600
IVCVLNREVE RVAMTAEAC                                                619

SEQ ID NO: 55              moltype = AA  length = 625
FEATURE                   Location/Qualifiers
REGION                    1..625
                          note = Chimeric Tim - Tim1IgV - Tim1Mucin - CD28TM - TRAF2SD
source                    1..625
                          mol_type = protein
                          organism = synthetic construct
SEQUENCE: 55
MHPQVVILSL ILHLADSVAG SVKVGGEAGP SVTLPCHYSG AVTSMCWNRG SCSLFTCQNG    60
IVWTNGTHVT YRKDTRYKLL GDLSRRDVSL TIENTAVSDS GVYCCRVEHR GWFNDMKITV   120
SLEIVPPKVT TTPIVTTVPT VTTVRTSTTV PTTTTVPMTT VPTTTVPTTM SIPTTTTVLT   180
TMTVSTTTSV PTTTSIPTTT SVPVTTTVST FVPPMPLPRQ NHEPVATSPS SPQPAETHPT   240
TLQGAIRREP TSSPLYSYTT DGNDTVTESS DGLWNNNQTQ LFLEHSLLTA NTTKGFWVLV   300
VVGGVLACYS LLVTVAFIIF WVMAAASVTP PGSLELLQPG FSKTLLGTKL EAKYLCSACR   360
NVLRRPFQAQ CGHRYCSFCL ASILSSGPQN CAACVHEGIY EEGISILESS SAFPDNAARR   420
EVESLPAVCP SDGCTWKGTL KEYESCHEGR CPLMLTECPA CKGLVRLGEK ERHLEHECPE   480
RSLSCRHCRA PCCGADVKAH HEVCPKFPLT CDGCGKKKIP REKFQDHVKT CGKCRVPCRF   540
HAIGCLETVE GEKQQEHEVQ WLREHLAMLL SSVLEAKPLL GDQSHAGSEL LQRCESLEKK   600
TATFENIVCV LNREVERVAM TAEAC                                         625

SEQ ID NO: 56              moltype = AA  length = 621
FEATURE                   Location/Qualifiers
REGION                    1..621
                          note = Chimeric Tim - Tim1IgV - Tim1Mucin - Tim1TM - TLR8SD
                           - CD3zSD
source                    1..621
                          mol_type = protein
                          organism = synthetic construct
SEQUENCE: 56
MHPQVVILSL ILHLADSVAG SVKVGGEAGP SVTLPCHYSG AVTSMCWNRG SCSLFTCQNG    60
IVWTNGTHVT YRKDTRYKLL GDLSRRDVSL TIENTAVSDS GVYCCRVEHR GWFNDMKITV   120
SLEIVPPKVT TTPIVTTVPT VTTVRTSTTV PTTTTVPMTT VPTTTVPTTM SIPTTTTVLT   180
TMTVSTTTSV PTTTSIPTTT SVPVTTTVST FVPPMPLPRQ NHEPVATSPS SPQPAETHPT   240
TLQGAIRREP TSSPLYSYTT DGNDTVTESS DGLWNNNQTQ LFLEHSLLTA NTTKGIYAGV   300
CISVLVLLAL LGVIIAHHLF YWDVWFIYNV CLAKVKGYRS LSTSQTFYDA YISYDTKDAS   360
VTDWVINELR YHLEESRDKN VLLCLEERDW DPGLAIIDNL MQSINQSKKT VFVLTKKYAK   420
SWNFKTAFYL ALQRLMDENM DVIIFILLEP VLQHSQYLRL RQRICKSSIL QWPDNPKAEG   480
LFWQTLRNVV LTENDSRYNN MYVDSIKQYR VKFSRSADAP AYQQGQNQLY NELNLGRREE   540
YDVLDKRRGR DPEMGGKPRR KNPQEGLYNE LQKDKMAEAY SEIGMKGERR RGKGHDGLYQ   600
```

```
GLSTATKDTY DALHMQALPP R                                                     621

SEQ ID NO: 57           moltype = AA   length = 415
FEATURE                 Location/Qualifiers
REGION                  1..415
                        note = Chimeric Tim - Tim1IgV - Tim1Mucin - CD28TM - CD28SD
                        - DAP12SD
source                  1..415
                        mol_type = protein
                        organism = synthetic construct
SEQUENCE: 57
MHPQVVILSL ILHLADSVAG SVKVGGEAGP SVTLPCHYSG AVTSMCWNRG SCSLFTCQNG  60
IWTNGTHVT YRKDTRYKLL GDLSRRDVSL TIENTAVSDS GVYCCRVEHR GWFNDMKITV   120
SLEIVPPKVT TTPIVTTVPT VTTVRTSTTV PTTTTVPMTT VPTTTVPTTM SIPTTTTVLT  180
TMTVSTTTSV PTTTSIPTTT SVPVTTTVST FVPPMPLPRQ NHEPVATSPS SPQPAETHPT  240
TLQGAIRREP TSSPLYSYTT DGNDTVTESS DGLWNNNQTQ LFLEHSLLTA NTTKGFWVLV  300
VVGGVLACYS LLVTVAFIIF WVRSKRSRLL HSDYMNMTPR RPGPTRKHYQ PYAPPRDFAA  360
YRSYFLGRLV PRGRGAAEAA TRKQRITETE SPYQELQGGR SDVYSDLNTQ RPYYK       415

SEQ ID NO: 58           moltype = AA   length = 409
FEATURE                 Location/Qualifiers
REGION                  1..409
                        note = Chimeric Tim - Tim1IgV - Tim1Mucin - Tim1TM - CD28SD
                        - DAP12SD
source                  1..409
                        mol_type = protein
                        organism = synthetic construct
SEQUENCE: 58
MHPQVVILSL ILHLADSVAG SVKVGGEAGP SVTLPCHYSG AVTSMCWNRG SCSLFTCQNG  60
IWTNGTHVT YRKDTRYKLL GDLSRRDVSL TIENTAVSDS GVYCCRVEHR GWFNDMKITV   120
SLEIVPPKVT TTPIVTTVPT VTTVRTSTTV PTTTTVPMTT VPTTTVPTTM SIPTTTTVLT  180
TMTVSTTTSV PTTTSIPTTT SVPVTTTVST FVPPMPLPRQ NHEPVATSPS SPQPAETHPT  240
TLQGAIRREP TSSPLYSYTT DGNDTVTESS DGLWNNNQTQ LFLEHSLLTA NTTKGIYAGV  300
CISVLVLLAL LGVIIARSKR SRLLHSDYMN MTPRRPGPTR KHYQPYAPPR DFAAYRSYFL  360
GRLVPRGRGA AEAATRKQRI TETESPYQEL QGQRSDVYSL NTQRPYYK              409

SEQ ID NO: 59           moltype = AA   length = 490
FEATURE                 Location/Qualifiers
REGION                  1..490
                        note = Chimeric Tim - Tim4IgV - Tim4Mucin - Tim4TM - Tim4SD
                        - CD3zSD
source                  1..490
                        mol_type = protein
                        organism = synthetic construct
SEQUENCE: 59
MSKEPLILWL MIEFWWLYLT PVTSETVVTE VLGHRVTLPC LYSSWSHNSN SMCWGKDQCP  60
YSGCKEALIR TDGMRVTSRK SAKYRLQGTI PRGDVSLTIL NPSESDSGVY CCRIEVPGWF  120
NDVKINVRLN LQRASTTTHR TATTTTRRTT TTSPTTTRQM TTTPAALPTT VVTTPDLTTG  180
TPLQMTTIAV FTTANTCLSL TPSTLPEEAT GLLTPEPSKE GPILTAESET VLPSDSWSSV  240
ESTSADTVLL TSKESKVWDL PSTSHVSMWK TSDSVSSPQP GASDTAVPEQ NKTTKTGQMD  300
GIPMSMKNEM PISQLLMIIA PSLGFVLFAL FVAFLLRGKL METYCSQKHT RLDYIGDSKN  360
VLNDVQHGRE DEDGLFTLRV KFSRSADAPA YQQGQNQLYN ELNLGRREEY DVLDKRRGRD  420
PEMGGKPRRK NPQEGLYNEL QKDKMAEAYS EIGMKGERRR GKGHDGLYQG LSTATKDTYD  480
ALHMQALPPR                                                         490

SEQ ID NO: 60           moltype = AA   length = 495
FEATURE                 Location/Qualifiers
REGION                  1..495
                        note = Chimeric Tim - Tim4IgV - Tim4Mucin - Tim4TM - Tim1SD
                        - CD3zSD
source                  1..495
                        mol_type = protein
                        organism = synthetic construct
SEQUENCE: 60
MSKEPLILWL MIEFWWLYLT PVTSETVVTE VLGHRVTLPC LYSSWSHNSN SMCWGKDQCP  60
YSGCKEALIR TDGMRVTSRK SAKYRLQGTI PRGDVSLTIL NPSESDSGVY CCRIEVPGWF  120
NDVKINVRLN LQRASTTTHR TATTTTRRTT TTSPTTTRQM TTTPAALPTT VVTTPDLTTG  180
TPLQMTTIAV FTTANTCLSL TPSTLPEEAT GLLTPEPSKE GPILTAESET VLPSDSWSSV  240
ESTSADTVLL TSKESKVWDL PSTSHVSMWK TSDSVSSPQP GASDTAVPEQ NKTTKTGQMD  300
GIPMSMKNEM PISQLLMIIA PSLGFVLFAL FVAFLKKYFF KKEVQQLSVS FSSLQIKALQ  360
NAVEKEVQAE DNIYIENSLY ATDRVKFSRS ADAPAYQQGQ NQLYNELNLG RREEYDVLDK  420
RRGRDPEMGG KPRRKNPQEG LYNELQKDKM AEAYSEIGMK GERRRGKGHD GLYQGLSTAT  480
KDTYDALHMQ ALPPR                                                   495

SEQ ID NO: 61           moltype = AA   length = 382
FEATURE                 Location/Qualifiers
REGION                  1..382
                        note = Chimeric Tim - Tim4IgV - Tim4Mucin - CD28TM - CD28SD
source                  1..382
```

```
                        mol_type = protein
                        organism = synthetic construct
SEQUENCE: 61
MSKEPLILWL MIEFWWLYLT PVTSETVVTE VLGHRVTLPC LYSSWSHNSN SMCWGKDQCP    60
YSGCKEALIR TDGMRVTSRK SAKYRLQGTI PRGDVSLTIL NPSESDSGVY CCRIEVPGWF   120
NDVKINVRLN LQRASTTTHR TATTTTRRTT TTSPTTTRQM TTTPAALPTT VVTTPDLTTG   180
TPLQMTTIAV FTTANTCLSL TPSTLPEEAT GLLTPEPSKE GPILTAESET VLPSDSWSSV   240
ESTSADTVLL TSKESKVWDL PSTSHVSMWK TSDSVSSPQP GASDTAVPEQ NKTTKTGQMD   300
GIPMSMKNEM PISQFWVLVV VGGVLACYSL LVTVAFIIFW VRSKRSRLLH SDYMNMTPRR   360
PGPTRKHYQP YAPPRDFAAY RS                                           382

SEQ ID NO: 62          moltype = AA   length = 609
FEATURE                Location/Qualifiers
REGION                 1..609
                       note = Chimeric Tim - Tim4IgV - Tim4Mucin - Tim4TM - TRAF6SD
source                 1..609
                       mol_type = protein
                       organism = synthetic construct
SEQUENCE: 62
MSKEPLILWL MIEFWWLYLT PVTSETVVTE VLGHRVTLPC LYSSWSHNSN SMCWGKDQCP    60
YSGCKEALIR TDGMRVTSRK SAKYRLQGTI PRGDVSLTIL NPSESDSGVY CCRIEVPGWF   120
NDVKINVRLN LQRASTTTHR TATTTTRRTT TTSPTTTRQM TTTPAALPTT VVTTPDLTTG   180
TPLQMTTIAV FTTANTCLSL TPSTLPEEAT GLLTPEPSKE GPILTAESET VLPSDSWSSV   240
ESTSADTVLL TSKESKVWDL PSTSHVSMWK TSDSVSSPQP GASDTAVPEQ NKTTKTGQMD   300
GIPMSMKNEM PISQLLMIIA PSLGFVLFAL FVAFLMSLLN CENSCGSSQS ESDCCVAMAS   360
SCSAVTKDDS VGGTASTGNL SSSFMEEIQG YDVEFDPPLE SKYECPICLM ALREAVQTPC   420
GHRFCKACII KSIRDAGHKC PVDNEILLEN QLFPDNFAKR EILSLMVKCP NEGCLHKMEL   480
RHLEDHQAHC EFALMDCPQC QRPFQKFHIN IHILKDCPRR QVSCDNCAAS MAFEDKEIHD   540
QNCPLANVIC EYCNTILIRE QMPNHYDLDC PTAPIPCTFS TFGCHEKMQR NHLARHLQEN   600
TQSHMRMLA                                                          609

SEQ ID NO: 63          moltype = AA   length = 615
FEATURE                Location/Qualifiers
REGION                 1..615
                       note = Chimeric Tim - Tim4IgV - Tim4Mucin - CD28TM - TRAF6SD
source                 1..615
                       mol_type = protein
                       organism = synthetic construct
SEQUENCE: 63
MSKEPLILWL MIEFWWLYLT PVTSETVVTE VLGHRVTLPC LYSSWSHNSN SMCWGKDQCP    60
YSGCKEALIR TDGMRVTSRK SAKYRLQGTI PRGDVSLTIL NPSESDSGVY CCRIEVPGWF   120
NDVKINVRLN LQRASTTTHR TATTTTRRTT TTSPTTTRQM TTTPAALPTT VVTTPDLTTG   180
TPLQMTTIAV FTTANTCLSL TPSTLPEEAT GLLTPEPSKE GPILTAESET VLPSDSWSSV   240
ESTSADTVLL TSKESKVWDL PSTSHVSMWK TSDSVSSPQP GASDTAVPEQ NKTTKTGQMD   300
GIPMSMKNEM PISQFWVLVV VGGVLACYSL LVTVAFIIFW VMSLLNCENS CGSSQSESDC   360
CVAMASSCSA VTKDDSVGGT ASTGNLSSSF MEEIQGYDVE FDPPLESKYE CPICLMALRE   420
AVQTPCGHRF CKACIIKSIR DAGHKCPVDN EILLENQLFP DNFAKREILS LMVKCPNEGC   480
LHKMELRHLE DHQAHCEFAL MDCPQCQRPF QKFHINIHIL KDCPRRQVSC DNCAASMAFE   540
DKEIHDQNCP LANVICEYCN TILIREQMPN HYDLDCPTAP IPCTFSTFGC HEKMQRNHLA   600
RHLQENTQSH MRMLA                                                   615

SEQ ID NO: 64          moltype = AA   length = 638
FEATURE                Location/Qualifiers
REGION                 1..638
                       note = Chimeric Tim - Tim4IgV - Tim4Mucin - Tim4TM - TRAF2SD
source                 1..638
                       mol_type = protein
                       organism = synthetic construct
SEQUENCE: 64
MSKEPLILWL MIEFWWLYLT PVTSETVVTE VLGHRVTLPC LYSSWSHNSN SMCWGKDQCP    60
YSGCKEALIR TDGMRVTSRK SAKYRLQGTI PRGDVSLTIL NPSESDSGVY CCRIEVPGWF   120
NDVKINVRLN LQRASTTTHR TATTTTRRTT TTSPTTTRQM TTTPAALPTT VVTTPDLTTG   180
TPLQMTTIAV FTTANTCLSL TPSTLPEEAT GLLTPEPSKE GPILTAESET VLPSDSWSSV   240
ESTSADTVLL TSKESKVWDL PSTSHVSMWK TSDSVSSPQP GASDTAVPEQ NKTTKTGQMD   300
GIPMSMKNEM PISQLLMIIA PSLGFVLFAL FVAFLMAAAS VTPPGSLELL QPGFSKTLLG   360
TKLEAKYLCS ACRNVLRRPF QAQCGHRYCS FCLASILSSG PQNCAACVHE GIYEEGISIL   420
ESSSAFPDNA ARREVESLPA VCPSDGCTWK GTLKEYESCH EGRCPLMLTE CPACKGLVRL   480
GEKERHLEHE CPERSLSCRH CRAPCCGADV KAHHEVCPKF PLTCDGCGKK KIPREKFQDH   540
VKTCGKCRVP CRFHAIGCLE TVEGEKQQEH EVQWLREHLA MLLSSVLEAK PLLGDQSHAG   600
SELLQRCESL EKKTATFENI VCVLNREVER VAMTAEAC                          638

SEQ ID NO: 65          moltype = AA   length = 644
FEATURE                Location/Qualifiers
REGION                 1..644
                       note = Chimeric Tim - Tim4IgV - Tim4Mucin - CD28TM - TRAF2SD
source                 1..644
                       mol_type = protein
                       organism = synthetic construct
SEQUENCE: 65
```

```
MSKEPLILWL MIEFWWLYLT PVTSETVVTE VLGHRVTLPC LYSSWSHNSN SMCWGKDQCP   60
YSGCKEALIR TDGMRVTSRK SAKYRLQGTI PRGDVSLTIL NPSESDSGVY CCRIEVPGWF  120
NDVKINVRLN LQRASTTTHR TATTTTRRTT TTSPTTTRQM TTTPAALPTT VVTTPDLTTG  180
TPLQMTTIAV FTTANTCLSL TPSTLPEEAT GLLTPEPSKE GPILTAESET VLPSDSWSSV  240
ESTSADTVLL TSKESKVVDL PSTSHVSMWK TSDSVSSPQP GASDTAVPEQ NKTTKTGQMD  300
GIPMSMKNEM PISQFWVLVV VGGVLACYSL LVTVAFIIFW VMAAASVTPP GSLELLQPGF  360
SKTLLGTKLE AKYLCSACRN VLRRPFQAQC GHRYCSFCLA SILSSGPQNC AACVHEGIYE  420
EGISILESSS AFPDNAARRE VESLPAVCPS DGCTWKGTLK EYESCHEGRC PLMLTECPAC  480
KGLVRLGEKE RHLEHECPER SLSCRHCRAP CCGADVKAHH EVCPKFPLTC DGCGKKKIPR  540
EKFQDHVKTC GKCRVPCRFH AIGCLETVEG EKQQEHEVQW LREHLAMLLS SVLEAKPLLG  600
DQSHAGSELL QRCESLEKKT ATFENIVCVL NREVERVAMT AEAC               644

SEQ ID NO: 66              moltype = AA   length = 640
FEATURE                    Location/Qualifiers
REGION                     1..640
                           note = Chimeric Tim - Tim4IgV - Tim4Mucin - Tim1TM - TLR8SD
                           - CD3zSD
source                     1..640
                           mol_type = protein
                           organism = synthetic construct
SEQUENCE: 66
MSKEPLILWL MIEFWWLYLT PVTSETVVTE VLGHRVTLPC LYSSWSHNSN SMCWGKDQCP   60
YSGCKEALIR TDGMRVTSRK SAKYRLQGTI PRGDVSLTIL NPSESDSGVY CCRIEVPGWF  120
NDVKINVRLN LQRASTTTHR TATTTTRRTT TTSPTTTRQM TTTPAALPTT VVTTPDLTTG  180
TPLQMTTIAV FTTANTCLSL TPSTLPEEAT GLLTPEPSKE GPILTAESET VLPSDSWSSV  240
ESTSADTVLL TSKESKVVDL PSTSHVSMWK TSDSVSSPQP GASDTAVPEQ NKTTKTGQMD  300
GIPMSMKNEM PISQIYAGVC ISVLVLLALL GVIIAHHLFY WDVWFIYNVC LAKVKGYRSL  360
STSQTFYDAY ISYDTKDASV TDWVINELRY HLEESRDKNV LLCLEERDWD PGLAIIDNLM  420
QSINQSKKTV FVLTKKYAKS WNFKTAFYLA LQRLMDENMD VIIFILLEPV LQHSQYLRLR  480
QRICKSSILQ WPDNPKAEGL FWQTLRNVVL TENDSRYNNM YVDSIKQYRV KFPSRSADAPA  540
YQQGQNQLYN ELNLGRREEY DVLDKRRGRD PEMGGKPRRK NPQEGLYNEL QKDKMAEAYS  600
EIGMKGERRR GKGHDGLYQG LSTATKDTYD ALHMQALPPR               640

SEQ ID NO: 67              moltype = AA   length = 628
FEATURE                    Location/Qualifiers
REGION                     1..628
                           note = Chimeric Tim - Tim4IgV - Tim1Mucin - Tim1TM - TLR8SD
                           - CD3zSD
source                     1..628
                           mol_type = protein
                           organism = synthetic construct
SEQUENCE: 67
MSKEPLILWL MIEFWWLYLT PVTSETVVTE VLGHRVTLPC LYSSWSHNSN SMCWGKDQCP   60
YSGCKEALIR TDGMRVTSRK SAKYRLQGTI PRGDVSLTIL NPSESDSGVY CCRIEVPGWF  120
NDVKINVRLN LQRASVTTTP IVTTVPTVTT VRTSTTVPTT TTVPMTTVPT TTVPTTMSIP  180
TTTTVLTTMT VSTTTSVPTT TSIPTTTSVP VTTTVSTFVP PMPLPRQNHE PVATSPSSPQ  240
PAETHPTTLQ GAIRREPTSS PLYSYTTDGN DTVTESSDGL WNNNQTQLFL EHSLLTANTT  300
KGIYAGVCIS VLVLLALLGV IIAHHLFYWD VWFIYNVCLA KVKGYRSLST SQTFYDAYIS  360
YDTKDASVTD WVINELRYHL EESRDKNVLL CLEERDWDPG LAIIDNLMQS INQSKKTVFV  420
LTKKYAKSWN FKTAFYLALQ RLMDENMDVI IFILLEPVLQ HSQYLRLRQR ICKSSILQWP  480
DNPKAEGLFW QTLRNVVLTE NDSRYNNMYV DSIKQYRVKF SRSADAPAYQ QGQNQLYNEL  540
NLGRREEYDV LDKRRGRDPE MGGKPRRKNP QEGLYNELQK DKMAEAYSEI GMKGERRGK  600
GHDGLYQGLS TATKDTYDAL HMQALPPR               628

SEQ ID NO: 68              moltype = AA   length = 416
FEATURE                    Location/Qualifiers
REGION                     1..416
                           note = Chimeric Tim - Tim4IgV - Tim1Mucin - Tim1TM - CD28SD
                           - DAP12SD
source                     1..416
                           mol_type = protein
                           organism = synthetic construct
SEQUENCE: 68
MSKEPLILWL MIEFWWLYLT PVTSETVVTE VLGHRVTLPC LYSSWSHNSN SMCWGKDQCP   60
YSGCKEALIR TDGMRVTSRK SAKYRLQGTI PRGDVSLTIL NPSESDSGVY CCRIEVPGWF  120
NDVKINVRLN LQRASVTTTP IVTTVPTVTT VRTSTTVPTT TTVPMTTVPT TTVPTTMSIP  180
TTTTVLTTMT VSTTTSVPTT TSIPTTTSVP VTTTVSTFVP PMPLPRQNHE PVATSPSSPQ  240
PAETHPTTLQ GAIRREPTSS PLYSYTTDGN DTVTESSDGL WNNNQTQLFL EHSLLTANTT  300
KGIYAGVCIS VLVLLALLGV IIARSKRSRL LHSDYMNMTP RRPGPTRKHY QPYAPPRDFA  360
AYRSYFLGRL VPRGRGAAEA ATRKQRITET ESPYQELQGQ RSDVYSDLNT QRPYYK      416

SEQ ID NO: 69              moltype = AA   length = 422
FEATURE                    Location/Qualifiers
REGION                     1..422
                           note = Chimeric Tim - Tim4IgV - Tim1Mucin - CD28TM - CD28SD
                           - DAP12SD
source                     1..422
                           mol_type = protein
                           organism = synthetic construct
```

```
SEQUENCE: 69
MSKEPLILWL MIEFWWLYLT PVTSETVVTE VLGHRVTLPC LYSSWSHNSN SMCWGKDQCP   60
YSGCKEALIR TDGMRVTSRK SAKYRLQGTI PRGDVSLTIL NPSESDSGVY CCRIEVPGWF  120
NDVKINVRLN LQRASVTTTP IVTTVPTVTT VRTSTTVPTT TTVPMTTVPT TTVPTTMSIP  180
TTTTVLTTMT VSTTTSVPTT TSIPTTTSVP VTTTVSTFVP PMPLPRQNHE PVATSPSSPQ  240
PAETHPTTLQ GAIRREPTSS PLYSYTTDGN DTVTESSDGL WNNNQTQLFL EHSLLTANTT  300
KGFWVLVVVG GVLACYSLLV TVAFIIFWVR SKRSRLLHSD YMNMTPRRPG PTRKHYQPYA  360
PPRDFAAYRS YFLGRLVPRG RGAAEAATRK QRITETESPY QELQGQRSDV YSDLNTQRPY  420
YK                                                                 422

SEQ ID NO: 70            moltype = AA  length = 45
FEATURE                  Location/Qualifiers
REGION                   1..45
                         note = CD8a hinge region
source                   1..45
                         mol_type = protein
                         organism = synthetic construct
SEQUENCE: 70
TTTPAPRPPT PAPTIASQPL SLRPEACRPA AGGAVHTRGL DFACD                   45

SEQ ID NO: 71            moltype = AA  length = 5
FEATURE                  Location/Qualifiers
REGION                   1..5
                         note = Sc02-004 HCDR1
source                   1..5
                         mol_type = protein
                         organism = synthetic construct
SEQUENCE: 71
GYLMS                                                                5

SEQ ID NO: 72            moltype = AA  length = 17
FEATURE                  Location/Qualifiers
REGION                   1..17
                         note = Sc02-004 HCDR2
source                   1..17
                         mol_type = protein
                         organism = synthetic construct
SEQUENCE: 72
VISYDGSNKY YADSVKG                                                  17

SEQ ID NO: 73            moltype = AA  length = 10
FEATURE                  Location/Qualifiers
REGION                   1..10
                         note = Sc02-004 HCDR3
source                   1..10
                         mol_type = protein
                         organism = synthetic construct
SEQUENCE: 73
ARRDTNLFDY                                                          10

SEQ ID NO: 74            moltype = AA  length = 11
FEATURE                  Location/Qualifiers
REGION                   1..11
                         note = Sc02-004 LCDR1
source                   1..11
                         mol_type = protein
                         organism = synthetic construct
SEQUENCE: 74
RASQSISSYL N                                                        11

SEQ ID NO: 75            moltype = AA  length = 7
FEATURE                  Location/Qualifiers
REGION                   1..7
                         note = Sc02-004 LCDR2
source                   1..7
                         mol_type = protein
                         organism = synthetic construct
SEQUENCE: 75
AASSLQS                                                             7

SEQ ID NO: 76            moltype = AA  length = 9
FEATURE                  Location/Qualifiers
REGION                   1..9
                         note = Sc02-004 LCDR3
source                   1..9
                         mol_type = protein
                         organism = synthetic construct
SEQUENCE: 76
QQSYSTPPT                                                           9
```

-continued

```
SEQ ID NO: 77            moltype = AA   length = 5
FEATURE                  Location/Qualifiers
REGION                   1..5
                         note = Sc02-025 HCDR1
source                   1..5
                         mol_type = protein
                         organism = synthetic construct
SEQUENCE: 77
SYYMH                                                                   5

SEQ ID NO: 78            moltype = AA   length = 17
FEATURE                  Location/Qualifiers
REGION                   1..17
                         note = Sc02-025 HCDR2
source                   1..17
                         mol_type = protein
                         organism = synthetic construct
SEQUENCE: 78
IINPSGGGTS YAQKFQG                                                      17

SEQ ID NO: 79            moltype = AA   length = 12
FEATURE                  Location/Qualifiers
REGION                   1..12
                         note = Sc02-025 HCDR3
source                   1..12
                         mol_type = protein
                         organism = synthetic construct
SEQUENCE: 79
DYYVTYDSWF DS                                                           12

SEQ ID NO: 80            moltype = AA   length = 11
FEATURE                  Location/Qualifiers
REGION                   1..11
                         note = Sc02-025 LCDR1
source                   1..11
                         mol_type = protein
                         organism = synthetic construct
SEQUENCE: 80
QGDSLRSYYA S                                                            11

SEQ ID NO: 81            moltype = AA   length = 7
FEATURE                  Location/Qualifiers
REGION                   1..7
                         note = Sc02-025 LCDR2
source                   1..7
                         mol_type = protein
                         organism = synthetic construct
SEQUENCE: 81
GKNNRPS                                                                 7

SEQ ID NO: 82            moltype = AA   length = 11
FEATURE                  Location/Qualifiers
REGION                   1..11
                         note = Sc02-025 LCDR3
source                   1..11
                         mol_type = protein
                         organism = synthetic construct
SEQUENCE: 82
NSRDSSGNHV V                                                            11

SEQ ID NO: 83            moltype = AA   length = 114
FEATURE                  Location/Qualifiers
REGION                   1..114
                         note = Sc02-004 VH
source                   1..114
                         mol_type = protein
                         organism = synthetic construct
SEQUENCE: 83
LVESGGGLVQ PGGSLRLSCA ASGFTFSGYL MSWVRQAPGK GLEWVAVISY DGSNKYYADS   60
VKGRFTISRD NSKNTLYLQM DSLRAEDTAV YYCARARRDT NLFDYWGQGT LVTV         114

SEQ ID NO: 84            moltype = AA   length = 104
FEATURE                  Location/Qualifiers
REGION                   1..104
                         note = Sc02-004 VL
source                   1..104
                         mol_type = protein
                         organism = synthetic construct
```

-continued

```
SEQUENCE: 84
ELTQSPSSLS ASVGDRVTIT CRASQSISSY LNWYQQKPGK APKLLIYAAS SLQSGVPSRF  60
SGSGSGTDFT LTISSLQPED FATYYCQQSY STPPTFGQGT KVEI                    104

SEQ ID NO: 85          moltype = AA   length = 117
FEATURE                Location/Qualifiers
REGION                 1..117
                       note = Sc02-025 VH
source                 1..117
                       mol_type = protein
                       organism = synthetic construct
SEQUENCE: 85
LVQSGAEVKK PGASVKVSCK ASGYTFTSYY MHWVRQAPGQ GLEWMGIINP SGGGTSYAQK  60
FQGRVTMTRD TSTSTVYMEL SSLRSEDTAV YYCARDYYVT YDSWFDSWGQ GTLVTVS     117

SEQ ID NO: 86          moltype = AA   length = 98
FEATURE                Location/Qualifiers
REGION                 1..98
                       note = Sc02-025 VL
source                 1..98
                       mol_type = protein
                       organism = synthetic construct
SEQUENCE: 86
VSVALGQTVR ITCQGDSLRS YYASWYQQKP GQAPVLVIYG KNNRPSGIPD RFSGSSSGNT  60
ASLTITGAQA EDEADYYCNS RDSSGNHVVF GGGTKLTV                          98

SEQ ID NO: 87          moltype = AA   length = 244
FEATURE                Location/Qualifiers
REGION                 1..244
                       note = Sc02-004 scFv
source                 1..244
                       mol_type = protein
                       organism = synthetic construct
SEQUENCE: 87
AEVQLVESGG GLVQPGGSLR LSCAASGFTF SGYLMSWVRQ APGKGLEWVA VISYDGSNKY  60
YADSVKGRFT ISRDNSKNTL YLQMDSLRAE DTAVYYCARA RRDTNLFDYW GQGTLVTVLE  120
GTGGSGGTGS GTGTSELTQS PSSLSASVGD RVTITCRASQ SISSYLNWYQ QKPGKAPKLL  180
IYAASSLQSG VPSRFSGSGS GTDFTLTISS LQPEDFATYY CQQSYSTPPT FGQGTKVEIK  240
RAAA                                                              244

SEQ ID NO: 88          moltype = AA   length = 248
FEATURE                Location/Qualifiers
REGION                 1..248
                       note = Sc02-025 scFv
source                 1..248
                       mol_type = protein
                       organism = synthetic construct
SEQUENCE: 88
AQVQLVQSGA EVKKPGASVK VSCKASGYTF TSYYMHWVRQ APGQGLEWMG IINPSGGGTS  60
YAQKFQGRVT MTRDTSTSTV YMELSSLRSE DTAVYYCARD YYVTYDSWFD SWGQGTLVTV  120
SRGGGGSGGG GSGGGGSSEL TQDPAVSVAL GQTVRITCQG DSLRSYYASW YQQKPGQAPV  180
LVIYGKNNRP SGIPDRFSGS SSGNTASLTI TGAQAEDEAD YYCNSRDSSG NHVVFGGGTK  240
LTVLGAAA                                                          248

SEQ ID NO: 89          moltype = AA   length = 15
FEATURE                Location/Qualifiers
REGION                 1..15
                       note = Flexible linker
source                 1..15
                       mol_type = protein
                       organism = synthetic construct
SEQUENCE: 89
GGGGSGGGGS GGGGS                                                   15

SEQ ID NO: 90          moltype = AA   length = 15
FEATURE                Location/Qualifiers
REGION                 1..15
                       note = Flexible linker
source                 1..15
                       mol_type = protein
                       organism = synthetic construct
SEQUENCE: 90
GTGGSGGTGS GTGTS                                                   15

SEQ ID NO: 91          moltype = AA   length = 12
FEATURE                Location/Qualifiers
REGION                 1..12
                       note = IgG4 hinge region (short)
source                 1..12
```

-continued

```
                          mol_type = protein
                          organism = synthetic construct
SEQUENCE: 91
ESKYGPPCPP CP                                                         12

SEQ ID NO: 92             moltype = AA   length = 45
FEATURE                   Location/Qualifiers
REGION                    1..45
                          note = CD8a hinge region
source                    1..45
                          mol_type = protein
                          organism = synthetic construct
SEQUENCE: 92
TTTPAPRPPT PAPTIASQPL SLRPEACRPA AGGAVHTRGL DFACD                     45

SEQ ID NO: 93             moltype = AA   length = 38
FEATURE                   Location/Qualifiers
REGION                    1..38
                          note = CD28 hinge region
source                    1..38
                          mol_type = protein
                          organism = synthetic construct
SEQUENCE: 93
IEVMYPPPYL DNEKSNGTII HVKGKHLCPS PLFPGPKP                             38

SEQ ID NO: 94             moltype = AA   length = 24
FEATURE                   Location/Qualifiers
REGION                    1..24
                          note = CD8a transmembrane region
source                    1..24
                          mol_type = protein
                          organism = synthetic construct
SEQUENCE: 94
IYIWAPLAGT CGVLLLSLVI TLYC                                            24

SEQ ID NO: 95             moltype = AA   length = 27
FEATURE                   Location/Qualifiers
REGION                    1..27
                          note = CD28 transmembrane region
source                    1..27
                          mol_type = protein
                          organism = synthetic construct
SEQUENCE: 95
FWVLVVVGGV LACYSLLVTV AFIIFWV                                         27

SEQ ID NO: 96             moltype = AA   length = 113
FEATURE                   Location/Qualifiers
REGION                    1..113
                          note = wildtype CD3z signaling domain
source                    1..113
                          mol_type = protein
                          organism = synthetic construct
SEQUENCE: 96
RVKFSRSADA PAYQQGQNQL YNELNLGRRE EYDVLDKRRG RDPEMGGKPQ RRKNPQEGLY 60
NELQKDKMAE AYSEIGMKGE RRRGKGHDGL YQGLSTATKD TYDALHMQAL PPR          113

SEQ ID NO: 97             moltype = AA   length = 112
FEATURE                   Location/Qualifiers
REGION                    1..112
                          note = variant CD3z signaling domain
source                    1..112
                          mol_type = protein
                          organism = synthetic construct
SEQUENCE: 97
RVKFSRSADA PAYQQGQNQL YNELNLGRRE EYDVLDKRRG RDPEMGGKPR RKNPQEGLYN 60
ELQKDKMAEA YSEIGMKGER RRGKGHDGLY QGLSTATKDT YDALHMQALP PR           112

SEQ ID NO: 98             moltype = AA   length = 41
FEATURE                   Location/Qualifiers
REGION                    1..41
                          note = wildtype CD28 costimulatory signaling domain
source                    1..41
                          mol_type = protein
                          organism = synthetic construct
SEQUENCE: 98
RSKRSRLLHS DYMNMTPRRP GPTRKHYQPY APPRDFAAYR S                         41

SEQ ID NO: 99             moltype = AA   length = 41
FEATURE                   Location/Qualifiers
```

-continued

```
REGION                 1..41
                       note = variant CD28 costimulatory signaling domain with
                       L186G/L187G substitutions with positions in reference to
                       full length protein
source                 1..41
                       mol_type = protein
                       organism = synthetic construct
SEQUENCE: 99
RSKRSRGGHS DYMNMTPRRP GPTRKHYQPY APPRDFAAYR S                        41

SEQ ID NO: 100         moltype = AA   length = 42
FEATURE                Location/Qualifiers
REGION                 1..42
                       note = 4-1BB costimulatory signaling domain
source                 1..42
                       mol_type = protein
                       organism = synthetic construct
SEQUENCE: 100
KRGRKKLLYI FKQPFMRPVQ TTQEEDGCSC RFPEEEEGGC EL                       42

SEQ ID NO: 101         moltype = AA   length = 458
FEATURE                Location/Qualifiers
REGION                 1..458
                       note = pCTX206 CAR: GMSCFR signal peptide (amino acids
                       1-21) - sc02-004 scFv - IgG4 Hinge - CD28 TM - CD28 ICD -
                       CD3z
SIGNAL                 1..21
source                 1..458
                       mol_type = protein
                       organism = synthetic construct
SEQUENCE: 101
MLLVTSLLLC ELPHPAFLLI PAEVQLVESG GGLVQPGGSL RLSCAASGFT FSGYLMSWVR  60
QAPGKGLEWV AVISYDGSNK YYADSVKGRF TISRDNSKNT LYLQMDSLRA EDTAVYYCAR  120
ARRDTNLFDY WGQGTLVTVL EGTGGSGGTG SGTGTSELTQ SPSSLSASVG DRVTITCRAS  180
QSISSYLNWY QQKPGKAPKL LIYAASSLQS GVPSRFSGSG SGTDFTLTIS SLQPEDFATY  240
YCQQSYSTPP TFGQGTKVEI KRAAAESKYG PPCPPCPFWV LVVVGGVLAC YSLLVTVAFI  300
IFWVRSKRSR LLHSDYMNMT PRRPGPTRKH YQPYAPPRDF AAYRSRVKFS RSADAPAYQQ  360
GQNQLYNELN LGRREEYDVL DKRRGRDPEM GGKPQRRKNP QEGLYNELQK DKMAEAYSEI  420
GMKGERRRGK GHDGLYQGLS TATKDTYDAL HMQALPPR                          458

SEQ ID NO: 102         moltype = AA   length = 462
FEATURE                Location/Qualifiers
REGION                 1..462
                       note = pCTX208 CAR: GMSCFR signal peptide (amino acids
                       1-21) - sc02-025 scFv - IgG4 Hinge - CD28 TM - CD28 ICD -
                       CD3z
SIGNAL                 1..21
source                 1..462
                       mol_type = protein
                       organism = synthetic construct
SEQUENCE: 102
MLLVTSLLLC ELPHPAFLLI PAQVQLVQSG AEVKKPGASV KVSCKASGYT FTSYYMHWVR  60
QAPGQGLEWM GIINPSGGGT SYAQKFQGRV TMTRDTSTST VYMELSSLRS EDTAVYYCAR  120
DYYVTYDSWF DSWGQGTLVT VSRGGGGSGG GGSGGGGSSE LTQDPAVSVA LGQTVRITCQ  180
GDSLRSYYAS WYQQKPGQAP VLVIYGKNNR PSGIPDRFSG SSSGNTASLT ITGAQAEDEA  240
DYYCNSRDSS GNHVVFGGGT KLTVLGAAAE SKYGPPCPPC PFWVLVVVGG VLACYSLLVT  300
VAFIIFWVRS KRSRLLHSDY MNMTPRRPGP TRKHYQPYAP PRDFAAYRSR VKFSRSADAP  360
AYQQGQNQLY NELNLGRREE YDVLDKRRGR DPEMGGKPQR RKNPQEGLYN ELQKDKMAEA  420
YSEIGMKGER RRGKGHDGLY QGLSTATKDT YDALHMQALP PR                     462

SEQ ID NO: 103         moltype = AA   length = 459
FEATURE                Location/Qualifiers
REGION                 1..459
                       note = CAR: GMSCFR signal peptide (amino acids 1-21) -
                       sc02-004 scFv - IgG4 Hinge - CD28 TM - 4-1BB ICD - CD3z
SIGNAL                 1..21
source                 1..459
                       mol_type = protein
                       organism = synthetic construct
SEQUENCE: 103
MLLVTSLLLC ELPHPAFLLI PAEVQLVESG GGLVQPGGSL RLSCAASGFT FSGYLMSWVR  60
QAPGKGLEWV AVISYDGSNK YYADSVKGRF TISRDNSKNT LYLQMDSLRA EDTAVYYCAR  120
ARRDTNLFDY WGQGTLVTVL EGTGGSGGTG SGTGTSELTQ SPSSLSASVG DRVTITCRAS  180
QSISSYLNWY QQKPGKAPKL LIYAASSLQS GVPSRFSGSG SGTDFTLTIS SLQPEDFATY  240
YCQQSYSTPP TFGQGTKVEI KRAAAESKYG PPCPPCPFWV LVVVGGVLAC YSLLVTVAFI  300
IFWVKRGRKK LLYIFKQPFM RPVQTTQEED GCSCRFPEEE EGGCELRVKF SRSADAPAYQ  360
QGQNQLYNEL NLGRREEYDV LDKRRGRDPE MGGKPQRRKN PQEGLYNELQ KDKMAEAYSE  420
IGMKGERRRG KGHDGLYQGL STATKDTYDA LHMQALPPR                         459
```

```
SEQ ID NO: 104           moltype = AA   length = 463
FEATURE                  Location/Qualifiers
REGION                   1..463
                         note = CAR: GMSCFR signal peptide (amino acids 1-21) -
                           sc02-025 scFv - IgG4 Hinge - CD28 TM - 4-1BB ICD - CD3z
SIGNAL                   1..21
source                   1..463
                         mol_type = protein
                         organism = synthetic construct
SEQUENCE: 104
MLLVTSLLLC ELPHPAFLLI PAQVQLVQSG AEVKKPGASV KVSCKASGYT FTSYYMHWVR   60
QAPGQGLEWM GIINPSGGGT SYAQKFQGRV TMTRDTSTST VYMELSSLRS EDTAVYYCAR  120
DYYVTYDSWF DSWGQGTLVT VSRGGGGSGG GGSGGGGSSE LTQDPAVSVA LGQTVRITCQ  180
GDSLRSYYAS WYQQKPGQAP VLVIYGKNNR PSGIPDRFSG SSSGNTASLT ITGAQAEDEA  240
DYYCNSRDSS GNHVVFGGGT KLTVLGAAAE SKYGPPCPPC PFWVLVVVGG VLACYSLLVT  300
VAFIIFWVKR GRKKLLYIFK QPFMRPVQTT QEEDGCSCRF PEEEGGCEL RVKFSRSADA   360
PAYQQGQNQL YNELNLGRRE EYDVLDKRRG RDPEMGGKPQ RRKNPQEGLY NELQKDKMAE  420
AYSEIGMKGE RRRGKGHDGL YQGLSTATKD TYDALHMQAL PPR                    463

SEQ ID NO: 105           moltype = AA   length = 485
FEATURE                  Location/Qualifiers
REGION                   1..485
                         note = CAR: GMSCFR signal peptide (amino acids 1-21) -
                           sc02-004 scFv - CD28 Hinge - CD28 TM - CD28 ICD - CD3z
SIGNAL                   1..21
source                   1..485
                         mol_type = protein
                         organism = synthetic construct
SEQUENCE: 105
MLLVTSLLLC ELPHPAFLLI PAEVQLVESG GGLVQPGGSL RLSCAASGFT FSGYLMSWVR   60
QAPGKGLEWV AVISYDGSNK YYADSVKGRF TISRDNSKNT LYLQMDSLRA EDTAVYYCAR  120
ARRDTNLFDY WGQGTLVTVL EGTGGSGGTG SGTGTSELTQ SPSSLSASVG DRVTITCRAS  180
QSISSYLNWY QQKPGKAPKL LIYAASSLQS GVPSRFSGSG SGTDFTLTIS SLQPEDFATY  240
YCQQSYSTPP TFGQGTKVEI KRAAAIEVMY PPPYLDNEKS NGTIIHVKGK HLCPSPLFPG  300
PSKPFWVLVV VGGVLACYSL LVTVAFIIFW VRSKRSRLLH SDYMNMTPRR PGPTRKHYQP  360
YAPPRDFAAY RSRVKFSRSA DAPAYQQGQN QLYNELNLGR REEYDVLDKR RGRDPEMGGK  420
PQRRKNPQEG LYNELQKDKM AEAYSEIGMK GERRRGKGHD GLYQGLSTAT KDTYDALHMQ  480
ALPPR                                                              485

SEQ ID NO: 106           moltype = AA   length = 489
FEATURE                  Location/Qualifiers
REGION                   1..489
                         note = CAR: GMSCFR signal peptide (amino acids 1-21) -
                           sc02-025 scFv - CD28 Hinge - CD28 TM - CD28 ICD - CD3z
SIGNAL                   1..21
source                   1..489
                         mol_type = protein
                         organism = synthetic construct
SEQUENCE: 106
MLLVTSLLLC ELPHPAFLLI PAQVQLVQSG AEVKKPGASV KVSCKASGYT FTSYYMHWVR   60
QAPGQGLEWM GIINPSGGGT SYAQKFQGRV TMTRDTSTST VYMELSSLRS EDTAVYYCAR  120
DYYVTYDSWF DSWGQGTLVT VSRGGGGSGG GGSGGGGSSE LTQDPAVSVA LGQTVRITCQ  180
GDSLRSYYAS WYQQKPGQAP VLVIYGKNNR PSGIPDRFSG SSSGNTASLT ITGAQAEDEA  240
DYYCNSRDSS GNHVVFGGGT KLTVLGAAAI EVMYPPPYLD NEKSNGTIIH VKGKHLCPSP  300
LFPGPSKPFW VLVVVGGVLA CYSLLVTVAF IIFWVRSKRS RLLHSDYMNM TPRRPGPTRK  360
HYQPYAPPRD FAAYRSRVKF SRSADAPAYQ QGQNQLYNEL NLGRREEYDV LDKRRGRDPE  420
MGGKPQRRKN PQEGLYNELQ KDKMAEAYSE IGMKGERRRG KGHDGLYQGL STATKDTYDA  480
LHMQALPPR                                                          489

SEQ ID NO: 107           moltype = AA   length = 486
FEATURE                  Location/Qualifiers
REGION                   1..486
                         note = CAR: GMSCFR signal peptide (amino acids 1-21) -
                           sc02-004 scFv - CD28 Hinge - CD28 TM - 4-1BB ICD - CD3z
SIGNAL                   1..21
source                   1..486
                         mol_type = protein
                         organism = synthetic construct
SEQUENCE: 107
MLLVTSLLLC ELPHPAFLLI PAEVQLVESG GGLVQPGGSL RLSCAASGFT FSGYLMSWVR   60
QAPGKGLEWV AVISYDGSNK YYADSVKGRF TISRDNSKNT LYLQMDSLRA EDTAVYYCAR  120
ARRDTNLFDY WGQGTLVTVL EGTGGSGGTG SGTGTSELTQ SPSSLSASVG DRVTITCRAS  180
QSISSYLNWY QQKPGKAPKL LIYAASSLQS GVPSRFSGSG SGTDFTLTIS SLQPEDFATY  240
YCQQSYSTPP TFGQGTKVEI KRAAAIEVFW PPPYLDNEKS NGTIIHVKGK HLCPSPLFPG  300
PSKPFWVLVV VGGVLACYSL LVTVAFIIFW VKRGRKKLLY IFKQPFMRPV QTTQEEDGCS  360
CRFPEEEEGG CELRVKFSRS ADAPAYQQGQ NQLYNELNLG RREEYDVLDK RRGRDPEMGG  420
KPQRRKNPQE GLYNELQKDK MAEAYSEIGM KGERRRGKGH DGLYQGLSTA TKDTYDALHM  480
QALPPR                                                             486
```

-continued

```
SEQ ID NO: 108              moltype = AA  length = 490
FEATURE                     Location/Qualifiers
REGION                      1..490
                            note = CAR: GMSCFR signal peptide (amino acids 1-21) -
                            sc02-025 scFv - CD28 Hinge - CD28 TM - 4-1BB ICD - CD3z
SIGNAL                      1..21
source                      1..490
                            mol_type = protein
                            organism = synthetic construct
SEQUENCE: 108
MLLVTSLLLC ELPHPAFLLI PAQVQLVQSG AEVKKPGASV KVSCKASGYT FTSYYMHWVR   60
QAPGQGLEWM GIINPSGGGT SYAQKFQGRV TMTRDTSTST VYMELSSLRS EDTAVYYCAR  120
DYYVTYDSWF DSWGQGTLVT VSRGGGGSGG GGSGGGGSSE LTQDPAVSVA LGQTVRITCQ  180
GDSLRSYYAS WYQQKPGQAP VLVIYGKNNR PSGIPDRFSG SSSGNTASLT ITGAQAEDEA  240
DYYCNSRDSS GNHVVFGGGT KLTVLGAAAI EVMYPPPYLD NEKSNGTIIH VKGKHLCPSP  300
LFPGPSKPFW VLVVVGGVLA CYSLLVTVAF IIFWVKRGRK KLLYIFKQPF MRPVQTTQEE  360
DGCSCRFPEE EEGGCELRVK FSRSADAPAY QQGQNQLYNE LNLGRREEYD VLDKRRGRDP  420
EMGGKPQRRK NPQEGLYNEL QKDKMAEAYS EIGMKGERRR GKGHDGLYQG LSTATKDTYD  480
ALHMQALPPR                                                         490

SEQ ID NO: 109              moltype = AA  length = 455
FEATURE                     Location/Qualifiers
REGION                      1..455
                            note = CAR: GMSCFR signal peptide (amino acids 1-21)-
                            sc02-004 scFv - IgG4 Hinge - CD8a TM - CD28 ICD - CD3z
SIGNAL                      1..21
source                      1..455
                            mol_type = protein
                            organism = synthetic construct
SEQUENCE: 109
MLLVTSLLLC ELPHPAFLLI PAEVQLVESG GGLVQPGGSL RLSCAASGFT FSGYLMSWVR   60
QAPGKGLEWV AVISYDGSNK YYADSVKGRF TISRDNSKNT LYLQMDSLRA EDTAVYYCAR  120
ARRDTNLFDY WGQGTLVTVL EGTGGSGGTG SGTGSELTQ SPSSLSASVG DRVTITCRAS  180
QSISSYLNWY QQKPGKAPKL LIYAASSLQS GVPSRFSGSG GVPSRFSGSG SLQPEDFATY  240
YCQQSYSTPP TFGQGTKVEI KRAAAESKYG PPCPPCPIYI WAPLAGTCGV LLLSLVITLY  300
CRSKRSRLLH SDYMNMTPRR PGPTRKHYQP YAPPRDFAAY RSRVKFSRSA DAPAYQQGQN  360
QLYNELNLGR REEYDVLDKR RGRDPEMGGK PQRRKNPQEG LYNELQKDKM AEAYSEIGMK  420
GERRRGKGHD GLYQGLSTAT KDTYDALHMQ ALPPR                             455

SEQ ID NO: 110              moltype = AA  length = 459
FEATURE                     Location/Qualifiers
REGION                      1..459
                            note = CAR: GMSCFR signal peptide (amino acids 1-21)-
                            sc02-025 scFv - IgG4 Hinge - CD8a TM - CD28 ICD - CD3z
SIGNAL                      1..21
source                      1..459
                            mol_type = protein
                            organism = synthetic construct
SEQUENCE: 110
MLLVTSLLLC ELPHPAFLLI PAQVQLVQSG AEVKKPGASV KVSCKASGYT FTSYYMHWVR   60
QAPGQGLEWM GIINPSGGGT SYAQKFQGRV TMTRDTSTST VYMELSSLRS EDTAVYYCAR  120
DYYVTYDSWF DSWGQGTLVT VSRGGGGSGG GGSGGGGSSE LTQDPAVSVA LGQTVRITCQ  180
GDSLRSYYAS WYQQKPGQAP VLVIYGKNNR PSGIPDRFSG SSSGNTASLT ITGAQAEDEA  240
DYYCNSRDSS GNHVVFGGGT KLTVLGAAAE SKYGPPCPPC PIYIWAPLAG TCGVLLLSLV  300
ITLYCRSKRS RLLHSDYMNM TPRRPGPTRK HYQPYAPPRD FAAYRSRVKF SRSADAPAYQ  360
QGQNQLYNEL NLGRREEYDV LDKRRGRDPE MGGKPQRRKN PQEGLYNELQ KDKMAEAYSE  420
IGMKGERRRG KGHDGLYQGL STATKDTYDA LHMQALPPR                          459

SEQ ID NO: 111              moltype = AA  length = 488
FEATURE                     Location/Qualifiers
REGION                      1..488
                            note = CAR: GMSCFR signal peptide (amino acids 1-21) -
                            sc02-004 scFv - CD8a Hinge - CD8a TM - CD28 ICD - CD3z
SIGNAL                      1..21
source                      1..488
                            mol_type = protein
                            organism = synthetic construct
SEQUENCE: 111
MLLVTSLLLC ELPHPAFLLI PAEVQLVESG GGLVQPGGSL RLSCAASGFT FSGYLMSWVR   60
QAPGKGLEWV AVISYDGSNK YYADSVKGRF TISRDNSKNT LYLQMDSLRA EDTAVYYCAR  120
ARRDTNLFDY WGQGTLVTVL EGTGGSGGTG SGTGSELTQ SPSSLSASVG DRVTITCRAS  180
QSISSYLNWY QQKPGKAPKL LIYAASSLQS GVPSRFSGSG SGTDFTLTIS SLQPEDFATY  240
YCQQSYSTPP TFGQGTKVEI KRAAATTTPA PRPPTPAPTI ASQPLSLRPE ACRPAAGGAV  300
HTRGLDFACD IYIWAPLAGT CGVLLLSLVI TLYCRSKRSR LLHSDYMNMT PRRPGPTRKH  360
YQPYAPPRDF AAYRSRVKFS RSADAPAYQQ GQNQLYNELN LGRREEYDVL DKRRGRDPEM  420
GGKPQRRKNP QEGLYNELQK DKMAEAYSEI GMKGERRRGK GHDGLYQGLS TATKDTYDAL  480
HMQALPPR                                                           488

SEQ ID NO: 112              moltype = AA  length = 492
```

-continued

```
FEATURE              Location/Qualifiers
REGION               1..492
                     note = CAR: GMSCFR signal peptide (amino acids 1-21) -
                       sc02-025 scFv - CD8a Hinge - CD8a TM - CD28 ICD - CD3z
SIGNAL               1..21
source               1..492
                     mol_type = protein
                     organism = synthetic construct
SEQUENCE: 112
MLLVTSLLLC ELPHPAFLLI PAQVQLVQSG AEVKKPGASV KVSCKASGYT FTSYYMHWVR  60
QAPGQGLEWM GIINPSGGGT SYAQKFQGRV TMTRDTSTST VYMELSSLRS EDTAVYYCAR  120
DYYVTYDSWF DSWGQGTLVT VSRGGGGSGG GGSGGGGSSE LTQDPAVSVA LGQTVRITCQ  180
GDSLRSYYAS WYQQKPGQAP VLVIYGKNNR PSGIPDRFSG SSSGNTASLT ITGAQAEDEA  240
DYYCNSRDSS GNHVVFGGGT KLTVLGAAAT TTPAPRPPTP APTIASQPLS LRPEACRPAA  300
GGAVHTRGLD FACDIYIWAP LAGTCGVLLL SLVITLYCRS KRSRLLHSDY MNMTPRRPGP  360
TRKHYQPYAP PRDFAAYRSR VKFSRSADAP AYQQGQNQLY NELNLGRREE YDVLDKRRGR  420
DPEMGGKPQR RKNPQEGLYN ELQKDKMAEA YSEIGMKGER RRGKGHDGLY QGLSTATKDT  480
YDALHMQALP PR                                                     492

SEQ ID NO: 113          moltype = AA   length = 456
FEATURE                 Location/Qualifiers
REGION                  1..456
                        note = CAR: GMSCFR signal peptide (amino acids 1-21) -
                          sc02-004 scFv - IgG4 Hinge - CD8a TM - 4-1BB ICD - CD3z
SIGNAL                  1..21
source                  1..456
                        mol_type = protein
                        organism = synthetic construct
SEQUENCE: 113
MLLVTSLLLC ELPHPAFLLI PAEVQLVESG GGLVQPGGSL RLSCAASGFT FSGYLMSWVR  60
QAPGKGLEWV AVISYDGSNK YYADSVKGRF TISRDNSKNT LYLQMDSLRA EDTAVYYCAR  120
ARRDTNLFDY WGQGTLVTVL EGTGGSGGTG SGTGTSELTQ SPSSLSASVG DRVTITCRAS  180
QSISSYLNWY QQKPGKAPKL LIYAASSLQS GVPSRFSGSG SGTDFTLTIS SLQPEDFATY  240
YCQQSYSTPP TFGQGTKVEI KRAAAESKYG PPCPPCPIYI WAPLAGTCGV LLLSLVITLY  300
CKRGRKKLLY IFKQPFMRPV QTTQEEDGCS CRFPEEEGG CELRVKFSRS ADAPAYQQGQ  360
NQLYNELNLG RREEYDVLDK RRGRDPEMGG KPQRRKNPQE GLYNELQKDK MAEAYSEIGM  420
KGERRRGKGH DGLYQGLSTA TKDTYDALHM QALPPR                          456

SEQ ID NO: 114          moltype = AA   length = 460
FEATURE                 Location/Qualifiers
REGION                  1..460
                        note = CAR: GMSCFR signal peptide (amino acids 1-21) -
                          sc02-025 scFv - IgG4 Hinge - CD8a TM - 4-1BB ICD - CD3z
SIGNAL                  1..21
source                  1..460
                        mol_type = protein
                        organism = synthetic construct
SEQUENCE: 114
MLLVTSLLLC ELPHPAFLLI PAQVQLVQSG AEVKKPGASV KVSCKASGYT FTSYYMHWVR  60
QAPGQGLEWM GIINPSGGGT SYAQKFQGRV TMTRDTSTST VYMELSSLRS EDTAVYYCAR  120
DYYVTYDSWF DSWGQGTLVT VSRGGGGSGG GGSGGGGSSE LTQDPAVSVA LGQTVRITCQ  180
GDSLRSYYAS WYQQKPGQAP VLVIYGKNNR PSGIPDRFSG SSSGNTASLT ITGAQAEDEA  240
DYYCNSRDSS GNHVVFGGGT KLTVLGAAAE SKYGPPCPPC PIYIWAPLAG TCGVLLLSLV  300
ITLYCKRGRK KLLYIFKQPF MRPVQTTQEE DGCSCRFPEE EEGGCELRVK FSRSADAPAY  360
QQGQNQLYNE LNLGRREEYD VLDKRRGRDP EMGGKPQRRK NPQEGLYNEL QKDKMAEAYS  420
EIGMKGERRR GKGHDGLYQG LSTATKDTYD ALHMQALPPR                       460

SEQ ID NO: 115          moltype = AA   length = 489
FEATURE                 Location/Qualifiers
REGION                  1..489
                        note = CAR: GMSCFR signal peptide (amino acids 1-21) -
                          sc02-004 scFv- CD8a Hinge - CD8a TM - 4-1BB ICD - CD3z
SIGNAL                  1..21
source                  1..489
                        mol_type = protein
                        organism = synthetic construct
SEQUENCE: 115
MLLVTSLLLC ELPHPAFLLI PAEVQLVESG GGLVQPGGSL RLSCAASGFT FSGYLMSWVR  60
QAPGKGLEWV AVISYDGSNK YYADSVKGRF TISRDNSKNT LYLQMDSLRA EDTAVYYCAR  120
ARRDTNLFDY WGQGTLVTVL EGTGGSGGTG SGTGTSELTQ SPSSLSASVG DRVTITCRAS  180
QSISSYLNWY QQKPGKAPKL LIYAASSLQS GVPSRFSGSG SGTDFTLTIS SLQPEDFATY  240
YCQQSYSTPP TFGQGTKVEI KRAAATTTPA PRPPTPAPTI ASQPLSLRPE ACRPAAGGAV  300
HTRGLDFACD IYIWAPLAGT CGVLLLSLVI TLYCKRGRKK LLYIFKQPFM RPVQTTQEED  360
GCSCRFPEEE EGGCELRVKF SRSADAPAYQ QGQNQLYNEL NLGRREEYDV LDKRRGRDPE  420
MGGKPQRRKN PQEGLYNELQ KDKMAEAYSE IGMKGERRRG KGHDGLYQGL STATKDTYDA  480
LHMQALPPR                                                        489

SEQ ID NO: 116          moltype = AA   length = 493
FEATURE                 Location/Qualifiers
```

-continued

```
REGION                    1..493
                          note = CAR: GMSCFR signal peptide (amino acids 1-21) -
                           sc02-025 scFv- CD8a Hinge - CD8a TM - 4-1BB ICD - CD3z
SIGNAL                    1..21
source                    1..493
                          mol_type = protein
                          organism = synthetic construct
SEQUENCE: 116
MLLVTSLLLC ELPHPAFLLI PAQVQLVQSG AEVKKPGASV KVSCKASGYT FTSYYMHWVR   60
QAPGQGLEWM GIINPSGGGT SYAQKFQGRV TMTRDTSTST VYMELSSLRS EDTAVYYCAR  120
DYYVTYDSWF DSWGQGTLVT VSRGGGGSGG GGSGGGGSSE LTQDPAVSVA LGQTVRITCQ  180
GDSLRSYYAS WYQQKPGQAP VLVIYGKNNR PSGIPDRFSG SSSGNTASLT ITGAQAEDEA  240
DYYCNSRDSS GNHVVFGGGT KLTVLGAAAT TTPAPRPPTP APTIASQPLS LRPEACRPAA  300
GGAVHTRGLD FACDIYIWAP LAGTCGVLLL SLVITLYCKR GRKKLLYIFK QPFMRPVQTT  360
QEEDGCSCRF PEEEEGGCEL RVKFSRSADA PAYQQGQNQL YNELNLGRRE EYDVLDKRRG  420
RDPEMGGKPQ RRKNPQEGLY NELQKDKMAE AYSEIGMKGE RRRGKGHDGL YQGLSTATKD  480
TYDALHMQAL PPR                                                    493

SEQ ID NO: 117            moltype = AA  length = 21
FEATURE                   Location/Qualifiers
REGION                    1..21
                          note = GMCSFR_Signal Peptide
source                    1..21
                          mol_type = protein
                          organism = synthetic construct
SEQUENCE: 117
MLLVTSLLLC ELPHPAFLLI P                                            21

SEQ ID NO: 118            moltype = AA  length = 24
FEATURE                   Location/Qualifiers
source                    1..24
                          mol_type = protein
                          organism = Homo sapiens
SEQUENCE: 118
MSKEPLILWL MIEFWWLYLT PVTS                                         24

SEQ ID NO: 119            moltype = AA  length = 290
FEATURE                   Location/Qualifiers
source                    1..290
                          mol_type = protein
                          organism = Homo sapiens
SEQUENCE: 119
ETVVTEVLGH RVTLPCLYSS WSHNSNSMCW GKDQCPYSGC KEALIRTDGM RVTSRKSAKY   60
RLQGTIPRGD VSLTILNPSE SDSGVYCCRI EVPGWFNDVK INVRLNLQRA STTTHRTATT  120
TTRRTTTTSP TTTRQMTTTP AALPTTVVTT PDLTTGTPLQ MTTIAVFTTA NTCLSLTPST  180
LPEEATGLLT PEPSKEGPIL TAESETVLPS DSWSSVESTS ADTVLLTSKE SKVWDLPSTS  240
HVSMWKTSDS VSSPQPGASD TAVPEQNKTT KTGQMDGIPM SMKNEMPISQ            290

SEQ ID NO: 120            moltype = AA  length = 27
FEATURE                   Location/Qualifiers
source                    1..27
                          mol_type = protein
                          organism = Homo sapiens
SEQUENCE: 120
FWVLVVVGGV LACYSLLVTV AFIIFWV                                      27

SEQ ID NO: 121            moltype = AA  length = 21
FEATURE                   Location/Qualifiers
source                    1..21
                          mol_type = protein
                          organism = Homo sapiens
SEQUENCE: 121
LLMIIAPSLG FVLFALFVAF L                                            21

SEQ ID NO: 122            moltype = AA  length = 175
FEATURE                   Location/Qualifiers
source                    1..175
                          mol_type = protein
                          organism = Homo sapiens
SEQUENCE: 122
HRFHGLWYMK MMWAWLQAKR KPRKAPSRNI CYDAFVSYSE RDAYWVENLM VQELENFNPP   60
FKLCLHKRDF IPGKWIIDNI IDSIEKSHKT VFVLSENFVK SEWCKYELDF SHFRLFDENN  120
DAAILILLEP IEKKAIPQRF CKLRKIMNTK TYLEWPMDEA QREGFWVNLR AAIKS       175

SEQ ID NO: 123            moltype = AA  length = 193
FEATURE                   Location/Qualifiers
source                    1..193
                          mol_type = protein
                          organism = Homo sapiens
```

-continued

```
SEQUENCE: 123
HHLFYWDVWF IYNVCLAKVK GYRSLSTSQT FYDAYISYDT KDASVTDWVI NELRYHLEES    60
RDKNVLLCLE ERDWDPGLAI IDNLMQSINQ SKKTVFVLTK KYAKSWNFKT AFYLALQRLM   120
DENMDVIIFI LLEPVLQHSQ YLRLRQRICK SSILQWPDNP KAEGLFWQTL RNVVLTENDS   180
RYNNMYVDSI KQY                                                      193

SEQ ID NO: 124            moltype = AA  length = 42
FEATURE                   Location/Qualifiers
source                    1..42
                          mol_type = protein
                          organism = Homo sapiens
SEQUENCE: 124
RGKLMETYCS QKHTRLDYIG DSKNVLNDVQ HGREDEDGLF TL                       42

SEQ ID NO: 125            moltype = AA  length = 43
FEATURE                   Location/Qualifiers
source                    1..43
                          mol_type = protein
                          organism = Homo sapiens
SEQUENCE: 125
MRGKLMETYC SQKHTRLDYI GDSKNVLNDV QHGREDEDGL FTL                      43

SEQ ID NO: 126            moltype =    length =
SEQUENCE: 126
000

SEQ ID NO: 127            moltype = AA  length = 495
FEATURE                   Location/Qualifiers
REGION                    1..495
                          note = hTIM4-TIM4-CD28tm-CD28icd-CD3zICD
SIGNAL                    1..24
source                    1..495
                          mol_type = protein
                          organism = synthetic construct
SEQUENCE: 127
MSKEPLILWL MIEFWWLYLT PVTSETVVTE VLGHRVTLPC LYSSWSHNSN SMCWGKDQCP    60
YSGCKEALIR TDGMRVTSRK SAKYRLQGTI PRGDVSLTIL NPSESDSGVY CCRIEVPGWF   120
NDVKINVRLN LQRASTTTHR TATTTTRRTT TTSPTTTRQM TTTPAALPTT VVTTPDLTTG   180
TPLQMTTIAV FTTANTCLSL TPSTLPEEAT GLLTPEPSKE GPILTAESET VLPSDSWSSV   240
ESTSADTVLL TSKESKVWDL PSTSHVSMWK TSDSVSSPQP GASDTAVPEQ NKTTKTGQMD   300
GIPMSMKNEM PISQFWVLVV VGGVLACYSL LVTVAFIIFW VRSKRSRLLH SDYMNMTPRR   360
PGPTRKHYQP YAPPRDFAAY RSRVKFSRSA DAPAYQQGQN QLYNELNLGR REEYDVLDKR   420
RGRDPEMGGK PQRRKNPQEG LYNELQKDKM AEAYSEIGMK GERRRGKGHD GLYQGLSTAT   480
KDTYDALHMQ ALPPR                                                    495

SEQ ID NO: 128            moltype = AA  length = 670
FEATURE                   Location/Qualifiers
REGION                    1..670
                          note = hTIM4-TIM4-CD28tm-CD28icd-TLR2ICD-CD3zICD
SIGNAL                    1..24
source                    1..670
                          mol_type = protein
                          organism = synthetic construct
SEQUENCE: 128
MSKEPLILWL MIEFWWLYLT PVTSETVVTE VLGHRVTLPC LYSSWSHNSN SMCWGKDQCP    60
YSGCKEALIR TDGMRVTSRK SAKYRLQGTI PRGDVSLTIL NPSESDSGVY CCRIEVPGWF   120
NDVKINVRLN LQRASTTTHR TATTTTRRTT TTSPTTTRQM TTTPAALPTT VVTTPDLTTG   180
TPLQMTTIAV FTTANTCLSL TPSTLPEEAT GLLTPEPSKE GPILTAESET VLPSDSWSSV   240
ESTSADTVLL TSKESKVWDL PSTSHVSMWK TSDSVSSPQP GASDTAVPEQ NKTTKTGQMD   300
GIPMSMKNEM PISQFWVLVV VGGVLACYSL LVTVAFIIFW VRSKRSRLLH SDYMNMTPRR   360
PGPTRKHYQP YAPPRDFAAY RSHRFHGLWY MKMMWAWLQA KRKPRKAPSR NICYDAFVSY   420
SERDAYWVEN LMVQELENFN PPFKLCLHKR DFIPGKWIID NIIDSIEKSH KTVFVLSENF   480
VKSEWCKYEL DFSHFRLFDE NNDAAILILL EPIEKKAIPQ RFCKLRKIMN TKTYLEWPMD   540
EAQREGFWVN LRAAIKSRVK FSRSADAPAY QQGQNQLYNE LNLGRREEYD VLDKRRGRDP   600
EMGGKPQRRK NPQEGLYNEL QKDKMAEAYS EIGMKGERRR GKGHDGLYQG LSTATKDTYD   660
ALHMQALPPR                                                          670

SEQ ID NO: 129            moltype = AA  length = 670
FEATURE                   Location/Qualifiers
REGION                    1..670
                          note = hTIM4-TIM4-CD28tm-CD28icd-CD3zICD-TLR2ICD
SIGNAL                    1..24
source                    1..670
                          mol_type = protein
                          organism = synthetic construct
SEQUENCE: 129
MSKEPLILWL MIEFWWLYLT PVTSETVVTE VLGHRVTLPC LYSSWSHNSN SMCWGKDQCP    60
YSGCKEALIR TDGMRVTSRK SAKYRLQGTI PRGDVSLTIL NPSESDSGVY CCRIEVPGWF   120
NDVKINVRLN LQRASTTTHR TATTTTRRTT TTSPTTTRQM TTTPAALPTT VVTTPDLTTG   180
```

```
TPLQMTTIAV FTTANTCLSL TPSTLPEEAT GLLTPEPSKE GPILTAESET VLPSDSWSSV  240
ESTSADTVLL TSKESKVWDL PSTSHVSMWK TSDSVSSPQP GASDTAVPEQ NKTTKTGQMD  300
GIPMSMKNEM PISQFWVLVV VGGVLACYSL LVTVAFIIFW VRSKRSRLLH SDYMNMTPRR  360
PGPTRKHYQP YAPPRDFAAY RSRVKFSRSA DAPAYQQGQN QLYNELNLGR REEYDVLDKR  420
RGRDPEMGGK PQRRKNPQEG LYNELQKDKM AEAYSEIGMK GERRRGKGHD GLYQGLSTAT  480
KDTYDALHMQ ALPPRHRFHG LWYMKMMWAW LQAKRKPRKA PSRNICYDAF VSYSERDAYW  540
VENLMVQELE NFNPPPKLCL HKRDFIPGKW IIDNIIDSIE KSHKTVFVLS ENFVKSEWCK  600
YELDFSHFRL FDENNDAAIL ILLEPIEKKA IPQRFCKLRK IMNTKTYLEW PMDEAQREGF  660
WVNLRAAIKS                                                        670

SEQ ID NO: 130          moltype = AA  length = 688
FEATURE                 Location/Qualifiers
REGION                  1..688
                        note = hTIM4-TIM4-CD28tm-CD28icd-TLR8ICD-CD3zICD
SIGNAL                  1..24
source                  1..688
                        mol_type = protein
                        organism = synthetic construct
SEQUENCE: 130
MSKEPLILWL MIEFWWLYLT PVTSETVVTE VLGHRVTLPC LYSSWSHNSN SMCWGKDQCP  60
YSGCKEALIR TDGMRVTSRK SAKYRLQGTI PRGDVSLTIL NPSESDSGVY CCRIEVPGWF  120
NDVKINVRLN LQRASTTTHR TATTTTRRTT TTSPTTTRQM TTTPAALPTT VVTTPDLTTG  180
TPLQMTTIAV FTTANTCLSL TPSTLPEEAT GLLTPEPSKE GPILTAESET VLPSDSWSSV  240
ESTSADTVLL TSKESKVWDL PSTSHVSMWK TSDSVSSPQP GASDTAVPEQ NKTTKTGQMD  300
GIPMSMKNEM PISQFWVLVV VGGVLACYSL LVTVAFIIFW VRSKRSRLLH SDYMNMTPRR  360
PGPTRKHYQP YAPPRDFAAY RSHHLFYWDV WFIYNVCLAK VKGYRSLSTS QTFYDAYISY  420
DTKDASVTDW VINELRYHLE ESRDKNVLLC LEERDWDPGL AIIDNLMQSI NQSKKTVFVL  480
TKKYAKSWNF KTAFYLALQR LMDENMDVII FILLEPVLQH SQYLRLRQRI CKSSILQWPD  540
NPKAEGLFWQ TLRNVVLTEN DSRYNNMYVD SIKQYRVKFS RSADAPAYQQ GQNQLYNELN  600
LGRREEYDVL DKRRGRDPEM GGKPQRRKNP QEGLYNELQK DKMAEAYSEI GMKGERRRGK  660
GHDGLYQGLS TATKDTYDAL HMQALPPR                                    688

SEQ ID NO: 131          moltype = AA  length = 688
FEATURE                 Location/Qualifiers
REGION                  1..688
                        note = hTIM4-TIM4-CD28tm-CD28icd-CD3zICD-TLR8ICD
SIGNAL                  1..24
source                  1..688
                        mol_type = protein
                        organism = synthetic construct
SEQUENCE: 131
MSKEPLILWL MIEFWWLYLT PVTSETVVTE VLGHRVTLPC LYSSWSHNSN SMCWGKDQCP  60
YSGCKEALIR TDGMRVTSRK SAKYRLQGTI PRGDVSLTIL NPSESDSGVY CCRIEVPGWF  120
NDVKINVRLN LQRASTTTHR TATTTTRRTT TTSPTTTRQM TTTPAALPTT VVTTPDLTTG  180
TPLQMTTIAV FTTANTCLSL TPSTLPEEAT GLLTPEPSKE GPILTAESET VLPSDSWSSV  240
ESTSADTVLL TSKESKVWDL PSTSHVSMWK TSDSVSSPQP GASDTAVPEQ NKTTKTGQMD  300
GIPMSMKNEM PISQFWVLVV VGGVLACYSL LVTVAFIIFW VRSKRSRLLH SDYMNMTPRR  360
PGPTRKHYQP YAPPRDFAAY RSRVKFSRSA DAPAYQQGQN QLYNELNLGR REEYDVLDKR  420
RGRDPEMGGK PQRRKNPQEG LYNELQKDKM AEAYSEIGMK GERRRGKGHD GLYQGLSTAT  480
KDTYDALHMQ ALPPRHHLFY WDVWFIYNVC LAKVKGYRSL STSQTFYDAY ISYDTKDASV  540
TDWVINELRY HLEESRDKNV LLCLEERDWD PGLAIIDNLM QSINQSKKTV FVLTKKYAKS  600
WNFKTAFYLA LQRLMDENMD VIIFILLEPV LQHSQYLRLR QRICKSSILQ WPDNPKAEGL  660
FWQTLRNVVL TENDSRYNNM YVDSIKQY                                    688

SEQ ID NO: 132          moltype = AA  length = 629
FEATURE                 Location/Qualifiers
REGION                  1..629
                        note = hTIM4-TIM4-CD28tm-TLR2ICD-CD3zICD
SIGNAL                  1..24
source                  1..629
                        mol_type = protein
                        organism = synthetic construct
SEQUENCE: 132
MSKEPLILWL MIEFWWLYLT PVTSETVVTE VLGHRVTLPC LYSSWSHNSN SMCWGKDQCP  60
YSGCKEALIR TDGMRVTSRK SAKYRLQGTI PRGDVSLTIL NPSESDSGVY CCRIEVPGWF  120
NDVKINVRLN LQRASTTTHR TATTTTRRTT TTSPTTTRQM TTTPAALPTT VVTTPDLTTG  180
TPLQMTTIAV FTTANTCLSL TPSTLPEEAT GLLTPEPSKE GPILTAESET VLPSDSWSSV  240
ESTSADTVLL TSKESKVWDL PSTSHVSMWK TSDSVSSPQP GASDTAVPEQ NKTTKTGQMD  300
GIPMSMKNEM PISQFWVLVV VGGVLACYSL LVTVAFIIFW VHRFHGLWYM KMMWAWLQAK  360
RKPRKAPSRN ICYDAFVSYS ERDAYWVENL MVQELENFNP PFKLCLHKRD FIPGKWIIDN  420
IIDSIEKSHK TVFVLSENFV KSEWCKYELD FSHFRLFDEN NDAAILILLE PIEKKAIPQR  480
FCKLRKIMNT KTYLEWPMDE AQREGFWVNL RAAIKSRVKF SRSADAPAYQ QGQNQLYNEL  540
NLGRREEYDV LDKRRGRDPE MGGKPQRRKN PQEGLYNELQ KDKMAEAYSE IGMKGERRRG  600
KGHDGLYQGL STATKDTYDA LHMQALPPR                                   629

SEQ ID NO: 133          moltype = AA  length = 629
FEATURE                 Location/Qualifiers
REGION                  1..629
                        note = hTIM4-TIM4-CD28tm-CD3zICD-TLR2ICD
```

```
SIGNAL                      1..24
source                      1..629
                            mol_type = protein
                            organism = synthetic construct
SEQUENCE: 133
MSKEPLILWL MIEFWWLYLT PVTSETVVTE VLGHRVTLPC LYSSWSHNSN SMCWGKDQCP   60
YSGCKEALIR TDGMRVTSRK SAKYRLQGTI PRGDVSLTIL NPSESDSGVY CCRIEVPGWF  120
NDVKINVRLN LQRASTTTHR TATTTTRRTT TTSPTTTRQM TTTPAALPTT VVTTPDLTTG  180
TPLQMTTIAV FTTANTCLSL TPSTLPEEAT GLLTPEPSKE GPILTAESET VLPSDSWSSV  240
ESTSADTVLL TSKESKVWDL PSTSHVSMWK TSDSVSSPQP GASDTAVPEQ NKTTKTGQMD  300
GIPMSMKNEM PISQFWVLVV VGGVLACYSL LVTVAFIIFW VRVKFSRSAD APAYQQGQNQ  360
LYNELNLGRR EEYDVLDKRR GRDPEMGGKP QRRKNPQEGL YNELQKDKMA EAYSEIGMKG  420
ERRRGKGHDG LYQGLSTATK DTYDALHMQA LPPRHRFHGL WYMKMMWAWL QAKRKPRKAP  480
SRNICYDAFV SYSERDAYWV ENLMVQELEN FNPPFKLCLH KRDFIPGKWI IDNIIDSIEK  540
SHKTVFVLSE NFVKSEWCKY ELDFSHFRLF DENNDAAILI LLEPIEKKAI PQRFCKLRKI  600
MNTKTYLEWP MDEAQREGFW VNLRAAIKS                                    629

SEQ ID NO: 134              moltype = AA  length = 647
FEATURE                     Location/Qualifiers
REGION                      1..647
                            note = hTIM4-TIM4-CD28tm-TLR8ICD-CD3zICD
SIGNAL                      1..24
source                      1..647
                            mol_type = protein
                            organism = synthetic construct
SEQUENCE: 134
MSKEPLILWL MIEFWWLYLT PVTSETVVTE VLGHRVTLPC LYSSWSHNSN SMCWGKDQCP   60
YSGCKEALIR TDGMRVTSRK SAKYRLQGTI PRGDVSLTIL NPSESDSGVY CCRIEVPGWF  120
NDVKINVRLN LQRASTTTHR TATTTTRRTT TTSPTTTRQM TTTPAALPTT VVTTPDLTTG  180
TPLQMTTIAV FTTANTCLSL TPSTLPEEAT GLLTPEPSKE GPILTAESET VLPSDSWSSV  240
ESTSADTVLL TSKESKVWDL PSTSHVSMWK TSDSVSSPQP GASDTAVPEQ NKTTKTGQMD  300
GIPMSMKNEM PISQFWVLVV VGGVLACYSL LVTVAFIIFW VHHLFYWDVW FIYNVCLAKV  360
KGYRSLSTSQ TFYDAYISYD TKDASVTDWV INELRYHLEE SRDKNVLLCL EERDWDPGLA  420
IIDNLMQSIN QSKKTVFVLT KKYAKSWNFK TAFYLALQRL MDENMDVIIF ILLEPVLQHS  480
QYLRLRQRIC KSSILQWPDN PKAEGLFWQT LRNVVLTEND SRYNNMYVDS IKQYRVKFSR  540
SADAPAYQQG QNQLYNELNL GRREEYDVLD KRRGRDPEMG GKPQRRKNPQ EGLYNELQKD  600
KMAEAYSEIG MKGERRRGKG HDGLYQGLST ATKDTYDALH MQALPPR                647

SEQ ID NO: 135              moltype = AA  length = 647
FEATURE                     Location/Qualifiers
REGION                      1..647
                            note = hTIM4-TIM4-CD28tm-CD3zICD-TLR8ICD
SIGNAL                      1..24
source                      1..647
                            mol_type = protein
                            organism = synthetic construct
SEQUENCE: 135
MSKEPLILWL MIEFWWLYLT PVTSETVVTE VLGHRVTLPC LYSSWSHNSN SMCWGKDQCP   60
YSGCKEALIR TDGMRVTSRK SAKYRLQGTI PRGDVSLTIL NPSESDSGVY CCRIEVPGWF  120
NDVKINVRLN LQRASTTTHR TATTTTRRTT TTSPTTTRQM TTTPAALPTT VVTTPDLTTG  180
TPLQMTTIAV FTTANTCLSL TPSTLPEEAT GLLTPEPSKE GPILTAESET VLPSDSWSSV  240
ESTSADTVLL TSKESKVWDL PSTSHVSMWK TSDSVSSPQP GASDTAVPEQ NKTTKTGQMD  300
GIPMSMKNEM PISQFWVLVV VGGVLACYSL LVTVAFIIFW VRVKFSRSAD APAYQQGQNQ  360
LYNELNLGRR EEYDVLDKRR GRDPEMGGKP QRRKNPQEGL YNELQKDKMA EAYSEIGMKG  420
ERRRGKGHDG LYQGLSTATK DTYDALHMQA LPPRHHLFYW DVWFIYNVCL AKVKGYRSLS  480
TSQTFYDAYI SYDTKDASVT DWVINELRYH LEESRDKNVL LCLEERDWDP GLAIIDNLMQ  540
SINQSKKTVF VLTKKYAKSW NFKTAFYLAL QRLMDENMDV IIFILLEPVL QHSQYLRLRQ  600
RICKSSILQW PDNPKAEGLF WQTLRNVVLT ENDSRYNNMY VDSIKQY                647

SEQ ID NO: 136              moltype = AA  length = 728
FEATURE                     Location/Qualifiers
REGION                      1..728
                            note = hTIM4-TIM4-CD28tm-TRAF6ICD-CD3zICD
SIGNAL                      1..24
source                      1..728
                            mol_type = protein
                            organism = synthetic construct
SEQUENCE: 136
MSKEPLILWL MIEFWWLYLT PVTSETVVTE VLGHRVTLPC LYSSWSHNSN SMCWGKDQCP   60
YSGCKEALIR TDGMRVTSRK SAKYRLQGTI PRGDVSLTIL NPSESDSGVY CCRIEVPGWF  120
NDVKINVRLN LQRASTTTHR TATTTTRRTT TTSPTTTRQM TTTPAALPTT VVTTPDLTTG  180
TPLQMTTIAV FTTANTCLSL TPSTLPEEAT GLLTPEPSKE GPILTAESET VLPSDSWSSV  240
ESTSADTVLL TSKESKVWDL PSTSHVSMWK TSDSVSSPQP GASDTAVPEQ NKTTKTGQMD  300
GIPMSMKNEM PISQFWVLVV VGGVLACYSL LVTVAFIIFW VMSLLNCENS CGSSQSESDC  360
CVAMASSCSA VTKDDSVGGT ASTGNLSSSF MEEIQGYDVE FDPPLESKYE CPICLMALRE  420
AVQTPCGHRF CKACIIKSIR DAGHKCPVDN EILLENQLFP DNFAKREILS LMVKCPNEGC  480
LHKMELRHLE DHQAHCEFAL MDCPQCQRPF QKFHINIHIL KDCPRRQVSC DNCAASMAFE  540
DKEIHDQNCP LANVICEYCN TILIREQMPN HYDLDCPTAP IPCTFSTFGC HEKMQRNHLA  600
RHLQENTQSH MRMLARVKFS RSADAPAYQQ GQNQLYNELN LGRREEYDVL DKRRGRDPEM  660
```

-continued

```
GGKPQRRKNP QEGLYNELQK DKMAEAYSEI GMKGERRRGK GHDGLYQGLS TATKDTYDAL    720
HMQALPPR                                                             728

SEQ ID NO: 137          moltype = AA  length = 728
FEATURE                 Location/Qualifiers
REGION                  1..728
                        note = hTIM4-TIM4-CD28tm-CD3zICD-TRAF6ICD
SIGNAL                  1..24
source                  1..728
                        mol_type = protein
                        organism = synthetic construct
SEQUENCE: 137
MSKEPLILWL MIEFWWLYLT PVTSETVVTE VLGHRVTLPC LYSSWSHNSN SMCWGKDQCP    60
YSGCKEALIR TDGMRVTSRK SAKYRLQGTI PRGDVSLTIL NPSESDSGVY CCRIEVPGWF    120
NDVKINVRLN LQRASTTTHR TATTTTRRTT TTSPTTTRQM TTTPAALPTT VVTTPDLTTG    180
TPLQMTTIAV FTTANTCLSL TPSTLPEEAT GLLTPEPSKE GPILTAESET VLPSDSWSSV    240
ESTSADTVLL TSKESKVWDL PSTSHVSMWK TSDSVSSPQP GASDTAVPEQ NKTTKTGQMD    300
GIPMSMKNEM PISQFWVLVV VGGVLACYSL LVTVAFIIFW VRVKFSRSAD APAYQQGQNQ    360
LYNELNLGRR EEYDVLDKRR GRDPEMGGKP QRRKNPQEGL YNELQKDKMA EAYSEIGMKG    420
ERRRGKGHDG LYQGLSTATK DTYDALHMQA LPPRMSLLNC ENSCGSSQSE SDCCVAMASS    480
CSAVTKDDSV GGTASTGNLS SSFMEEIQGY DVEFDPPLES KYECPICLMA LREAVQTPCG    540
HRFCKACIIK SIRDAGHKCP VDNEILLENQ LFPDNFAKRE ILSLMVKCPN EGCLHKMELR    600
HLEDHQAHCE FALMDCPQCQ RPFQKFHINI HILKDCPRRQ VSCDNCAASM AFEDKEIHDQ    660
NCPLANVICE YCNTILIREQ MPNHYDLDCP TAPIPCTFST FGCHEKMQRN HLARHLQENT    720
QSHMRMLA                                                             728

SEQ ID NO: 138          moltype = AA  length = 489
FEATURE                 Location/Qualifiers
REGION                  1..489
                        note = hTIM4-TIM4-TIM4tm-CD28icd-CD3zICD
SIGNAL                  1..24
source                  1..489
                        mol_type = protein
                        organism = synthetic construct
SEQUENCE: 138
MSKEPLILWL MIEFWWLYLT PVTSETVVTE VLGHRVTLPC LYSSWSHNSN SMCWGKDQCP    60
YSGCKEALIR TDGMRVTSRK SAKYRLQGTI PRGDVSLTIL NPSESDSGVY CCRIEVPGWF    120
NDVKINVRLN LQRASTTTHR TATTTTRRTT TTSPTTTRQM TTTPAALPTT VVTTPDLTTG    180
TPLQMTTIAV FTTANTCLSL TPSTLPEEAT GLLTPEPSKE GPILTAESET VLPSDSWSSV    240
ESTSADTVLL TSKESKVWDL PSTSHVSMWK TSDSVSSPQP GASDTAVPEQ NKTTKTGQMD    300
GIPMSMKNEM PISQLLMIIA PSLGFVLFAL FVAFLRSKRS RLLHSDYMNM TPRRPGPTRK    360
HYQPYAPPRD FAAYRSRVKF SRSADAPAYQ QGQNQLYNEL NLGRREEYDV LDKRRGRDPE    420
MGGKPQRRKN PQEGLYNELQ KDKMAEAYSE IGMKGERRRG KGHDGLYQGL STATKDTYDA    480
LHMQALPPR                                                           489

SEQ ID NO: 139          moltype = AA  length = 664
FEATURE                 Location/Qualifiers
REGION                  1..664
                        note = hTIM4-TIM4-TIM4tm-CD28icd-TLR2ICD-CD3zICD
SIGNAL                  1..24
source                  1..664
                        mol_type = protein
                        organism = synthetic construct
SEQUENCE: 139
MSKEPLILWL MIEFWWLYLT PVTSETVVTE VLGHRVTLPC LYSSWSHNSN SMCWGKDQCP    60
YSGCKEALIR TDGMRVTSRK SAKYRLQGTI PRGDVSLTIL NPSESDSGVY CCRIEVPGWF    120
NDVKINVRLN LQRASTTTHR TATTTTRRTT TTSPTTTRQM TTTPAALPTT VVTTPDLTTG    180
TPLQMTTIAV FTTANTCLSL TPSTLPEEAT GLLTPEPSKE GPILTAESET VLPSDSWSSV    240
ESTSADTVLL TSKESKVWDL PSTSHVSMWK TSDSVSSPQP GASDTAVPEQ NKTTKTGQMD    300
GIPMSMKNEM PISQLLMIIA PSLGFVLFAL FVAFLRSKRS RLLHSDYMNM TPRRPGPTRK    360
HYQPYAPPRD FAAYRSHRFH GLWYMKMMWA WLQAKRKPRK APSRNICYDA FVSYSERDAY    420
WVENLMVQEL ENFNPPFKLC LHKRDFIPGK WIIDNIIDSI EKSHKTVFVL SENFVKSEWC    480
KYELDFSHFR LFDENNDAAI LILLEPIEKK AIPQRFCKLR KIMNTKTYLE WPMDEAQREG    540
FWVNLRAAIK SRVKFSRSAD APAYQQGQNQ LYNELNLGRR EEYDVLDKRR GRDPEMGGKP    600
QRRKNPQEGL YNELQKDKMA EAYSEIGMKG ERRRGKGHDG LYQGLSTATK DTYDALHMQA    660
LPPR                                                                664

SEQ ID NO: 140          moltype = AA  length = 664
FEATURE                 Location/Qualifiers
REGION                  1..664
                        note = hTIM4-TIM4-TIM4tm-CD28icd-CD3zICD-TLR2ICD
SIGNAL                  1..24
source                  1..664
                        mol_type = protein
                        organism = synthetic construct
SEQUENCE: 140
MSKEPLILWL MIEFWWLYLT PVTSETVVTE VLGHRVTLPC LYSSWSHNSN SMCWGKDQCP    60
YSGCKEALIR TDGMRVTSRK SAKYRLQGTI PRGDVSLTIL NPSESDSGVY CCRIEVPGWF    120
NDVKINVRLN LQRASTTTHR TATTTTRRTT TTSPTTTRQM TTTPAALPTT VVTTPDLTTG    180
```

-continued

```
TPLQMTTIAV FTTANTCLSL TPSTLPEEAT GLLTPEPSKE GPILTAESET VLPSDSWSSV   240
ESTSADTVLL TSKESKVWDL PSTSHVSMWK TSDSVSSPQP GASDTAVPEQ NKTTKTGQMD   300
GIPMSMKNEM PISQLLMIIA PSLGFVLFAL FVAFLRSKRS RLLHSDYMNM TPRRPGPTRK   360
HYQPYAPPRD FAAYRSRVKF SRSADAPAYQ QGQNQLYNEL NLGRREEYDV LDKRRGRDPE   420
MGGKPQRRKN PQEGLYNELQ KDKMAEAYSE IGMKGERRRG KGHDGLYQGL STATKDTYDA   480
LHMQALPPRH RFHGLWYKM MWAWLQAKRK PRKAPSRNIC YDAFVSYSER DAYWVENLMV   540
QELENFNPPF KLCLHKRDFI PGKWIIDNII DSIEKSHKTV FVLSENFVKS EWCKYELDFS   600
HFRLFDENND AAILILLEPI EKKAIPQRFC KLRKIMNTKT YLEWPMDEAQ REGFWVNLRA   660
AIKS                                                                664

SEQ ID NO: 141          moltype = AA  length = 682
FEATURE                 Location/Qualifiers
REGION                  1..682
                        note = hTIM4-TIM4-TIM4tm-CD28icd-TLR8ICD-CD3zICD
SIGNAL                  1..24
source                  1..682
                        mol_type = protein
                        organism = synthetic construct
SEQUENCE: 141
MSKEPLILWL MIEFWWLYLT PVTSETVVTE VLGHRVTLPC LYSSWSHNSN SMCWGKDQCP   60
YSGCKEALIR TDGMRVTSRK SAKYRLQGTI PRGDVSLTIL NPSESDSGVY CCRIEVPGWF   120
NDVKINVRLN LQRASTTTHR TATTTTRRTT TTSPTTTRQM TTTPAALPTT VVTTPDLTTG   180
TPLQMTTIAV FTTANTCLSL TPSTLPEEAT GLLTPEPSKE GPILTAESET VLPSDSWSSV   240
ESTSADTVLL TSKESKVWDL PSTSHVSMWK TSDSVSSPQP GASDTAVPEQ NKTTKTGQMD   300
GIPMSMKNEM PISQLLMIIA PSLGFVLFAL FVAFLRSKRS RLLHSDYMNM TPRRPGPTRK   360
HYQPYAPPRD FAAYRSHHLF YWDVWFIYNV CLAKVKGYRS LSTSQTFYDA YISYDTKDAS   420
VTDWVINELR YHLEESRDKN VLLCLEERDW DPGLAIIDNL MQSINQSKKT VFVLTKKYAK   480
SWNFKTAFYL ALQRLMDENM DVIIFILLEP VLQHSQYLRL RQRICKSSIL QWPDNPKAEG   540
LFWQTLRNVV LTENDSRYNN MYVDSIKQYR VKFSRSADAP AYQQGQNQLY NELNLGRREE   600
YDVLDKRRGR DPEMGGKPQR RKNPQEGLYN ELQKDKMAEA YSEIGMKGER RRGKGHDGLY   660
QGLSTATKDT YDALHMQALP PR                                            682

SEQ ID NO: 142          moltype = AA  length = 682
FEATURE                 Location/Qualifiers
REGION                  1..682
                        note = hTIM4-TIM4-TIM4tm-CD28icd-CD3zICD-TLR8ICD
SIGNAL                  1..24
source                  1..682
                        mol_type = protein
                        organism = synthetic construct
SEQUENCE: 142
MSKEPLILWL MIEFWWLYLT PVTSETVVTE VLGHRVTLPC LYSSWSHNSN SMCWGKDQCP   60
YSGCKEALIR TDGMRVTSRK SAKYRLQGTI PRGDVSLTIL NPSESDSGVY CCRIEVPGWF   120
NDVKINVRLN LQRASTTTHR TATTTTRRTT TTSPTTTRQM TTTPAALPTT VVTTPDLTTG   180
TPLQMTTIAV FTTANTCLSL TPSTLPEEAT GLLTPEPSKE GPILTAESET VLPSDSWSSV   240
ESTSADTVLL TSKESKVWDL PSTSHVSMWK TSDSVSSPQP GASDTAVPEQ NKTTKTGQMD   300
GIPMSMKNEM PISQLLMIIA PSLGFVLFAL FVAFLRSKRS RLLHSDYMNM TPRRPGPTRK   360
HYQPYAPPRD FAAYRSRVKF SRSADAPAYQ QGQNQLYNEL NLGRREEYDV LDKRRGRDPE   420
MGGKPQRRKN PQEGLYNELQ KDKMAEAYSE IGMKGERRRG KGHDGLYQGL STATKDTYDA   480
LHMQALPPRH HLFYWDVWFI YNVCLAKVKG YRSLSTSQTF YDAYISYDTK DASVTDWVIN   540
ELRYHLEESR DKNVLLCLEE RDWDPGLAII DNLMQSINQS KKTVFVLTKK YAKSWNFKTA   600
FYLALQRLMD ENMDVIIFIL LEPVLQHSQY LRLRQRICKS SILQWPDNPK AEGLFWQTLR   660
NVVLTENDSR YNNMYVDSIK QY                                            682

SEQ ID NO: 143          moltype = AA  length = 623
FEATURE                 Location/Qualifiers
REGION                  1..623
                        note = hTIM4-TIM4-TIM4tm-TLR2ICD-CD3zICD
SIGNAL                  1..24
source                  1..623
                        mol_type = protein
                        organism = synthetic construct
SEQUENCE: 143
MSKEPLILWL MIEFWWLYLT PVTSETVVTE VLGHRVTLPC LYSSWSHNSN SMCWGKDQCP   60
YSGCKEALIR TDGMRVTSRK SAKYRLQGTI PRGDVSLTIL NPSESDSGVY CCRIEVPGWF   120
NDVKINVRLN LQRASTTTHR TATTTTRRTT TTSPTTTRQM TTTPAALPTT VVTTPDLTTG   180
TPLQMTTIAV FTTANTCLSL TPSTLPEEAT GLLTPEPSKE GPILTAESET VLPSDSWSSV   240
ESTSADTVLL TSKESKVWDL PSTSHVSMWK TSDSVSSPQP GASDTAVPEQ NKTTKTGQMD   300
GIPMSMKNEM PISQLLMIIA PSLGFVLFAL FVAFLHRFHG LWYMKMMWAW LQAKRKPRKA   360
PSRNICYDAF VSYSERDAYW VENLMVQELE NFNPPFKLCL HKRDFIPGKW IIDNIIDSIE   420
KSHKTVFVLS ENFVKSEWCK YELDFSHFRL FDENNDAAIL ILLEPIEKKA IPQRFCKLRK   480
IMNTKTYLEW PMDEAQREGF WVNLRAAIKS RVKFSRSADA PAYQQGQNQL YNELNLGRRE   540
EYDVLDKRRG RDPEMGGKPQ RRKNPQEGLY NELQKDKMAE AYSEIGMKGE RRRGKGHDGL   600
YQGLSTATKD TYDALHMQAL PPR                                           623

SEQ ID NO: 144          moltype = AA  length = 623
FEATURE                 Location/Qualifiers
REGION                  1..623
                        note = hTIM4-TIM4-TIM4tm-CD3zICD-TLR2ICD
```

```
SIGNAL                  1..24
source                  1..623
                        mol_type = protein
                        organism = synthetic construct
SEQUENCE: 144
MSKEPLILWL MIEFWWLYLT PVTSETVVTE VLGHRVTLPC LYSSWSHNSN SMCWGKDQCP  60
YSGCKEALIR TDGMRVTSRK SAKYRLQGTI PRGDVSLTIL NPSESDSGVY CCRIEVPGWF  120
NDVKINVRLN LQRASTTTHR TATTTTRRTT TTSPTTTRQM TTTPAALPTT VVTTPDLTTG  180
TPLQMTTIAV FTTANTCLSL TPSTLPEEAT GLLTPEPSKE GPILTAESET VLPSDSWSSV  240
ESTSADTVLL TSKESKVWDL PSTSHVSMWK TSDSVSSPQP GASDTAVPEQ NKTTKTGQMD  300
GIPMSMKNEM PISQLLMIIA PSLGFVLFAL FVAFLRVKFS RSADAPAYQQ GQNQLYNELN  360
LGRREEYDVL DKRRGRDPEM GGKPQRRKNP QEGLYNELQK DKMAEAYSEI GMKGERRRGK  420
GHDGLYQGLS TATKDTYDAL HMQALPPRHR FHGLWYMKMM WAWLQAKRKP RKAPSRNICY  480
DAFVSYSERD AYWVENLMVQ ELENFNPPFK LCLHKRDFIP GKWIIDNIID SIEKSHKTVF  540
VLSENFVKSE WCKYELDFSH FRLFDENNDA AILILLEPIE KKAIPQRFCK LRKIMNTKTY  600
LEWPMDEAQR EGFWVNLRAA IKS                                          623

SEQ ID NO: 145          moltype = AA  length = 641
FEATURE                 Location/Qualifiers
REGION                  1..641
                        note = hTIM4-TIM4-TIM4tm-TLR8ICD-CD3zICD
SIGNAL                  1..24
source                  1..641
                        mol_type = protein
                        organism = synthetic construct
SEQUENCE: 145
MSKEPLILWL MIEFWWLYLT PVTSETVVTE VLGHRVTLPC LYSSWSHNSN SMCWGKDQCP  60
YSGCKEALIR TDGMRVTSRK SAKYRLQGTI PRGDVSLTIL NPSESDSGVY CCRIEVPGWF  120
NDVKINVRLN LQRASTTTHR TATTTTRRTT TTSPTTTRQM TTTPAALPTT VVTTPDLTTG  180
TPLQMTTIAV FTTANTCLSL TPSTLPEEAT GLLTPEPSKE GPILTAESET VLPSDSWSSV  240
ESTSADTVLL TSKESKVWDL PSTSHVSMWK TSDSVSSPQP GASDTAVPEQ NKTTKTGQMD  300
GIPMSMKNEM PISQLLMIIA PSLGFVLFAL FVAFLHHLFY WDVWFIYNVC LAKVKGYRSL  360
STSQTFYDAY ISYDTKDASV TDWVINELRY HLEESRDKNV LLCLEERDWD PGLAIIDNLM  420
QSINQSKKTV FVLTKKYAKS WNFKTAFYLA LQRLMDENMD VIIFILLEPV LQHSQYLRLR  480
QRICKSSILQ WPDNPKAEGL FWQTLRNVVL TENDSRYNNM YVDSIKQYRV KFSRSADAPA  540
YQQGQNQLYN ELNLGRREEY DVLDKRRGRD PEMGGKPQRR KNPQEGLYNE LQKDKMAEAY  600
SEIGMKGERR RGKGHDGLYQ GLSTATKDTY DALHMQALPP R                      641

SEQ ID NO: 146          moltype = AA  length = 641
FEATURE                 Location/Qualifiers
REGION                  1..641
                        note = hTIM4-TIM4-TIM4tm-CD3zICD-TLR8ICD
SIGNAL                  1..24
source                  1..641
                        mol_type = protein
                        organism = synthetic construct
SEQUENCE: 146
MSKEPLILWL MIEFWWLYLT PVTSETVVTE VLGHRVTLPC LYSSWSHNSN SMCWGKDQCP  60
YSGCKEALIR TDGMRVTSRK SAKYRLQGTI PRGDVSLTIL NPSESDSGVY CCRIEVPGWF  120
NDVKINVRLN LQRASTTTHR TATTTTRRTT TTSPTTTRQM TTTPAALPTT VVTTPDLTTG  180
TPLQMTTIAV FTTANTCLSL TPSTLPEEAT GLLTPEPSKE GPILTAESET VLPSDSWSSV  240
ESTSADTVLL TSKESKVWDL PSTSHVSMWK TSDSVSSPQP GASDTAVPEQ NKTTKTGQMD  300
GIPMSMKNEM PISQLLMIIA PSLGFVLFAL FVAFLRVKFS RSADAPAYQQ GQNQLYNELN  360
LGRREEYDVL DKRRGRDPEM GGKPQRRKNP QEGLYNELQK DKMAEAYSEI GMKGERRRGK  420
GHDGLYQGLS TATKDTYDAL HMQALPPRHH LFYWDVWFIY NVCLAKVKGY RSLSTSQTFY  480
DAYISYDTKD ASVTDWVINE LRYHLEESRD KNVLLCLEER DWDPGLAIID NLMQSINQSK  540
KTVFVLTKKY AKSWNFKTAF YLALQRLMDE NMDVIIFILL EPVLQHSQYL RLRQRICKSS  600
ILQWPDNPKA EGLFWQTLRN VVLTENDSRY NNMYVDSIKQ Y                      641

SEQ ID NO: 147          moltype = AA  length = 722
FEATURE                 Location/Qualifiers
REGION                  1..722
                        note = hTIM4-TIM4-TIM4tm-TRAF6ICD-CD3zICD
SIGNAL                  1..24
source                  1..722
                        mol_type = protein
                        organism = synthetic construct
SEQUENCE: 147
MSKEPLILWL MIEFWWLYLT PVTSETVVTE VLGHRVTLPC LYSSWSHNSN SMCWGKDQCP  60
YSGCKEALIR TDGMRVTSRK SAKYRLQGTI PRGDVSLTIL NPSESDSGVY CCRIEVPGWF  120
NDVKINVRLN LQRASTTTHR TATTTTRRTT TTSPTTTRQM TTTPAALPTT VVTTPDLTTG  180
TPLQMTTIAV FTTANTCLSL TPSTLPEEAT GLLTPEPSKE GPILTAESET VLPSDSWSSV  240
ESTSADTVLL TSKESKVWDL PSTSHVSMWK TSDSVSSPQP GASDTAVPEQ NKTTKTGQMD  300
GIPMSMKNEM PISQLLMIIA PSLGFVLFAL FVAFLMSLLN CENSCGSSQS ESDCCVAMAS  360
SCSAVTKDDS VGGTASTGNL SSSFMEEIQG YDVEFDPPLE SKYECPICLM ALREAVQTPC  420
GHRFCKACII KSIRDAGHKC PVDNEILLEN QLFPDNFAKR EILSLMVKCP NEGCLHKMEL  480
RHLEDHQAHC EFALMDCPQC QRPFQKFHIN IHILKDCPRR QVSCDNCAAS MAFEDKEIHD  540
QNCPLANVIC EYCNTILIRE QMPNHYDLDC PTAPIPCTFS TFGCHEKMQR NHLARHLQEN  600
TQSHMRMLAR VKFSRSADAP AYQQGQNQLY NELNLGRREE YDVLDKRRGR DPEMGGKPQR  660
```

```
RKNPQEGLYN ELQKDKMAEA YSEIGMKGER RRGKGHDGLY QGLSTATKDT YDALHMQALP   720
PR                                                                               722

SEQ ID NO: 148          moltype = AA  length = 722
FEATURE                 Location/Qualifiers
REGION                  1..722
                        note = hTIM4-TIM4-TIM4tm-CD3zICD-TRAF6ICD
SIGNAL                  1..24
source                  1..722
                        mol_type = protein
                        organism = synthetic construct
SEQUENCE: 148
MSKEPLILWL MIEFWWLYLT PVTSETVVTE VLGHRVTLPC LYSSWSHNSN SMCWGKDQCP   60
YSGCKEALIR TDGMRVTSRK SAKYRLQGTI PRGDVSLTIL NPSESDSGVY CCRIEVPGWF   120
NDVKINVRLN LQRASTTTHR TATTTTRRTT TTSPTTTRQM TTTPAALPTT VVTTPDLTTG   180
TPLQMTTIAV FTTANTCLSL TPSTLPEEAT GLLTPEPSKE GPILTAESET VLPSDSWSSV   240
ESTSADTVLL TSKESKVVDL PSTSHVSMWK TSDSVSSPQP GASDTAVPEQ NKTTKTGQMD   300
GIPMSMKNEM PISQLLMIIA PSLGFVLFAL FVAFLRVKFS RSADAPAYQQ GQNQLYNELN   360
LGRREEYDVL DKRRGRDPEM GGKPQRRKNP QEGLYNELQK DKMAEAYSEI GMKGERRRGK   420
GHDGLYQGLS TATKDTYDAL HMQALPPRMS LLNCENSCGS SQSESDCCVA MASSCSAVTK   480
DDSVGGTAST GNLSSSFMEE IQGYDVEFDP PLESKYECPI CLMALREAVQ TPCGHRFCKA   540
CIIKSIRDAG HKCPVDNEIL LENQLFPDNF AKREILSLMV KCPNEGCLHK MELRHLEDHQ   600
AHCEFALMDC PQCQRPFQKF HINIHILKDC PRRQVSCDNC AASMAFEDKE IHDQNCPLAN   660
VICEYCNTIL IREQMPNHYD LDCPTAPIPC TFSTFGCHEK MQRNHLARHL QENTQSHMRM   720
LA                                                                               722

SEQ ID NO: 149          moltype = AA  length = 378
FEATURE                 Location/Qualifiers
REGION                  1..378
                        note = hTIM4-TIM4-TIM4tm-TIM4ICD
SIGNAL                  1..24
source                  1..378
                        mol_type = protein
                        organism = synthetic construct
SEQUENCE: 149
MSKEPLILWL MIEFWWLYLT PVTSETVVTE VLGHRVTLPC LYSSWSHNSN SMCWGKDQCP   60
YSGCKEALIR TDGMRVTSRK SAKYRLQGTI PRGDVSLTIL NPSESDSGVY CCRIEVPGWF   120
NDVKINVRLN LQRASTTTHR TATTTTRRTT TTSPTTTRQM TTTPAALPTT VVTTPDLTTG   180
TPLQMTTIAV FTTANTCLSL TPSTLPEEAT GLLTPEPSKE GPILTAESET VLPSDSWSSV   240
ESTSADTVLL TSKESKVVDL PSTSHVSMWK TSDSVSSPQP GASDTAVPEQ NKTTKTGQMD   300
GIPMSMKNEM PISQLLMIIA PSLGFVLFAL FVAFLMRGKL METYCSQKHT RLDYIGDSKN   360
VLNDVQHGRE DEDGLFTL                                                         378

SEQ ID NO: 150          moltype = AA  length = 665
FEATURE                 Location/Qualifiers
REGION                  1..665
                        note = hTIM4-TIM4-TIM4tm-TIM4ICD-TLR2-CD3z
SIGNAL                  1..24
source                  1..665
                        mol_type = protein
                        organism = synthetic construct
SEQUENCE: 150
MSKEPLILWL MIEFWWLYLT PVTSETVVTE VLGHRVTLPC LYSSWSHNSN SMCWGKDQCP   60
YSGCKEALIR TDGMRVTSRK SAKYRLQGTI PRGDVSLTIL NPSESDSGVY CCRIEVPGWF   120
NDVKINVRLN LQRASTTTHR TATTTTRRTT TTSPTTTRQM TTTPAALPTT VVTTPDLTTG   180
TPLQMTTIAV FTTANTCLSL TPSTLPEEAT GLLTPEPSKE GPILTAESET VLPSDSWSSV   240
ESTSADTVLL TSKESKVVDL PSTSHVSMWK TSDSVSSPQP GASDTAVPEQ NKTTKTGQMD   300
GIPMSMKNEM PISQLLMIIA PSLGFVLFAL FVAFLRGKLM ETYCSQKHTR LDYIGDSKNV   360
LNDVQHGRED EDGLFTLHRF HGLWYMKMMW AWLQAKRKPR KAPSRNICYD AFVSYSERDA   420
YWVENLMVQE LENFNPPFKL CLHKRDFIPG KWIIDNIIDS IEKSHKTVFV LSENFVKSEW   480
CKYELDFSHF RLFDENNDAA ILILLEPIEK KAIPQRFCKL RKIMNTKTYL EWPMDEAQRE   540
GFWVNLRAAI KSRVKFSRSA DAPAYQQGQN QLYNELNLGR REEYDVLDKR RGRDPEMGGK   600
PQRRKNPQEG LYNELQKDKM AEAYSEIGMK GERRRGKGHD GLYQGLSTAT KDTYDALHMQ   660
ALPPR                                                                            665

SEQ ID NO: 151          moltype = AA  length = 665
FEATURE                 Location/Qualifiers
REGION                  1..665
                        note = hTIM4-TIM4-TIM4tm-TIM4ICD-CD3z-TLR2
SIGNAL                  1..24
source                  1..665
                        mol_type = protein
                        organism = synthetic construct
SEQUENCE: 151
MSKEPLILWL MIEFWWLYLT PVTSETVVTE VLGHRVTLPC LYSSWSHNSN SMCWGKDQCP   60
YSGCKEALIR TDGMRVTSRK SAKYRLQGTI PRGDVSLTIL NPSESDSGVY CCRIEVPGWF   120
NDVKINVRLN LQRASTTTHR TATTTTRRTT TTSPTTTRQM TTTPAALPTT VVTTPDLTTG   180
TPLQMTTIAV FTTANTCLSL TPSTLPEEAT GLLTPEPSKE GPILTAESET VLPSDSWSSV   240
ESTSADTVLL TSKESKVVDL PSTSHVSMWK TSDSVSSPQP GASDTAVPEQ NKTTKTGQMD   300
```

-continued

```
GIPMSMKNEM PISQLLMIIA PSLGFVLFAL FVAFLRGKLM ETYCSQKHTR LDYIGDSKNV    360
LNDVQHGRED EDGLFTLRVK FSRSADAPAY QQGQNQLYNE LNLGRREEYD VLDKRRGRDP    420
EMGGKPQRRK NPQEGLYNEL QKDKMAEAYS EIGMKGERRR GKGHDGLYQG LSTATKDTYD    480
ALHMQALPPR HRFHGLWYMK MMWAWLQAKR KPRKAPSRNI CYDAFVSYSE RDAYWVENLM    540
VQELENFNPP FKLCLHKRDF IPGKWIIDNI IDSIEKSHKT VFVLSENFVK SEWCKYELDF    600
SHFRLFDENN DAAILILLEP IEKKAIPQRF CKLRKIMNTK TYLEWPMDEA QREGFWVNLR    660
AAIKS                                                               665

SEQ ID NO: 152            moltype = AA   length = 683
FEATURE                   Location/Qualifiers
REGION                    1..683
                          note = hTIM4-TIM4-TIM4tm-TIM4ICD-TLR8-CD3z
SIGNAL                    1..24
source                    1..683
                          mol_type = protein
                          organism = synthetic construct
SEQUENCE: 152
MSKEPLILWL MIEFWWLYLT PVTSETVVTE VLGHRVTLPC LYSSWSHNSN SMCWGKDQCP    60
YSGCKEALIR TDGMRVTSRK SAKYRLQGTI PRGDVSLTIL NPSESDSGVY CCRIEVPGWF    120
NDVKINVRLN LQRASTTTHR TATTTTRRTT TTSPTTTRQM TTTPAALPTT VVTTPDLTTG    180
TPLQMTTIAV FTTANTCLSL TPSTLPEEAT GLLTPEPSKE GPILTAESET VLPSDSWSSV    240
ESTSADTVLL TSKESKVWDL PSTSHVSMWK TSDSVSSPQP GASDTAVPEQ NKTTKTGQMD    300
GIPMSMKNEM PISQLLMIIA PSLGFVLFAL FVAFLRGKLM ETYCSQKHTR LDYIGDSKNV    360
LNDVQHGRED EDGLFTLHHL FYWDVWFIYN VCLAKVKGYR SLSTSQTFYD AYISYDTKDA    420
SVTDWVINEL RYHLEESRDK NVLLCLEERD WDPGLAIIDN LMQSINQSKK TVFVLTKKYA    480
KSWNFKTAFY LALQRLMDEN MDVIIFILLE PVLQHSQYLR LRQRICKSSI LQWPDNPKAE    540
GLFWQTLRNV VLTENDSRYN NMYVDSIKQY RVKFSRSADA PAYQQGQNQL YNELNLGRRE    600
EYDVLDKRRG RDPEMGGKPQ RRKNPQEGLY NELQKDKMAE AYSEIGMKGE RRRGKGHDGL    660
YQGLSTATKD TYDALHMQAL PPR                                           683

SEQ ID NO: 153            moltype = AA   length = 683
FEATURE                   Location/Qualifiers
REGION                    1..683
                          note = hTIM4-TIM4-TIM4tm-TIM4ICD-CD3z-TLR8
SIGNAL                    1..24
source                    1..683
                          mol_type = protein
                          organism = synthetic construct
SEQUENCE: 153
MSKEPLILWL MIEFWWLYLT PVTSETVVTE VLGHRVTLPC LYSSWSHNSN SMCWGKDQCP    60
YSGCKEALIR TDGMRVTSRK SAKYRLQGTI PRGDVSLTIL NPSESDSGVY CCRIEVPGWF    120
NDVKINVRLN LQRASTTTHR TATTTTRRTT TTSPTTTRQM TTTPAALPTT VVTTPDLTTG    180
TPLQMTTIAV FTTANTCLSL TPSTLPEEAT GLLTPEPSKE GPILTAESET VLPSDSWSSV    240
ESTSADTVLL TSKESKVWDL PSTSHVSMWK TSDSVSSPQP GASDTAVPEQ NKTTKTGQMD    300
GIPMSMKNEM PISQLLMIIA PSLGFVLFAL FVAFLRGKLM ETYCSQKHTR LDYIGDSKNV    360
LNDVQHGRED EDGLFTLRVK FSRSADAPAY QQGQNQLYNE LNLGRREEYD VLDKRRGRDP    420
EMGGKPQRRK NPQEGLYNEL QKDKMAEAYS EIGMKGERRR GKGHDGLYQG LSTATKDTYD    480
ALHMQALPPR HHLFYWDVWF IYNVCLAKVK GYRSLSTSQT FYDAYISYDT KDASVTDWVI    540
NELRYHLEES RDKNVLLCLE ERDWDPGLAI IDNLMQSINQ SKKTVFVLTK KYAKSWNFKT    600
AFYLALQRLM DENMDVIIFI LLEPVLQHSQ YLRLRQRICK SSILQWPDNP KAEGLFWQTL    660
RNVVLTENDS RYNNMYVDSI KQY                                           683

SEQ ID NO: 154            moltype = AA   length = 552
FEATURE                   Location/Qualifiers
REGION                    1..552
                          note = hTIM4-TIM4-TIM4tm-TLR2ICD
SIGNAL                    1..24
source                    1..552
                          mol_type = protein
                          organism = synthetic construct
SEQUENCE: 154
MSKEPLILWL MIEFWWLYLT PVTSETVVTE VLGHRVTLPC LYSSWSHNSN SMCWGKDQCP    60
YSGCKEALIR TDGMRVTSRK SAKYRLQGTI PRGDVSLTIL NPSESDSGVY CCRIEVPGWF    120
NDVKINVRLN LQRASTTTHR TATTTTRRTT TTSPTTTRQM TTTPAALPTT VVTTPDLTTG    180
TPLQMTTIAV FTTANTCLSL TPSTLPEEAT GLLTPEPSKE GPILTAESET VLPSDSWSSV    240
ESTSADTVLL TSKESKVWDL PSTSHVSMWK TSDSVSSPQP GASDTAVPEQ NKTTKTGQMD    300
GIPMSMKNEM PISQLLMIIA PSLGFVLFAL FVAFLRGKLM ETYCSQKHTR LDYIGDSKNV    360
LNDVQHGRED EDGLFTLHRF HGLWYMKMMW AWLQAKRKPR KAPSRNICYD AFVSYSERDA    420
YWVENLMVQE LENFNPPFKL CLHKRDFIPG KWIIDNIIDS IEKSHKTVFV LSENFVKSEW    480
CKYELDFSHF RLFDENNDAA ILILLEPIEK KAIPQRFCKL RKIMNTKTYL EWPMDEAQRE    540
GFWVNLRAAI KS                                                       552

SEQ ID NO: 155            moltype = AA   length = 570
FEATURE                   Location/Qualifiers
REGION                    1..570
                          note = hTIM4-TIM4-TIM4tm-TLR8ICD
SIGNAL                    1..24
source                    1..570
                          mol_type = protein
```

```
                        organism = synthetic construct
SEQUENCE: 155
MSKEPLILWL MIEFWWLYLT PVTSETVVTE VLGHRVTLPC LYSSWSHNSN SMCWGKDQCP  60
YSGCKEALIR TDGMRVTSRK SAKYRLQGTI PRGDVSLTIL NPSESDSGVY CCRIEVPGWF  120
NDVKINVRLN LQRASTTTHR TATTTTRRTT TTSPTTTRQM TTTPAALPTT VVTTPDLTTG  180
TPLQMTTIAV FTTANTCLSL TPSTLPEEAT GLLTPEPSKE GPILTAESET VLPSDSWSSV  240
ESTSADTVLL TSKESKVWDL PSTSHVSMWK TSDSVSSPQP GASDTAVPEQ NKTTKTGQMD  300
GIPMSMKNEM PISQLLMIIA PSLGFVLFAL FVAFLRGKLM ETYCSQKHTR LDYIGDSKNV  360
LNDVQHGRED EDGLFTLHHL FYWDVWFIYN VCLAKVKGYR SLSTSQTFYD AYISYDTKDA  420
SVTDWVINEL RYHLEESRDK NVLLCLEERD WDPGLAIIDN LMQSINQSKK TVFVLTKKYA  480
KSWNFKTAFY LALQRLMDEN MDVIIFILLE PVLQHSQYLR LRQRICKSSI LQWPDNPKAE  540
GLFWQTLRNV VLTENDSRYN NMYVDSIKQY                                    570

SEQ ID NO: 156         moltype = AA  length = 598
FEATURE                Location/Qualifiers
REGION                 1..598
                       note = HPV16 E7 TCRB chain-P2A-TCRa chain; amino acids
                        309-335 P2A sequence
source                 1..598
                       mol_type = protein
                       organism = synthetic construct
SEQUENCE: 156
MAPGLLCWAL LCLLGAGLVD AGVTQSPTHL IKTRGQQVTL RCSPKSGHDT VSWYQQALGQ  60
GPQFIFQYYE EEERQRGNFP DRFSGHQFPN YSSELNVNAL LLGDSALYLC ASSLGWRGGR  120
YNEQFFGPGT RLTVLEDLRN VTPPKVSLFE PSKAEIANKQ KATLVCLARG FFPDHVELSW  180
WVNGKEVHSG VCTDPQAYKE SNYSYCLSSR LRVSATFWHN PRNHFRCQVQ FHGLSEEDKW  240
PEGSPKPVTQ NISAEAWGRA DCGITSASYQ QGVLSATILY EILLGKATLY AVLVSTLVVM  300
AMVKRKNSRA KRSGSGATNF SLLKQAGDVE ENPGPMWGVF LLYVSMKMGG TTGQNIDQPT  360
EMTATEGAIV QINCTYQTSG FNGLFWYQQH AGEAPTFLSY NVLDGLEEKG RFSSFLSRSK  420
GYSYLLLKEL QMKDSASYLC ASVDGNNRLA FGKGNQVVVI PNIQNPEPAV YQLKDPRSQD  480
STLCLFTDFD SQINVPKTME SGTFITDKCV LDMKAMDSKS NGAIAWSNQT SFTCQDIFKE  540
TNATYPSSDV PCDATLTEKS FETDMNLNFQ NLLVIVLRIL LLKVAGFNLL MTLRLWSS    598

SEQ ID NO: 157         moltype = AA  length = 510
FEATURE                Location/Qualifiers
REGION                 1..510
                       note = hTIM4-TIM4-TIM4tm-TLR2ICD
SIGNAL                 1..24
source                 1..510
                       mol_type = protein
                       organism = synthetic construct
SEQUENCE: 157
MSKEPLILWL MIEFWWLYLT PVTSETVVTE VLGHRVTLPC LYSSWSHNSN SMCWGKDQCP  60
YSGCKEALIR TDGMRVTSRK SAKYRLQGTI PRGDVSLTIL NPSESDSGVY CCRIEVPGWF  120
NDVKINVRLN LQRASTTTHR TATTTTRRTT TTSPTTTRQM TTTPAALPTT VVTTPDLTTG  180
TPLQMTTIAV FTTANTCLSL TPSTLPEEAT GLLTPEPSKE GPILTAESET VLPSDSWSSV  240
ESTSADTVLL TSKESKVWDL PSTSHVSMWK TSDSVSSPQP GASDTAVPEQ NKTTKTGQMD  300
GIPMSMKNEM PISQLLMIIA PSLGFVLFAL FVAFLHRFHG LWYMKMMWAW LQAKRKPRKA  360
PSRNICYDAF VSYSERDAYW VENLMVQELE NFNPPFKLCL HKRDFIPGKW IIDNIIDSIE  420
KSHKTVFVLS ENFVKSEWCK YELDFSHFRL FDENNDAAIL ILLEPIEKKA IPQRFCKLRK  480
IMNTKTYLEW PMDEAQREGF WVNLRAAIKS                                    510

SEQ ID NO: 158         moltype = AA  length = 528
FEATURE                Location/Qualifiers
REGION                 1..528
                       note = hTIM4-TIM4-TIM4tm-TLR8ICD
SIGNAL                 1..24
source                 1..528
                       mol_type = protein
                       organism = synthetic construct
SEQUENCE: 158
MSKEPLILWL MIEFWWLYLT PVTSETVVTE VLGHRVTLPC LYSSWSHNSN SMCWGKDQCP  60
YSGCKEALIR TDGMRVTSRK SAKYRLQGTI PRGDVSLTIL NPSESDSGVY CCRIEVPGWF  120
NDVKINVRLN LQRASTTTHR TATTTTRRTT TTSPTTTRQM TTTPAALPTT VVTTPDLTTG  180
TPLQMTTIAV FTTANTCLSL TPSTLPEEAT GLLTPEPSKE GPILTAESET VLPSDSWSSV  240
ESTSADTVLL TSKESKVWDL PSTSHVSMWK TSDSVSSPQP GASDTAVPEQ NKTTKTGQMD  300
GIPMSMKNEM PISQLLMIIA PSLGFVLFAL FVAFLHHLFY WDVWFIYNVC LAKVKGYRSL  360
STSQTFYDAY ISYDTKDASV TDWVINELRY HLEESRDKNV LLCLEERDWD PGLAIIDNLM  420
QSINQSKKTV FVLTKKYAKS WNFKTAFYLA LQRLMDENMD VIIFILLEPV LQHSQYLRLR  480
QRICKSSILQ WPDNPKAEGL FWQTLRNVVL TENDSRYNNM YVDSIKQY                528
```

CHIMERIC TIM RECEPTORS AND USES THEREOF

STATEMENT REGARDING SEQUENCE LISTING

This application contains a Sequence Listing which has been submitted electronically in xml format and is hereby incorporated by reference in its entirety. Said xml copy, created on Jan. 13, 2025, is named SeqList-368779-41411.xml and is 238,020 bytes in size.

BACKGROUND

Upon exposure to antigen, naïve antigen-specific T cells undergo activation that promotes their clonal expansion, differentiation, and development into functional, effector T cells that can kill cells expressing the cognate antigen (e.g., tumor cells). Following antigen clearance, the majority of effector T cells undergo apoptosis, and a subset of the surviving effector T cells differentiate into memory T cells that can confer long-term protection against antigen re-exposure. However, prolonged antigen exposure may result in T cell exhaustion, enabling the persistence of tumor cells. T cell exhaustion refers to a dysfunctional state acquired by T cells experiencing persistent TCR stimulation characterized by upregulated expression of immune checkpoint molecules (e.g., PD-1, CTLA-4, Tim-3), impaired effector function, poor proliferation, and metabolic defects. Engineered T cells expressing chimeric antigen receptors (CARs) can also develop exhaustion.

BRIEF DESCRIPTION OF THE SEVERAL VIEWS OF THE DRAWINGS

FIG. 1A: a schematic of pCTX247 and pCTX1107 chimeric Tim4 receptors and pCTX1107 T cells pulsed with E7 peptides and co-cultured with E7-specific T cells to evaluate their antigen presentation capacity. FIG. 1B: E7-specific proliferation responses were measured by CT Violet dye dilution after 6 days in the presence of autologous CER-T (TLR containing or non-containing CERs) pulsed with E7 peptides. FIG. 1C: The addition of a TLR-2 ICD (pCTX1107) triggered proliferation responses of E7-specific TCRs whereas non-TLR containing CERs were less stimulatory. All data collected by FACS. Cell tracing show E7 TCR-T cells using an anti-mouse TCRb. E7 TCR-T cells were labeled with CT Violet at the time of co-culture.

Figure 4:
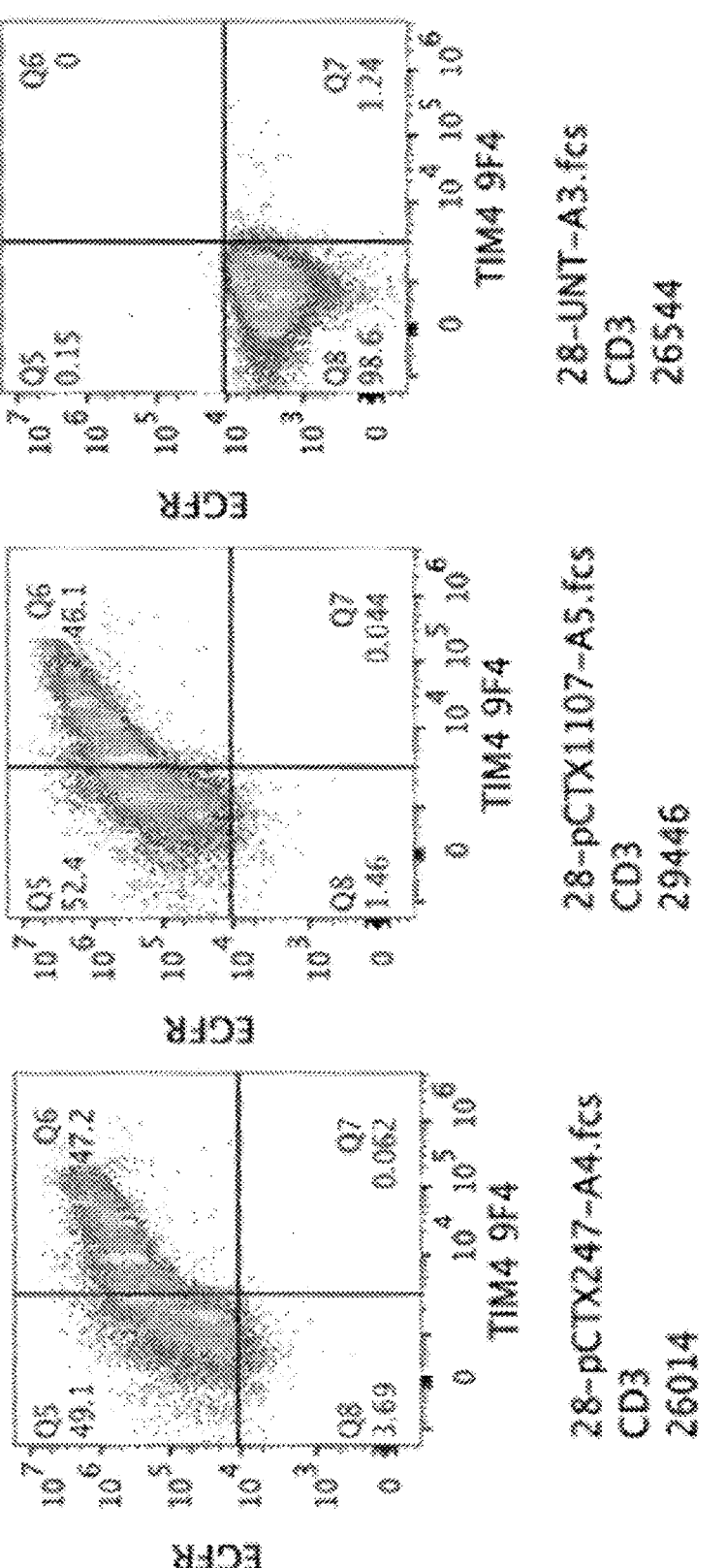

FIG. 4: Robust Cell Surface Chimeric Tim4 Receptor Expression and Detection Using anti-Tim-4 antibodies. Chimeric Tim4 Receptor cell surface staining was evaluated using an anti-Tim-4 antibody (9F4) on day 5 post-transduction. pCTX1107 contains a TLR-2 intracellular sequence. The lentiviral cassette contains a p2A fragment followed by a truncated EGFRt polypeptide.

Figures 5A, 5C:
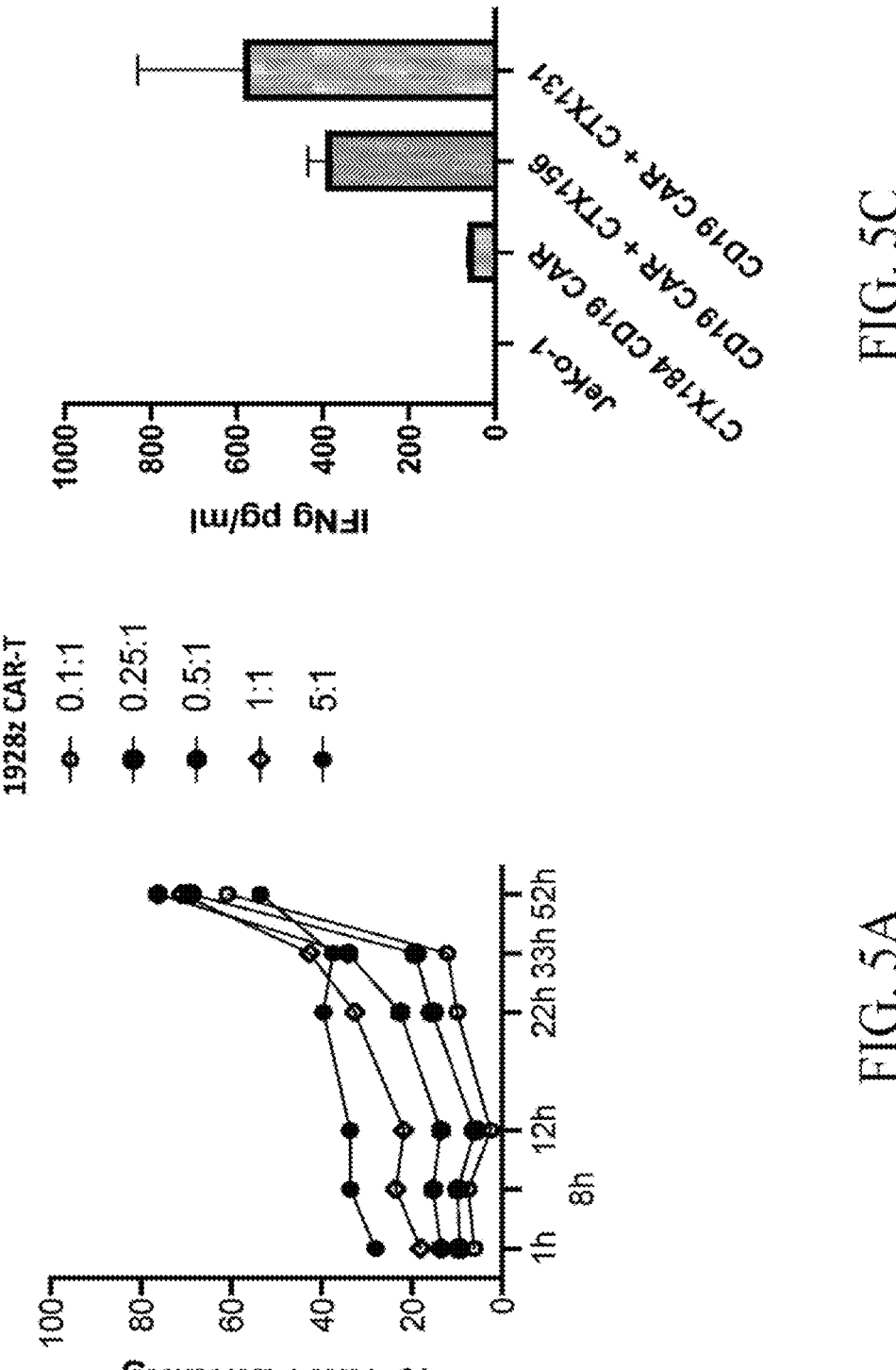
Figure 5B:
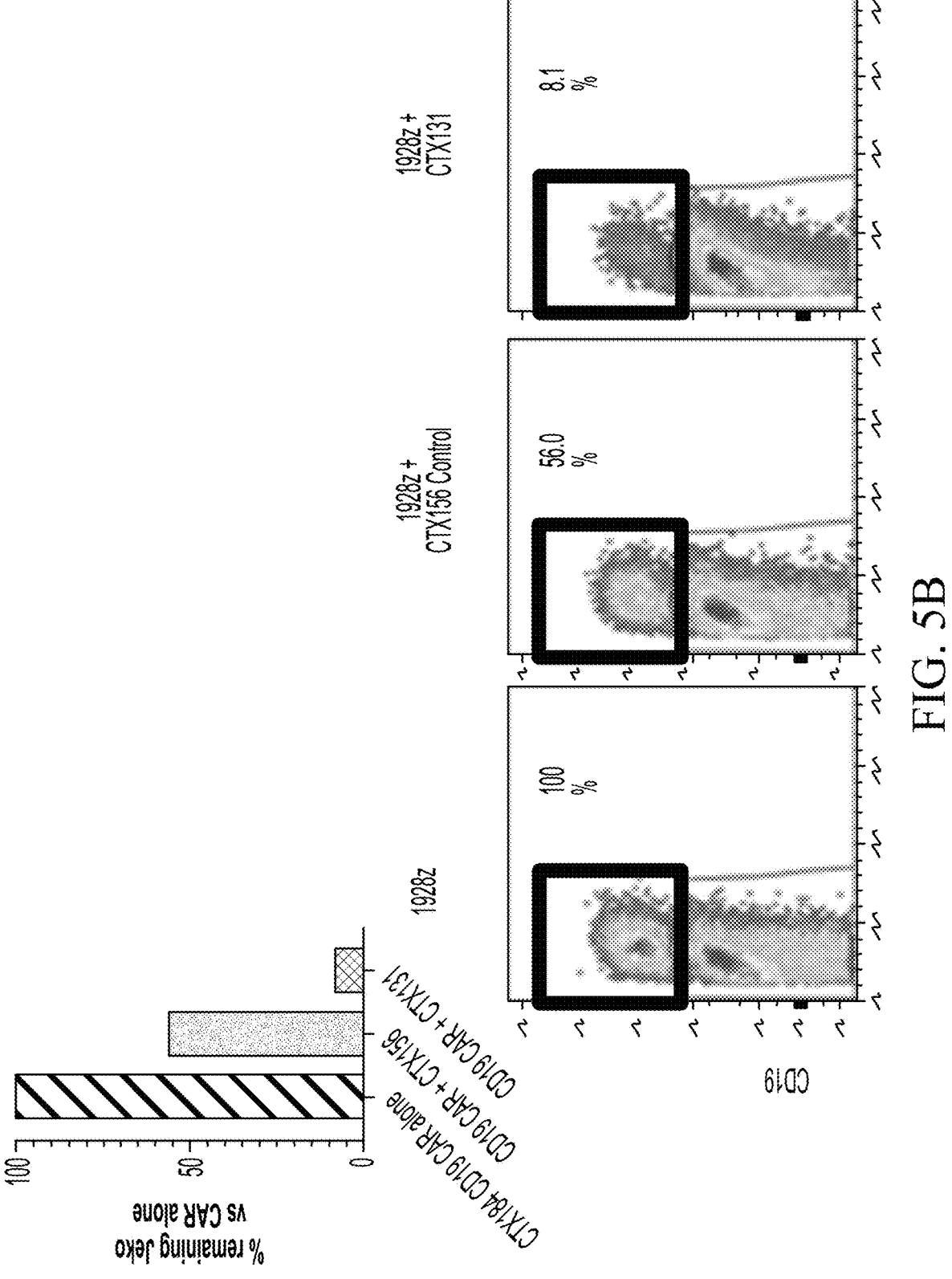

FIGS. 5A-5C: pCTX131 CER-T cells enhance the potency CD1928z CAR-T cell. FIG. 5A: Kinetics of Ptd-Ser induction on JeKo-1 MCL cells in response to CD1928z CAR-T cells. JeKo-1 MCL cells were co-cultured at increasing effector:target ratios and evaluated for Ptd-Ser induction over time. Kinetic curves represent the percentage of viable JeKo-1 targets that bind to rTim-4, a Ptd-Ser binding protein. FIG. 5B top: JeKo-1 cells were co-cultured with pCTX184 (1928z)+pCTX131, pCTX184+CTX156 Control T cells or pCTX184 cells alone for 48 hrs at a 1:1 T cell:JeKo-1 ratio. Samples treated with CTX184+CER 131 exhibited substantially fewer tumor cells in culture ~2 days later when compared to samples treated with CTX184 alone, or CTX184+CTX156 Control T cells. All data were collected via FACs. FIG. 5B bottom: Representative flow plots for enumeration of remaining JeKo-1 cells after 48 h co-culture. FIG. 5B top: Raw flow data from FIG. 5B bottom used to calculate bar graph of remaining JeKo-1 cells. FIG. 5C: JeKo-1 cells were co-cultured with pCTX184 (1928z)+pCTX131, pCTX184+CTX156 Control T cells or pCTX184 cells alone for 48 hrs at a 0.5:1 T cell:JeKo-1 ratio. Samples treated with CTX184+CER 131 exhibited increased IFN-γ secretion as compared to samples treated with CTX184 alone, or CTX184+CTX156 Control T cells.

Figure 6A:
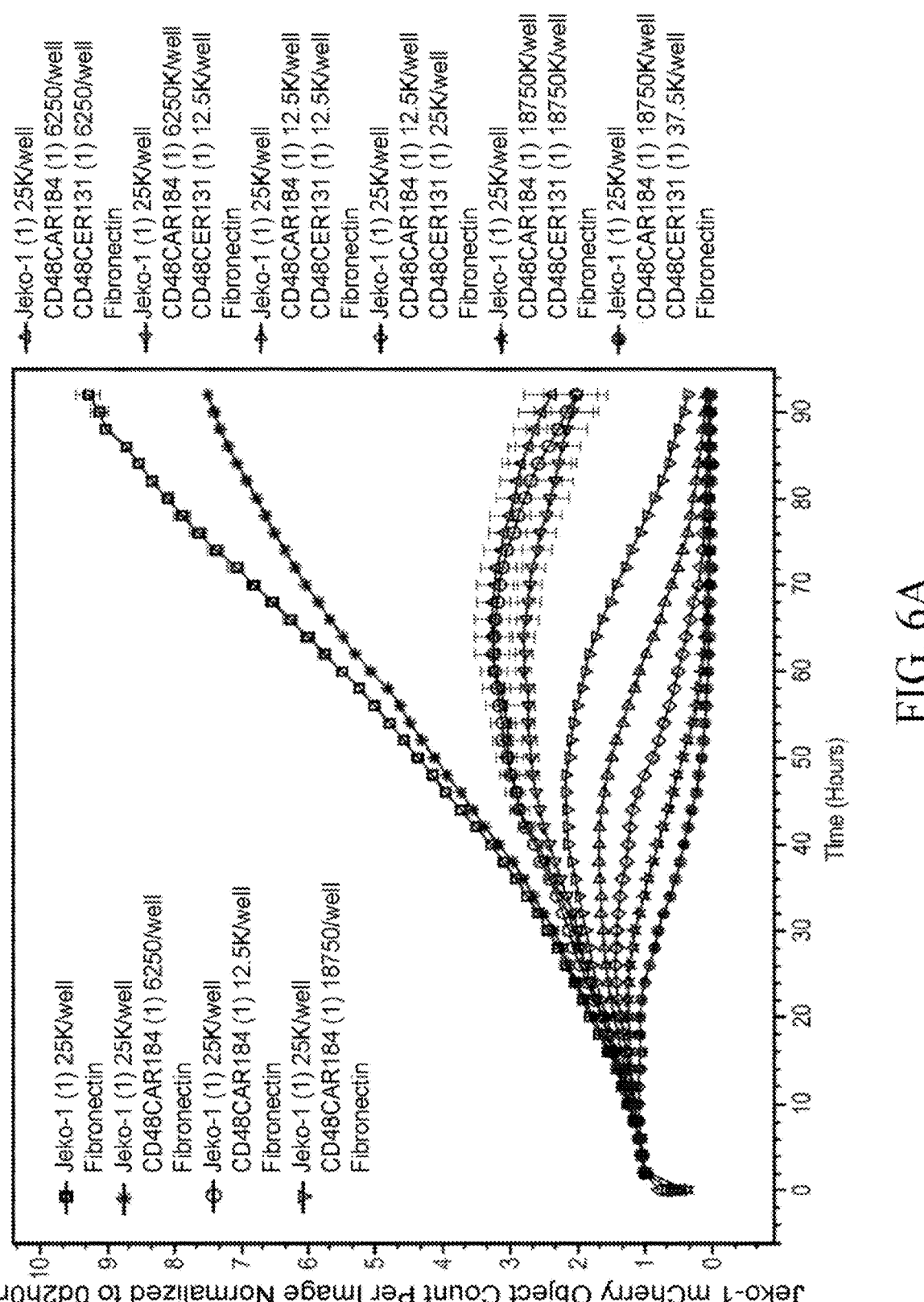
Figure 6B:
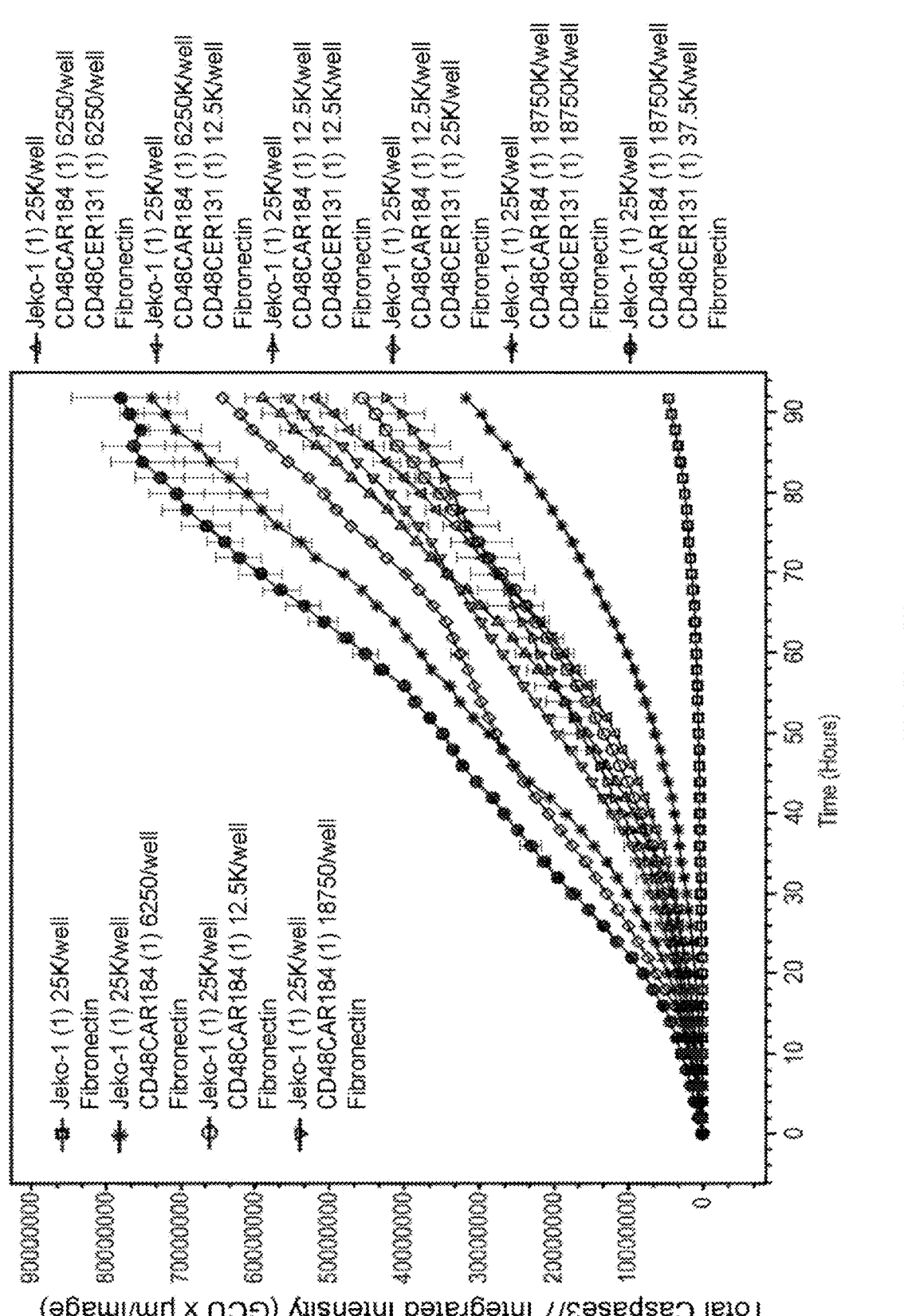

FIGS. 6A-6B: pCTX131 Chimeric Tim4 Receptor-T cells enhance the potency CD1928z CAR-T cells. Cytotoxic responses evaluating mixtures of CD1928z CAR-T (pCTX184, also called CAR184)+pCTX131 Chimeric Tim4 Receptor-T cells. FIG. 6A: pCTX131 Chimeric Tim4 Receptor-T cells were combined with CD1928z CAR-T cells (pCTX184) at varying ratios and JekO-1 cell counts were quantified over time. FIG. 6B: Caspase 3/7 responses. All data were collected via incucyte.

Figure 7A:
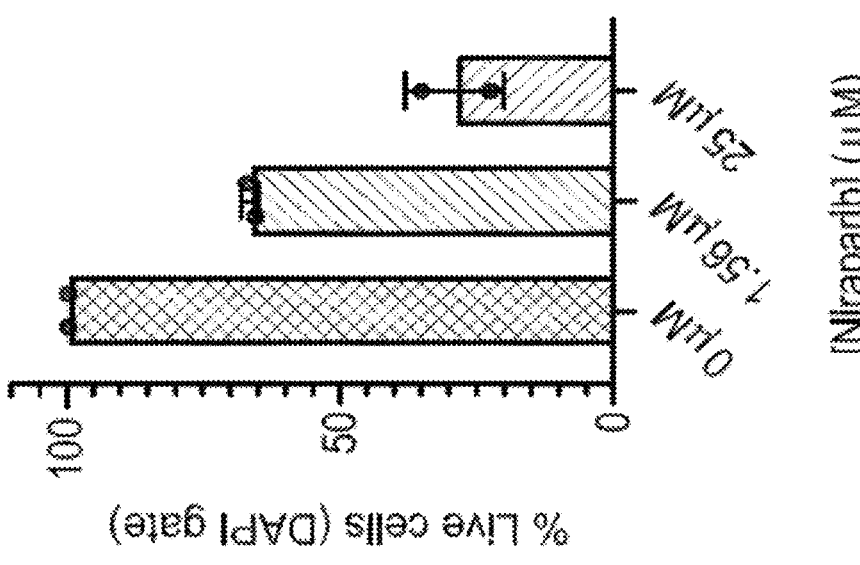
Figure 7A:
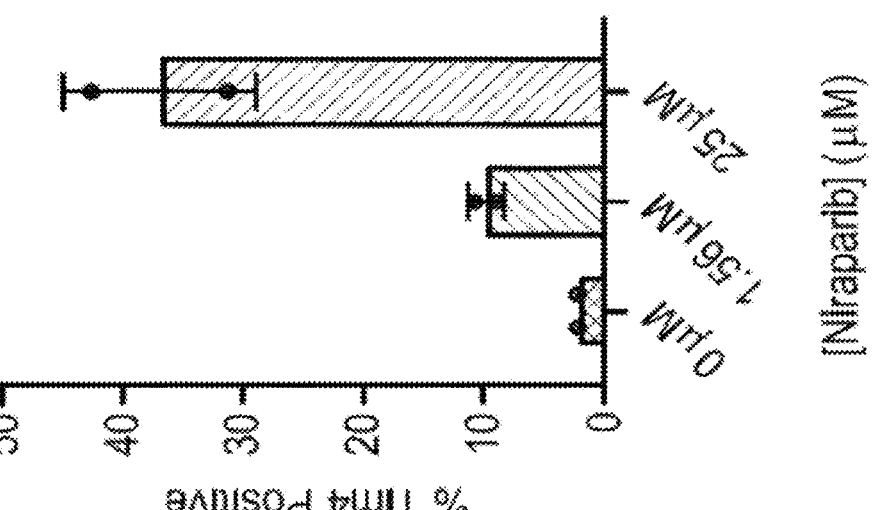
Figure 7B:
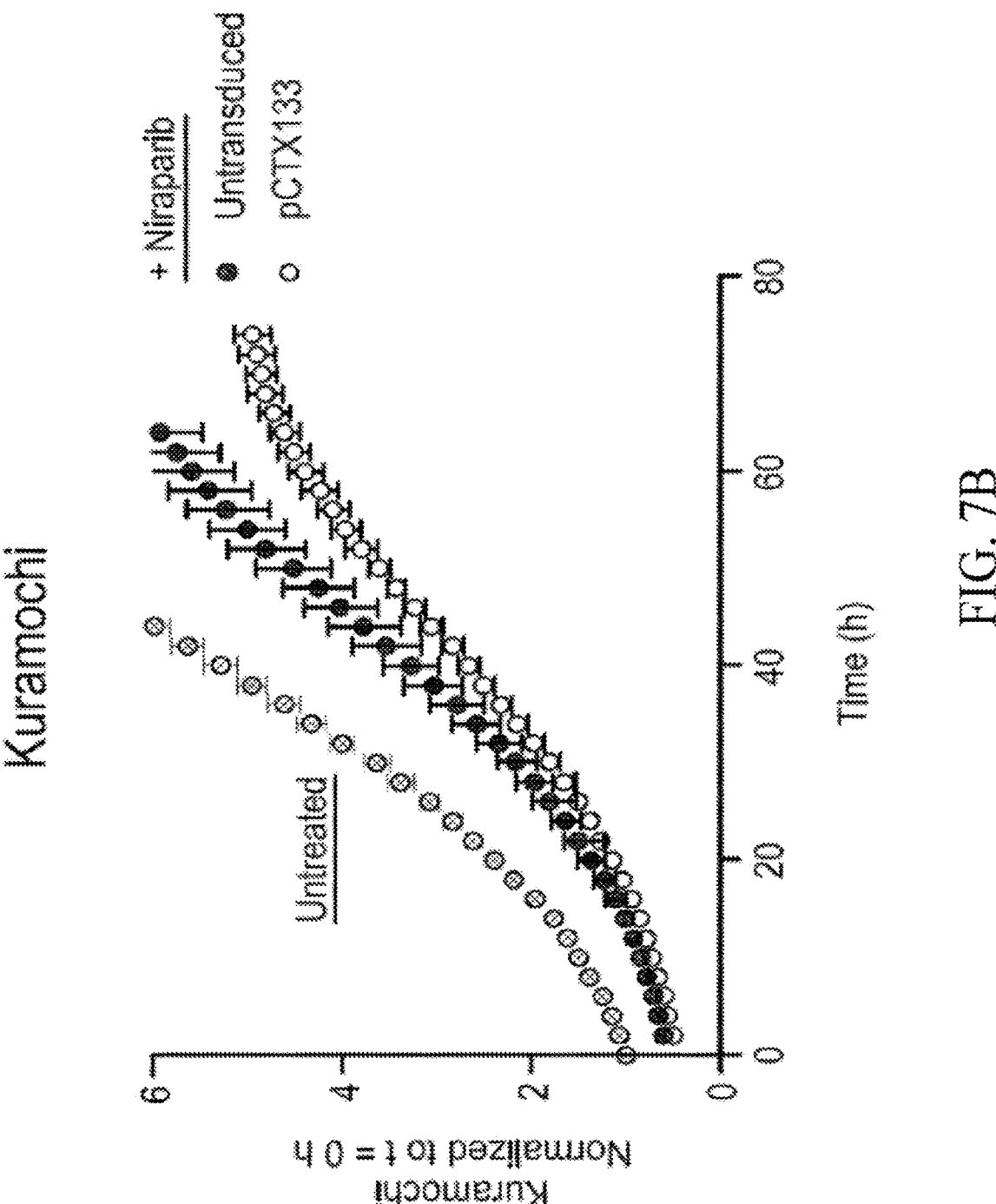

FIGS. 7A-7B: pCTX133, a TLR-2 containing Chimeric Tim4 Receptor Enhances Potency of Niraparib in an Ovarian Cancer Model. FIG. 7A: Flow cytometry measurement of surface PtdSer. Kuramochi cells were treated with 1.56 or 25 μM Niraparib or with equivalent volume of DMSO (control). 48 hours later samples were trypsinized and stained using a Tim4-Fc followed by a fluorescently-labeled secondary antibody to the Tim4-Fc. FIG. 7B: Kuramochi cells pre-treated for ~20 hours with 1.56 μM Niraparib were co-cultured with pCTX133 and Untransduced CD4 T cells from donor 32 at a 2:1 T cell:Kuramochi ratio and a final Niraparib concentration of 1.56 μM. Samples treated with Niraparib+pCTX133 exhibited substantially fewer tumor cells in culture ~3 days later when compared to samples treated with Niraparib alone, or Niraparib+untransduced T cells. All data were collected via IncuCyte.

Figure 8A:
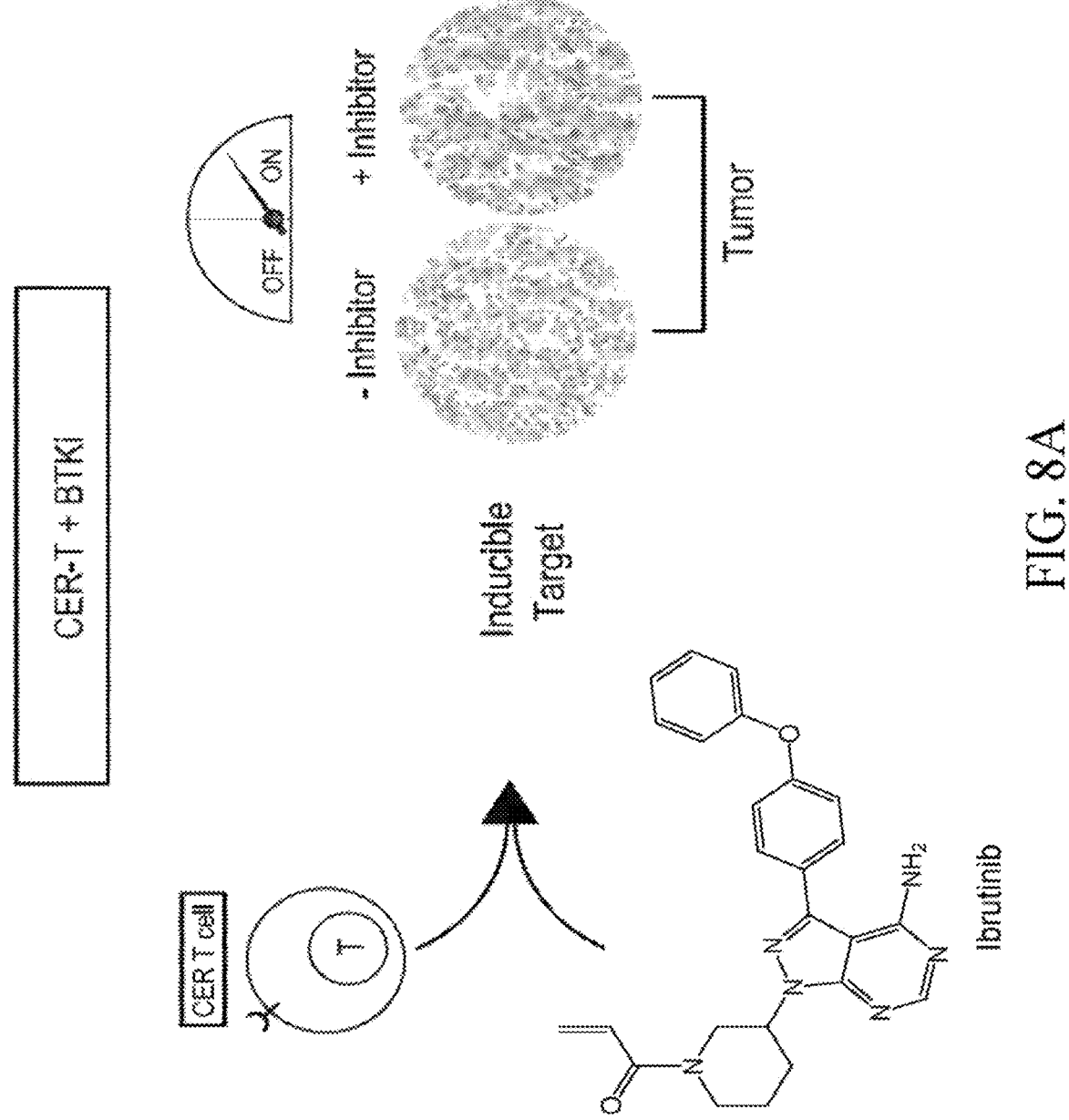
Figure 8B:
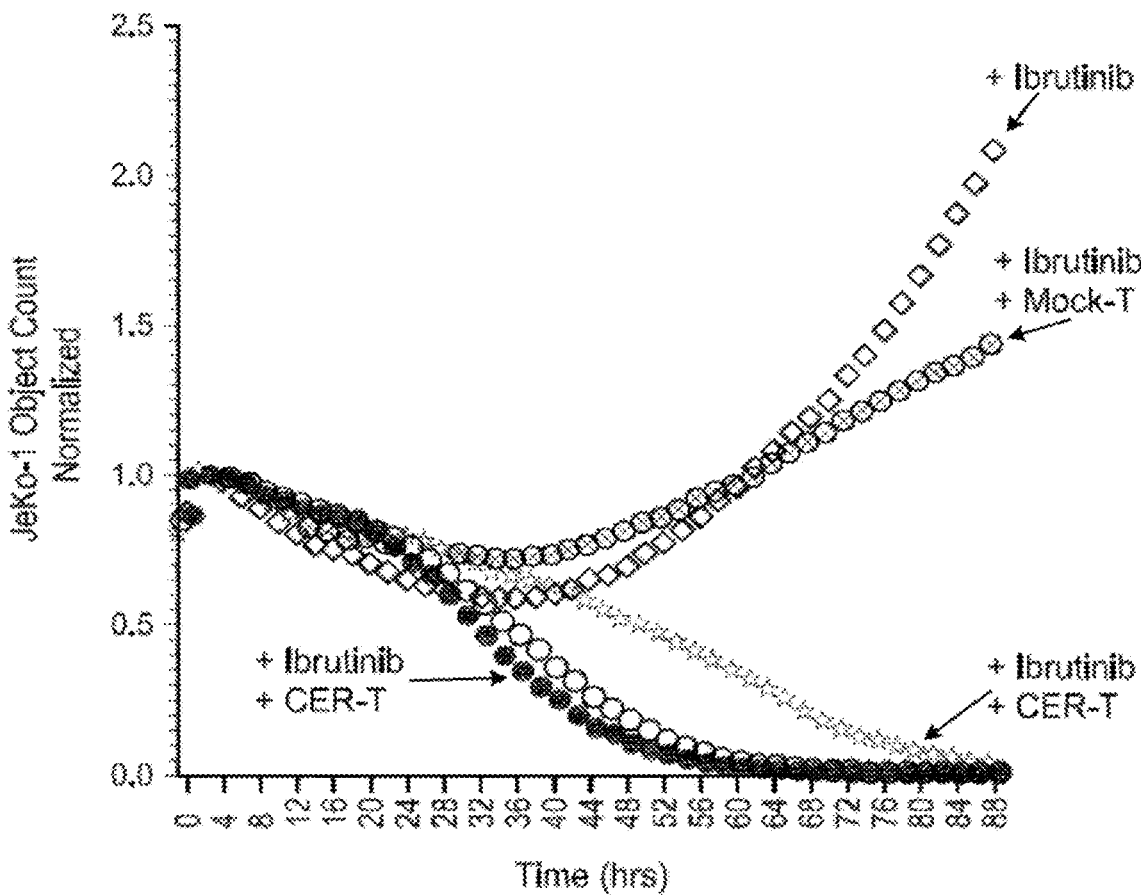

FIGS. 8A-8B: Chimeric Tim4 Receptor-T Cell+BTK inhibitor (ibrutinib) combination for hematologic malignancy. FIG. 8A: Ibrutinib induces expression of phosphatidylserine on target cells. FIG. 8B: Synergistic Chimeric Tim4 Receptor-T cell mediated cell killing in combination with BTK inhibitor small molecule. CTX136 (Tim4-CD28-CD3z) T cells co-cultured at a 3:1, 2:1, and 1:1 E:T in presence of Ibrutinib showed a substantial increase in killing as compared to empty vector transduced cells or Ibrutinib treatment alone.

Figure 9A:
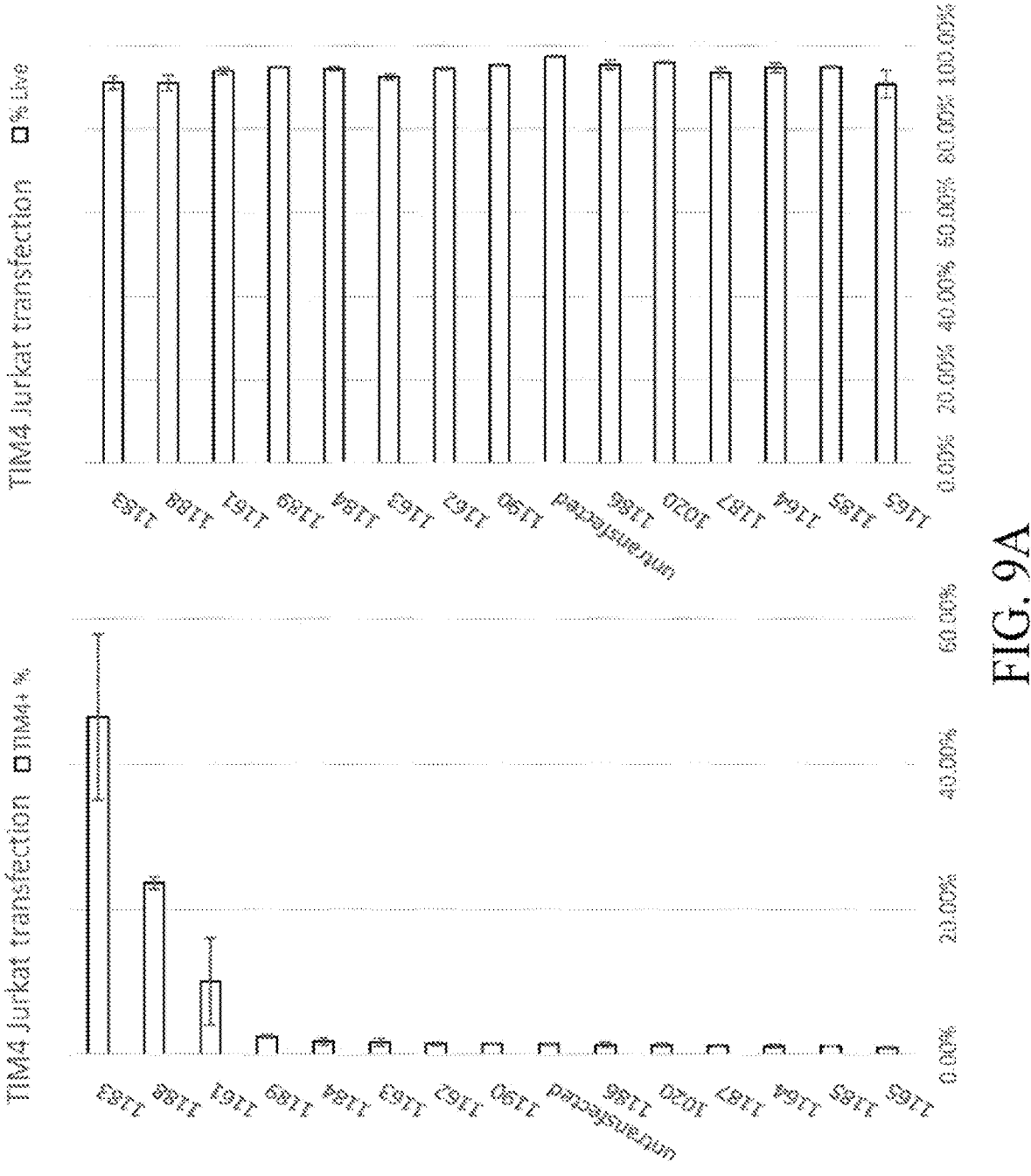
Figure 9B:
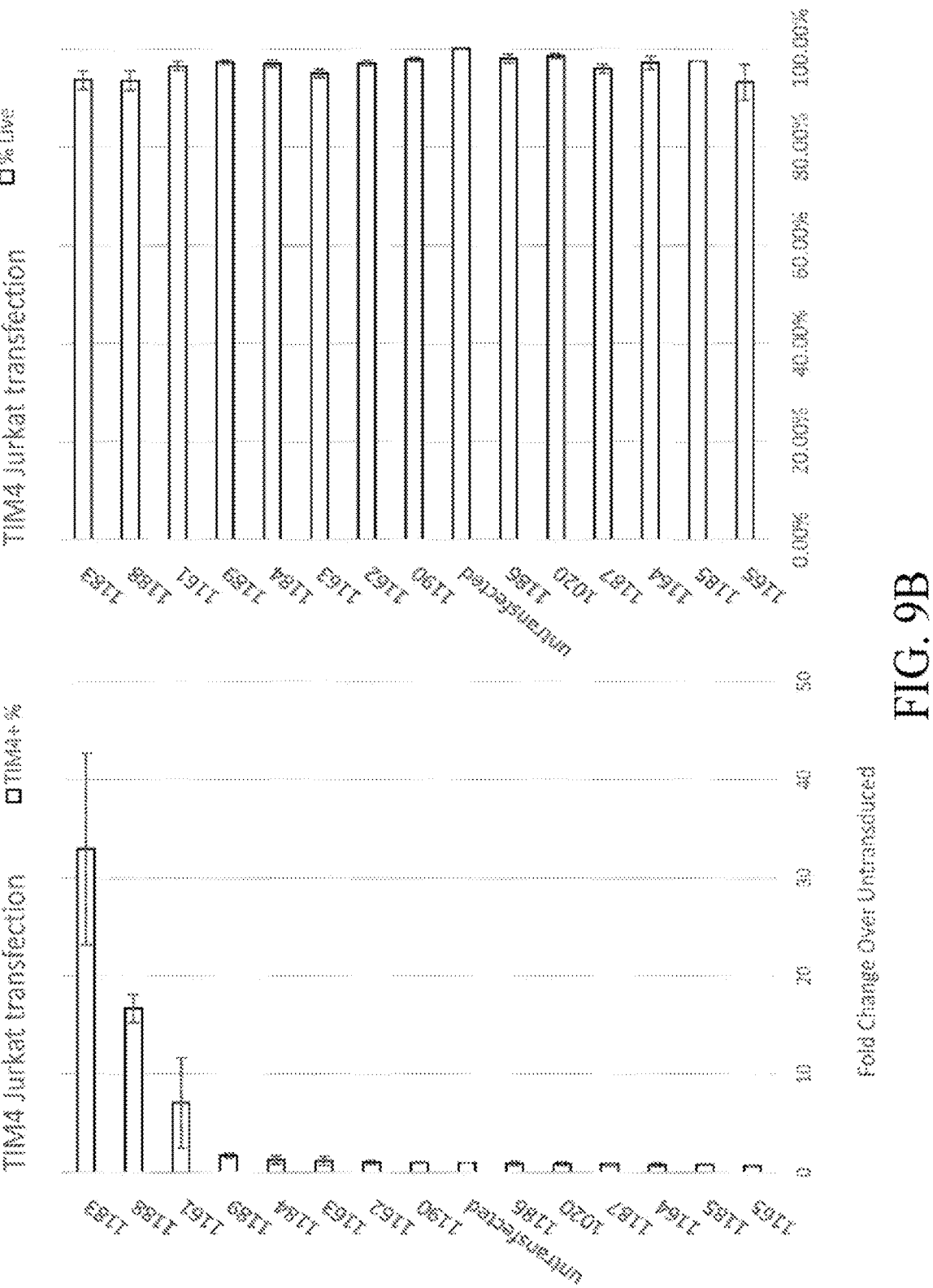

FIGS. 9A-9B show transfection of Jurkat cells with various chimeric Tim4 receptor constructs, pCTX1183, pCTX1161, pCTX1189, pCTX1184, pCTX1163, pCTX1162, pCTX1190, pCTX1186, pCTX1187, pCTX1164, pCTX1185, and pCTX1165. FIG. 9B is normalized to untransfected cells.

Figure 10:
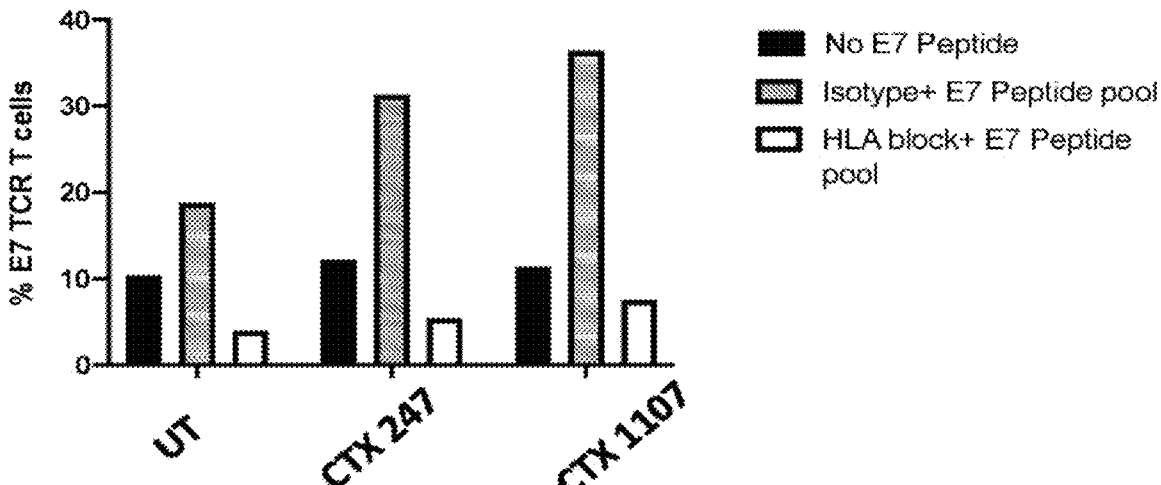

FIG. 10 is a bar graph showing activation of HPV E7 TCR T cells mediated by antigen presentation by chimeric Tim4-T cells is blocked by anti-HLA-I antibodies.

DETAILED DESCRIPTION

In one aspect, the present disclosure provides chimeric T-cell immunoglobulin mucin protein (Tim) receptors, also referred to as chimeric engulfment receptors (CERs). Chimeric Tim receptors of the present disclosure confer engulfment and/or cytotoxic activity to chimeric Tim receptor-modified host cells (e.g., T cells), with the cytotoxic activity being induced upon binding of the chimeric Tim receptor to its target antigen, phosphatidylserine. In some embodiments, chimeric Tim receptors confer engulfment, cytotoxicity, and enhanced antigen capture, antigen processing, and antigen presentation activity to modified host cells (e.g., T cells).

In some embodiments, chimeric Tim receptors described herein comprise a single chain chimeric protein, the single chain chimeric protein comprising: (a) an extracellular domain comprising a binding domain comprising: (i) a Tim4 IgV domain and a Tim1 mucin domain; or (ii) a Tim1 IgV domain and a Tim4 mucin domain; (b) an intracellular signaling domain, wherein the intracellular signaling domain comprises a primary intracellular signaling domain and optionally a secondary intracellular signaling domain; and (c) a transmembrane domain positioned between and connecting the extracellular domain and the intracellular signaling domain.

In some embodiments, chimeric Tim receptors described herein comprise a single chain chimeric protein, the single chain chimeric protein comprising: (a) an extracellular domain comprising a binding domain comprising a Tim1 IgV domain and a Tim1 mucin domain; (b) an intracellular signaling domain, wherein the intracellular signaling domain comprises a primary intracellular signaling domain and optionally a secondary intracellular signaling domain; and (c) a transmembrane domain positioned between and connecting the extracellular domain and the intracellular signaling domain.

In some embodiments, chimeric Tim receptors described herein comprise a single chain chimeric protein, the single chain chimeric protein comprising: (a) an extracellular domain comprising a binding domain comprising: (i) a Tim1 IgV domain and a Tim1 mucin domain; (ii) a Tim4 IgV domain and a Tim4 mucin domain; (iii) a Tim1 IgV domain and a Tim4 mucin domain; or (iv) a Tim4 IgV domain and a Tim1 mucin domain; (b) an intracellular signaling domain, wherein the intracellular signaling domain comprises a primary intracellular signaling domain selected from a Tim1 signaling domain or a Tim4 signaling domain, and optionally a secondary intracellular signaling domain; and (c) a transmembrane domain positioned between and connecting the extracellular domain and the intracellular signaling domain.

In some embodiments, chimeric Tim receptors described herein comprise a single chain chimeric protein, the single chain chimeric protein comprising: (a) an extracellular domain comprising a binding domain comprising: (i) a Tim4 IgV domain and a Tim4 mucin domain; (b) an intracellular signaling domain, wherein the intracellular signaling domain comprises a primary intracellular signaling domain selected from a CD28 signaling domain, a CD3ζ signaling domain, and a 4-1BB signaling domain, and a secondary intracellular signaling domain selected from a TLR signaling domain; and (c) a transmembrane domain positioned between and connecting the extracellular domain and the intracellular signaling domain.

In some embodiments, chimeric Tim receptors described herein comprise a single chain chimeric protein, the single chain chimeric protein comprising: (a) an extracellular domain comprising a binding domain comprising: (i) a Tim4 IgV domain and a Tim4 mucin domain; (b) an intracellular signaling domain, wherein the intracellular signaling domain comprises a primary intracellular signaling domain comprises an immunoreceptor tyrosine-based activation motif (ITAM) containing signaling domain; the secondary intracellular signaling domain comprises a costimulatory signaling domain, Tim1 signaling domain, or Tim4 signaling domain; and the tertiary intracellular signaling domain comprises a TLR signaling domain.

In some embodiments, the extracellular domain of the chimeric Tim receptors described herein optionally includes an extracellular spacer domain positioned between and connecting the binding domain and transmembrane domain.

In some embodiments, chimeric Tim receptors may also be capable of costimulating T cells via a different signaling pathway than the "classical" T cell costimulation pathways (e.g., CD28). For example, in addition to binding phosphatidylserine, Tim4 is also a ligand for Tim1, which is expressed on the surface of activated T cells. Tim1 is also capable of binding to phosphatidylserine. Tim4-induced Tim1 signaling has been found to costimulate T cell proliferation and survival (Hartt Meyers et al., 2005, Nat. Immunol. 6:455). Thus, in certain embodiments, cytotoxic chimeric Tim receptors may reduce or inhibit T cell exhaustion, or restore exhausted T cells by providing costimulatory signals via at least one signaling pathway. In certain embodiments, cytotoxic chimeric Tim receptors provide costimulatory signals via at least two distinct signaling pathways (e.g., via the selected costimulatory signaling domain in the cytotoxic chimeric Tim receptor and Tim1).

In some embodiments, when expressed in a host cell, the chimeric Tim receptors of the present disclosure also confer engulfment activity to the host cell. For example, in certain such embodiments, binding of the chimeric Tim receptor expressed in a host cell to a phosphatidylserine target may induce both cytolytic and engulfment responses by the host cell. In particular embodiments of the modified host cells described herein, the host cell does not naturally exhibit an engulfment phenotype prior to modification with the chimeric Tim receptor.

In another aspect, host cells modified with chimeric Tim receptors of the present disclosure can be used in methods for eliminating target cells bearing surface exposed phosphatidylserine, e.g., for the treatment of cancer. In normal, healthy cells phosphatidylserine is located in the inner leaflet of the plasma membrane. However, certain cellular events, such as damage, apoptosis, necrosis, and stress, activates a "scramblase" that quickly exposes phosphatidylserine on the cell surface, where it can bind to receptors such as Tim4 or Tim1. Endogenous tumor-specific effector T cells can induce exposure of phosphatidylserine on the outer membrane of targeted tumor cells during cytolysis. Furthermore, certain cancer therapies (e.g., chemotherapy, radiotherapy, CAR-T cells, etc.) can induce exposure of phosphatidylserine on targeted tumor cells or cells in the tumor microenvironment by inducing apoptosis, cellular stress, cellular damage, etc. Engineered host cells expressing the presently disclosed chimeric Tim receptors may clear damaged, stressed, apoptotic, or necrotic tumor cells bearing surface exposed phosphatidylserine by inducing apoptosis in the tumor cells bearing surface exposed phosphatidylserine. In certain embodiments, host cells expressing chimeric Tim receptors disclosed herein clear damaged, stressed, apoptotic, or necrotic tumor cells bearing surface exposed phosphatidylserine by inducing apoptosis and by engulfment. Engineered host cells comprising chimeric Tim receptors according to the present description may be administered to a subject alone, or in combination with one or more additional therapeutic agents, including for example CAR-T cells, TCRs, antibodies, radiation therapy, chemotherapies, small molecules, oncolytic viruses, electropulse therapy, etc.

In another aspect, host cells modified with chimeric Tim receptors of the present disclosure can be used in methods for enhancing an effector response (e.g., a tumor specific immune response). In embodiments, host cells modified with chimeric Tim receptors of the present disclosure can be used in methods for enhancing anti-tumor efficacy (e.g., tumor trafficking, expansion, and persistence). Embodiments of the chimeric Tim receptors of the present disclosure are capable of costimulating T cells via at least one costimulatory signaling pathway upon binding phosphatidylserine. In certain embodiments, the chimeric Tim receptors described herein provide costimulatory signals via at least two distinct signaling pathways. In certain embodiments, the enhanced effector response is enhanced T cell proliferation, cytokine production, cytotoxic activity, persistence, or any combination thereof. Host cells expressing chimeric Tim receptors according to the present description may be administered to a subject alone, or in combination with one or more additional therapeutic agents, including for example CAR-T cells, TCRs, antibodies, radiation therapy, chemotherapies, small molecules, oncolytic viruses, electropulse therapy, etc.

In another aspect, host cells modified with chimeric Tim receptors of the present disclosure can be used in methods for inhibiting or reducing immune cell exhaustion. In certain embodiments, immune cell exhaustion refers to T cell exhaustion, NK cell exhaustion, or both. Tumor cells may provide continuous antigen stimulation to immune cells, often in the absence of costimulatory ligands, which may result in immune cell exhaustion (e.g., reduced proliferative capacity, reduced effector function, and upregulation of immunosuppressive molecules). Cancer therapies, such as chemotherapy, radiotherapy, CAR-T cell therapy, etc., can also provide prolonged antigen stimulation in the absence of costimulatory signals or when the strength or duration of costimulatory signals is limited. Chimeric Tim receptors of the present disclosure are capable of costimulating immune cells via at least one costimulatory signaling domain upon binding phosphatidylserine. In certain embodiments, chimeric Tim receptors provide costimulatory signals via at least two distinct signaling pathways. Host cells expressing chimeric Tim receptors may be administered to a subject alone, or in combination with one or more additional therapeutic agents, including for example CAR-T cells, TCRs, antibodies, radiation therapy, chemotherapies, small molecules, oncolytic viruses, electropulse therapy, etc.

In some embodiments, host cells (e.g., T cells) modified with chimeric Tim receptors of the present disclosure exhibit enhanced antigen capture, antigen processing, and antigen presentation activity. Ligand-binding to the phagocytic receptor portion of the chimeric Tim receptor mediates a cascade of events including: T cell activation, signal transduction, cytolytic function, production of cytokines and chemokines, partial engulfment of target cells, and downstream transcriptional programs that lead to presentation of target cell antigens. Expression of chimeric Tim receptors in non- or weakly phagocytic immune cells such as mature polyclonal T cells can enable and enhance antigen-specific capture through engulfment of target cell fragments. In some embodiments, the added functionality of chimeric Tim receptor-mediated antigen capture supports enhanced presentation of non-targeted antigens while also eliciting direct cytolytic activity against primed tumor cell targets.

For combination therapy compositions and methods comprising a chimeric Tim receptor according to the present description and cellular immunotherapy, e.g., CARs or TCRs, the chimeric Tim receptor and cellular immunotherapy agent (e.g., CAR or TCR) can be expressed on separate engineered cells or expressed on the same engineered cell to produce a bispecific, multifunctional engineered cell. Chimeric Tim receptor and a cellular immunotherapy agent expressed on the same engineered cell can be expressed from separate vectors, or on the same vector as a multicistronic construct.

In another aspect, host cells modified with chimeric Tim receptors of the present disclosure can be used to enhance the effect of a therapeutic agent that induces cellular stress, damage, necrosis, or apoptosis. For example, certain therapeutic agents, such as chemotherapy, specific inhibitors of driver mutations associated with cancer (targeted therapy such as BRAF inhibitors, EGRF inhibitors, ALK/ROS1 kinase inhibitors, BTK inhibitors), radiation therapy, UV light therapy, electropulse therapy, adoptive cellular immunotherapy (e.g., CAR-T cells, TCRs) and oncolytic viral therapy, can induce cell damage or death in tumor cells or diseased cells. Cells expressing a chimeric Tim receptor as presently described can bind to the phosphatidylserine moieties exposed on the outer leaflet of damaged or dying cells resulting from any one or more of such therapeutic agents and induce cytolysis or both cytolysis and engulfment of the targeted cells.

Prior to setting forth this disclosure in more detail, it may be helpful to an understanding thereof to provide definitions of certain terms to be used herein.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means ±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

Terms understood by those in the art of antibody technology are each given the meaning acquired in the art, unless expressly defined differently herein. The term "antibody" is used in the broadest sense and includes polyclonal and monoclonal antibodies. An "antibody" may refer to an intact antibody comprising at least two heavy (H) chains and two light (L) chains inter-connected by disulfide bonds, as well as an antigen-binding portion (or antigen-binding domain) of an intact antibody that has or retains the capacity to bind a target molecule. An antibody may be naturally occurring, recombinantly produced, genetically engineered, or modified forms of immunoglobulins, for example intrabodies, peptibodies, nanobodies, single domain antibodies, SMIPs, multispecific antibodies (e.g., bispecific antibodies, diabodies, triabodies, tetrabodies, tandem di-scFV, tandem tri-scFv, ADAPTIR). A monoclonal antibody or antigen-binding portion thereof may be non-human, chimeric, humanized, or human, preferably humanized or human. Immunoglobulin structure and function are reviewed, for example, in Harlow et al., Eds., Antibodies: A Laboratory Manual, Chapter 14 (Cold Spring Harbor Laboratory, Cold Spring Harbor, 1988). "Antigen-binding portion" or "antigen-binding domain" of an intact antibody is meant to encompass an "antibody fragment," which indicates a portion of an intact antibody and refers to the antigenic determining variable regions or complementary determining regions of an intact antibody. Examples of antibody fragments include, but are not limited to, Fab, Fab', F(ab')$_2$, and Fv fragments, Fab'-SH, F(ab')$_2$, diabodies, linear antibodies, scFv antibodies, VH, and multispecific antibodies formed from antibody fragments. A "Fab" (fragment antigen binding) is a portion of an antibody that binds to antigens and includes the variable region and CH1 of the heavy chain linked to the light chain via an inter-chain disulfide bond. An antibody may be of any class or subclass, including IgG and subclasses thereof (IgG$_1$, IgG$_2$, IgG$_3$, IgG$_4$), IgM, IgE, IgA, and IgD.

The term "variable region" or "variable domain" refers to the domain of an antibody heavy or light chain that is involved in binding of the antibody to antigen. The variable domains of the heavy chain and light chain (VH and VL, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007)). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

The terms "complementarity determining region" and "CDR," which are synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (HCDR1, HCDR2, HCDR3) and three CDRs in each light chain variable region (LCDR1, LCDR2, LCDR3).

As used herein, the terms "binding domain", "binding region", and "binding moiety" refer to a molecule, such as a peptide, oligopeptide, polypeptide, or protein that possesses the ability to specifically and non-covalently bind, associate, unite, recognize, or combine with a target molecule (e.g., phosphatidylserine). A binding domain includes any naturally occurring, synthetic, semi-synthetic, or recombinantly produced binding partner for a biological molecule or other target of interest. In some embodiments, the binding domain is an antigen-binding domain, such as an antibody or functional binding domain or antigen-binding portion thereof. Exemplary binding domains include single chain antibody variable regions (e.g., domain antibodies, sFv, scFv, Fab), receptor ectodomains (e.g., Tim4), ligands (e.g., cytokines, chemokines), or synthetic polypeptides selected for the specific ability to bind to a biological molecule.

"T cell receptor" (TCR) refers to a molecule found on the surface of T cells (also referred to as T lymphocytes) that is generally responsible for recognizing antigens bound to major histocompatibility complex (MHC) molecules. The TCR is generally composed of a disulfide-linked heterodimer of the highly variable a and β chains (also known as TCRα and TCRβ, respectively) in most T cells. In a small subset of T cells, the TCR is made up of a heterodimer of γ and δ chains (also known as TCRγ and TCRδ, respectively). Each chain of the TCR is a member of the immunoglobulin superfamily and possesses one N-terminal immunoglobulin variable domain, one immunoglobulin constant domain, a transmembrane region, and a short cytoplasmic tail at the C-terminal end (see Janeway et al., *Immunobiology: The Immune System in Health and Disease*, 3$^{rd}$ Ed., Current Biology Publications, p. 4:33, 1997). TCRs of the present disclosure may be from various animal species, including human, mouse, rat, cat, dog, goat, horse, or other mammals. TCRs may be cell-bound (i.e., have a transmembrane region or domain) or in soluble form. TCRs include recombinantly produced, genetically engineered, fusion, or modified forms of TCRs, including for example, scTCRs, soluble TCRs, TCR fusion constructs (TRuC™; see, U.S. Patent Publication No. 2017/0166622).

The term "variable region" or "variable domain" of a TCR α-chain (Vα) and β-chain (Vβ), or Vγ and Vδ for γδ TCRs, are involved in binding of the TCR to antigen. The V$_\alpha$ and V$_\beta$ of a native TCR generally have similar structures, with each variable domain comprising four conserved FRs and three CDRs. The V$_\alpha$ domain is encoded by two separate DNA segments, the variable gene segment (V gene) and the joining gene segment (J gene); the V$_\beta$ domain is encoded by three separate DNA segments, the variable gene segment (V gene), the diversity gene segment (D gene), and the joining gene segment (J gene). A single V$_\alpha$ or V$_\beta$ domain may be sufficient to confer antigen-binding specificity. "Major histocompatibility complex molecule" (MHC molecule) refers to a glycoprotein that delivers a peptide antigen to a cell surface. MHC class I molecules are heterodimers composed of a membrane spanning α chain (with three a domains) and a non-covalently associated β2 microglobulin. MHC class II molecules are composed of two transmembrane glycoproteins, α and β, both of which span the membrane. Each chain has two domains. MHC class I molecules deliver peptides originating in the cytosol to the cell surface, where peptide: MHC complex is recognized by CD8$^+$ T cells. MHC class II molecules deliver peptides originating in the vesicular system to the cell surface, where they are recognized by CD4$^+$ T cells. An MHC molecule may be from various animal species, including human, mouse, rat, or other mammals.

"Chimeric antigen receptor" (CAR) refers to a chimeric protein comprising two or more distinct domains and can function as a receptor when expressed on the surface of a cell. CARs are generally composed of an extracellular domain comprising a binding domain that binds a target antigen, an optional extracellular spacer domain, a transmembrane domain, and an intracellular signaling domain (e.g., an immunoreceptor tyrosine-based activation motif (ITAM)-containing T cell activating motif, and optionally an intracellular costimulatory domain). In certain embodiments, an intracellular signaling domain of a CAR has an ITAM-containing T cell activating domain (e.g., CD3ζ) and an intracellular costimulatory domain (e.g., CD28). In certain embodiments, a CAR is synthesized as a single polypeptide chain or is encoded by a nucleic acid molecule as a single chain polypeptide.

A variety of assays are known for identifying binding domains of the present disclosure that specifically bind a particular target, as well as determining binding domain affinities, such as Western blot, ELISA, and BIACORE® analysis (see also, e.g., Scatchard et al., *Ann. N.Y. Acad. Sci.* 51:660, 1949; and U.S. Pat. Nos. 5,283,173, 5,468,614, or the equivalent). As used herein, "specifically binds" refers to an association or union of a binding domain, or a fusion protein thereof, to a target molecule with an affinity or $K_a$ (i.e., an equilibrium association constant of a particular binding interaction with units of 1/M) equal to or greater than $10^5$ $M^{-1}$, while not significantly associating or uniting with any other molecules or components in a sample.

The terms "antigen" and "Ag" refer to a molecule that is capable of inducing an immune response. The immune response that is induced may involve antibody production, the activation of specific immunologically-competent cells, or both. Macromolecules, including proteins, glycoproteins, and glycolipids, can serve as an antigen. Antigens can be derived from recombinant or genomic DNA. As contemplated herein, an antigen need not be encoded (i) solely by a full-length nucleotide sequence of a gene or (ii) by a "gene" at all. An antigen can be generated or synthesized, or an antigen can be derived from a biological sample. Such a biological sample can include, but is not limited, to a tissue sample, a tumor sample, a cell, or a biological fluid.

The term "epitope" or "antigenic epitope" includes any molecule, structure, amino acid sequence or protein determinant within an antigen that is specifically bound by a cognate immune binding molecule, such as an antibody or fragment thereof (e.g., scFv), T cell receptor (TCR), chimeric Tim receptor, or other binding molecule, domain or protein. Epitopic determinants generally contain chemically active surface groupings of molecules, such as amino acids or sugar side chains, and can have specific three-dimensional structural characteristics, as well as specific charge characteristics. An epitope may be a linear epitope or a conformational epitope.

As used herein, the term "Tim4" (T-cell immunoglobulin and mucin domain containing protein 4), also known as "TimD4", refers to a phosphatidylserine receptor that is typically expressed on antigen presenting cells, such as macrophages and dendritic cells. Tim4 mediates the phagocytosis of apoptotic, necrotic, damaged, injured, or stressed cells, which present phosphatidylserine (PtdSer) on the exofacial (outer) leaflet of the cell membrane. Tim4 is also capable of binding to Tim1 expressed on the surface of T cells and inducing proliferation and survival. In certain embodiments, Tim4 refers to human Tim4. An exemplary human Tim4 protein comprises an amino acid sequence of SEQ ID NO:1.

As used herein, the term "Tim4 binding domain" refers to the N-terminal immunoglobulin-fold domain of Tim4 that possesses a metal ion-dependent pocket that selectively binds PtdSer. An exemplary human Tim4 binding domain comprises an amino acid sequence of SEQ ID NO:2, and an exemplary mouse Tim4 binding domain comprises an amino acid sequence of SEQ ID NO:24.

A Tim4 binding domain includes a variable immunoglobulin (IgV) like domain (referred to herein as an "IgV domain") and a Mucin like domain ("referred to herein as a "mucin domain"). An exemplary human Tim4 IgV domain comprises an amino acid sequence of SEQ ID NO:34, and an exemplary human Tim4 mucin domain comprises an amino acid sequence of SEQ ID NO:35. In certain embodiments, the Tim4 binding domain does not include a signal peptide. An exemplary human Tim4 signal peptide has the amino acid sequences of SEQ ID NO:11. An exemplary mouse Tim4 signal peptide has the amino acid sequences of SEQ ID NO:25.

As used herein, the term "Tim1" (T-cell immunoglobulin and mucin domain containing protein 1), refers to a phosphatidylserine receptor that is expressed on the surface of T cells. Tim1, as noted above is also capable of binding to Tim4 expressed on the surface of antigen presenting cells. In certain embodiments, Tim1 refers to human Tim1. An exemplary human Tim1 protein comprises an amino acid sequence of SEQ ID NO:36.

As used herein, the term "Tim1 binding domain" refers to the N-terminal immunoglobulin-fold domain of Tim1 that selectively binds PtdSer. An exemplary human Tim1 binding domain comprises an amino acid sequence of SEQ ID NO:37.

A Tim1 binding domain includes an IgV domain and a mucin domain. An exemplary human Tim1 IgV domain comprises an amino acid sequence of SEQ ID NO: 38, and an exemplary human Tim1 mucin domain comprises an amino acid sequence of SEQ ID NO:39. In certain embodiments, the Tim1 binding domain does not include a signal peptide. An exemplary human Tim1 signal peptide has the amino acid sequences of SEQ ID NO:40.

As used herein, an "effector domain" is an intracellular portion of a fusion protein or receptor that can directly or indirectly promote a biological or physiological response in a cell expressing the effector domain when receiving the appropriate signal. In certain embodiments, an effector domain is part of a protein or protein complex that receives a signal when bound, or it binds directly to a target molecule, which triggers a signal from the effector domain. An effector domain may directly promote a cellular response when it contains one or more signaling domains or motifs, such as an immunoreceptor tyrosine-based activation motif (ITAM). In other embodiments, an effector domain will indirectly promote a cellular response by associating with one or more other proteins that directly promote a cellular response.

As used herein, a "costimulatory signaling domain" refers to an intracellular signaling domain, or functional portion thereof, of a costimulatory molecule, which, when activated in conjunction with a primary or classic (e.g., ITAM-driven) activation signal (provided by, for example, a CD3ζ intracellular signaling domain), promotes or enhances a T cell response, such as T cell activation, cytokine production, proliferation, differentiation, survival, effector function, or combinations thereof. Costimulatory signaling domains include, for example, CD27, CD28, CD40L, GITR, NKG2C, CARD1, CD2, CD7, CD27, CD30, CD40, CD54 (ICAM), CD83, CD134 (OX-40), CD137 (4-1BB), CD150 (SLAMF1), CD152 (CTLA4), CD223 (LAG3), CD226, CD270 (HVEM), CD273 (PD-L2), CD274 (PD-L1), CD278 (ICOS), DAP10, LAT, LFA-1, LIGHT, NKG2C, SLP76, TRIM, or any combination thereof.

As used herein, an "immunoreceptor tyrosine-based activation motif (ITAM) activating domain" refers to an intracellular signaling domain or functional portion thereof which is naturally or endogenously present on an immune cell receptor or a cell surface marker and contains at least one immunoreceptor tyrosine-based activation motif (ITAM). ITAM refers to a conserved motif of YXXL/I-$X_{6-8}$-YXXL/I. In certain embodiments an ITAM signaling domain contains one, two, three, four, or more ITAMs. An ITAM signaling domain may initiate T cell activation signaling following antigen binding or ligand engagement. ITAM-signaling domains include, for example, intracellular signaling domains of CD3γ, CD3δ, CD3ε, CD3ζ, CD79a, and CD66d.

"Junction amino acids" or "junction amino acid residues" refer to one or more (e.g., about 2-20) amino acid residues between two adjacent motifs, regions or domains of a polypeptide. Junction amino acids may result from the construct design of a chimeric protein (e.g., amino acid residues resulting from the use of a restriction enzyme site during the construction of a nucleic acid molecule encoding a chimeric protein).

"Nucleic acid molecule" and "polynucleotide" can be in the form of RNA or DNA, which includes cDNA, genomic DNA, and synthetic DNA. A nucleic acid molecule may be composed of naturally occurring nucleotides (such as deoxyribonucleotides and ribonucleotides), analogs of naturally occurring nucleotides (e.g., α-enantiomeric forms of naturally occurring nucleotides), or a combination of both. Modified nucleotides can have modifications in or replacement of sugar moieties, or pyrimidine or purine base moieties. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. A nucleic acid molecule may be double stranded or single stranded, and if single stranded, may be the coding strand or non-coding (anti-sense strand). A coding molecule may have a coding sequence identical to a coding sequence known in the art or may have a different coding sequence, which, as the result of the redundancy or degeneracy of the genetic code, or by splicing, can encode the same polypeptide.

"Encoding" refers to the inherent property of specific polynucleotide sequences, such as DNA, cDNA, and mRNA polynucleotide sequences, such as DNA, cDNA, and mRNA sequences, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a polynucleotide encodes a protein if transcription and translation of mRNA corresponding to that polynucleotide produces the protein in a cell or other biological system. Both a coding strand and a non-coding strand can be referred to as encoding a protein or other product of the polynucleotide. Unless otherwise specified, a "nucleotide sequence encoding an amino acid sequence" includes all nucleotide sequences that are degenerate versions of each other and that encode the same amino acid sequence.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, the term "mature polypeptide" or "mature protein" refers to a protein or polypeptide that is secreted or localized in the cell membrane or inside certain cell organelles (e.g., the endoplasmic reticulum, golgi, or endosome) and does not include an N-terminal signal peptide.

A "signal peptide", also referred to as "signal sequence", "leader sequence", "leader peptide", "localization signal" or "localization sequence", is a short peptide (usually 15-30 amino acids in length) present at the N-terminus of newly synthesized proteins that are destined for the secretory pathway. A signal peptide typically comprises a short stretch of hydrophilic, positively charged amino acids at the N-terminus, a central hydrophobic domain of 5-15 residues, and a C-terminal region with a cleavage site for a signal peptidase. In eukaryotes, a signal peptide prompts translocation of the newly synthesized protein to the endoplasmic reticulum where it is cleaved by the signal peptidase, creating a mature protein that then proceeds to its appropriate destination.

The term "chimeric" refers to any nucleic acid molecule or protein that is not endogenous and comprises sequences joined or linked together that are not normally found joined or linked together in nature. For example, a chimeric nucleic acid molecule may comprise regulatory sequences and coding sequences that are derived from different sources, or regulatory sequences and coding sequences that are derived from the same source but arranged in a manner different than that found in nature.

As used herein, the term "endogenous" or "native" refers to a gene, protein, compound, molecule, or activity that is normally present in a host or host cell, including naturally occurring variants of the gene, protein, compound, molecule, or activity.

As used herein, "homologous" or "homolog" refers to a molecule or activity from a host cell that is related by ancestry to a second gene or activity, e.g., from the same host cell, from a different host cell, from a different organism, from a different strain, from a different species. For example, a heterologous molecule or heterologous gene encoding the molecule may be homologous to a native host cell molecule or gene that encodes the molecule, respectively, and may optionally have an altered structure, sequence, expression level or any combination thereof.

As used herein, "heterologous" nucleic acid molecule, construct or sequence refers to a nucleic acid molecule or portion of a nucleic acid molecule that is not native to a host cell, but can be homologous to a nucleic acid molecule or portion of a nucleic acid molecule from the host cell. The source of the heterologous nucleic acid molecule, construct or sequence can be from a different genus or species. In some embodiments, the heterologous nucleic acid molecules are not naturally occurring. In certain embodiments, a heterologous nucleic acid molecule is added (i.e., not endogenous or native) into a host cell or host genome by, for example, conjugation, transformation, transfection, transduction, electroporation, or the like, wherein the added molecule can integrate into the host cell genome or exist as extra-chromosomal genetic material (e.g., as a plasmid or other form of self-replicating vector), and can be present in multiple copies. In addition, "heterologous" refers to a non-native enzyme, protein or other activity encoded by a non-endogenous nucleic acid molecule introduced into the host cell, even if the host cell encodes a homologous protein or activity.

As used herein, the term "engineered," "recombinant," "modified" or "non-natural" refers to an organism, micro-organism, cell, nucleic acid molecule, or vector that has been modified by introduction of a heterologous nucleic acid molecule, or refers to a cell or microorganism that has been genetically engineered by human intervention—that is, modified by introduction of a heterologous nucleic acid molecule, or refers to a cell or microorganism that has been altered such that expression of an endogenous nucleic acid molecule or gene is controlled, deregulated or constitutive, where such alterations or modifications can be introduced by genetic engineering. Human-generated genetic alterations can include, for example, modifications introducing nucleic acid molecules (which may include an expression control element, such as a promoter) encoding one or more proteins, chimeric receptors, or enzymes, or other nucleic acid molecule additions, deletions, substitutions, or other functional disruption of or addition to a cell's genetic material. Exemplary modifications include those in coding regions or functional fragments thereof heterologous or homologous polypeptides from a reference or parent molecule. Additional exemplary modifications include, for example, modifications in non-coding regulatory regions in which the modifications alter expression of a gene or operon.

As used herein, the term "transgene" refers to a gene or polynucleotide encoding a protein of interest (e.g., chimeric Tim receptor) whose expression is desired in a host cell and that has been transferred by genetic engineering techniques into a cell. A transgene may encode proteins of therapeutic interest as well as proteins that are reporters, tags, markers, suicide proteins, etc. A transgene may be from a natural source, modification of a natural gene, or a recombinant or synthetic molecule. In certain embodiments, a transgene is a component of a vector.

The term "overexpressed" or "overexpression" of an antigen refers to an abnormally high level of antigen expression in a cell. Overexpressed antigen or overexpression of antigen is often associated with a disease state, such as in hematological malignancies and cells forming a solid tumor within a specific tissue or organ of a subject. Solid tumors or hematological malignancies characterized by overexpression of a tumor antigen can be determined by standard assays known in the art.

The "percent identity" between two or more nucleic acid or amino acid sequences is a function of the number of identical positions shared by the sequences (i.e., % identity=number of identical positions/total number of positions×100), taking into account the number of gaps, and the length of each gap that needs to be introduced to optimize alignment of two or more sequences. The comparison of sequences and determination of percent identity between two or more sequences can be accomplished using a mathematical algorithm, such as BLAST and Gapped BLAST programs at their default parameters (e.g., Altschul et al., *J. Mol. Biol.* 215:403, 1990; see also BLASTN at www.ncbi.nlm.nih.gov/BLAST).

A "conservative substitution" is recognized in the art as a substitution of one amino acid for another amino acid that has similar properties. Exemplary conservative substitutions are well known in the art (see, e.g., WO 97/09433, page 10, published Mar. 13, 1997; Lehninger, Biochemistry, Second Edition; Worth Publishers, Inc. NY:NY (1975), pp. 71-77; Lewin, Genes IV, Oxford University Press, NY and Cell Press, Cambridge, MA (1990), p. 8).

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements that are required for expression of the gene product. The promoter/regulatory sequence may, for example, be one that expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

The phrase "under transcriptional control" or "operatively linked" as used herein means that a promoter is in the correct location and orientation in relation to a polynucleotide to control the initiation of transcription by RNA polymerase and expression of the polynucleotide.

A "vector" is a nucleic acid molecule that is capable of transporting another nucleic acid. Vectors may be, for example, plasmids, cosmids, viruses, or phage. The term should also be construed to include non-plasmid and non-viral compounds which facilitate transfer of nucleic acid into cells. An "expression vector" is a vector that is capable of directing the expression of a protein encoded by one or more genes carried by the vector when it is present in the appropriate environment.

In certain embodiments, the vector is a viral vector. Examples of viral vectors include, but are not limited to, adenovirus vectors, adeno-associated virus vectors, retrovirus vectors, gamma retrovirus vectors, and lentivirus vectors. "Retroviruses" are viruses having an RNA genome. "Gamma retrovirus" refers to a genus of the retroviridae family. Examples of gamma retroviruses include mouse stem cell virus, murine leukemia virus, feline leukemia virus, feline sarcoma virus, and avian reticuloendotheliosis viruses. "Lentivirus" refers to a genus of retroviruses that are capable of infecting dividing and non-dividing cells. Examples of lentiviruses include but are not limited to HIV (human immunodeficiency virus), including HIV type 1 and HIV type 2, equine infectious anemia virus, feline immunodeficiency virus (FIV), bovine immune deficiency virus (BIV), and simian immunodeficiency virus (SIV).

In other embodiments, the vector is a non-viral vector. Examples of non-viral vectors include lipid-based DNA vectors, modified mRNA (modRNA), self-amplifying mRNA, closed-ended linear duplex (CELiD) DNA, and transposon-mediated gene transfer (PiggyBac, Sleeping Beauty). Where a non-viral delivery system is used, the delivery vehicle can be a liposome. Lipid formulations can be used to introduce nucleic acids into a host cell in vitro, ex vivo, or in vivo. The nucleic acid may be encapsulated in the interior of a liposome, interspersed within the lipid bilayer of a liposome, attached to a liposome via a linking molecule that is associated with both the liposome and the nucleic acid, contained or complexed with a micelle, or otherwise associated with a lipid.

As used herein, the term "engulfment" refers to a receptor-mediated process wherein endogenous or exogenous cells or particles greater than 100 nm in diameter are internalized by a phagocyte or host cell of the present disclosure. Engulfment is typically composed of multiple steps: (1) tethering of the target cell or particle via binding of an engulfment receptor to a pro-engulfment marker or antigenic marker directly or indirectly (via a bridging molecule) on a target cell or particle; and (2) internalization or engulfment of the whole target cell or particle, or a portion thereof. In certain embodiments, internalization may occur via cytoskeletal rearrangement of a phagocyte or host cell to form a phagosome, a membrane-bound compartment containing the internalized target. Engulfment may further include maturation of the phagosome, wherein the phagosome becomes increasingly acidic and fuses with lysosomes (to form a phagolysosome), whereupon the engulfed target is degraded (e.g., "phagocytosis"). Alternatively, phagosome-lysosome fusion may not be observed in engulfment. In yet another embodiment, a phagosome may regurgitate or discharge its contents to the extracellular environment before complete degradation. In some embodiments, engulfment refers to phagocytosis. In some embodiments, engulfment includes tethering of the target cell or particle by the phagocyte of host cell of the present disclosure, but not internalization. In some embodiments, engulfment includes tethering of the target cell or particle by the phagocyte of host cell of the present disclosure and internalization of part of the target cell or particle.

As used herein, the term "phagocytosis" refers to an engulfment process of cells or large particles (≥0.5 μm) wherein tethering of a target cell or particle, engulfment of the target cell or particle, and degradation of the internalized target cell or particle occurs. In certain embodiments, phagocytosis comprises formation of a phagosome that encompasses the internalized target cell or particle and phagosome fusion with a lysosome to form a phagolysosome, wherein the contents therein are degraded. In certain embodiments, during phagocytosis, following binding of a chimeric Tim receptor expressed on a host cell of the present disclosure to a phosphatidylserine expressed by a target cell or particle, a phagocytic synapse is formed; an actin-rich phagocytic cup is generated at the phagocytic synapse; phagocytic arms are extended around the target cell or particle through cytoskeletal rearrangements; and ultimately, the target cell or particle is pulled into the phagocyte or host cell through force generated by motor proteins. As used herein, "phagocytosis" includes the process of "efferocytosis", which specifically refers to the phagocytosis of apoptotic or necrotic cells in a non-inflammatory manner.

The term "immune system cell" or "immune cell" means any cell of the immune system that originates from a hematopoietic stem cell in the bone marrow. Hematopoietic stem cells give rise to two major lineages, a myeloid progenitor cell (which give rise to myeloid cells such as monocytes, macrophages, dendritic cells, megakaryocytes and granulocytes) and a lymphoid progenitor cell (which give rise to lymphoid cells such as T cells, B cells and natural killer (NK) cells). Exemplary immune system cells include a CD4+ T cell, a CD8+ T cell, a CD4− CD8− double negative T cell, a γδ T cell, a regulatory T cell, a natural killer cell, and a dendritic cell. Macrophages and dendritic cells may also be referred to as "antigen presenting cells" or "APCs," which are specialized cells that can activate T cells when a major histocompatibility complex (MHC) receptor on the surface of the APC complexed with a peptide interacts with a TCR on the surface of a T cell.

The term "T cells" refers to cells of T cell lineage. "Cells of T cell lineage" refer to cells that show at least one phenotypic characteristic of a T cell or a precursor or progenitor thereof that distinguishes the cells from other lymphoid cells, and cells of the erythroid or myeloid lineages. Such phenotypic characteristics can include expression of one or more proteins specific for T cells (e.g., $CD3^+$, $CD4^+$, $CD8^+$), or a physiological, morphological, functional, or immunological feature specific for a T cell. For example, cells of the T cell lineage may be progenitor or precursor cells committed to the T cell lineage; $CD25^+$ immature and inactivated T cells; cells that have undergone CD4 or CD8 linage commitment; thymocyte progenitor cells that are $CD4^+CD8^+$ double positive; single positive $CD4^+$ or $CD8^+$; TCRαβ or TCR γδ; or mature and functional or activated T cells. The term "T cells" encompasses naïve T cells (CD45 RA+, CCR7+, CD62L+, CD27+, CD45RO−), central memory T cells ($CD45RO^+$, $CD62L^+$, $CD8^+$), effector memory T cells (CD45RA+, CD45RO−, CCR7−, CD62L−, CD27−), mucosal-associated invariant T (MAIT) cells, Tregs, natural killer T cells, and tissue resident T cells.

The term "B cells" refers to cells of the B cell lineage. "Cells of B cell lineage" refer to cells that show at least one phenotypic characteristic of a B cell or a precursor or progenitor thereof that distinguishes the cells from other lymphoid cells, and cells of the erythroid or myeloid lineages. Such phenotypic characteristics can include expression of one or more proteins specific for B cells (e.g., $CD19^+$, CD72+, CD24+, $CD20^+$), or a physiological, morphological, functional, or immunological feature specific for a B cell. For example, cells of the B cell lineage may be progenitor or precursor cells committed to the B cell lineage (e.g., pre-pro-B cells, pro-B cells, and pre-B cells), immature and inactivated B cells or mature and functional or activated B cells. Thus, "B cells" encompass naïve B cells, plasma cells, regulatory B cells, marginal zone B cells, follicular B cells, lymphoplasmacytoid cells, plasmablast cells, and memory B cells (e.g., $CD27^+$, $IgD^-$).

The term "cytotoxic activity," also referred to as "cytolytic activity," with respect to a cell (e.g., a T cell or NK cell) expressing an immune receptor (e.g., a TCR) or a chimeric Tim receptor according to the present disclosure on its surface, means that upon antigen-specific signaling (e.g., via the TCR, chimeric Tim receptor), the cell induces a target cell to undergo apoptosis. In some embodiments, a cytotoxic cell may induce apoptosis in a target cell via the release of cytotoxins, such as perforin, granzyme, and granulysin, from granules. Perforins insert into the target cell membrane and form pores that allow water and salts to rapidly enter the target cell. Granzymes are serine proteases that induce apoptosis in the target cell. Granulysin is also capable of forming pores in the target cell membrane and is a proinflammatory molecule. In some embodiments, a cytotoxic cell may induce apoptosis in a target cell via interaction of Fas ligand, which is upregulated on T cell following antigen-specific signaling, with Fas molecules expressed on the target cell. Fas is an apoptosis-signaling receptor molecule on the surface of a number of different cells.

The term "exhaustion" with respect to immune cells refers to a state of immune cell dysfunction defined by poor effector function (e.g., reduced cytokine production, reduced cytotoxic activity), reduced proliferative capacity, increased expression of immune checkpoint molecules, and a transcriptional state distinct from that of functional effector or memory cells. In certain embodiments, an exhausted immune cell becomes unresponsive to the presence of its target antigen. Immune cell exhaustion may result from chronic exposure to a target antigen (e.g., as may result from chronic infection) or when it enters an immunosuppressive environment (e.g., a tumor microenvironment). In certain embodiments, immune cell exhaustion refers to T cell exhaustion, NK cell exhaustion, or both. In certain embodiments, exhausted T cells exhibit; (a) increased expression of PD-1, TIGIT, LAG3, TIM3, or any combination thereof; (b) decreased production of IFN-γ, IL-2, TNF-α, or any combination thereof; or both (a) and (b). In certain embodiments, exhausted NK cells exhibit; (a) increased expression of PD-1, NKG2A, TIM3, or any combination thereof; (b) decreased production of IFN-γ, TNF-α, or both; or both (a) and (b).

A "disease" is a state of health of a subject wherein the subject cannot maintain homeostasis, and wherein, if the disease is not ameliorated, then the subject's health continues to deteriorate. In contrast, a "disorder" or "undesirable condition" in a subject is a state of health in which the subject is able to maintain homeostasis, but in which the subject's state of health is less favorable than it would be in the absence of the disorder or undesirable condition. Left untreated, a disorder or undesirable condition does not necessarily result in a further decrease in the subject's state of health.

The term "cancer" as used herein is defined as disease characterized by the rapid and uncontrolled growth of aberrant cells. The aberrant cells may form solid tumors or constitute a hematological malignancy. Cancer cells can spread locally or through the bloodstream and lymphatic system to other parts of the body. Examples of various cancers include, but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

The term "subject," "patient" and "individual" are used interchangeably herein and are intended to include living organisms in which an immune response can be elicited (e.g., mammals). Examples of subjects include humans, primates, cows, horses, sheep, dogs, cats, mice, rats, rabbits, guinea pigs, pigs, and transgenic species thereof.

"Adoptive cellular immunotherapy" or "adoptive immunotherapy" refers to the administration of naturally occurring or genetically engineered disease antigen-specific immune cells (e.g., T cells). Adoptive cellular immunotherapy may be autologous (immune cells are from the recipient), allogeneic (immune cells are from a donor of the same species) or syngeneic (immune cells are from a donor genetically identical to the recipient).

"Autologous" refers to any material (e.g., a graft of organ, tissue, cells) derived from the same subject to which it is later to be re-introduced.

"Allogeneic" refers to a graft derived from a different subject of the same species.

A "therapeutically effective amount" or "effective amount" of a chimeric protein or cell expressing a chimeric protein of this disclosure (e.g., a chimeric Tim receptor or a cell expressing a chimeric Tim receptor) refers to that amount of protein or cells sufficient to result in amelioration of one or more symptoms of the disease, disorder, or undesired condition being treated. When referring to an individual active ingredient or a cell expressing a single active ingredient, administered alone, a therapeutically effective dose refers to the effects of that ingredient or cell expressing that ingredient alone. When referring to a combination, a therapeutically effective dose refers to the combined amounts of active ingredients or combined adjunctive active ingredient with a cell expressing an active ingredient that results in a therapeutic effect, whether administered serially or simultaneously.

"Treat" or "treatment" or "ameliorate" refers to medical management of a disease, disorder, or undesired condition of a subject. In general, an appropriate dose or treatment regimen comprising a host cell expressing a chimeric protein of this disclosure is administered in an amount sufficient to elicit a therapeutic or prophylactic benefit. Therapeutic or prophylactic/preventive benefit includes improved clinical outcome; lessening or alleviation of symptoms associated with a disease, disorder, or undesired condition; decreased occurrence of symptoms; improved quality of life; longer disease-free status; diminishment of extent of disease, disorder, or undesired condition; stabilization of disease state; delay of disease progression; remission; survival; prolonged survival; or any combination thereof.

The term "anti-tumor effect" refers to a biological effect which can be manifested by a decrease in tumor volume, a decrease in the number of tumor cells, a decrease in the number of metastases, an increase in life expectancy, or amelioration of various physiological symptoms associated with a cancerous condition. An "anti-tumor effect" can also be manifested by prevention of a hematological malignancy or tumor formation.

"Autoimmune disease" refers to a disorder that results from an autoimmune response. An autoimmune disease is the result of an inappropriately excessive response to a self-antigen. An autoimmune response may involve self-reactive B-cells that produce autoantibodies, self-reactive T-cells, or both. An "autoantibody" as used herein is an antibody produced by a subject that binds to a self-antigen also produced by the subject.

Additional definitions are provided throughout the present disclosure.

Chimeric Tim Receptors

In some embodiments, the present disclosure provides a chimeric Tim receptor comprising a single chain chimeric protein, the single chain chimeric protein comprising: (a) an extracellular domain comprising a binding domain comprising: (i) a Tim4 IgV domain and a Tim1 mucin domain; or (ii) a Tim1 IgV domain and a Tim4 mucin domain; (b) an intracellular signaling domain, wherein the intracellular signaling domain comprises a primary intracellular signaling domain and optionally a secondary intracellular signaling domain; and (c) a transmembrane domain positioned between and connecting the extracellular domain and the intracellular signaling domain.

In some embodiments, the present disclosure provides a chimeric Tim receptor comprising a single chain chimeric protein, the single chain chimeric protein comprising: (a) an extracellular domain comprising a binding domain comprising a Tim1 IgV domain and a Tim1 mucin domain; (b) an intracellular signaling domain, wherein the intracellular signaling domain comprises a primary intracellular signaling domain and optionally a secondary intracellular signaling domain; and (c) a transmembrane domain positioned between and connecting the extracellular domain and the intracellular signaling domain.

In some embodiments, the present disclosure provides a chimeric Tim receptor comprising a single chain chimeric protein, the single chain chimeric protein comprising: (a) an extracellular domain comprising a binding domain comprising: (i) a Tim1 IgV domain and a Tim1 mucin domain; (ii) a Tim4 IgV domain and a Tim4 mucin domain; (iii) a Tim1 IgV domain and a Tim4 mucin domain; or (iv) a Tim4 IgV domain and a Tim1 mucin domain; (b) an intracellular signaling domain, wherein the intracellular signaling domain comprises a primary intracellular signaling domain selected from a Tim1 signaling domain or a Tim4 signaling domain, and optionally a secondary intracellular signaling domain; and (c) a transmembrane domain positioned between and connecting the extracellular domain and the intracellular signaling domain.

In some embodiments, the present disclosure provides chimeric Tim receptors comprising a single chain chimeric protein, the single chain chimeric protein comprising: (a) an extracellular domain comprising a binding domain comprising: (i) a Tim4 IgV domain and a Tim4 mucin domain; (b) an intracellular signaling domain, wherein the intracellular signaling domain comprises a primary intracellular signaling domain selected from a CD28 signaling domain, a CD3ζ signaling domain, and a 4-1BB signaling domain, and a secondary intracellular signaling domain selected from a TLR signaling domain; and (c) a transmembrane domain positioned between and connecting the extracellular domain and the intracellular signaling domain.

In some embodiments, the present disclosure provides chimeric Tim receptors comprising a single chain chimeric protein, the single chain chimeric protein comprising: (a) an extracellular domain comprising a binding domain comprising: (i) a Tim4 IgV domain and a Tim4 mucin domain; (b) an intracellular signaling domain, wherein the intracellular signaling domain comprises a primary intracellular signaling domain comprises an immunoreceptor tyrosine-based activation motif (ITAM) containing signaling domain; the secondary intracellular signaling domain comprises a costimulatory signaling domain, Tim1 signaling domain, or Tim4 signaling domain; and the tertiary intracellular signaling domain comprises a TLR signaling domain.

Additional chimeric Tim receptors are provided in the present disclosure.

In certain embodiments, the extracellular domain of the chimeric Tim receptors described herein optionally includes an extracellular spacer domain positioned between and connecting the binding domain and transmembrane domain.

When expressed in a host cell, chimeric Tim receptors of the present disclosure can confer a phosphatidylserine-specific, cytotoxic phenotype to the modified host cell (e.g., the host cell becomes cytotoxic to a stressed, damaged, injured, apoptotic, or necrotic cell expressing phosphatidyl-serine on its surface). In some embodiments, the chimeric Tim receptors induce apoptosis in targeted cells via release of granzymes, perforin, granulysin, or any combination thereof. In some embodiments, cells expressing a chimeric Tim receptor according to the present description exhibit an engulfment phenotype specific to phosphatidylserine presenting cells. In some embodiments, cells, e.g., T cells, expressing a chimeric Tim receptor according to the present disclosure exhibit enhanced antigen presenting activity.

The intracellular signaling domain can include one or more effector domains that are capable of transmitting functional signals to a cell in response to binding of the extracellular domain of the chimeric Tim receptor and phosphatidylserine. Signaling by the intracellular signaling domain(s) is triggered by binding of the extracellular domain to phosphatidylserine. The signals transduced by the intracellular signaling domain promote effector function of the chimeric Tim receptor containing cell. Examples of effector function include cytotoxic activity, secretion of cytokines, proliferation, anti-apoptotic signaling, persistence, expansion, engulfment of a target cell or particle expressing phosphatidylserine on its surface, antigen presentation, or any combination thereof.

In certain embodiments, the intracellular signaling domain comprises a first intracellular signaling domain. In embodiments, the intracellular signaling domain comprises a first intracellular signaling domain and a second intracellular signaling domain. In some embodiments, the intracellular signaling domain comprises a first intracellular signaling domain, a second intracellular signaling domain, and a third intracellular signaling domain. Chimeric Tim receptors according to the present disclosure can be used in a variety of therapeutic methods where clearance of apoptotic, necrotic, damaged, or stressed cells is beneficial, while providing costimulation that enhances cellular immune response, reduces immune cell exhaustion, or both.

Component parts of the fusion proteins of the present disclosure are further described in detail herein.

Extracellular Domain

As described herein, a chimeric Tim receptor comprises an extracellular domain comprising a Tim binding domain. The Tim binding domain confers specificity to phosphatidylserine (PtdSer), which is a phospholipid with a negatively charged head-group and a component of the cell membrane. In healthy cells, phosphatidylserine is preferentially found in the inner leaflet of the cell membrane. However, when cells are stressed, damaged or undergo apoptosis or necrosis, phosphatidylserine is exposed on the outer leaflet of the cell membrane. Thus, phosphatidylserine may be used as a marker to distinguish stressed, damaged, apoptotic, necrotic, pyroptotic, or oncotic cells. Binding of phosphatidylserine by the Tim binding domain may block the interaction between the phosphatidylserine and another molecule and, for example, interfere with, reduce or eliminate certain functions of the phosphatidylserine (e.g., signal transduction). In some embodiments, the binding of a phosphatidylserine may induce certain biological pathways or identify the phosphatidylserine molecule or a cell expressing phosphatidylserine for elimination.

A Tim binding domain suitable for use in a chimeric Tim receptor of the present disclosure may be any polypeptide or peptide derived from a Tim1 and/or Tim4 molecule that specifically binds phosphatidylserine. In embodiments, a Tim binding domain comprises an IgV domain from Tim1 or Tim4, and a mucin domain from Tim1 or Tim4. For example, a Tim binding domain may comprise a Tim1 IgV domain and a Tim1 mucin domain. In another example, a Tim binding domain may comprise a Tim1 IgV domain and a Tim4 mucin domain. In another example, a Tim binding domain may comprise a Tim4 IgV domain and a Tim 1 mucin domain. In another example, a Tim binding domain may comprise a Tim4 IgV domain and a Tim4 mucin domain.

Phosphatidylserine binding is generally regulated by the IgV domain. The core phosphatidylserine binding domain is a four amino acid sequence in the IgV domain (e.g., amino acids 95-98 of SEQ ID NO:34 or amino acids 92-95 of SEQ ID NO: 38). A Tim4 binding domain binds minimally to cells with low phosphatidylserine density. A Tim1 binding domain binds more strongly to a lower phosphatidylserine density, resulting in a lower threshold for response. A summary of Tim1 and Tim4 binding to phosphatidylserine is provided in Table 1. By combining Tim1 IgV domain and Tim4 mucin domain, or Tim4 IgV domain and Tim1 mucin domain, the binding affinity of the binding domain to phosphatidylserine can be modulated. Further, such a combination in the Tim binding domain also provides a combination of the sensitivity to phosphatidylserine of Tim4 and the stability in protein expression of Tim1.

TABLE 1

|  | Low PtdSer | Moderate PtdSer | High PtdSer | Cooperativity |
|---|---|---|---|---|
| Tim-1 | Moderate binding | Strong binding | Strong binding |  |
| Tim-4 | Minimal binding | Moderate binding | Strong binding | Yes |

Additionally, an RGD domain (e.g., amino acids 68-70 of SEQ ID NO: 34) in an IgV domain may regulate integrin binding as a co-receptor for engulfment.

In some embodiments, the Tim binding domain is obtained or derived from human Tim 1 and/or Tim4. An exemplary human Tim1 molecule is provided in Uniprot. Ref. Q96D42 (SEQ ID NO:36). An exemplary human Tim1 binding domain comprises or consists of the amino acid sequence of SEQ ID NO:37 or SEQ ID NO:43. In some embodiments, the Tim1 binding domain comprises or consists of an amino acid sequence having at least about 75%, 80%, 85%, 90%, 91%, 92%, 93%, 94%, 95%, 96%, 97%, 98%, 99%, 99.5%, or 100% identity to SEQ ID NO:37 or SEQ ID NO:43. In certain embodiments, the Tim1 binding domain comprises an amino acid sequence having at least about 1, 2, 3, 4, 5, 6, 7, 8, 9, 10, 11, 12, 13, 14, 15, 16, 17, 18, 19, or 20 amino acid modifications (e.g., deletions, additions, substitutions) to an amino acid sequence of SEQ ID NO:37 or SEQ ID NO:43.

An exemplary human Tim4 molecule is provided in Uniprot. Ref. Q96H15 (SEQ ID NO:1). An exemplary human Tim4 binding domain comprises or consists of the amino acid sequence of SEQ ID NO:2, SEQ ID NO:42, or SEQ ID NO: 119. An exemplary mouse Tim4 binding domain comprises or consists of an amino acid sequence of SEQ ID NO:24 or amino acids 23-279 of SEQ ID NO:24. In certain embodiments, the Tim4 binding domain comprises or consists of an amino acid sequence having at least about 75%, 80%, 85%, 90%, 91%, 92%, 93%, 94%, 95%, 96%, 97%, 98%, 99%, 99.5%, or 100% identity to SEQ ID NO:2, SEQ ID NO:42, SEQ ID NO:119, or SEQ ID NO:24 or amino acids 23-279 of SEQ ID NO:24. In certain embodiments, the Tim4 binding domain comprises an amino acid sequence having at least about 1, 2, 3, 4, 5, 6, 7, 8, 9, 10, 11, 12, 13, 14, 15, 16, 17, 18, 19, or 20 amino acid modifications (e.g., deletions, additions, substitutions) to an amino acid sequence of SEQ ID NO:2, SEQ ID NO:42, SEQ ID NO:119, or SEQ ID NO:24 or amino acids 23-279 of SEQ ID NO:24.

In embodiments, the Tim binding domain comprises an IgV domain from Tim1. An exemplary human Tim1 IgV domain is provided in SEQ ID NO:38. In some embodiments, the Tim1 IgV domain is a modified Tim1 IgV domain comprising a R66G substitution in SEQ ID NO:38. The R66G substitution (e.g., amino acids 68-70 of SEQ ID NO:34) confers a RGD domain in Tim1 IgV domain, which may regulate integrin binding as a co-receptor for engulfment. In particular embodiments, the modified Tim1 IgV domain comprises the amino acid sequence of SEQ ID NO:41. In some embodiments, this modified Tim1 domain may increase phagocytic activity while preserving Tim1 sensitivity. In some embodiments, the Tim1 IgV domain comprises or consists of an amino acid sequence having at least about 75%, 80%, 85%, 90%, 91%, 92%, 93%, 94%, 95%, 96%, 97%, 98%, 99%, 99.5%, or 100% identity to SEQ ID NO: 38, SEQ ID NO:38 with a R66G substitution, or SEQ ID NO:41. In certain embodiments, the Tim1 IgV comprises an amino acid sequence having at least about 1, 2, 3, 4, 5, 6, 7, 8, 9, 10, 11, 12, 13, 14, 15, 16, 17, 18, 19, or 20 amino acid modifications (e.g., deletions, additions, substitutions) to an amino acid sequence of SEQ ID NO:38, SEQ ID NO:38 with a R66G substitution, or SEQ ID NO:41.

In some embodiments, the Tim binding domain comprises an IgV domain from Tim4. An exemplary human Tim4 IgV domain is provided in SEQ ID NO: 34. In some embodiments, the Tim4 IgV domain comprises or consists of an amino acid sequence having at least about 75%, 80%, 85%, 90%, 91%, 92%, 93%, 94%, 95%, 96%, 97%, 98%, 99%, 99.5%, or 100% identity to SEQ ID NO:34. In certain embodiments, the Tim4 IgV domain comprises an amino acid sequence having at least about 1, 2, 3, 4, 5, 6, 7, 8, 9, 10, 11, 12, 13, 14, 15, 16, 17, 18, 19, or 20 amino acid modifications (e.g., deletions, additions, substitutions) to an amino acid sequence of SEQ ID NO:34.

In embodiments, the Tim binding domain comprises a mucin domain from Tim1. An exemplary human Tim1 mucin domain is provided in SEQ ID NO:39. In certain embodiments, the Tim1 mucin domain comprises or consists of an amino acid sequence having at least about 75%, 80%, 85%, 90%, 91%, 92%, 93%, 94%, 95%, 96%, 97%, 98%, 99%, 99.5%, or 100% identity to SEQ ID NO:39. In certain embodiments, the Tim1 mucin domain comprises an amino acid sequence having at least about 1, 2, 3, 4, 5, 6, 7, 8, 9, 10, 11, 12, 13, 14, 15, 16, 17, 18, 19, or 20 amino acid modifications (e.g., deletions, additions, substitutions) to an amino acid sequence of SEQ ID NO:39.

In other embodiments, the Tim binding domain comprises a mucin domain from Tim4. An exemplary human Tim4 mucin domain is provided in SEQ ID NO: 35. In certain embodiments, the Tim4 mucin domain comprises or consists of an amino acid sequence having at least about 75%, 80%, 85%, 90%, 91%, 92%, 93%, 94%, 95%, 96%, 97%, 98%, 99%, 99.5%, or 100% identity to SEQ ID NO:35. In certain embodiments, the Tim4 mucin domain comprises an amino acid sequence having at least about 1, 2, 3, 4, 5, 6, 7, 8, 9, 10, 11, 12, 13, 14, 15, 16, 17, 18, 19, or 20 amino acid modifications (e.g., deletions, additions, substitutions) to an amino acid sequence of SEQ ID NO:35.

In some embodiments, the Tim binding domain comprises a Tim1 IgV domain and a Tim1 mucin domain. In some embodiments, the Tim1 IgV domain comprises or consists of the amino acid sequence set forth in SEQ ID NO:38 and the Tim1 mucin domain comprises or consists of the amino acid sequence set forth in SEQ ID NO: 39. In some embodiments, the Tim1 IgV domain comprises or consists of the amino acid sequence set forth in SEQ ID NO:38 with a R66G substitution and the Tim1 mucin domain comprises or consists of the amino acid sequence set forth in SEQ ID NO: 39. In some embodiments, the Tim1 IgV domain comprises or consists of the amino acid sequence set forth in SEQ ID NO:41 and the Tim1 mucin domain comprises or consists of the amino acid sequence set forth in SEQ ID NO:39. In some embodiments, the Tim1 IgV domain and Tim1 mucin domain together comprise or consist of the amino acid sequence set forth in SEQ ID NO:37 or SEQ ID NO:43.

In some embodiments, the Tim binding domain comprises a Tim4 IgV domain and a Tim4 mucin domain. In some embodiments, the Tim4 IgV domain comprises or consists of the amino acid sequence set forth in SEQ ID NO:34 and the Tim4 mucin domain comprises or consists of the amino acid sequence set forth in SEQ ID NO: 35. In some embodiments, the Tim4 IgV domain and Tim4 mucin domain together comprise or consist of the amino acid sequence set forth in SEQ ID NO:2 or SEQ ID NO:42.

In some embodiments, the Tim binding domain comprises a Tim1 IgV domain and a Tim4 mucin domain. In some embodiments, the Tim1 IgV domain comprises or consists of the amino acid sequence set forth in SEQ ID NO:38 and the Tim4 mucin domain comprises or consists of the amino acid sequence set forth in SEQ ID NO: 35. In some embodiments, the Tim1 IgV domain comprises or consists of the amino acid sequence set forth in SEQ ID NO:38 with a R66G substitution and the Tim4 mucin domain comprises or consists of the amino acid sequence set forth in SEQ ID NO: 35. In some embodiments, the Tim1 IgV domain comprises or consists of the amino acid sequence set forth in SEQ ID NO:41 and the Tim4 mucin domain comprises or consists of the amino acid sequence set forth in SEQ ID NO:35. In some embodiments, the Tim1 IgV domain further comprises the Tim1 signal sequence of SEQ ID NO:40.

In some embodiments, the Tim binding domain comprises a Tim4 IgV domain and a Tim1 mucin domain. In some embodiments, the Tim4 IgV domain comprises or consists of the amino acid sequence set forth in SEQ ID NO:34 and the Tim1 mucin domain comprises or consists of the amino acid sequence set forth in SEQ ID NO: 39. In some embodiments, the Tim4 IgV domain further comprises the Tim4 signal sequence of SEQ ID NO:11.

In some embodiments, the extracellular domain optionally comprises an extracellular, non-signaling spacer or linker domain. Where included, such a spacer or linker domain may position the binding domain away from the host cell surface to further enable proper cell/cell contact, binding, and activation. When included in a chimeric receptor as described herein, an extracellular spacer domain is generally located between the extracellular binding domain and the transmembrane domain of the chimeric Tim receptor. The length of the extracellular spacer may be varied to optimize target molecule binding based on the selected target molecule, selected binding epitope, binding domain size and affinity (see, e.g., Guest et al., *J. Immunother.* 28:203-11, 2005; PCT Publication No. WO 2014/031687). In some embodiments, an extracellular spacer domain is an immunoglobulin hinge region (e.g., IgG1, IgG2, IgG3, IgG4, IgA, IgD). An immunoglobulin hinge region may be a wild type immunoglobulin hinge region or an altered wild type immunoglobulin hinge region. An altered IgG4 hinge region is described in PCT Publication No. WO 2014/031687, which hinge region is incorporated herein by reference in its entirety. In some embodiments, an extracellular spacer domain comprises a modified IgG4 hinge region having an amino acid sequence of ESKYGPPCPPCP (SEQ ID NO:3). Other examples of hinge regions that may be used in the chimeric Tim receptors described herein include the hinge region from the extracellular regions of type 1 membrane proteins, such as CD8a, CD4, CD28 and CD7, which may be wild-type or variants thereof. In some embodiments, an extracellular spacer domain comprises a CD28 hinge region having an amino acid sequence of SEQ ID NO: 32. In some embodiments, an extracellular spacer domain comprises all or a portion of an immunoglobulin Fc domain selected from: a CH1 domain, a CH2 domain, a CH3 domain, or combinations thereof (see, e.g., PCT Publication WO2014/031687, which spacers are incorporated herein by reference in their entirety). In some embodiments, an extracellular spacer domain may comprise a stalk region of a type II C-lectin (the extracellular domain located between the C-type lectin domain and the transmembrane domain). Type II C-lectins include CD23, CD69, CD72, CD94, NKG2A, and NKG2D.

In some embodiments, an extracellular domain comprises amino acid sequences derived from any mammalian species, including humans, primates, cows, horses, goats, sheep, dogs, cats, mice, rats, rabbits, guinea pigs, pigs, transgenic species thereof, or any combination thereof. In certain embodiments, an extracellular domain is murine, human, or chimeric.

Intracellular Signaling Domain

The intracellular signaling domain of a chimeric Tim receptor as described herein is an intracellular effector domain and is capable of transmitting functional signals to a cell in response to binding of the extracellular domain of the chimeric Tim receptor and phosphatidylserine. The signals transduced by the intracellular signaling domain promote effector function of the chimeric Tim receptor containing cell. Examples of effector function include cytotoxic activity, secretion of cytokines, proliferation, anti-apoptotic signaling, persistence, expansion, engulfment of a target cell or particle expressing phosphatidylserine on its surface, antigen capture, antigen processing, antigen presentation, or any combination thereof.

An intracellular signaling domain comprises a primary intracellular signaling domain. In some embodiments, an intracellular signaling domain comprises a primary intracellular signaling domain, a secondary intracellular signaling domain. In some embodiments, an intracellular signaling domain comprises a primary intracellular signaling domain, a secondary intracellular signaling domain, and a tertiary intracellular signaling domain. The primary, secondary, and/or tertiary intracellular signaling domains may independently be any portion of a signaling molecule that retains sufficient signaling activity. In some embodiments, a full-length signaling molecule or full-length intracellular component of a signaling molecule is used. In some embodiments, a truncated portion of a signaling molecule or intracellular component of a signaling molecule is used, provided that the truncated portion retains sufficient signal transduction activity. In some embodiments, a signaling domain is a variant of a whole or truncated portion of a signaling molecule, provided that the variant retains sufficient signal transduction activity (i.e., is a functional variant).

In some embodiments, the primary intracellular signaling domain comprises a Tim1 signaling domain, a Tim4 signaling domain, a TRAF2 signaling domain, a TRAF6 signaling domain, a CD28 signaling domain, a DAP12 signaling domain, a CD3ζ signaling domain, 4-1BB signaling domain, TLR2 signaling domain, or a TLR8 signaling domain.

In some embodiments, the secondary intracellular signaling domain comprises a Tim1 signaling domain, a Tim4 signaling domain, a TRAF2 signaling domain, a TRAF6 signaling domain, a CD28 signaling domain, a DAP12 signaling domain, a CD3ζ signaling domain, 4-1BB signaling domain, TLR2 signaling domain or a TLR8 signaling domain.

In some embodiments, the tertiary intracellular signaling domain comprises a Tim1 signaling domain, a Tim4 signaling domain, a TRAF2 signaling domain, a TRAF6 signaling domain, a CD28 signaling domain, a DAP12 signaling domain, a CD3, signaling domain, 4-1BB signaling domain, TLR2 signaling domain or a TLR8 signaling domain.

In some embodiments, the primary intracellular signaling domain comprises an immunoreceptor tyrosine-based activation motif (ITAM) containing signaling domain; the secondary intracellular signaling domain comprises a costimulatory signaling domain, Tim1 signaling domain, or Tim4 signaling domain; and the tertiary intracellular signaling domain comprises a TLR signaling domain. An ITAM containing signaling domain generally contains at least one (one, two, three, four, or more) ITAMs, which refer to a conserved motif of YXXL/I-X$_{6-8}$-YXXL/I. An ITAM containing signaling domain may initiate T cell activation signaling following antigen binding or ligand engagement. ITAM-signaling domains include, for example, intracellular signaling domains of CD3γ, CD3δ, CD3ε, CD3ζ, CD5, CD22, CD79a, CD278 (ICOS), DAP12, FcRγ, and CD66d. A costimulatory signaling domain, which, when activated in conjunction with a primary or classic (e.g., ITAM-driven) activation signal, promotes or enhances T cell response, such as T cell activation, cytokine production, proliferation, differentiation, survival, effector function, or combinations thereof. Costimulatory signaling domains for use in chimeric Tim receptors include, for example, CD27, CD28, CD40L, GITR, NKG2C, CARD1, CD2, CD7, CD27, CD30, CD40, CD54 (ICAM), CD83, CD134 (OX-40), CD137 (4-1BB), CD150 (SLAMF1), CD152 (CTLA4), CD223 (LAG3), CD226, CD270 (HVEM), CD273 (PD-L2), CD274 (PD-L1), CD278 (ICOS), DAP10, LAT, LFA-1, LIGHT, NKG2C, SLP76, TRIM, ZAP70, or any combination thereof. In some embodiments, the costimulatory signaling domain comprises a OX40, CD2, CD27, CD28, ICAM-1, LFA-1 (CD11a/CD18), ICOS (CD278), or 4-1BB (CD137) signaling domain. A TLR signaling domain may be a TLR1, TLR2, TLR3, TLR4, TLR5, TLR6, TLR7, TLR8, or TLR9 signaling domain. In some embodiments, the TLR signaling domain is a TLR2 signaling domain or TLR8 signaling domain.

As used herein, the designation of primary, secondary, and tertiary intracellular signaling domains includes but is not limited to arrangements of the primary intracellular signaling domain at the N-terminus, secondary intracellular signaling domain in the middle, and tertiary intracellular signaling domain at the C-terminus of the intracellular portion of the chimeric Tim receptor. Thus, designation of the primary intracellular signaling domain does not limit the use of the selected intracellular signaling domain at the N-terminus of the intracellular portion of the chimeric Tim receptor. Designation of the secondary intracellular signaling domain does not limit the use of the selected intracellular signaling domain in the middle (or at the C-terminus for those chimeric Tim receptors only having two intracellular signaling domains) of the intracellular portion of the chimeric Tim receptor. Designation of the tertiary intracellular signaling domain does not limit the use of the selected intracellular signaling domain at the C-terminus of the intracellular portion of the chimeric Tim receptor. Thus, different arrangements of the primary, secondary, and/or tertiary intracellular signaling domains within the intracellular portion of the chimeric Tim receptor are contemplated.

An exemplary Tim1 signaling domain comprises or consists of the amino acid sequence of SEQ ID NO:44. An exemplary Tim4 signaling domain comprises or consists of the amino acid sequence of SEQ ID NO:45, SEQ ID NO:124, or SEQ ID NO:125. An exemplary TRAF2 signaling domain comprises or consists of the amino acid sequence of SEQ ID NO:48. An exemplary TRAF6 signaling domain comprises or consists of the amino acid sequence of SEQ ID NO:46. An exemplary CD28 signaling domain comprises or consists of the amino acid sequence of SEQ ID NO: 4 or 26. An exemplary DAP12 signaling domain comprises or consists of the amino acid sequence of SEQ ID NO:9. An exemplary CD3ζ signaling domain comprises or consists of the amino acid sequence of SEQ ID NO:27 or 5. An exemplary 4-1BB signaling domain comprises or consists of the amino acid sequence of SEQ ID NO:100. An exemplary TLR2 signaling domain comprises or consists of the amino acid sequence of SEQ ID NO:122. An exemplary TLR8 signaling domain comprises or consists of the amino acid sequence of SEQ ID NO:47.

In some embodiments, the Tim1 signaling domain comprises the amino acid sequence set forth in SEQ ID NO:44. In some embodiments, the Tim4 signaling domain comprises the amino acid sequence set forth in SEQ ID NO:45, SEQ ID NO: 124, or SEQ ID NO:125. In some embodiments, the TRAF2 signaling domain comprises the amino acid sequence set forth in SEQ ID NO:48. In some embodiments, the TRAF6 signaling domain comprises the amino acid sequence set forth in SEQ ID NO: 46. In some embodiments, the CD28 signaling domain comprises the amino acid sequence set forth in SEQ ID NO:4. In some embodiments, the CD28 signaling domain comprises the amino acid sequence set forth in SEQ ID NO:26. In some embodiments, the DAP12 signaling domain comprises the amino acid sequence set forth in SEQ ID NO: 9. In some embodiments, the CD3ζ signaling domain comprises the amino acid sequence set forth in SEQ ID NO:27. In some embodiments, the CD3ζ signaling domain comprises the amino acid sequence set forth in SEQ ID NO:5. In some embodiments, the 4-1BB signaling domain comprises the amino acid sequence of SEQ ID NO: 100. In some embodiments, the TLR2 signaling domain comprises the amino acid sequence of SEQ ID NO:122. In some embodiments, the TLR8 signaling domain comprises the amino acid sequence set forth in SEQ ID NO:47.

In some embodiments, the primary and/or secondary signaling domain comprises or consists of an amino acid sequence having at least about 75%, 80%, 85%, 90%, 91%, 92%, 93%, 94%, 95%, 96%, 97%, 98%, 99%, 99.5%, or 100% identity to any one of SEQ ID NOS: 4, 5, 9, 26, 27, 44-48, 100, 122 124, and 125. In some embodiments, the primary and/or secondary signaling domains comprises an amino acid sequence having at least about 1, 2, 3, 4, 5, 6, 7, 8, 9, 10, 11, 12, 13, 14, 15, 16, 17, 18, 19, or 20 amino acid modifications (e.g., deletions, additions, substitutions) to an amino acid sequence of any one of SEQ ID NOS: 4, 5, 9, 26, 27, 44-48, 100, 122, 124, and 125. In some embodiments, the primary signaling domain and secondary signaling domain are the same or different.

In some embodiments, the primary, secondary, and/or tertiary intracellular signaling domain comprises or consists of an amino acid sequence having at least about 75%, 80%, 85%, 90%, 91%, 92%, 93%, 94%, 95%, 96%, 97%, 98%, 99%, 99.5%, or 100% identity to any one of SEQ ID NOS: 4, 5, 7, 9, 26, 27, 44-48, 122, and 124. In some embodiments, the primary, secondary, and/or tertiary intracellular signaling domains comprises an amino acid sequence having at least about 1, 2, 3, 4, 5, 6, 7, 8, 9, 10, 11, 12, 13, 14, 15, 16, 17, 18, 19, or 20 amino acid modifications (e.g., deletions, additions, substitutions) to an amino acid sequence of any one of SEQ ID NOS: 4, 5, 9, 26, 27, 44-48, 100, 122, 124, and 125. In some embodiments, the primary, secondary, and tertiary intracellular signaling domain are the same. In some embodiments, two or three of the primary, secondary, and tertiary intracellular signaling domains are different.

In some embodiments, an intracellular signaling domain comprises a Tim1 intracellular signaling domain. In some embodiments, an intracellular signaling domain comprises a Tim4 intracellular signaling domain. In some embodiments, an intracellular signaling domain comprises a CD3ζ intracellular signaling domain. In some embodiments, an intracellular signaling domain comprises a CD28 intracellular signaling domain. In some embodiments, an intracellular signaling domain comprises a 4-1BB intracellular signaling domain. In some embodiments, an intracellular signaling domain comprises a TRAF6 intracellular signaling domain. In some embodiments, an intracellular signaling domain comprises a TRAF2 intracellular signaling domain. In some embodiments, an intracellular signaling domain comprises a TLR2 intracellular signaling domain. In some embodiments, an intracellular signaling domain comprises a TLR8 intracellular signaling domain.

In some embodiments, an intracellular signaling domain comprises a Tim1 primary intracellular signaling domain and a CD3ζ secondary intracellular signaling domain. In some embodiments, an intracellular signaling domain comprises a Tim4 primary intracellular signaling domain and a CD3ζ secondary intracellular signaling domain. In some embodiments, an intracellular signaling domain comprises a TLR8 primary intracellular signaling domain and a CD3ζ secondary intracellular signaling domain. In some embodiments, an intracellular signaling domain comprises a CD28 primary intracellular signaling domain and a DAP12 secondary intracellular signaling domain. In some embodiments, an intracellular signaling domain comprises a CD28 primary intracellular signaling domain and a CD3ζ secondary intracellular signaling domain. In some embodiments, an intracellular signaling domain comprises a CD28 primary intracellular signaling domain, a TLR2 secondary intracellular signaling domain, and a CD3ζ tertiary intracellular signaling domain. In some embodiments, an intracellular signaling domain comprises a CD28 primary intracellular signaling domain, a CD3ζ secondary intracellular signaling domain, and a TLR2 tertiary intracellular signaling domain. In some embodiments, an intracellular signaling domain comprises a CD28 primary intracellular signaling domain, a TLR8 secondary intracellular signaling domain, and a CD3ζ tertiary intracellular signaling domain. In some embodiments, an intracellular signaling domain comprises a CD28 primary intracellular signaling domain, a CD3ζ secondary intracellular signaling domain, and a TLR8 tertiary intracellular signaling domain. In some embodiments, an intracellular signaling domain comprises a TLR2 primary intracellular signaling domain and a CD3ζ secondary intracellular signaling domain. In some embodiments, an intracellular signaling domain comprises a CD3ζ primary intracellular signaling domain and a TLR2 secondary intracellular signaling domain. In some embodiments, an intracellular signaling domain comprises a TLR8 primary intracellular signaling domain and a CD3ζ secondary intracellular signaling domain. In some embodiments, an intracellular signaling domain comprises a CD3ζ primary intracellular signaling domain and a TLR8 secondary intracellular signaling domain. In some embodiments, an intracellular signaling domain comprises a TRAF6 primary intracellular signaling domain and a CD3ζ secondary intracellular signaling domain. In some embodiments, an intracellular signaling domain comprises a CD3ζ primary intracellular signaling domain and a TRAF6 secondary intracellular signaling domain. In some embodiments, an intracellular signaling domain comprises a CD28 primary intracellular signaling domain and a CD3ζ secondary intracellular signaling domain. In some embodiments, an intracellular signaling domain comprises a CD28 primary intracellular signaling domain, a TLR2 secondary intracellular signaling domain, and a CD3ζ tertiary intracellular signaling domain. In some embodiments, an intracellular signaling domain comprises a CD28 primary intracellular signaling domain, a CD3ζ secondary intracellular signaling domain, and a TLR2 tertiary intracellular signaling domain. In some embodiments, an intracellular signaling domain comprises a CD28 primary intracellular signaling domain, a TLR8 secondary intracellular signaling domain, and a CD3ζ tertiary intracellular signaling domain. In some embodiments, an intracellular signaling domain comprises a CD28 primary intracellular signaling domain, a CD3ζ secondary intracellular signaling domain, and a TLR8 tertiary intracellular signaling domain. In some embodiments, an intercellular signaling domain comprises a CD3ζ primary intracellular signaling domain and a TLR2 secondary intracellular signaling domain. In some embodiments, an intercellular signaling domain comprises a TLR2 primary intracellular signaling domain and a CD3ζ secondary intracellular signaling domain. In some embodiments, an intercellular signaling domain comprises a CD3ζ primary intracellular signaling domain and a TLR8 secondary intracellular signaling domain. In some embodiments, an intercellular signaling domain comprises a TLR8 primary intracellular signaling domain and a CD3ζ secondary intracellular signaling domain. In some embodiments, an intercellular signaling domain comprises a CD3ζ primary intracellular signaling domain and a TRAF6 secondary intracellular signaling domain. In some embodiments, an intercellular signaling domain comprises a TRAF6 primary intracellular signaling domain and a CD3ζ secondary intracellular signaling domain. In some embodiments, an intracellular signaling domain comprises a Tim4 primary intracellular signaling domain, a TLR2 secondary intracellular signaling domain, and a CD3ζ tertiary intracellular signaling domain. In some embodiments, an intracellular signaling domain comprises a Tim4 primary intracellular signaling domain, a CD3ζ secondary intracellular signaling domain, and a TLR2 tertiary intracellular signaling domain. In some embodiments, an intracellular signaling domain comprises a Tim4 primary intracellular signaling domain, a TLR8 secondary intracellular signaling domain, and a CD3ζ tertiary intracellular signaling domain. In some embodiments, an intracellular signaling domain comprises a Tim4 primary intracellular signaling domain, a CD3ζ secondary intracellular signaling domain, and a TLR8 tertiary intracellular signaling domain.

In some embodiments, an intracellular signaling domain comprises a Tim1 primary intracellular signaling domain comprising the amino acid sequence of SEQ ID NO:44 and a CD3ζ secondary intracellular signaling domain comprising the amino acid sequence of SEQ ID NO:27 or 5. In some embodiments, an intracellular signaling domain comprises a Tim4 primary intracellular signaling domain comprising the amino acid sequence of SEQ ID NO:45, 124, or 125, and a CD3ζ secondary intracellular signaling domain comprising the amino acid sequence of SEQ ID NO:27 or 5. In some embodiments, an intracellular signaling domain comprises a TLR8 primary intracellular signaling domain comprising the amino acid sequence of SEQ ID NO: 47 and a CD3ζ secondary intracellular signaling domain comprising the amino acid sequence of SEQ ID NO:27 or 5. In some embodiments, an intracellular signaling domain comprises a CD28 primary intracellular signaling domain comprising the amino acid sequence of SEQ ID NO:4 or 26 and a DAP12 secondary intracellular signaling domain comprising the amino acid sequence of SEQ ID NO:9. In some embodiments, an intracellular signaling domain comprises a combination of primary, secondary, and optionally tertiary intracellular signaling domain as shown in Table 8.

Intracellular signaling domains may be derived from a mammalian species, including humans, primates, cows, horses, goats, sheep, dogs, cats, mice, rats, rabbits, guinea pigs, pigs, and transgenic species thereof.

Transmembrane Domain

The transmembrane domain of a chimeric Tim receptor connects and is positioned between the extracellular domain and the intracellular signaling domain. The transmembrane domain is a hydrophobic alpha helix that transverses the host cell membrane. The transmembrane domain may be directly fused to the binding domain or to the extracellular spacer domain if present. In certain embodiments, the transmembrane domain is derived from an integral membrane protein (e.g., receptor, cluster of differentiation (CD) molecule, enzyme, transporter, cell adhesion molecule, or the like). In one embodiment, the transmembrane domain is selected from the same molecule as the molecule from which the extracellular domain is derived. In another embodiment, the transmembrane domain is selected from the same molecule as the molecule from which the intracellular signaling domain is derived. For example, a chimeric Tim receptor may comprise a Tim4 binding domain and a Tim4 transmembrane domain. In another example, a chimeric Tim receptor may comprise a CD28 transmembrane domain and a CD28 costimulatory signaling domain. In certain embodiments, the transmembrane domain and the extracellular domain are derived from different molecules; the transmembrane domain and the intracellular signaling domain are derived from different molecules; or the transmembrane domain, extracellular domain, and intracellular signaling domain are all derived from different molecules. Examples of transmembrane domains that may be used in chimeric Tim receptors of the present disclosure include transmembrane domains from Tim1, Tim4, and CD28. An exemplary Tim1 transmembrane domain comprises or consists of an amino acid sequence of SEQ ID NO:8. An exemplary Tim4 transmembrane domain comprises or consists of an amino acid sequence of SEQ ID NO:6, SEQ ID NO:23 or SEQ ID NO:121. An exemplary CD28 transmembrane domain comprises or consists of an amino acid sequence of SEQ ID NO:7 or SEQ ID NO:120. In certain embodiments, the transmembrane domain comprises or consists of an amino acid sequence having at least about 75%, 80%, 85%, 90%, 91%, 92%, 93%, 94%, 95%, 96%, 97%, 98%, 99%, 99.5%, or 100% identity to any one of SEQ ID NOS: 6-8, 23, 120, and 121. In certain embodiments, the transmembrane domain comprises an amino acid sequence having at least about 1, 2, 3, 4, 5, 6, 7, 8, 9, or 10 amino acid modifications (e.g., deletion, additions, substitutions) to the amino acid sequence of any one of SEQ ID NOS: 6-8, 23, 120, and 121.

Transmembrane domains may be derived from any mammalian species, including humans, primates, cows, horses, goats, sheep, dogs, cats, mice, rats, rabbits, guinea pigs, pigs, and transgenic species thereof.

In certain embodiments, a chimeric Tim receptor is encoded by polynucleotide sequences derived from any mammalian species, including humans, primates, cows, horses, goats, sheep, dogs, cats, mice, rats, rabbits, guinea pigs, pigs, transgenic species thereof, or any combination thereof. In certain embodiments, a chimeric Tim receptor is murine, chimeric, human, or humanized.

It is understood that direct fusion of one domain to another domain of a chimeric Tim receptor described herein does not preclude the presence of intervening junction amino acids. Junction amino acids may be natural or non-natural (e.g., resulting from the construct design of a chimeric protein). For example, junction amino acids may result from restriction enzyme sites used for joining one domain to another domain or cloning polynucleotides encoding chimeric Tim receptors into vectors.

Exemplary Chimeric Tim Receptors

The component parts of a chimeric Tim receptor as disclosed herein can be selected and arranged in various combinations to provide a desired specificity and effector phenotype to a host cell.

Exemplary chimeric Tim receptors of the present disclosure are described in Table 2.

TABLE 2

| Construct No. | IgV Domain | Mucin Domain | Transmembrane Domain | Primary Signaling Domain | Secondary Signaling Domain |
|---|---|---|---|---|---|
| 1 | Tim1 | Tim1 | Tim1 | Tim1 | CD3ζ |
| 2 | Tim1 | Tim1 | Tim1 | Tim4 | CD3ζ |
| 3 | Tim1 | Tim1 | CD28 | CD28 | |
| 4 | Tim1 | Tim1 | Tim1 | TRAF6 | |
| 5 | Tim1 | Tim1 | CD28 | TRAF6 | |
| 6 | Tim1 | Tim1 | Tim1 | TRAF2 | |
| 7 | Tim1 | Tim1 | CD28 | TRAF2 | |
| 8 | Tim1 | Tim1 | Tim1 | TLR8 | CD3ζ |
| 9 | Tim1 | Tim1 | CD28 | CD28 | DAP12 |
| 10 | Tim1 | Tim1 | Tim1 | CD28 | DAP12 |

Further exemplary chimeric Tim receptors are described in Table 3.

TABLE 3

| Construct No. | IgV Domain | Mucin Domain | Transmembrane Domain | Primary Signaling Domain | Secondary Signaling Domain |
|---|---|---|---|---|---|
| 1' | SEQ ID NO: 38 | SEQ ID NO: 39 | SEQ ID NO: 8 | SEQ ID NO: 44 | SEQ ID NO: 5 |
| 2' | SEQ ID NO: 38 | SEQ ID NO: 39 | SEQ ID NO: 8 | SEQ ID NO: 45 | SEQ ID NO: 5 |
| 3' | SEQ ID NO: 38 | SEQ ID NO: 39 | SEQ ID NO: 7 | SEQ ID NO: 4 | |
| 4' | SEQ ID NO: 38 | SEQ ID NO: 39 | SEQ ID NO: 8 | SEQ ID NO: 46 | |
| 5' | SEQ ID NO: 38 | SEQ ID NO: 39 | SEQ ID NO: 7 | SEQ ID NO: 46 | |
| 6' | SEQ ID NO: 38 | SEQ ID NO: 39 | SEQ ID NO: 8 | SEQ ID NO: 48 | |
| 7' | SEQ ID NO: 38 | SEQ ID NO: 39 | SEQ ID NO: 7 | SEQ ID NO: 48 | |
| 8' | SEQ ID NO: 38 | SEQ ID NO: 39 | SEQ ID NO: 8 | SEQ ID NO: 47 | SEQ ID NO: 5 |
| 9' | SEQ ID NO: 38 | SEQ ID NO: 39 | SEQ ID NO: 7 | SEQ ID NO: 4 | SEQ ID NO: 9 |
| 10' | SEQ ID NO: 38 | SEQ ID NO: 39 | SEQ ID NO: 8 | SEQ ID NO: 4 | SEQ ID NO: 9 |

In some embodiments, a chimeric Tim receptor of the present disclosure comprises a construct of Table 2. In some embodiments, a chimeric Tim receptor of the present disclosure comprises a construct of Table 3.

In some embodiments, a chimeric Tim receptor of Construct 1 or Construct 1' comprises amino acids 21-456 of SEQ ID NO:49. In a specific embodiment, a chimeric Tim receptor of Construct 1 or Construct 1' comprises an amino acid sequence of SEQ ID NO:49.

In some embodiments, a chimeric Tim receptor of Construct 2 or Construct 2' comprises amino acids 21-471 of SEQ ID NO:50. In a specific embodiment, a chimeric Tim receptor of Construct 2 or Construct 2' comprises an amino acid sequence of SEQ ID NO:50.

In some embodiments, a chimeric Tim receptor of Construct 3 or Construct 3' comprises amino acids 21-363 of SEQ ID NO:51. In a specific embodiment, a chimeric Tim receptor of Construct 3 or Construct 3' comprises an amino acid sequence of SEQ ID NO:51.

In some embodiments, a chimeric Tim receptor of Construct 4 or Construct 4' comprises amino acids 21-590 of SEQ ID NO:52. In a specific embodiment, a chimeric Tim receptor of Construct 4 or Construct 4' comprises an amino acid sequence of SEQ ID NO:52.

In some embodiments, a chimeric Tim receptor of Construct 5 or Construct 5' comprises amino acids 21-596 of receptor of Construct 10 or Construct 10' comprises an amino acid sequence of SEQ ID NO:58.

Further exemplary chimeric Tim receptors of the present disclosure are described in Table 4.

TABLE 4

| Construct No. | IgV Domain | Mucin Domain | Transmembrane Domain | Primary Signaling Domain | Secondary Signaling Domain |
|---|---|---|---|---|---|
| 11 | Tim4 | Tim4 | Tim4 | Tim4 | CD3ζ |
| 12 | Tim4 | Tim4 | Tim4 | Tim1 | CD3ζ |
| 13 | Tim4 | Tim4 | CD28 | CD28 | |
| 14 | Tim4 | Tim4 | Tim4 | TRAF6 | |
| 15 | Tim4 | Tim4 | CD28 | TRAF6 | |
| 16 | Tim4 | Tim4 | Tim4 | TRAF2 | |
| 17 | Tim4 | Tim4 | CD28 | TRAF2 | |
| 18 | Tim4 | Tim4 | Tim1 | TLR8 | CD3ζ |

Further exemplary chimeric Tim receptors are described in Table 5.

TABLE 5

| Construct No. | IgV Domain | Mucin Domain | Transmembrane Domain | Primary Signaling Domain | Secondary Signaling Domain |
|---|---|---|---|---|---|
| 11' | SEQ ID NO: 34 | SEQ ID NO: 35 | SEQ ID NO: 6 | SEQ ID NO: 45 | SEQ ID NO: 5 |
| 12' | SEQ ID NO: 34 | SEQ ID NO: 35 | SEQ ID NO: 6 | SEQ ID NO: 44 | SEQ ID NO: 5 |
| 13' | SEQ ID NO: 34 | SEQ ID NO: 35 | SEQ ID NO: 7 | SEQ ID NO: 4 | |
| 14' | SEQ ID NO: 34 | SEQ ID NO: 35 | SEQ ID NO: 6 | SEQ ID NO: 46 | |
| 15' | SEQ ID NO: 34 | SEQ ID NO: 35 | SEQ ID NO: 7 | SEQ ID NO: 46 | |
| 16' | SEQ ID NO: 34 | SEQ ID NO: 35 | SEQ ID NO: 6 | SEQ ID NO: 48 | |
| 17' | SEQ ID NO: 34 | SEQ ID NO: 35 | SEQ ID NO: 7 | SEQ ID NO: 48 | |
| 18' | SEQ ID NO: 34 | SEQ ID NO: 35 | SEQ ID NO: 8 | SEQ ID NO: 47 | SEQ ID NO: 5 |

SEQ ID NO:53. In a specific embodiment, a chimeric Tim receptor of Construct 5 or Construct 5' comprises an amino acid sequence of SEQ ID NO:53.

In some embodiments, a chimeric Tim receptor of Construct 6 or Construct 6' comprises amino acids 21-619 of SEQ ID NO:54. In a specific embodiment, a chimeric Tim receptor of Construct 6 or Construct 6' comprises an amino acid sequence of SEQ ID NO:54.

In some embodiments, a chimeric Tim receptor of Construct 7 or Construct 7' comprises amino acids 21-625 of SEQ ID NO:55. In a specific embodiment, a chimeric Tim receptor of Construct 7 or Construct 7' comprises an amino acid sequence of SEQ ID NO:55.

In some embodiments, a chimeric Tim receptor of Construct 8 or Construct 8' comprises amino acids 21-621 of SEQ ID NO:56. In a specific embodiment, a chimeric Tim receptor of Construct 8 or Construct 8' comprises an amino acid sequence of SEQ ID NO:56.

In some embodiments, a chimeric Tim receptor of Construct 9 or Construct 9' comprises amino acids 21-415 of SEQ ID NO:57. In a specific embodiment, a chimeric Tim receptor of Construct 9 or Construct 9' comprises an amino acid sequence of SEQ ID NO:57.

In some embodiments, a chimeric Tim receptor of Construct 10 or Construct 10' comprises amino acids 21-409 of SEQ ID NO:58. In a specific embodiment, a chimeric Tim In some embodiments, a chimeric Tim receptor of the present disclosure comprises a construct of Table 4. In some embodiments, a chimeric Tim receptor of the present disclosure comprises a construct of Table 5

In some embodiments, a chimeric Tim receptor of Construct 11 or Construct 11' comprises amino acids 25-490 of SEQ ID NO:59. In a specific embodiment, a chimeric Tim receptor of Construct 11 or Construct 11' comprises an amino acid sequence of SEQ ID NO:59.

In some embodiments, a chimeric Tim receptor of Construct 12 or Construct 12' comprises amino acids 25-495 of SEQ ID NO:60. In a specific embodiment, a chimeric Tim receptor of Construct 12 or Construct 12' comprises an amino acid sequence of SEQ ID NO:60.

In some embodiments, a chimeric Tim receptor of Construct 13 or Construct 13' comprises amino acids 25-382 of SEQ ID NO:61. In a specific embodiment, a chimeric Tim receptor of Construct 13 or Construct 13' comprises an amino acid sequence of SEQ ID NO:61.

In some embodiments, a chimeric Tim receptor of Construct 14 or Construct 14' comprises amino acids 25-609 of SEQ ID NO:62. In a specific embodiment, a chimeric Tim receptor of Construct 14 or Construct 14' comprises an amino acid sequence of SEQ ID NO:62.

In some embodiments, a chimeric Tim receptor of Construct 15 or Construct 15' comprises amino acids 25-615 of SEQ ID NO:63. In a specific embodiment, a chimeric Tim receptor of Construct 15 or Construct 15' comprises an amino acid sequence of SEQ ID NO:63.

In some embodiments, a chimeric Tim receptor of Construct 16 or Construct 16' comprises amino acids 25-638 of SEQ ID NO:64. In a specific embodiment, a chimeric Tim receptor of Construct 16 or Construct 16' comprises an amino acid sequence of SEQ ID NO:64.

In some embodiments, a chimeric Tim receptor of Construct 17 or Construct 17' comprises amino acids 25-644 of SEQ ID NO:65. In a specific embodiment, a chimeric Tim receptor of Construct 17 or Construct 17' comprises an amino acid sequence of SEQ ID NO:65.

In some embodiments, a chimeric Tim receptor of Construct 18 or Construct 18' comprises amino acids 25-640 of SEQ ID NO:66. In a specific embodiment, a chimeric Tim receptor of Construct 18 or Construct 18' comprises an amino acid sequence of SEQ ID NO:66.

In some embodiments, a chimeric Tim receptor of the present disclosure is not a construct of Table 4. In some embodiments, a chimeric Tim receptor of the present disclosure is not a construct of Table 5. In some embodiments a chimeric Tim receptor of the present disclosure does not have a configuration of any one of Constructs 13, 14, 15, 16, and 17, or any combination thereof. In some embodiments, a chimeric Tim receptor of the present disclosure does not have an amino acid sequence of any one of SEQ ID NOS: 61, 62, 63, 64, and 65, or any combination thereof.

Further exemplary chimeric Tim receptors of the present disclosure are described in Table 6.

TABLE 6

| Construct No. | IgV Domain | Mucin Domain | Transmembrane Domain | Primary Signaling Domain | Secondary Signaling Domain |
|---|---|---|---|---|---|
| 19 | Tim4 | Tim1 | Tim1 | TLR8 | CD3ζ |
| 20 | Tim4 | Tim1 | Tim1 | CD28 | DAP12 |
| 21 | Tim4 | Tim1 | CD28 | CD28 | DAP12 |

Further exemplary chimeric Tim receptors are described in Table 7.

TABLE 7

| Construct No. | IgV Domain | Mucin Domain | Transmembrane Domain | Primary Signaling Domain | Secondary Signaling Domain |
|---|---|---|---|---|---|
| 19 | SEQ ID NO: 34 | SEQ ID NO: 39 | SEQ ID NO: 8 | SEQ ID NO: 47 | SEQ ID NO: 5 |
| 20 | SEQ ID NO: 34 | SEQ ID NO: 39 | SEQ ID NO: 8 | SEQ ID NO: 4 | SEQ ID NO: 9 |
| 21 | SEQ ID NO: 34 | SEQ ID NO: 39 | SEQ ID NO: 7 | SEQ ID NO: 4 | SEQ ID NO: 9 |

In some embodiments, a chimeric Tim receptor of the present disclosure comprises a construct of Table 6. In some embodiments, a chimeric Tim receptor of the present disclosure comprises a construct of Table 7.

In some embodiments, a chimeric Tim receptor of Construct 19 or Construct 19' comprises amino acids 25-628 of SEQ ID NO:67. In a specific embodiment, a chimeric Tim receptor of Construct 19 or Construct 19' comprises an amino acid sequence of SEQ ID NO:67.

In some embodiments, a chimeric Tim receptor of Construct 20 or Construct 20' comprises amino acids 25-416 of SEQ ID NO:68. In a specific embodiment, a chimeric Tim receptor of Construct 20 or Construct 20' comprises an amino acid sequence of SEQ ID NO:68.

In some embodiments, a chimeric Tim receptor of Construct 21 or Construct 21' comprises amino acids 25-422 of SEQ ID NO:69. In a specific embodiment, a chimeric Tim receptor of Construct 21 or Construct 21' comprises an amino acid sequence of SEQ ID NO:69.

Further exemplary chimeric Tim receptors are described in Table 8. In some embodiments, a chimeric Tim receptor of the present disclosure comprises a construct of Table 8. In some embodiments, a chimeric Tim receptor of the present disclosure does not include a chimeric Tim receptor having the amino acid sequence of SEQ ID NO:127, 138, 149, 157, or 158. In some embodiments, a chimeric Tim receptor of the present disclosure does not include a chimeric Tim receptor having the combination of components as described for constructs SEQ ID NO:127, 138, 149, 157, or 158.

In some embodiments, a chimeric Tim 4 receptor comprises the amino acid sequence of SEQ ID NO:127 or the amino acid sequence of SEQ ID NO:127 absent the signal sequence (amino acids 1-24). In some embodiments, a chimeric Tim 4 receptor comprises the amino acid sequence of SEQ ID NO:128 or the amino acid sequence of SEQ ID NO:128 absent the signal sequence (amino acids 1-24). In some embodiments, a chimeric Tim 4 receptor comprises the amino acid sequence of SEQ ID NO: 129 or the amino acid sequence of SEQ ID NO:129 absent the signal sequence (amino acids 1-24). In some embodiments, a chimeric Tim 4 receptor comprises the amino acid sequence of SEQ ID NO:130 or the amino acid sequence of SEQ ID NO: 130 absent the signal sequence (amino acids 1-24). In some embodiments, a chimeric Tim 4 receptor comprises the amino acid sequence of SEQ ID NO:131 or the amino acid sequence of SEQ ID NO:131 absent the signal sequence (amino acids 1-24). In some embodiments, a chimeric Tim 4 receptor comprises the amino acid sequence of SEQ ID NO:132 or the amino acid sequence of SEQ ID NO:132 absent the signal sequence (amino acids 1-24). In some embodiments, a chimeric Tim 4 receptor comprises the amino acid sequence of SEQ ID NO:133 or the amino acid sequence of SEQ ID NO:133 absent the signal sequence (amino acids 1-24). In some embodiments, a chimeric Tim 4 receptor comprises the amino acid sequence of SEQ ID NO: 134 or the amino acid sequence of SEQ ID NO:134 absent the signal sequence (amino acids 1-24). In some embodiments, a chimeric Tim 4 receptor comprises the amino acid sequence of SEQ ID NO:135 or the amino acid sequence of SEQ ID NO:135 absent the signal sequence (amino acids 1-24). In some embodiments, a chimeric Tim 4 receptor comprises the amino acid sequence of SEQ ID NO: 136 or the amino acid sequence of SEQ ID NO:136 absent the signal sequence (amino acids 1-24). In some embodiments, a chimeric Tim 4 receptor comprises the amino acid sequence of SEQ ID NO: 137 or the amino acid sequence of SEQ ID NO:137 absent the signal sequence (amino acids 1-24). In some embodiments, a chimeric Tim 4 receptor comprises the amino acid sequence of SEQ ID NO:138 or the amino acid sequence of SEQ ID NO:138 absent the signal sequence (amino acids 1-24). In some embodiments, a chimeric Tim 4 receptor comprises the amino acid sequence of SEQ ID NO:139 or the amino acid sequence of SEQ ID NO:139 absent the signal sequence (amino acids 1-24). In some embodiments, a chimeric Tim 4 receptor comprises the amino acid sequence of SEQ ID NO: 140 or the amino acid sequence of SEQ ID NO:140 absent the signal sequence (amino acids 1-24). In some embodiments, a chimeric Tim 4 receptor comprises the amino acid sequence of SEQ ID NO:141 or the amino acid sequence of SEQ ID NO:141 absent the signal sequence (amino acids 1-24). In some embodiments, a chimeric Tim 4 receptor comprises the amino acid sequence of SEQ ID NO: 142 or the amino acid sequence of SEQ ID NO:142 absent the signal sequence (amino acids 1-24). In some embodiments, a chimeric Tim 4 receptor comprises the amino acid sequence of SEQ ID NO:143 or the amino acid sequence of SEQ ID NO:143 absent the signal sequence (amino acids 1-24). In some embodiments, a chimeric Tim 4 receptor comprises the amino acid sequence of SEQ ID NO:144 or the amino acid sequence of SEQ ID NO:144 absent the signal sequence (amino acids 1-24). In some embodiments, a chimeric Tim 4 receptor comprises the amino acid sequence of SEQ ID NO: 145 or the amino acid sequence of SEQ ID NO:145 absent the signal sequence (amino acids 1-24). In some embodiments, a chimeric Tim 4 receptor comprises the amino acid sequence of SEQ ID NO:146 or the amino acid sequence of SEQ ID NO:146 absent the signal sequence (amino acids 1-24). In some embodiments, a chimeric Tim 4 receptor comprises the amino acid sequence of SEQ ID NO:147 or the amino acid sequence of SEQ ID NO:147 absent the signal sequence (amino acids 1-24). In some embodiments, a chimeric Tim 4 receptor comprises the amino acid sequence of SEQ ID NO:148 or the amino acid sequence of SEQ ID NO:148 absent the signal sequence (amino acids 1-24). In some embodiments, a chimeric Tim 4 receptor comprises the amino acid sequence of SEQ ID NO: 149 or the amino acid sequence of SEQ ID NO:149 absent the signal sequence (amino acids 1-24). In some embodiments, a chimeric Tim 4 receptor comprises the amino acid sequence of SEQ ID NO:150 or the amino acid sequence of SEQ ID NO:150 absent the signal sequence (amino acids 1-24). In some embodiments, a chimeric Tim 4 receptor comprises the amino acid sequence of SEQ ID NO:151 or the amino acid sequence of SEQ ID NO:151 absent the signal sequence (amino acids 1-24). In some embodiments, a chimeric Tim 4 receptor comprises the amino acid sequence of SEQ ID NO: 152 or the amino acid sequence of SEQ ID NO:152 absent the signal sequence (amino acids 1-24). In some embodiments, a chimeric Tim 4 receptor comprises the amino acid sequence of SEQ ID NO:153 or the amino acid sequence of SEQ ID NO:153 absent the signal sequence (amino acids 1-24). In some embodiments, a chimeric Tim 4 receptor comprises the amino acid sequence of SEQ ID NO: 154 or the amino acid sequence of SEQ ID NO:154 absent the signal sequence (amino acids 1-24). In some embodiments, a chimeric Tim 4 receptor comprises the amino acid sequence of SEQ ID NO: 155 or the amino acid sequence of SEQ ID NO:155 absent the signal sequence (amino acids 1-24).

TABLE 8

| Construct Number | Construct Description | Signal Peptide | Extracellular Domain | Transmembrane Domain | Intracellular Domain #1 | Intracellular Domain #2 | Intracellular Domain #3 |
|---|---|---|---|---|---|---|---|
| pCTX1161 [SEQ ID NO: 127] | hTIM4-TIM4-CD28tm-CD28icd-CD3zICD | hTIM4 [SEQ ID NO: 118] | TIM4 [SEQ ID NO: 119] | CD28 [SEQ ID NO: 120] | CD28 [SEQ ID NO: 4] | CD3z [SEQ ID NO: 27] | |
| pCTX1162 [SEQ ID NO: 128] | hTIM4-TIM4-CD28tm-CD28icd-TLR2ICD-CD3zICD | hTIM4 [SEQ ID NO: 118] | TIM4 [SEQ ID NO: 119] | CD28 [SEQ ID NO: 120] | CD28 [SEQ ID NO: 4] | TLR2 [SEQ ID NO: 122] | CD3z [SEQ ID NO: 27] |
| pCTX1163 [SEQ ID NO: 129] | hTIM4-TIM4-CD28tm-CD28icd-CD3zICD-TLR2ICD | hTIM4 [SEQ ID NO: 118] | TIM4 [SEQ ID NO: 119] | CD28 [SEQ ID NO: 120] | CD28 [SEQ ID NO: 4] | CD3z [SEQ ID NO: 27] | TLR2 [SEQ ID NO: 122] |
| pCTX1164 [SEQ ID NO: 130] | hTIM4-TIM4-CD28tm-CD28icd-TLR8ICD-CD3zICD | hTIM4 [SEQ ID NO: 118] | TIM4 [SEQ ID NO: 119] | CD28 [SEQ ID NO: 120] | CD28 [SEQ ID NO: 4] | TLR8 [SEQ ID NO: 47] | CD3z [SEQ ID NO: 27] |
| pCTX1165 [SEQ ID NO: 131] | hTIM4-TIM4-CD28tm-CD28icd-CD3zICD-TLR8ICD | hTIM4 [SEQ ID NO: 118] | TIM4 [SEQ ID NO: 119] | CD28 [SEQ ID NO: 120] | CD28 [SEQ ID NO: 4] | CD3z [SEQ ID NO: 27] | TLR8 [SEQ ID NO: 47] |
| pCTX1166 [SEQ ID NO: 132] | hTIM4-TIM4-CD28tm-TLR2ICD-CD3zICD | hTIM4 [SEQ ID NO: 118] | TIM4 [SEQ ID NO: 119] | CD28 [SEQ ID NO: 120] | TLR2 [SEQ ID NO: 122] | CD3z [SEQ ID NO: 27] | |
| pCTX1167 [SEQ ID NO: 133] | hTIM4-TIM4-CD28tm-CD3zICD-TLR2ICD | hTIM4 [SEQ ID NO: 118] | TIM4 [SEQ ID NO: 119] | CD28 [SEQ ID NO: 120] | CD3z [SEQ ID NO: 27] | TLR2 [SEQ ID NO: 122] | |
| pCTX1168 [SEQ ID NO: 134] | hTIM4-TIM4-CD28tm-TLR8ICD-CD3zICD | hTIM4 [SEQ ID NO: 118] | TIM4 [SEQ ID NO: 119] | CD28 [SEQ ID NO: 120] | TLR8 [SEQ ID NO: 47] | CD3z [SEQ ID NO: 27] | |
| pCTX1169 [SEQ ID NO: 135] | hTIM4-TIM4-CD28tm-CD3zICD-TLR8ICD | hTIM4 [SEQ ID NO: 118] | TIM4 [SEQ ID NO: 119] | CD28 [SEQ ID NO: 120] | CD3z [SEQ ID NO: 27] | TLR8 [SEQ ID NO: 47] | |
| pCTX1170 [SEQ ID NO: 136] | hTIM4-TIM4-CD28tm-TRAF6ICD-CD3zICD | hTIM4 [SEQ ID NO: 118] | TIM4 [SEQ ID NO: 119] | CD28 [SEQ ID NO: 120] | TRAF6 [SEQ ID NO: 46] | CD3z [SEQ ID NO: 27] | |
| pCTX1171 [SEQ ID NO: 137] | hTIM4-TIM4-CD28tm-CD3zICD-TRAF6ICD | hTIM4 [SEQ ID NO: 118] | TIM4 [SEQ ID NO: 119] | CD28 [SEQ ID NO: 120] | CD3z [SEQ ID NO: 27] | TRAF6 [SEQ ID NO: 46] | |
| pCTX1172 [SEQ ID NO: 138] | hTIM4-TIM4-TIM4tm-CD28icd-CD3zICD | hTIM4 [SEQ ID NO: 118] | TIM4 [SEQ ID NO: 119] | TIM4 [SEQ ID NO: 121] | CD28 [SEQ ID NO: 4] | CD3z [SEQ ID NO: 27] | |

TABLE 8-continued

| Construct Number | Construct Description | Signal Peptide | Extracellular Domain | Transmembrane Domain | Intracellular Domain #1 | Intracellular Domain #2 | Intracellular Domain #3 |
|---|---|---|---|---|---|---|---|
| pCTX1173 [SEQ ID NO: 139] | hTIM4-TIM4-TIM4tm-CD28icd-TLR2ICD-CD3zICD | hTIM4 [SEQ ID NO: 118] | TIM4 [SEQ ID NO: 119] | TIM4 [SEQ ID NO: 121] | CD28 [SEQ ID NO: 4] | TLR2 [SEQ ID NO: 122] | CD3z [SEQ ID NO: 27] |
| pCTX1174 [SEQ ID NO: 140] | hTIM4-TIM4-TIM4tm-CD28icd-CD3zICD-TLR2ICD | hTIM4 [SEQ ID NO: 118] | TIM4 [SEQ ID NO: 119] | TIM4 [SEQ ID NO: 121] | CD28 [SEQ ID NO: 4] | CD3z [SEQ ID NO: 27] | TLR2 [SEQ ID NO: 122] |
| pCTX1175 [SEQ ID NO: 141] | hTIM4-TIM4-TIM4tm-CD28icd-TLR8ICD-CD3zICD | hTIM4 [SEQ ID NO: 118] | TIM4 [SEQ ID NO: 119] | TIM4 [SEQ ID NO: 121] | CD28 [SEQ ID NO: 4] | TLR8 [SEQ ID NO: 47] | CD3z [SEQ ID NO: 27] |
| pCTX1176 [SEQ ID NO: 142] | hTIM4-TIM4-TIM4tm-CD28icd-CD3zICD-TLR8ICD | hTIM4 [SEQ ID NO: 118] | TIM4 [SEQ ID NO: 119] | TIM4 [SEQ ID NO: 121] | CD28 [SEQ ID NO: 4] | CD3z [SEQ ID NO: 27] | TLR8 [SEQ ID NO: 47] |
| pCTX1177 [SEQ ID NO: 143] | hTIM4-TIM4-TIM4tm-TLR2ICD-CD3zICD | hTIM4 [SEQ ID NO: 118] | TIM4 [SEQ ID NO: 119] | TIM4 [SEQ ID NO: 121] | TLR2 [SEQ ID NO: 122] | CD3z [SEQ ID NO: 27] | |
| pCTX1178 [SEQ ID NO: 144] | hTIM4-TIM4-TIM4tm-CD3zICD-TLR2ICD | hTIM4 [SEQ ID NO: 118] | TIM4 [SEQ ID NO: 119] | TIM4 [SEQ ID NO: 121] | CD3z [SEQ ID NO: 27] | TLR2 [SEQ ID NO: 122] | |
| pCTX1179 [SEQ ID NO: 145] | hTIM4-TIM4-TIM4tm-TLR8ICD-CD3zICD | hTIM4 [SEQ ID NO: 118] | TIM4 [SEQ ID NO: 119] | TIM4 [SEQ ID NO: 121] | TLR8 [SEQ ID NO: 47] | CD3z [SEQ ID NO: 27] | |
| pCTX1180 [SEQ ID NO: 146] | hTIM4-TIM4-TIM4tm-CD3zICD-TLR8ICD | hTIM4 [SEQ ID NO: 118] | TIM4 [SEQ ID NO: 119] | TIM4 [SEQ ID NO: 121] | CD3z [SEQ ID NO: 27] | TLR8 [SEQ ID NO: 47] | |
| pCTX1181 [SEQ ID NO: 147] | hTIM4-TIM4-TIM4tm-TRAF6ICD-CD3zICD | hTIM4 [SEQ ID NO: 118] | TIM4 [SEQ ID NO: 119] | TIM4 [SEQ ID NO: 121] | TRAF6 [SEQ ID NO: 46] | CD3z [SEQ ID NO: 27] | |
| pCTX1182 [SEQ ID NO: 148] | hTIM4-TIM4-TIM4tm-CD3zICD-TRAF6ICD | hTIM4 [SEQ ID NO: 118] | TIM4 [SEQ ID NO: 119] | TIM4 [SEQ ID NO: 121] | CD3z [SEQ ID NO: 27] | TRAF6 [SEQ ID NO: 46] | |
| pCTX1183 [SEQ ID NO: 149] | hTIM4-TIM4-TIM4tm-TIM4ICD | hTIM4 [SEQ ID NO: 118] | TIM4 [SEQ ID NO: 119] | TIM4 [SEQ ID NO: 121] | TIM4 [SEQ ID NO: 125] | | |
| pCTX1184 [SEQ ID NO: 150] | hTIM4-TIM4-TIM4tm-TIM4ICD-TLR2-CD3z | hTIM4 [SEQ ID NO: 118] | TIM4 [SEQ ID NO: 119] | TIM4 [SEQ ID NO: 121] | TIM4 [SEQ ID NO: 124] | TLR2 [SEQ ID NO: 87] | CD3z [SEQ ID NO: 27] |
| pCTX1185 [SEQ ID NO: 151] | hTIM4-TIM4-TIM4tm-TIM4ICD-CD3z-TLR2 | hTIM4 [SEQ ID NO: 118] | TIM4 [SEQ ID NO: 119] | TIM4 [SEQ ID NO: 121] | TIM4 [SEQ ID NO: 124] | CD3z [SEQ ID NO: 27] | TLR2 [SEQ ID NO: 122] |
| pCTX1186 [SEQ ID NO: 152] | hTIM4-TIM4-TIM4tm-TIM4ICD-TLR8-CD3z | hTIM4 [SEQ ID NO: 118] | TIM4 [SEQ ID NO: 119] | TIM4 [SEQ ID NO: 121] | TIM4 [SEQ ID NO: 124] | TLR8 [SEQ ID NO: 47] | CD3z [SEQ ID NO: 27] |
| pCTX1187 [SEQ ID NO: 153] | hTIM4-TIM4-TIM4tm-TIM4ICD-CD3z-TLR8 | hTIM4 [SEQ ID NO: 118] | TIM4 [SEQ ID NO: 119] | TIM4 [SEQ ID NO: 121] | TIM4 [SEQ ID NO: 124] | CD3z [SEQ ID NO: 27] | TLR8 [SEQ ID NO: 47] |
| pCTX1189 [SEQ ID NO: 157] | hTIM4-TIM4-TIM4tm-TLR2ICD | hTIM4 [SEQ ID NO: 118] | TIM4 [SEQ ID NO: 119] | TIM4 [SEQ ID NO: 121] | TLR2 [SEQ ID NO: 122] | | |
| pCTX1190 [SEQ ID NO: 158] | hTIM4-TIM4-TIM4tm-TLR8ICD | hTIM4 [SEQ ID NO: 118] | TIM4 [SEQ ID NO: 119] | TIM4 [SEQ ID NO: 121] | TLR8 [SEQ ID NO: 47] | | |

Polynucleotides, Vectors, and Host Cells

The present disclosure provides nucleic acid molecules that encode any one or more of the chimeric Tim receptors described herein. A nucleic acid may refer to a single- or double-stranded DNA, cDNA, or RNA, and may include a positive and a negative strand of the nucleic acid which complement one another, including antisense DNA, cDNA, and RNA. A nucleic acid may be naturally occurring or synthetic forms of DNA or RNA. The nucleic acid sequences encoding a desired chimeric Tim receptor can be obtained or produced using recombinant methods known in the art using standard techniques, such as by screening libraries from cells expressing the desired sequence or a portion thereof, by deriving the sequence from a vector known to include the same, or by isolating the sequence or a portion thereof directly from cells or tissues containing the same as described in, for example, Sambrook et al. (1989 and 2001 editions; *Molecular Cloning: A Laboratory Manual*, Cold Spring Harbor Laboratory Press, NY) and Ausubel et al. (Current Protocols in Molecular Biology, 2003). Alternatively, the sequence of interest can be produced synthetically, rather than being cloned.

Polynucleotides encoding the chimeric Tim receptor compositions provided herein may be derived from any animal, such as humans, primates, cows, horses, sheep, dogs, cats, mice, rats, rabbits, guinea pigs, pigs, or a combination thereof. In certain embodiments, a polynucleotide encoding the chimeric Tim receptor is from the same animal species as the host cell into which the polynucleotide is inserted.

The polynucleotides encoding chimeric Tim receptors of the present disclosure may be operatively linked to expression control sequences. Expression control sequences may include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequences); sequences that enhance protein stability; and possibly sequences that enhance protein secretion.

In certain embodiments, a polynucleotide encoding a chimeric Tim receptor comprises a sequence encoding a signal peptide (also referred to as leader peptide or signal sequence) at the 5'-end for targeting of the precursor protein to the secretory pathway. The signal peptide is optionally cleaved from the N-terminus of the extracellular domain during cellular processing and localization of the chimeric Tim receptor to the host cell membrane. A polypeptide from which a signal peptide sequence has been cleaved or removed may also be called a mature polypeptide. Examples of signal peptides that may be used in the chimeric Tim receptors of the present disclosure include signal peptides derived from endogenous secreted proteins, including, e.g., GM-CSF (amino acid sequence of SEQ ID NO:10), Tim1 (amino acid sequence of SEQ ID NO:40), or Tim4 (amino acid sequence of SEQ ID NO:11, 25, or 118). In certain embodiments, a polynucleotide sequence encodes a mature chimeric Tim receptor polypeptide, or a polypeptide sequence comprises a mature chimeric Tim receptor polypeptide. It is understood by persons of skill in the art that for sequences disclosed herein that include a signal peptide sequence, the signal peptide sequence may be replaced with another signal peptide that is capable of trafficking the encoded protein to the extracellular membrane.

In certain embodiments, a chimeric Tim receptor encoding polynucleotide of the present disclosure is codon optimized for efficient expression in a target host cell comprising the polynucleotide (see, e.g., Scholten et al., *Clin. Immunol.* 119:135-145 (2006)). As used herein, a "codon optimized" polynucleotide comprises a heterologous polynucleotide having codons modified with silent mutations corresponding to the abundances of tRNA in a host cell of interest.

A single polynucleotide molecule may encode one, two, or more chimeric Tim receptors according to any of the embodiments disclosed herein. A polynucleotide encoding more than one transgene may comprise a sequence (e.g., IRES, viral 2A peptide) disposed between each gene for multicistronic expression.

Polynucleotides encoding at least two transgenes (e.g., a chimeric Tim receptor and CAR) provided in the present disclosure may be used to compose tandem expression cassettes. A tandem expression cassette refers to a component of a vector nucleic acid comprising at least two transgenes under the control of, or operatively linked to, the same set of regulatory sequences for tandem or co-expression of the at least two transgenes. Regulatory sequences that may be used in tandem expression cassettes of the present disclosure include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequences); sequences that enhance protein stability; sequences that enhance protein secretion, or any combination thereof.

In one aspect, the present disclosure provides a tandem expression cassette comprising a polynucleotide encoding a chimeric Tim receptor of the present disclosure and a polynucleotide encoding a cellular immunotherapy agent (e.g., a CAR, TCR, etc.).

In certain embodiments, a tandem expression cassette can be constructed to optimize spatial and temporal control. For example, a tandem expression cassette can include promoter elements to optimize spatial and temporal control. In some embodiments, a tandem expression cassette includes tissue specific promoters or enhancers that enable specific induction of a tandem expression cassette to an organ, a cell type (e.g., immune cell), or a pathologic microenvironment, such as a tumor or infected tissue. An "enhancer" is an additional promoter element that can function either cooperatively or independently to activate transcription. In certain embodiments, a tandem expression cassette includes a constitutive promoter. An exemplary constitutive promoter for use in tandem expression cassettes of the present disclosure is an EF-1α promoter. In certain embodiments, a tandem expression cassette includes an inducible promoter. In certain embodiments, a tandem expression cassette includes a tissue specific promoter.

The at least two transgenes contained within the tandem expression cassettes may be in any order. For example, a tandem expression cassette comprising a polynucleotide encoding a chimeric Tim receptor and a polynucleotide encoding a CAR may be arranged from 5' to 3': chimeric Tim receptor-CAR, or CAR-chimeric Tim receptor.

In certain embodiments, receptors that comprise two or more polypeptide chains that associate to form a multimer or complex may be encoded by two or more polynucleotide molecules within a tandem expression construct. Exemplary multimeric receptors contemplated for expression in tandem expression constructs of the present disclosure include multichain CARs, TCRs, TCR-CARs, and TRuC™ constructs. Accordingly, exemplary tandem expression cassette embodiments encoding a chimeric Tim receptor and a TCR may comprise a polynucleotide encoding a chimeric Tim receptor, a polynucleotide encoding a TCRα chain polypeptide, and a polynucleotide encoding a TCRβ chain polypeptide.

In certain embodiments, tandem expression cassettes of the present disclosure may comprise an internal ribosome entry site (IRES) or peptide cleavage site such as a furin cleavage site or viral 2A peptide, disposed between each polynucleotide contained within the tandem expression cassette to allow for co-expression of multiple proteins from a single mRNA. For example, an IRES, furin cleavage site, or viral 2A peptide may be disposed between a polynucleotide encoding a chimeric Tim receptor and a polynucleotide encoding a CAR within a tandem expression cassette. In another example, an IRES, furin cleavage site, or viral 2A peptide may be disposed between each of a polynucleotide encoding a chimeric Tim receptor, a polynucleotide encoding a TCRα chain polypeptide, and a polynucleotide encoding a TCRβ chain polypeptide. In certain embodiments, a viral 2A peptide is a porcine teschovirus-1 (P2A), Thosea asigna virus (T2A), equine rhinitis A virus (E2A), foot-and-mouth disease virus (F2A), or variant thereof. An exemplary T2A peptide comprises an amino acid sequence of any one of SEQ ID NOs:12, 28, 29, or 30. An exemplary P2A peptide comprises an amino acid sequence of SEQ ID NO: 13 or 31. An exemplary E2A peptide sequence comprises an amino acid sequence of SEQ ID NO: 14. An exemplary F2A peptide sequence comprises an amino acid sequence of SEQ ID NO:15.

Certain embodiments of tandem expression cassettes of the present disclosure comprise a polynucleotide encoding a CAR/or TCR specific for a target antigen (e.g., tumor antigen) and a polynucleotide encoding a chimeric Tim receptor of the present disclosure. Upon binding a target cell expressing the target antigen by the CAR/or TCR, a cell modified to express such a tandem expression cassette induces apoptosis of the target cell. Apoptosis induces exposure of pro-engulfment markers on the target cell, such as phosphatidylserine, which may then target the damaged or apoptotic cells for engulfment by the chimeric Tim receptor.

A polynucleotide encoding a desired chimeric Tim receptor can be inserted into an appropriate vector, e.g., a viral vector, non-viral plasmid vector, and non-viral vectors, such as lipid-based DNA vectors, modified mRNA (modRNA), self-amplifying mRNA, CELiD, and transposon-mediated gene transfer (PiggyBac, Sleeping Beauty), for introduction into a host cell of interest (e.g., an immune cell). Polynucleotides encoding a chimeric Tim receptor of the present disclosure can be cloned into any suitable vector, such as an expression vector, a replication vector, a probe generation vector, or a sequencing vector. In certain embodiments, a polynucleotide encoding the extracellular domain, a polynucleotide encoding the transmembrane domain, and a polynucleotide encoding the intracellular signaling domain are joined together into a single polynucleotide and then inserted into a vector. In other embodiments, a polynucleotide encoding the extracellular domain, a polynucleotide encoding the transmembrane domain, and a polynucleotide encoding the intracellular signaling domain may be inserted separately into a vector such that the expressed amino acid sequence produces a functional chimeric Tim receptor. A vector that encodes a chimeric Tim receptor is referred to herein as a "chimeric Tim receptor vector."

In certain embodiments, a vector comprises a polynucleotide encoding one chimeric Tim receptor. In certain embodiments, a vector comprises one polynucleotide encoding two or more chimeric Tim receptors. In certain embodiments, a single polynucleotide encoding two or more chimeric Tim receptors is cloned into a cloning site and expressed from a single promoter, with each chimeric Tim receptor sequence separated from each other by an internal ribosomal entry site (IRES), furin cleavage site, or viral 2A peptide to allow for co-expression of multiple genes from a single open reading frame (e.g., a multicistronic vector). In certain embodiments, a viral 2A peptide is a porcine teschovirus-1 (P2A), Thosea asigna virus (T2A), equine rhinitis A virus (E2A), foot-and-mouth disease virus (F2A), or variant thereof. An exemplary T2A peptide comprises an amino acid sequence of SEQ ID NO: 12, 28, 29, or 30. An exemplary P2A peptide comprises an amino acid sequence of SEQ ID NO:13 or 31. An exemplary E2A peptide sequence comprises an amino acid sequence of SEQ ID NO: 14. An exemplary F2A peptide sequence comprises an amino acid sequence of SEQ ID NO:15.

In certain embodiments, a vector comprises two or more polynucleotides, each polynucleotide encoding a chimeric Tim receptor. The two or more polynucleotides encoding chimeric Tim receptors may be cloned sequentially into a vector at different cloning sites, with each chimeric Tim receptor expressed under the regulation of different promoters. In certain embodiments, vectors that allow long-term integration of a transgene and propagation to daughter cells are utilized. Examples include viral vectors such as, adenovirus, adeno-associated virus, vaccinia virus, herpes viruses, cytomegalovirus, pox virus, or retroviral vectors, such as lentiviral vectors. Vectors derived from lentivirus can be used to achieve long-term gene transfer and have added advantages over vectors including the ability to transduce non-proliferating cells, such as hepatocytes, and low immunogenicity.

In certain embodiments, a vector comprises a polynucleotide encoding a chimeric Tim receptor and a polynucleotide encoding a cellular immunotherapy agent (e.g., chimeric antigen receptor, recombinant TCR, etc.). In certain embodiments, a single polynucleotide encoding the chimeric Tim receptor and cellular immunotherapy agent (e.g., CAR) is cloned into a cloning site and expressed from a single promoter, with the chimeric Tim receptor sequence and cellular immunotherapy agent (e.g., CAR) sequence separated from each other by an internal ribosomal entry site (IRES), furin cleavage site, or viral 2A peptide to allow for co-expression of multiple genes from a single open reading frame (e.g., a multicistronic vector). In certain embodiments, a viral 2A peptide is a porcine teschovirus-1 (P2A), Thosea asigna virus (T2A), equine rhinitis A virus (E2A), foot-and-mouth disease virus (F2A), or variant thereof. An exemplary T2A peptide comprises an amino acid sequence of SEQ ID NO:12, 28, 29, or 30. An exemplary P2A peptide comprises an amino acid sequence of SEQ ID NO:13 or 31. An exemplary E2A peptide sequence comprises an amino acid sequence of SEQ ID NO: 14. An exemplary F2A peptide sequence comprises an amino acid sequence of SEQ ID NO:15.

In certain embodiments, a polynucleotide encoding the chimeric Tim receptor and a polynucleotide encoding the cellular immunotherapy agent (e.g., CAR) binding protein are joined together into a single polynucleotide and then inserted into a vector. In other embodiments, a polynucleotide encoding the CER, and a polynucleotide encoding the CAR or TCR binding protein may be inserted separately into a vector in the same or different cloning sites, such that the expressed amino acid sequence produces a functional CER and CAR/or TCR. A vector that encodes a tandem expression cassette is referred to herein as a "tandem expression vector."

In certain embodiments, a vector comprises a polynucleotide encoding a chimeric Tim receptor and a polynucleotide encoding a cellular immunotherapy agent (e.g., CAR). The polynucleotides encoding the chimeric Tim receptor and cellular immunotherapy agent (e.g., CAR) may be cloned sequentially into a vector at different cloning sites, with the chimeric Tim receptor and cellular immunotherapy agent (e.g., CAR) expressed under the regulation of different promoters.

A vector that encodes a core virus is referred to herein as a "viral vector." There are a large number of available viral vectors suitable for use with the compositions of the instant disclosure, including those identified for human gene therapy applications (see Pfeifer and Verme, *Ann. Rev. Genomics Hum. Genet.* 2:177, 2001). Suitable viral vectors include vectors based on RNA viruses, such as retrovirus-derived vectors, e.g., Maloney murine leukemia virus (MLV)-derived vectors, and include more complex retrovirus-derived vectors, e.g., lentivirus-derived vectors. HIV-1-derived vectors belong to this category. Other examples include lentivirus vectors derived from HIV-2, FIV, equine infectious anemia virus, SIV, and Maedi-Visna virus (ovine lentivirus). Methods of using retroviral and lentiviral viral vectors and packaging cells for transducing mammalian host cells with viral particles containing chimeric receptor transgenes are known in the art and have been previous described, for example, in U.S. Pat. No. 8,119,772; Walchli et al., *PLOS One* 6:327930, 2011; Zhao et al., *J. Immunol.* 174:4415, 2005; Engels et al., *Hum. Gene Ther.* 14:1155, 2003; Frecha et al., *Mol. Ther.* 18:1748, 2010; Verhoeyen et al., *Methods Mol. Biol.* 506:97, 2009. Retroviral and lentiviral vector constructs and expression systems are also commercially available.

In certain embodiments, a viral vector is used to introduce a non-endogenous polynucleotide encoding a chimeric Tim receptor to a host cell. A viral vector may be a retroviral vector or a lentiviral vector. A viral vector may also include a nucleic acid sequence encoding a marker for transduction. Transduction markers for viral vectors are known in the art and include selection markers, which may confer drug resistance, or detectable markers, such as fluorescent markers or cell surface proteins that can be detected by methods such as flow cytometry. In particular embodiments, a viral vector further comprises a gene marker for transduction comprising a fluorescent protein (e.g., green, yellow), an extracellular domain of human CD2, or a truncated human EGFR (EGFRt or tEGFR; see Wang et al., *Blood* 118:1255, 2011). An exemplary tEGFR comprises an amino acid sequence of SEQ ID NO:16. When a viral vector genome comprises a plurality of genes to be expressed in a host cell as separate proteins from a single transcript, the viral vector may also comprise additional sequences between the two (or more) genes allowing for multicistronic expression. Examples of such sequences used in viral vectors include internal ribosome entry sites (IRES), furin cleavage sites, viral 2A peptides (e.g., T2A, P2A, E2A, F2A), or any combination thereof.

Other viral vectors also can be used for polynucleotide delivery including DNA viral vectors, including, for example adenovirus-based vectors and adeno-associated virus (AAV)-based vectors; vectors derived from herpes simplex viruses (HSVs), including amplicon vectors, replication-defective HSV and attenuated HSV (Krisky et al., *Gene Ther.* 5:1517, 1998).

Other viral vectors recently developed for gene therapy uses can also be used with the compositions and methods of this disclosure. Such vectors include those derived from baculoviruses and α-viruses. (Jolly, D J. 1999. Emerging Viral Vectors. pp 209-40 in Friedmann T. ed. The Development of Human Gene Therapy. New York: Cold Spring Harbor Lab), or plasmid vectors (such as sleeping beauty or other transposon vectors).

In certain embodiments, a chimeric Tim receptor vector can be constructed to optimize spatial and temporal control. For example, a chimeric Tim receptor vector can include promoter elements to optimize spatial and temporal control. In some embodiments, a chimeric Tim receptor vector includes tissue specific promoters or enhancers that enable specific induction of a chimeric Tim receptor to an organ, a cell type (e.g., immune cell), or a pathologic microenvironment, such as a tumor or infected tissue. An "enhancer" is an additional promoter element that can function either cooperatively or independently to activate transcription. In certain embodiments, a chimeric Tim receptor vector includes a constitutive promoter. In certain embodiments, a chimeric Tim receptor vector includes an inducible promoter. In certain embodiments, a chimeric Tim receptor vector includes a tissue specific promoter.

In certain embodiments, a chimeric Tim receptor vector can include a gene encoding a homing receptor, such as CCR4 or CXCR4, to improve homing and antitumor activity in vivo.

Where temporal control is desired, a chimeric Tim receptor vector may include an element that allows for inducible depletion of transduced cells. For example, such a vector may include an inducible suicide gene. A suicide gene may be an apoptotic gene or a gene that confers sensitivity to an agent (e.g., a drug). Exemplary suicide genes include chemically inducible caspase 9 (iCASP9) (U.S. Patent Publication No. 2013/0071414), chemically inducible Fas, or Herpes simplex virus thymidine kinase (HSV-TK), which confers sensitivity to ganciclovir. In further embodiments, a chimeric Tim receptor vector can be designed to express a known cell surface antigen that, upon infusion of an associated antibody, enables depletion of transduced cells. Examples of cell surface antigens and their associated antibodies that may be used for depletion of transduced cells include CD20 and Rituximab, RQR8 (combined CD34 and CD20 epitopes, allowing CD34 selection and anti-CD20 deletion) and Rituximab, and EGFR and Cetuximab.

Inducible vector systems, such as the tetracycline (Tet)-On vector system which activates transgene expression with doxycycline (Heinz et al., Hum. Gene Ther. 2011, 22:166-76) may also be used for inducible chimeric Tim receptor expression. Inducible chimeric Tim receptor expression may be also accomplished via retention using a selective hook (RUSH) system based on streptavidin anchored to the membrane of the endoplasmic reticulum through a hook and a streptavidin binding protein introduced into the chimeric Tim receptor structure, where addition of biotin to the system leads to the release of the chimeric Tim receptor from the endoplasmic reticulum (Agaugue et al., 2015, Mol. Ther. 23 (Suppl. 1): S88).

In certain embodiments, a chimeric Tim receptor modified host cell may also be modified to co-express one or more small GTPases. Rho GTPases, a family of small (~21 k Da) signaling G proteins and also a subfamily of the Ras superfamily, regulate actin cytoskeleton organization in various cell types and promote pseudopod extension and phagosome closure during phagocytosis (see, e.g., Castellano et al., 2000, J. Cell Sci. 113:2955-2961). Engulfment requires F-actin recruitment beneath tethered cells or particles, and F-actin rearrangement to allow membrane extension resulting in cell or particle internalization. RhoGTPases include RhoA, Rac1, Rac2, RhoG, and CDC42. Other small GTPases, such as Rap1, is involved in regulation of complement mediated phagocytosis. Co-expression of a small GTPase with the chimeric Tim receptor may promote target cell or particle internalization and/or phagosome formation by the host cell. In some embodiments, a recombinant nucleic acid molecule encoding a GTPase is encoded on a separate vector than the chimeric Tim receptor-containing vector. In other embodiments, a recombinant nucleic acid molecule encoding a GTPase is encoded on the same vector as the chimeric Tim receptor. The GTPase and chimeric Tim receptor may be expressed under the regulation of different promoters on the same vector (e.g., at different multiple cloning sites). Alternatively, the chimeric Tim receptor and GTPase may be expressed under the regulation of one promoter in a multicistronic vector. The polynucleotide sequence encoding the chimeric Tim receptor and the polynucleotide sequence encoding the small GTPase(s) may be separated from each other by an IRES or viral 2A peptide in a multicistronic vector. Exemplary 2A peptides include T2A (SEQ ID NO:12), P2A (SEQ ID NO:13), E2A (SEQ ID NO:14), F2A (SEQ ID NO:15). Examples of GTPases that may be co-expressed with a chimeric Tim receptor include Rac1, Rac2, Rab5 (also referred to as Rab5a), Rab7, Rap1, RhoA, RhoG, CDC42, or any combination thereof. In specific embodiments, the GTPase comprises or is a sequence that is at least 90%, at least 91%, at least 92%, at least 93%, at least 94%, at least 95%, at least 96%, at least 97%, at least 98%, at least 99%, at least 99.5%, or 100% identical to a Rac1 amino acid sequence of SEQ ID NO:17, a Rab5 amino acid sequence of SEQ ID NO:18, a Rab7 amino acid sequence of SEQ ID NO: 19, a Rap1 amino acid sequence of SEQ ID NO:20, a RhoA amino acid sequence of SEQ ID NO:21, a CDC42 amino acid sequence of SEQ ID NO:22, or any combination thereof.

In certain embodiments, a cell, such as an immune cell, obtained from a subject may be engineered into a non-natural or recombinant cell (e.g., a non-natural or recombinant immune cell) by introducing a polynucleotide that encodes a chimeric Tim receptor as described herein, whereby the cell expresses a cell surface localized chimeric Tim receptor. In certain embodiments, a host cell is an immune cell, such as a myeloid progenitor cell or a lymphoid progenitor cell. Exemplary immune cells that may be modified to comprise a polynucleotide encoding a chimeric Tim receptor or a vector comprising a polynucleotide encoding a chimeric Tim receptor include a T cell, a natural killer cell, a B cell, a lymphoid precursor cell, an antigen presenting cell, a dendritic cell, a Langerhans cell, a myeloid precursor cell, a mature myeloid cell, a monocyte, or a macrophage.

In certain embodiments, a B cell is genetically modified to express one or more chimeric Tim receptors. B cells possess certain properties that may be advantageous as host cells, including: trafficking to sites of inflammation, capable of internalizing and presenting antigen, capable of costimulating T cells, highly proliferative, and self-renewing (persist for life). In certain embodiments, a chimeric Tim receptor modified B cell is capable of digesting an engulfed target cell or engulfed target particle into smaller peptides and presenting them to T cells via an MHC molecule. Antigen presentation by a chimeric Tim receptor modified B cell may contribute to antigen spreading of the immune response to non-targeted antigens. B cells include progenitor or precursor cells committed to the B cell lineage (e.g., pre-pro-B cells, pro-B cells, and pre-B cells); immature and inactivated B cells; or mature and functional or activated B cells. In certain embodiments, B cells may be naïve B cells, plasma cells, regulatory B cells, marginal zone B cells, follicular B cells, lymphoplasmacytoid cell, plasmablast cell, memory B cells, or any combination thereof. Memory B cells may be distinguished from naïve B cells by expression of CD27, which is absent on naïve B cells. In certain embodiments, the B cells can be primary cells or cell lines derived from human, mouse, rat, or other mammals. B cell lines are well known in the art. If obtained from a mammal, a B cell can be obtained from numerous sources, including blood, bone marrow, spleen, lymph node, or other tissues or fluids. A B cell composition may be enriched or purified.

In certain embodiments, a T cell is genetically modified to express one or more chimeric Tim receptors. Exemplary T cells include CD4+ helper, CD8+ effector (cytotoxic), naïve (CD45 RA+, CCR7+, CD62L+, CD27+, CD45RO−), central memory (CD45RO+, CD62L+, CD8+), effector memory (CD45RA+, CD45RO−, CCR7−, CD62L−, CD27−), T memory stem, regulatory, mucosal-associated invariant (MAIT), γδ (gd), tissue resident T cells, natural killer T cells, or any combination thereof. In certain embodiments, the T cells can be primary cells or cell lines derived from human, mouse, rat, or other mammals. If obtained from a mammal, a T cell can be obtained from numerous sources, including blood, bone marrow, lymph node, thymus, or other tissues or fluids. A T cell composition may be enriched or purified. T cell lines are well known in the art, some of which are described in Sandberg et al., Leukemia 21:230, 2000. In certain embodiments, the T cells lack endogenous expression of a TCRα gene, TCRβ gene, or both. Such T cells may naturally lack endogenous expression of TCRα and β chains, or may have been modified to block expression (e.g., T cells from a transgenic mouse that does not express TCR α and β chains or cells that have been manipulated to inhibit expression of TCR α and β chains) or to knockout a TCRα chain, a TCRβ chain, or both genes.

In certain embodiments, host cells expressing a chimeric Tim protein of this disclosure on the cell surface are not T cells or cells of a T cell lineage, but cells that are progenitor cells, stem cells or cells that have been modified to express cell surface anti-CD3.

In certain embodiments, a chimeric Tim receptor modified host cell may also be modified to co-express a cellular immunotherapy agent (e.g., CAR, TCR, etc.). In some embodiments, the cellular immunotherapy agent comprises a chimeric antigen receptor (CAR). CARs are recombinant receptors that generally comprise: an extracellular domain comprising a binding domain that binds to a target antigen; an intracellular signaling domain (e.g., comprising an ITAM containing intracellular signaling domain and optionally an intracellular costimulatory domain), and a transmembrane domain positioned between and connecting the extracellular domain and the intracellular signaling domain.

Binding domains suitable for use in CARs of the present disclosure include any antigen-binding polypeptide. A binding domain may comprise an antibody or antigen binding fragment thereof, including for example, a full-length heavy chain, Fab fragment, Fab', F(ab')$_2$, sFv, VH domain, VL domain, dAb, VHH, CDR, and scFv. In certain embodiments, a CAR binding domain is murine, chimeric, human, or humanized.

In certain embodiments, the binding domain of the CAR targets a cancer or tumor antigen. Exemplary antigens that a CAR may target include CD138, CD3δ, CD33, CD123, CD72, CD79a, CD79b, mesothelin, PSMA, BCMA, ROR1, MUC-16, L1CAM, CD22, CD19, CD20, CD23, CD24, CD37, CD30, CA125, CD56, c-Met, EGFR, GD-3, HPV E6, HPV E7, MUC-1, HER2, folate receptor α, CD97, CD171, CD179a, CD44v6, WT1, VEGF-α, VEGFR1, IL-13Rα1, IL-13Rα2, IL-11Rα, PSA, FcRH5, NKG2D ligand, NY-ESO-1, TAG-72, CEA, ephrin A2, ephrin B2, Lewis A antigen, Lewis Y antigen, MAGE, MAGE-A1, RAGE-1, folate receptor β, EGFRviii, VEGFR-2, LGR5, SSX2, AKAP-4, FLT3, fucosyl GM1, GM3, o-acetyl-GD2, and GD2.

In certain embodiments, the extracellular domain of CARs provided in the present disclosure optionally comprises an extracellular, non-signaling spacer or linker domain. Where included, such a spacer or linker domain may position the binding domain away from the host cell surface to further enable proper cell to cell contact, binding, and activation. An extracellular spacer domain is generally located between the extracellular binding domain and the transmembrane domain of the CAR. The length of the extracellular spacer may be varied to optimize target molecule binding based on the selected target molecule, selected binding epitope, binding domain size and affinity (see, e.g., Guest et al., J. Immunother. 28:203-11, 2005; PCT Publication No. WO 2014/031687). In certain embodiments, an extracellular spacer domain is an immunoglobulin hinge region (e.g., IgG1, IgG2, IgG3, IgG4, IgA, IgD). An immunoglobulin hinge region may be a wild type immunoglobulin hinge region or an altered wild type immunoglobulin hinge region. An altered IgG4 hinge region is described in PCT Publication No. WO 2014/031687, which hinge region is incorporated herein by reference in its entirety. In a particular embodiment, an extracellular spacer domain comprises a modified IgG4 hinge region having an amino acid sequence of SEQ ID NO:3.

Other examples of hinge regions that may be used in the CARs described herein include the hinge region from the extracellular regions of type 1 membrane proteins, such as CD8a, CD4, CD28 and CD7, which may be wild-type or variants thereof. In a particular embodiment, an extracellular spacer domain comprises a CD8a hinge region having an amino acid sequence of SEQ ID NO:70. In another particular embodiment, an extracellular spacer domain comprises a CD28 hinge region having an amino acid sequence of SEQ ID NO:32. In further embodiments, an extracellular spacer domain comprises all or a portion of an immunoglobulin Fc domain selected from: a CH1 domain, a CH2 domain, a CH3 domain, or combinations thereof (see, e.g., PCT Publication WO2014/031687, which spacers are incorporated herein by reference in their entirety). In yet further embodiments, an extracellular spacer domain may comprise a stalk region of a type II C-lectin (the extracellular domain located between the C-type lectin domain and the transmembrane domain). Type II C-lectins include CD23, CD69, CD72, CD94, NKG2A, and NKG2D.

CARs of the present disclosure comprise a transmembrane domain that connects and is positioned between the extracellular domain and the intracellular signaling domain. The transmembrane domain ranges in length from about 15 amino acids to about 30 amino acids. The transmembrane domain is a hydrophobic alpha helix that transverses the host cell membrane and anchors the CAR in the host cell membrane. The transmembrane domain may be directly fused to the binding domain or to the extracellular spacer domain if present. In certain embodiments, the transmembrane domain is derived from an integral membrane protein (e.g., receptor, cluster of differentiation (CD) molecule, enzyme, transporter, cell adhesion molecule, or the like). The transmembrane domain can be selected from the same molecule as the extracellular domain or the intracellular signaling domain (e.g., a CAR comprises a CD28 costimulatory signaling domain and a CD28 transmembrane domain). In certain embodiments, the transmembrane domain and the extracellular domain are each selected from different molecules. In other embodiments, the transmembrane domain and the intracellular signaling domain are each selected from different molecules. In yet other embodiments, the transmembrane domain, the extracellular domain, and the intracellular signaling domain are each selected from different molecules.

Exemplary transmembrane domains for use in CARs of the present disclosure include a CD28, CD2, CD4, CD8a, CD5, CD3δ, CD3δ, CD3ζ, CD9, CD16, CD22, CD25, CD27, CD33, CD37, CD40, CD45, CD64, CD79A, CD79B, CD80, CD86, CD95 (Fas), CD134 (OX40), CD137 (4-1BB), CD150 (SLAMF1), CD152 (CTLA4), CD154 (CD40L), CD200R, CD223 (LAG3), CD270 (HVEM), CD272 (BTLA), CD273 (PD-L2), CD274 (PD-L1), CD278 (ICOS), CD279 (PD-1), CD300, CD357 (GITR), A2aR, DAP10, FcRα, FcRβ, FcRγ, Fyn, GAL9, KIR, Lck, LAT, LRP, NKG2D, NOTCH1, NOTCH2, NOTCH3, NOTCH4, PTCH2, ROR2, Ryk, Slp76, SIRPα, pTα, TCRα, TCRβ, TIM3, TRIM, LPA5, and Zap70 transmembrane domain. An exemplary CD28 transmembrane domain comprises an amino acid sequence of SEQ ID NO: 7. In a particular embodiment, a transmembrane domain comprises a CD8a transmembrane domain having an amino acid sequence of SEQ ID NO:33.

The intracellular signaling domain of a CAR is an intracellular effector domain and is capable of transmitting functional signals to a cell in response to binding of the extracellular domain of the CAR to a target molecule (e.g., cancer antigen) and activates at least one of the normal effector functions or responses of the immune cell, e.g., T cell engineered to express the CAR. In some embodiments, the CAR induces a function of a T cell such as cytolytic activity or T helper activity, such as secretion of cytokines or other factors. The intracellular signaling domain may be any portion of an intracellular signaling molecule that retains sufficient signaling activity. In some embodiments, the intracellular signaling domain is obtained from an antigen receptor component (e.g., TCR) or costimulatory molecule. In some embodiments, a full length intracellular signaling domain of an antigen receptor or costimulatory molecule is used. In some embodiments, a truncated portion of an intracellular signaling domain of an antigen receptor or costimulatory molecule is used, provided that the truncated portion retains sufficient signal transduction activity. In further embodiments, an intracellular signaling domain is a variant of a full length or truncated portion of an intracellular signaling domain of an antigen receptor co stimulatory molecule, provided that the variant retains sufficient signal transduction activity (i.e., is a functional variant).

In some embodiments, the intracellular signaling domain of a CAR comprises an immunoreceptor tyrosine-based activation motif (ITAM) containing signaling domain. An ITAM containing signaling domain generally contains at least one (one, two, three, four, or more) ITAMs, which refer to a conserved motif of $YXXL/I\text{-}X_{6-8}\text{-}YXXL/I$. An ITAM containing signaling domain may initiate T cell activation signaling following antigen binding or ligand engagement. ITAM-signaling domains include, for example, intracellular signaling domains of CD3γ, CD3δ, CD3δ, CD3ζ, CD5, CD22, CD79a, CD278 (ICOS), DAP12, FcRγ, and CD66d. Exemplary CD3ζ signaling domains that may be used in CARs of the present disclosure comprise the amino acid sequence of SEQ ID NO:27 or SEQ ID NO:5.

CAR intracellular signaling domains optionally comprise a costimulatory signaling domain, which, when activated in conjunction with a primary or classic (e.g., ITAM-driven) activation signal, promotes or enhances T cell response, such as T cell activation, cytokine production, proliferation, differentiation, survival, effector function, or combinations thereof. Costimulatory signaling domains for use in CARs include, for example, CD27, CD28, CD40L, GITR, NKG2C, CARD1, CD2, CD7, CD27, CD30, CD40, CD54 (ICAM), CD83, CD134 (OX-40), CD137 (4-1BB), CD150 (SLAMF1), CD152 (CTLA4), CD223 (LAG3), CD226, CD270 (HVEM), CD273 (PD-L2), CD274 (PD-L1), CD278 (ICOS), DAP10, LAT, LFA-1, LIGHT, NKG2C, SLP76, TRIM, ZAP70, or any combination thereof. In some embodiments, the costimulatory signaling domain comprises a OX40, CD2, CD27, CD28, ICAM-1, LFA-1 (CD11a/CD18), ICOS (CD278), or 4-1BB (CD137) signaling domain. Exemplary CD28 costimulatory signaling domains that may be used in CARs of the present disclosure comprise an amino acid sequence of SEQ ID NO:26 or 4. An exemplary 4-1BB costimulatory signaling domain comprises an amino acid sequence of SEQ ID NO:100. In certain embodiments, a CAR comprises one, two, or more costimulatory signaling domains.

In some embodiments, CARs are recombinant receptors composed of an scFv binding domain derived from an antibody, a transmembrane domain, and an intracellular signaling domain(s). In some embodiments, the intracellular signaling domain(s) are derived from a TCR.

In certain embodiments, a chimeric antigen receptor comprises an amino acid sequence derived from any mammalian species, including humans, primates, cows, horses, goats, sheep, dogs, cats, mice, rats, rabbits, guinea pigs, pigs, transgenic species thereof, or any combination thereof. In certain embodiments, chimeric antigen receptor is murine, chimeric, human, or humanized.

In certain embodiments, a CAR is a first-generation CAR, a second-generation CAR, or a third-generation CAR. A first-generation CAR generally has an intracellular signaling domain comprising an intracellular signaling domain of CD3ζ, FcγRI, or other ITAM-containing activating domain to provide a T cell activation signal. Second generation CARs further comprise a costimulatory signaling domain (e.g., a costimulatory signaling domain from an endogenous T cell costimulatory receptor, such as CD28, 4-1BB, or ICOS). Third-generation CARs comprise an ITAM-containing activating domain, a first costimulatory signaling domain and a second costimulatory signaling domain.

In some embodiments, one or more of the extracellular domain, the binding domain, the linker, the transmembrane domain, the intracellular signaling domain, or the costimulatory domain comprises junction amino acids. "Junction amino acids" or "junction amino acid residues" refer to one or more (e.g., about 2-20) amino acid residues between two adjacent domains, motifs, regions, modules, or fragments of a protein, such as between a binding domain and an adjacent linker, between a transmembrane domain and an adjacent extracellular or intracellular domain, or on one or both ends of a linker that links two domains, motifs, regions, modules, or fragments (e.g., between a linker and an adjacent binding domain or between a linker and an adjacent hinge). Junction amino acids may result from the construct design of a fusion protein (e.g., amino acid residues resulting from the use of a restriction enzyme site or self-cleaving peptide sequences during the construction of a polynucleotide encoding a fusion protein). For example, a transmembrane domain of a fusion protein may have one or more junction amino acids at the amino-terminal end, carboxy-terminal end, or both.

In certain embodiments, an engineered host cell co-expresses a chimeric Tim receptor and an anti-CD72 CAR.

In some embodiments, the binding domain of the anti-CD72 CAR comprises: (i) a heavy chain variable (VH) region, wherein the VH region comprises a heavy chain complementarity determining region 1 (HCDR-1) comprising the amino acid sequence set forth in SEQ ID NO:71; a heavy chain complementarity determining region 2 (HCDR-2) comprising the amino acid sequence set forth in SEQ ID NO:72; and a heavy chain complementarity determining region 3 (HCDR-3) comprising the amino acid sequence set forth in SEQ ID NO:73; and (ii) a light chain variable (VL) region, wherein the VL region comprises a light chain complementarity determining region 1 (LCDR-1) comprising the amino acid sequence set forth in SEQ ID NO:74; a light chain complementarity determining region 2 (LCDR-2) comprising the amino acid sequence set forth in SEQ ID NO:75; and a light chain complementarity determining region 3 (LCDR-3) comprising the amino acid sequence set forth in SEQ ID NO:76; or (iii) a heavy chain variable (VH) region, wherein the VH region comprises a heavy chain complementarity determining region 1 (HCDR-1) comprising the amino acid sequence set forth in SEQ ID NO:77; a heavy chain complementarity determining region 2 (HCDR-2) comprising the amino acid sequence set forth in SEQ ID NO:78; and a heavy chain complementarity determining region 3 (HCDR-3) comprising the amino acid sequence set forth in SEQ ID NO:79; and (iv) (ii) a light chain variable (VL) region, wherein the VL region comprises a light chain complementarity determining region 1 (LCDR-1) comprising the amino acid sequence set forth in SEQ ID NO: 80; a light chain complementarity determining region 2 (LCDR-2) comprising the amino acid sequence set forth in SEQ ID NO:81; and a light chain complementarity determining region 3 (LCDR-3) comprising the amino acid sequence set forth in SEQ ID NO: 82.

In some embodiments, the binding domain of the CAR comprises: (i) a VH region comprising the amino acid sequence set forth in SEQ ID NO:83 or a sequence having at least 90%, 91%, 92%, 93%, 94%, 95%, 96%, 97%, 98%, or 99% sequence identity to SEQ ID NO:83, and a VL region comprising the amino acid sequence set forth in SEQ ID NO:84 or a sequence having at least 90%, 91%, 92%, 93%, 94%, 95%, 96%, 97%, 98%, or 99% sequence identity to SEQ ID NO:84; or (ii) a VH region comprising the amino acid sequence set forth in SEQ ID NO:85 or a sequence having at least 90%, 91%, 92%, 93%, 94%, 95%, 96%, 97%, 98%, or 99% sequence identity to SEQ ID NO:85, and a VL region comprising the amino acid sequence set forth in SEQ ID NO:86 or a sequence having at least 90%, 91%, 92%, 93%, 94%, 95%, 96%, 97%, 98%, or 99% sequence identity to SEQ ID NO:86.

Exemplary binding domain, extracellular spacer, transmembrane, and intracellular signaling domain sequences for use in anti-CD72 CARs of the present disclosure and exemplary anti-CD72 CAR sequences are set forth in Table 9 and described in U.S. Provisional Application titled "Anti-CD72 Chimeric Receptors and Uses Thereof" filed on Aug. 14, 2020, which is incorporated herein by reference in its entirety.

TABLE 9

| Name | Amino Acid Sequence | SEQ ID NO: |
|---|---|---|
| Sc02-004 HCDR1 | GYLMS | 71 |
| Sc02-004 HCDR2 | VISYDGSNKYYADSVKG | 72 |
| Sc02-004 HCDR3 | ARRDTNLFDY | 73 |
| Sc02-004 LCDR1 | RASQSISSYLN | 74 |
| Sc02-004 LCDR2 | AASSLQS | 75 |
| Sc02-004 LCDR3 | QQSYSTPPT | 76 |
| Sc02-025 HCDR1 | SYYMH | 77 |

TABLE 9-continued

| Name | Amino Acid Sequence | SEQ ID NO: |
| --- | --- | --- |
| Sc02-025 HCDR2 | IINPSGGGTSYAQKFQG | 78 |
| Sc02-025 HCDR3 | DYYVTYDSWFDS | 79 |
| Sc02-025 LCDR1 | QGDSLRSYYAS | 80 |
| Sc02-025 LCDR2 | GKNNRPS | 81 |
| Sc02-025 LCDR3 | NSRDSSGNHVV | 82 |
| Sc02-004 VH | LVESGGGLVQPGGSLRLSCAASGFTFSGYLMS WVRQAPGKGLEWVAVISYDGSNKYYADSVKGR FTISRDNSKNTLYLQMDSLRAEDTAVYYCARA RRDTNLFDYWGQGTLVTV | 83 |
| Sc02-004 VL | ELTQSPSSLSASVGDRVTITCRASQSISSYLN WYQQKPGKAPKLLIYAASSLQSGVPSRFSGSG SGTDFTLTISSLQPEDFATYYCQQSYSTPPTF GQGTKVEI | 84 |
| Sc02-025 VH | LVQSGAEVKKPGASVKVSCKASGYTFTSYYMH WVRQAPGQGLEWMGIINPSGGGTSYAQKFQGR VTMTRDTSTSTVYMELSSLRSEDTAVYYCARD YYVTYDSWFDSWGQGTLVTVS | 85 |
| Sc02-025 VL | VSVALGQTVRITCQGDSLRSYYASWYQQKPGQ APVLVIYGKNNRPSGIPDRFSGSSSGNTASLT ITGAQAEDEADYYCNSRDSSGNHVVFGGGTKL TV | 86 |
| Sc02-004 scFv | AEVQLVESGGGLVQPGGSLRLSCAASGFTFSG YLMSWVRQAPGKGLEWVAVISYDGSNKYYADS VKGRFTISRDNSKNTLYLQMDSLRAEDTAVYY CARARRDTNLFDYWGQGTLVTVLEGTGGSGGT GSGTGTSELTQSPSSLSASVGDRVTITCRASQ SISSYLNWYQQKPGKAPKLLIYAASSLQSGVP SRFSGSGSGTDFTLTISSLQPEDFATYYCQQS YSTPPTFGQGTKVEIKRAAA | 87 |
| Sc02-025 scFv | AQVQLVQSGAEVKKPGASVKVSCKASGYTFTS YYMHWVRQAPGQGLEWMGIINPSGGGTSYAQK FQGRVTMTRDTSTSTVYMELSSLRSEDTAVYY CARDYYVTYDSWFDSWGQGTLVTVSRGGGGSG GGGSGGGGSSELTQDPAVSVALGQTVRITCQG DSLRSYYASWYQQKPGQAPVLVIYGKNNRPSG IPDRFSGSSSGNTASLTITGAQAEDEADYYCN SRDSSGNHVVFGGGTKLTVLGAAA | 88 |
| Flexible linker | GGGGSGGGGSGGGGS | 89 |
| Flexible linker | GTGGSGGTGSGTGTS | 90 |
| IgG4 hinge region (short) | ESKYGPPCPPCP | 91 |
| CD8a hinge region | TTTPAPRPPTPAPTIASQPLSLRPEACRPAAG GAVHTRGLDFACD | 92 |
| CD28 hinge region | IEVMYPPPYLDNEKSNGTIIHVKGKHLCPSPL FPGPSKP | 93 |
| CD8a transmembrane region | IYIWAPLAGTCGVLLLSLVITLYC | 94 |
| CD28 transmembrane region | FWVLVVVGGVLACYSLLVTVAFIIFWV | 95 |
| wildtype CD3ζ signaling domain | RVKFSRSADAPAYQQGQNQLYNELNLGRREEY DVLDKRRGRDPEMGGKPQRRKNPQEGLYNELQ KDKMAEAYSEIGMKGERRRGKGHDGLYQGLST ATKDTYDALHMQALPPR | 96 |

TABLE 9-continued

| Name | Amino Acid Sequence | SEQ ID NO: |
|---|---|---|
| variant CD3ζ signaling domain | RVKFSRSADAPAYQQGQNQLYNELNLGRREEY DVLDKRRGRDPEMGGKPRRKNPQEGLYNELQK DKMAEAYSEIGMKGERRRGKGHDGLYQGLSTA TKDTYDALHMQALPPR | 97 |
| wildtype CD28 costimulatory signaling domain | RSKRSRLLHSDYMNMTPRRPGPTRKHYQPYAP PRDFAAYRS | 98 |
| variant CD28 costimulatory signaling domain with L186G/L187G substitutions with positions in reference to full length protein | RSKRSRGGHSDYMNMTPRRPGPTRKHYQPYAP PRDFAAYRS | 99 |
| 4-1BB costimulatory signaling domain | KRGRKKLLYIFKQPFMRPVQTTQEEDGCSCRF PEEEEGGCEL | 100 |
| pCTX206 CAR: GMSCFR signal peptide (amino acids 1-21) - sc02-004 scFv - IgG4 Hinge - CD28 TM - CD28 ICD - CD3z | MLLVTSLLLCELPHPAFLLIPAEVQLVESGGG LVQPGGSLRLSCAASGFTFSGYLMSWVRQAPG KGLEWVAVISYDGSNKYYADSVKGRFTISRDN SKNTLYLQMDSLRAEDTAVYYCARARRDTNLF DYWGQGTLVTVLEGTGGSGGTGSGTGTSELTQ SPSSLSASVGDRVTITCRASQSISSYLNWYQQ KPGKAPKLLIYAASSLQSGVPSRFSGSGSGTD FTLTISSLQPEDFATYYCQQSYSTPPTFGQGT KVEIKRAAAESKYGPPCPPCPFWVLVVVGGVL ACYSLLVTVAFIIFWVRSKRSRLLHSDYMNMT PRRPGPTRKHYQPYAPPRDFAAYRSRVKFSRS ADAPAYQQGQNQLYNELNLGRREEYDVLDKRR GRDPEMGGKPQRRKNPQEGLYNELQKDKMAEA YSEIGMKGERRRGKGHDGLYQGLSTATKDTYD ALHMQALPPR31 | 101 |
| pCTX208 CAR: GMSCFR signal peptide - (amino acids 1-21) - sc02-025 scFv - IgG4 Hinge - CD28 TM - CD28 ICD - CD3z | MLLVTSLLLCELPHPAFLLIPAQVQLVQSGAE VKKPGASVKVSCKASGYTFTSYYMHWVRQAPG QGLEWMGIINPSGGGTSYAQKFQGRVTMTRDT STSTVYMELSSLRSEDTAVYYCARDYYVTYDS WFDSWGQGTLVTVSRGGGGSGGGGSGGGGSSE LTQDPAVSVALGQTVRITCQGDSLRSYYASWY QQKPGQAPVLVIYGKNNRPSGIPDRFSGSSSG NTASLTITGAQAEDEADYYCNSRDSSGNHVVF GGGTKLTVLGAAAESKYGPPCPPCPFWVLVVV GGVLACYSLLVTVAFIIFWVRSKRSRLLHSDY MNMTPRRPGPTRKHYQPYAPPRDFAAYRSRVK FSRSADAPAYQQGQNQLYNELNLGRREEYDVL DKRRGRDPEMGGKPQRRKNPQEGLYNELQKDK MAEAYSEIGMKGERRRGKGHDGLYQGLSTATK DTYDALHMQALPPR | 102 |
| CAR: GMSCFR signal peptide (amino acids 1-21) - sc02-004 scFv - IgG4 Hinge - CD28 TM - 4-1BB ICD - CD3z | MLLVTSLLLCELPHPAFLLIPAEVQLVESGGG LVQPGGSLRLSCAASGFTFSGYLMSWVRQAPG KGLEWVAVISYDGSNKYYADSVKGRFTISRDN SKNTLYLQMDSLRAEDTAVYYCARARRDTNLF DYWGQGTLVTVLEGTGGSGGTGSGTGTSELTQ SPSSLSASVGDRVTITCRASQSISSYLNWYQQ KPGKAPKLLIYAASSLQSGVPSRFSGSGSGTD FTLTISSLQPEDFATYYCQQSYSTPPTFGQGT KVEIKRAAAESKYGPPCPPCPFWVLVVVGGVL ACYSLLVTVAFIIFWV*KRGRKKLLYIFKQPFM RPVQTTQEEDGCSCRFPEEEEGGCEL*RVKFSR SADAPAYQQGQNQLYNELNLGRREEYDVLDKR RGRDPEMGGKPQRRKNPQEGLYNELQKDKMAE AYSEIGMKGERRRGKGHDGLYQGLSTATKDTY DALHMQALPPR | 103 |

TABLE 9-continued

| Name | Amino Acid Sequence | SEQ ID NO: |
|---|---|---|
| CAR: GMSCFR signal peptide (amino acids 1-21) - sc02-025 scFv - IgG4 Hinge - CD28 TM - 4-1BB ICD - CD3z | MLLVTSLLLCELPHPAFLLIPAQVQLVQSGAE VKKPGASVKVSCKASGYTFTSYYMHWVRQAPG QGLEWMGIINPSGGGTSYAQKFQGRVTMTRDT STSTVYMELSSLRSEDTAVYYCARDYYVTYDS WFDSWGQGTLVTVSRGGGGSGGGGSGGGGSSE LTQDPAVSVALGQTVRITCQGDSLRSYYASWY QQKPGQAPVLVIYGKNNRPSGIPDRFSGSSSG NTASLTITGAQAEDEADYYCNSRDSSGNHVVF GGGTKLTVLGAAAESKYGPPCPPCPFWVLVVV GGVLACYSLLVTVAFIIFWV*KRGRKKLLYIFK QPFMRPVQTTQEEDGCSCRFPEEEEGGCEL*RV KFSRSADAPAYQQGQNQLYNELNLGRREEYDV LDKRRGRDPEMGGKPQRRKNPQEGLYNELQKD KMAEAYSEIGMKGERRRGKGHDGLYQGLSTAT KDTYDALHMQALPPR | 104 |
| CAR: GMSCFR signal peptide (amino acids 1-21) - sc02-004 scFv - CD28 Hinge - CD28 TM - CD28 ICD - CD3z | MLLVTSLLLCELPHPAFLLIPAEVQLVESGGG LVQPGGSLRLSCAASGFTFSGYLMSWVRQAPG KGLEWVAVISYDGSNKYYADSVKGRFTISRDN SKNTLYLQMDSLRAEDTAVYYCARARRDTNLF DYWGQGTLVTVLEGTGGSGGTGSGTGTSELTQ SPSSLSASVGDRVTITCRASQSISSYLNWYQQ KPGKAPKLLIYAASSLQSGVPSRFSGSGSGTD FTLTISSLQPEDFATYYCQQSYSTPPTFGQGT KVEIKRAAA<u>IEVMYPPPYLDNEKSNGTIIHVK</u> <u>GKHLCPSPLFPGPSKPFWVLVVVGGVLACYSL</u> LVTVAFIIFWVRSKRSRLLHSDYMNMTPRRPG PTRKHYQPYAPPRDFAAYRSRVKFSRSADAPA YQQGQNQLYNELNLGRREEYDVLDKRRGRDPE MGGKPQRRKNPQEGLYNELQKDKMAEAYSEIG MKGERRRGKGHDGLYQGLSTATKDTYDALHMQ ALPPR | 105 |
| CAR: GMSCFR signal peptide (amino acids 1-21) - sc02-025 scFv - CD28 Hinge - CD28 TM - CD28 ICD - CD3z | MLLVTSLLLCELPHPAFLLIPAQVQLVQSGAE VKKPGASVKVSCKASGYTFTSYYMHWVRQAPG QGLEWMGIINPSGGGTSYAQKFQGRVTMTRDT STSTVYMELSSLRSEDTAVYYCARDYYVTYDS WFDSWGQGTLVTVSRGGGGSGGGGSGGGGSSE LTQDPAVSVALGQTVRITCQGDSLRSYYASWY QQKPGQAPVLVIYGKNNRPSGIPDRFSGSSSG NTASLTITGAQAEDEADYYCNSRDSSGNHVVF GGGTKLTVLGAAA<u>IEVMYPPPYLDNEKSNGTI</u> <u>IHVKGKHLCPSPLFPGPSKP</u>FWVLVVVGGVLA CYSLLVTVAFIIFWVRSKRSRLLHSDYMNMTP RRPGPTRKHYQPYAPPRDFAAYRSRVKFSRSA DAPAYQQGQNQLYNELNLGRREEYDVLDKRRG RDPEMGGKPQRRKNPQEGLYNELQKDKMAEAY SEIGMKGERRRGKGHDGLYQGLSTATKDTYDA LHMQALPPR | 106 |
| CAR: GMSCFR signal peptide (amino acids 1-21) - sc02-004 scFv - CD28 Hinge - CD28 TM - 4-1BB ICD - CD3z | MLLVTSLLLCELPHPAFLLIPAEVQLVESGGG LVQPGGSLRLSCAASGFTFSGYLMSWVRQAPG KGLEWVAVISYDGSNKYYADSVKGRFTISRDN SKNTLYLQMDSLRAEDTAVYYCARARRDTNLF DYWGQGTLVTVLEGTGGSGGTGSGTGTSELTQ SPSSLSASVGDRVTITCRASQSISSYLNWYQQ KPGKAPKLLIYAASSLQSGVPSRFSGSGSGTD FTLTISSLQPEDFATYYCQQSYSTPPTFGQGT KVEIKRAAA<u>IEVMYPPPYLDNEKSNGTIIHVK</u> <u>GKHLCPSPLFPGPSKPFWVLVVVGGVLACYSL</u> LVTVAFIIFWV*KRGRKKLLYIFKQPFMRPVQT TQEEDGCSCRFPEEEEGGCEL*RVKFSRSADAP AYQQGQNQLYNELNLGRREEYDVLDKRRGRDP EMGGKPQRRKNPQEGLYNELQKDKMAEAYSEI GMKGERRRGKGHDGLYQGLSTATKDTYDALHM QALPPR | 107 |

TABLE 9-continued

| Name | Amino Acid Sequence | SEQ ID NO: |
|---|---|---|
| CAR: GMSCFR signal peptide - (amino acids 1-21) - sc02-025 scFv - CD28 Hinge - CD28 TM - 4-1BB ICD - CD3z | MLLVTSLLLCELPHPAFLLIPAQVQLVQSGAE VKKPGASVKVSCKASGYTFTSYYMHWVRQAPG QGLEWMGIINPSGGGTSYAQKFQGRVTMTRDT STSTVYMELSSLRSEDTAVYYCARDYYVTYDS WFDSWGQGTLVTVSRGGGGSGGGGSGGGGSSE LTQDPAVSVALGQTVRITCQGDSLRSYYASWY QQKPGQAPVLVIYGKNNRPSGIPDRFSGSSSG NTASLTITGAQAEDEADYYCNSRDSSGNHVVF GGGTKLTVLGAAAIEVMYPPPYLDNEKSNGTI IHVKGKHLCPSPLFPGPSKPFWVLVVVGGVLA CYSLLVTVAFIIFWVKRGRKKLLYIFKQPFMR PVQTTQEEDGCSCRFPEEEEGGCELRVKFSRS ADAPAYQQGQNQLYNELNLGRREEYDVLDKRR GRDPEMGGKPQRRKNPQEGLYNELQKDKMAEA YSEIGMKGERRRGKGHDGLYQGLSTATKDTYD ALHMQALPPR | 108 |
| CAR: GMSCFR signal peptide (amino acids 1-21) - sc02-004 scFv - IgG4 Hinge - CD8a TM - CD28 ICD - CD3z | MLLVTSLLLCELPHPAFLLIPAEVQLVESGGG LVQPGGSLRLSCAASGFTFSGYLMSWVRQAPG KGLEWVAVISYDGSNKYYADSVKGRFTISRDN SKNTLYLQMDSLRAEDTAVYYCARARRDTNLF DYWGQGTLVTVLEGTGGSGGTGSGTGTSELTQ SPSSLSASVGDRVTITCRASQSISSYLNWYQQ KPGKAPKLLIYAASSLQSGVPSRFSGSGSGTD FTLTISSLQPEDFATYYCQQSYSTPPTFGQGT KVEIKRAAAESKYGPPCPPPCPIYIWAPLAGTC GVLLLSLVITLYCRSKRSRLLHSDYMNMTPRR PGPTRKHYQPYAPPRDFAAYRSRVKFSRSADA PAYQQGQNQLYNELNLGRREEYDVLDKRRGRD PEMGGKPQRRKNPQEGLYNELQKDKMAEAYSE IGMKGERRRGKGHDGLYQGLSTATKDTYDALH MQALPPR | 109 |
| CAR: GMSCFR signal peptide (amino acids 1-21) - sc02-025 scFv - IgG4 Hinge - CD8a TM - CD28 ICD - CD3z | MLLVTSLLLCELPHPAFLLIPAQVQLVQSGAE VKKPGASVKVSCKASGYTFTSYYMHWVRQAPG QGLEWMGIINPSGGGTSYAQKFQGRVTMTRDT STSTVYMELSSLRSEDTAVYYCARDYYVTYDS WFDSWGQGTLVTVSRGGGGSGGGGSGGGGSSE LTQDPAVSVALGQTVRITCQGDSLRSYYASWY QQKPGQAPVLVIYGKNNRPSGIPDRFSGSSSG NTASLTITGAQAEDEADYYCNSRDSSGNHVVF GGGTKLTVLGAAAESKYGPPCPPPCPIYIWAPL AGTCGVLLLSLVITLYCRSKRSRLLHSDYMNM TPRRPGPTRKHYQPYAPPRDFAAYRSRVKFSR SADAPAYQQGQNQLYNELNLGRREEYDVLDKR RGRDPEMGGKPQRRKNPQEGLYNELQKDKMAE AYSEIGMKGERRRGKGHDGLYQGLSTATKDTY DALHMQALPPR | 110 |
| CAR: GMSCFR signal peptide (amino acids 1-21) - sc02-004 scFv - CD8a Hinge - CD8a TM - CD28 ICD - CD3z | MLLVTSLLLCELPHPAFLLIPAEVQLVESGGG LVQPGGSLRLSCAASGFTFSGYLMSWVRQAPG KGLEWVAVISYDGSNKYYADSVKGRFTISRDN SKNTLYLQMDSLRAEDTAVYYCARARRDTNLF DYWGQGTLVTVLEGTGGSGGTGSGTGTSELTQ SPSSLSASVGDRVTITCRASQSISSYLNWYQQ KPGKAPKLLIYAASSLQSGVPSRFSGSGSGTD FTLTISSLQPEDFATYYCQQSYSTPPTFGQGT KVEIKRAAATTTPAPRPPTPAPTIASQPLSLR PEACRPAAGGAVHTRGLDFACDIYIWAPLAGT CGVLLLSLVITLYCRSKRSRLLHSDYMNMTPR RPGPTRKHYQPYAPPRDFAAYRSRVKFSRSAD APAYQQGQNQLYNELNLGRREEYDVLDKRRGR DPEMGGKPQRRKNPQEGLYNELQKDKMAEAYS EIGMKGERRRGKGHDGLYQGLSTATKDTYDAL HMQALPPR | 111 |
| CAR: GMSCFR signal peptide (amino acids 1-21) - sc02-025 scFv - CD8a Hinge - CD8a TM - CD28 ICD - CD3z | MLLVTSLLLCELPHPAFLLIPAQVQLVQSGAE VKKPGASVKVSCKASGYTFTSYYMHWVRQAPG QGLEWMGIINPSGGGTSYAQKFQGRVTMTRDT STSTVYMELSSLRSEDTAVYYCARDYYVTYDS WFDSWGQGTLVTVSRGGGGSGGGGSGGGGSSE LTQDPAVSVALGQTVRITCQGDSLRSYYASWY QQKPGQAPVLVIYGKNNRPSGIPDRFSGSSSG NTASLTITGAQAEDEADYYCNSRDSSGNHVVF GGGTKLTVLGAAATTTPAPRPPTPAPTIASQP LSLRPEACRPAAGGAVHTRGLDFACDIYIWAP LAGTCGVLLLSLVITLYCRSKRSRLLHSDYMN | 112 |

TABLE 9-continued

| Name | Amino Acid Sequence | SEQ ID NO: |
|---|---|---|
| | MTPRRPGPTRKHYQPYAPPRDFAAYRSRVKFS RSADAPAYQQGQNQLYNELNLGRREEYDVLDK RRGRDPEMGGKPQRRKNPQEGLYNELQKDKMA EAYSEIGMKGERRRGKGHDGLYQGLSTATKDT YDALHMQALPPR | |
| CAR: GMSCFR signal peptide (amino acids 1-21) - sc02-004 scFv - IgG4 Hinge - CD8a TM - 4-1BB ICD - CD3z | MLLVTSLLLCELPHPAFLLIPAEVQLVESGGG LVQPGGSLRLSCAASGFTFSGYLMSWVRQAPG KGLEWVAVISYDGSNKYYADSVKGRFTISRDN SKNTLYLQMDSLRAEDTAVYYCARARRDTNLF DYWGQGTLVTVLEGTGGSGGTGSGTGTSELTQ SPSSLSASVGDRVTITCRASQSISSYLNWYQQ KPGKAPKLLIYAASSLQSGVPSRFSGSGSGTD FTLTISSLQPEDFATYYCQQSYSTPPTFGQGT KVEIKRAAAESKYGPPCPPPCP*IYIWAPLAGTC GVLLLSLVITLYCKRGRKKLLYIFKQPFMRPV QTTQEEDGCSCRFPEEEEGGCELRVKFSRSAD APAYQQGQNQLYNELNLGRREEYDVLDKRRGR DPEMGGKPQRRKNPQEGLYNELQKDKMAEAYS EIGMKGERRRGKGHDGLYQGLSTATKDTYDAL HMQALPPR* | 113 |
| CAR: GMSCFR signal peptide (amino acids 1-21) - sc02-025 scFv - IgG4 Hinge - CD8a TM - 4-1BB ICD - CD3z | MLLVTSLLLCELPHPAFLLIPAQVQLVQSGAE VKKPGASVKVSCKASGYTFTSYYMHWVRQAPG QGLEWMGIINPSGGGTSYAQKFQGRVTMTRDT STSTVYMELSSLRSEDTAVYYCARDYYVTYDS WFDSWGQGTLVTVSRGGGGSGGGGSGGGGSSE LTQDPAVSVALGQTVRITCQGDSLRSYYASWY QQKPGQAPVLVIYGKNNRPSGIPDRFSGSSSG NTASLTITGAQAEDEADYYCNSRDSSGNHVVF GGGTKLTVLGAAAESKYGPPCPPPCP*IYIWAPL AGTCGVLLLSLVITLYCKRGRKKLLYIFKQPF MRPVQTTQEEDGCSCRFPEEEEGGCELRVKFS RSADAPAYQQGQNQLYNELNLGRREEYDVLDK RRGRDPEMGGKPQRRKNPQEGLYNELQKDKMA EAYSEIGMKGERRRGKGHDGLYQGLSTATKDT YDALHMQALPPR* | 114 |
| CAR: GMSCFR signal peptide (amino acids 1-21) - sc02-004 scFv- CD8a Hinge - CD8a TM - 4-1BB ICD - CD3z | MLLVTSLLLCELPHPAFLLIPAEVQLVESGGG LVQPGGSLRLSCAASGFTFSGYLMSWVRQAPG KGLEWVAVISYDGSNKYYADSVKGRFTISRDN SKNTLYLQMDSLRAEDTAVYYCARARRDTNLF DYWGQGTLVTVLEGTGGSGGTGSGTGTSELTQ SPSSLSASVGDRVTITCRASQSISSYLNWYQQ KPGKAPKLLIYAASSLQSGVPSRFSGSGSGTD FTLTISSLQPEDFATYYCQQSYSTPPTFGQGT KVEIKRAAATTTPAPRPPTPAPTIASQPLSLR PEACRPAAGGAVHTRGLDFACDIYIWAPLAGT CGVLLLSLVITLYCKRGRKKLLYIFKQPFMRP VQTTQEEDGCSCRFPEEEEGGCELRVKFSRSA DAPAYQQGQNQLYNELNLGRREEYDVLDKRRG RDPEMGGKPQRRKNPQEGLYNELQKDKMAEAY SEIGMKGERRRGKGHDGLYQGLSTATKDTYDA LHMQALPPR* | 115 |
| CAR: GMSCFR signal peptide (amino acids 1-21) - sc02-025 scFv- CD8a Hinge - CD8a TM - 4-1BB ICD - CD3z | MLLVTSLLLCELPHPAFLLIPAQVQLVQSGAE VKKPGASVKVSCKASGYTFTSYYMHWVRQAPG QGLEWMGIINPSGGGTSYAQKFQGRVTMTRDT STSTVYMELSSLRSEDTAVYYCARDYYVTYDS WFDSWGQGTLVTVSRGGGGSGGGGSGGGGSSE LTQDPAVSVALGQTVRITCQGDSLRSYYASWY QQKPGQAPVLVIYGKNNRPSGIPDRFSGSSSG NTASLTITGAQAEDEADYYCNSRDSSGNHVVF GGGTKLTVLGAAATTTPAPRPPTPAPTIASQP LSLRPEACRPAAGGAVHTRGLDFACDIYIWAP LAGTCGVLLLSLVITLYCKRGRKKLLYIFKQP FMRPVQTTQEEDGCCRFPEEEEGGCELRVKFS RSADAPAYQQGQNQLYNELNLGRREEYDVLDK RRGRDPEMGGKPQRRKNPQEGLYNELQKDKMA EAYSEIGMKGERRRGKGHDGLYQGLSTATKDT YDALHMQALPPR* | 116 |
| GMCSFR_Signal Peptide | MLLVTSLLLCELPHPAFLLIP | 117 |

In certain embodiments, a chimeric Tim receptor modified host cell co-expresses a recombinant TCR. Recombinant TCR proteins include "traditional" TCRs composed of a heterodimer of α chain polypeptide and β chain polypeptide or a heterodimer of a γ chain polypeptide and a δ chain polypeptide, binding fragments and fusion proteins thereof, including for example, single chain TCRs, single domain TCRs, soluble TCR fusion TCR proteins, and TCR fusion constructs (TRuC™). In certain embodiments, a tandem expression cassette comprises a polynucleotide encoding a recombinant TCR beta chain comprising a TCR beta variable region and a TCR beta constant region, and a polynucleotide encoding a recombinant TCR alpha chain comprising a TCR alpha variable region and a TCR alpha constant region. In certain embodiments, a recombinant TCR is an enhanced affinity TCR. In one embodiment, a recombinant TCR is an enhanced affinity TCR.

In certain embodiments, a recombinant TCR binding protein is a single chain TCR (scTCR) comprising a Vα joined to a Vβ by a flexible linker. In some embodiments, a scTCR comprises a Vα-linker-Vβ polypeptide. In other embodiments, a scTCR comprises a Vβ-linker-Vα polypeptide.

In certain embodiments, a chimeric Tim receptor modified host cell may also be modified to co-express a single chain TCR (scTCR) fusion protein. A scTCR fusion protein comprises a binding domain comprising a scTCR (a TCR Vα domain linked to a TCR Vβ domain), an optional extracellular spacer, a transmembrane domain, and an intracellular component comprising a single intracellular signaling domain providing an T cell activation signal (e.g., a CD3ζ ITAM-containing activating domain) and optionally a costimulatory signaling domain (see, Aggen et al., 2012, Gene Ther. 19:365-374; Stone et al., Cancer Immunol. Immunother. 2014, 63:1163-76).

In certain embodiments, a chimeric Tim receptor modified host cell may also be modified to co-express a T cell receptor-based chimeric antigen receptor (TCR-CAR). A TCR-CAR is a heterodimeric fusion protein generally comprising a soluble TCR (a polypeptide chain comprising a Vα domain and Cα domain and a polypeptide chain comprising a Vβ domain and a Cβ domain) wherein the VβCβ polypeptide chain is linked to a transmembrane domain and an intracellular signaling component (e.g., an ITAM-containing activating domain and optionally a costimulatory signaling domain) (see, e.g., Walseng et al., 2017 Scientific Reports 7:10713).

In certain embodiments, an engineered host cell that co-expresses a chimeric Tim receptor and a cellular immunotherapy agent (e.g., CAR, TCR, etc.) comprises a recombinant nucleic acid encoding the chimeric Tim receptor and a recombinant nucleic acid molecule encoding the cellular immunotherapy agent on separate vectors within the engineered host cell.

In some embodiments, an engineered host cell that co-expresses a chimeric Tim receptor and a cellular immunotherapy agent (e.g., CAR, TCR, etc.) comprises a recombinant nucleic acid encoding the chimeric Tim receptor and a recombinant nucleic acid molecule encoding the cellular immunotherapy agent on the same vector as the chimeric Tim receptor within an engineered host cell. The chimeric Tim receptor and cellular immunotherapy agent may be expressed under the regulation of different promoters on the same vector (e.g., at different multiple cloning sites). Alternatively, the chimeric Tim receptor and cellular immunotherapy agent may be expressed under the regulation of one promoter in a multicistronic vector (e.g., tandem expression vector). The polynucleotide sequence encoding the chimeric Tim receptor and the polynucleotide sequence encoding the cellular immunotherapy agent may be separated by an IRES or viral 2A peptide in a multicistronic vector.

Tandem expression cassettes, tandem expression vectors, and engineered host cells comprising the same are described in International Application Publication No. WO2019/191339, which is incorporated herein by reference in its entirety.

In certain embodiments, gene editing methods are used to modify the host cell genome to comprise a polynucleotide encoding a chimeric Tim receptor of the present disclosure. Gene editing, or genome editing, is a method of genetic engineering wherein DNA is inserted, replaced, or removed from a host cell's genome using genetically engineered endonucleases. The nucleases create specific double-stranded breaks at targeted loci in the genome. The host cell's endogenous DNA repair pathways then repair the induced break(s), e.g., by non-homologous ending joining (NHEJ) and homologous recombination. Exemplary endonucleases useful for gene editing include a zinc finger nuclease (ZFN), a transcription activator-like effector (TALE) nuclease, a clustered regularly interspaced short palindromic repeats (CRISPR)/Cas nuclease system (e.g., CRISPR-Cas9), a meganuclease, or combinations thereof. Methods of disrupting or knocking out genes or gene expression in immune cells including B cells and T cells, using gene editing endonucleases are known in the art and described, for example, in International Application Publication Nos. WO 2015/066262; WO 2013/074916; WO 2014/059173; Cheong et al., Nat. Comm. 2016 7:10934; Chu et al., Proc. Natl. Acad. Sci. USA 2016 113:12514-12519; methods from each of which are incorporated herein by reference in their entirety.

In certain embodiments, expression of an endogenous gene of the host cell is inhibited, knocked down, or knocked out. Examples of endogenous genes that may be inhibited, knocked down, or knocked out in a B cell include IGH, IGκ, IGλ, or any combination thereof. Examples of endogenous genes that may be inhibited, knocked down, or knocked out in a T cell include a TCR gene (TRA or TRB), an HLA gene (HLA class I gene or HLA class II gene), an immune checkpoint molecule (PD-L1, PD-L2, CD80, CD86, B7-H3, B7-H4, HVEM, adenosine, GAL9, VISTA, CEACAM-1, CEACAM-3, CEACAM-5, PVRL2, PD-1, CTLA-4, BTLA, KIR, LAG3, TIM3, A2aR, CD244/2B4, CD160, TIGIT, LAIR-1, or PVRIG/CD112R), or any combination thereof. Expression of an endogenous gene may be inhibited, knocked down, or knocked out at the gene level, transcriptional level, translational level, or a combination thereof. Methods of inhibiting, knocking down, or knocking out an endogenous gene may be accomplished, for example, by an RNA interference agent (e.g., siRNA, shRNA, miRNA, etc.) or an engineered endonuclease (e.g., CRISPR/Cas nuclease system, a zinc finger nuclease (ZFN), a Transcription Activator Like Effector nuclease (TALEN), a meganuclease), or any combination thereof. In certain embodiments, an endogenous B cell gene (e.g., IGH, IGκ, or IGλ) is knocked out by insertion of a polynucleotide encoding a chimeric Tim receptor of the present disclosure into the locus of the endogenous B cell gene, such as via an engineered endonuclease. In certain embodiments, an endogenous T cell gene (e.g., a TCR gene, an HLA gene, or an immune checkpoint molecule gene) is knocked out by insertion of a polynucleotide encoding a chimeric Tim receptor of the present disclosure into the locus of the endogenous T cell gene, such as via an engineered endonuclease.

In certain embodiments, a host cell may be genetically modified to express one type of chimeric Tim receptor. In other embodiments, a host cell may express at least two or more different chimeric Tim receptors.

The present disclosure also provides a composition comprising a population of chimeric Tim receptor modified host cells. In certain embodiments, the population of chimeric Tim receptor modified host cells may be a population of B cells, a population of T cells, a population of natural killer cells, a population of lymphoid precursor cells, a population of antigen presenting cells, a population of dendritic cells, a population of Langerhans cells, a population of myeloid precursor cells, a population of mature myeloid cells, or any combination thereof. Furthermore, a population of chimeric Tim receptor modified host cells of a particular cell type may be composed of one or more subtypes. For example, a population of B cells may be composed of chimeric Tim receptor modified naïve B cells, plasma cells, regulatory B cells, marginal zone B cells, follicular B cells, lymphoplasmacytoid cells, plasmablast cells, memory B cells, or any combination thereof. In another example, a population of T cells may be composed of chimeric Tim receptor modified CD4$^+$ helper T cells, CD8$^+$ effector (cytotoxic) T cells, naïve (CD45 RA+, CCR7+, CD62L+, CD27+, CD45RO−) T cells, central memory (CD45RO$^+$, CD62L$^+$, CD8$^+$) T cells, effector memory (CD45RA+, CD45RO−, CCR7−, CD62L−, CD27−) T cells, T memory stem cells, regulatory T cells, mucosal-associated invariant T cells (MAIT), γδ (gd) cells, tissue resident T cells, natural killer T cells, or any combination thereof.

In certain embodiments, a population of host cells is composed of cells that each expresses the same chimeric Tim receptor(s). In other embodiments, a population of host cells is composed of a mixture of two or more subpopulation of host cells, wherein each subpopulation expresses a different chimeric Tim receptor or set of chimeric Tim receptors.

In certain embodiments, when preparing chimeric Tim receptor modified host cells, e.g., B cells or T cells, one or more growth factor cytokines that promotes proliferation of the host cells, e.g., B cells or T cells, may be added to the cell culture. The cytokines may be human or non-human. Exemplary growth factor cytokines that may be used to promote T cell proliferation include IL-2, IL-15, or the like. Exemplary growth factor cytokines that may be used to promote B cell proliferation include CD40L, IL-2, IL-4, IL-15, IL-21, BAFF, or the like.

Prior to genetic modification of the host cells with a chimeric Tim receptor vector, a source of host cells (e.g., T cells, B cells, natural killer cells, etc.) is obtained from a subject (e.g., whole blood, peripheral blood mononuclear cells, bone marrow, lymph node tissue, cord blood, thymus tissue, tissue from a site of infection, ascites, pleural effusion, spleen tissue), from which host cells are isolated using methods known in the art. Specific host cell subsets can be collected in accordance with known techniques and enriched or depleted by known techniques, such as affinity binding to antibodies, flow cytometry and/or immunomagnetic selection. After enrichment and/or depletion steps and introduction of a chimeric Tim receptor, in vitro expansion of the desired modified host cells can be carried out in accordance with known techniques, or variations thereof that will be apparent those skilled in the art.

Chimeric Tim receptors of the present disclosure confer cytotoxic activity to host cells expressing the chimeric Tim receptors that is specific for phosphatidylserine. Thus, upon binding phosphatidylserine exposed on the surface of a target cell, a host cell expressing a chimeric Tim receptor is capable of inducing apoptosis of the target cell. In certain embodiments, the host cell expressing the chimeric Tim receptor induces apoptosis of the target cell via: release of granzymes, perforins, granulysin, or any combination thereof; Fas ligand-Fas interaction; or both. In further embodiments, the chimeric Tim receptor further confers phosphatidylserine specific engulfment activity to host cells expressing the chimeric Tim receptor. In yet further embodiments, the host cell does not naturally exhibit an engulfment phenotype prior to modification with the chimeric Tim receptor.

Chimeric Tim receptors of the present disclosure may also be capable of costimulating T cells via at least one signaling pathway. In certain embodiments, chimeric Tim receptors provide costimulatory signals to T cells via at least two distinct signaling pathways (e.g., via the selected costimulatory signaling domain(s) in the chimeric Tim receptor). For example, a chimeric Tim receptor comprising a CD28 costimulatory signaling domain may be capable of providing a costimulatory signal via CD28 and Tim1. In certain embodiments, host immune cells expressing the chimeric Tim receptors exhibit reduction or inhibition of immune cell exhaustion. In certain embodiments, the host immune cell is a T cell or NK cells. In certain embodiments, exhausted T cells exhibit; (a) increased expression of PD-1, TIGIT, LAG3, TIM3, or any combination thereof; (b) decreased production of IFN-γ, IL-2, TNF-α, or any combination thereof; or both (a) and (b). In certain embodiments, exhausted NK cells exhibit; (a) increased expression of PD-1, NKG2A, TIM3, or any combination thereof; (b) decreased production of IFN-γ, TNF-α, or both; or both (a) and (b).

In certain embodiments, host cells expressing the chimeric Tim receptors exhibit an enhanced effector response (e.g., tumor specific). In certain embodiments, the effector response is enhanced T cell proliferation, cytokine production (e.g., IFN-γ, IL-2, TNF-α), cytotoxic activity, persistence, or any combination thereof. Host cells expressing chimeric Tim receptors may be administered to a subject alone, or in combination with other therapeutic agents, including for example CAR-T cells, TCRs, antibodies, radiation therapy, chemotherapies, small molecules, oncolytic viruses, electropulse therapy, etc.

In certain embodiments host cells expressing the chimeric Tim receptors exhibit a reduced immunosuppressive response to phosphatidylserine. Phosphatidylserine is one of the primary apoptotic cell ligands that signal "eat me" to phagocytes. The removal of apoptotic cells by phagocytes generally reduces or prevents an inflammatory response via secretion of anti-inflammatory cytokines IL-10 and TGF-β and the decrease of secretion of inflammatory cytokines TNF-α, IL-1β, and IL-12. Thus, phosphatidylserine may act as an immunosuppressive signal during the clearance of apoptotic cells. In certain embodiments, upon binding phosphatidylserine, a chimeric Tim receptor modified host cell exhibits increased antigen-specific cytokine production (e.g., IFN-γ, IL-2, TNF-α), thereby reducing the immunosuppressive response to phosphatidylserine.

In some embodiments, T cells expressing the chimeric Tim receptors exhibit increased or enhance antigen capture, antigen processing, and/or antigen presentation activity. Methods of measuring the ability of chimeric Tim receptor T cells to present target peptide antigens and induce target peptide specific activation to target peptide specific T cells are described in Example 2.

The expression of chimeric Tim receptors on host cells may be functionally characterized according to any of a large number of art-accepted methodologies for assaying host cell (e.g., T cell) activity, including determination of T cell binding, activation or induction and also including determination of T cell responses that are antigen-specific. Examples include determination of T cell proliferation, T cell cytokine release, antigen-specific T cell stimulation, CTL activity (e.g., by detecting $^{51}$Cr or Europium release from pre-loaded target cells), changes in T cell phenotypic marker expression, and other measures of T cell functions. Procedures for performing these and similar assays may be found, for example, in Lefkovits (*Immunology Methods Manual: The Comprehensive Sourcebook of Techniques*, 1998). See, also, *Current Protocols in Immunology*; Weir, *Handbook of Experimental Immunology*, Blackwell Scientific, Boston, MA (1986); Mishell and Shigii (eds.) *Selected Methods in Cellular Immunology*, Freeman Publishing, San Francisco, CA (1979); Green and Reed, *Science* 281:1309 (1998) and references cited therein. Cytokine levels may be determined according to methods known in the art, including for example, ELISA, ELISPOT, intracellular cytokine staining, flow cytometry, and any combination thereof (e.g., intracellular cytokine staining and flow cytometry). Immune cell proliferation and clonal expansion resulting from an antigen-specific elicitation or stimulation of an immune response may be determined by isolating lymphocytes, such as circulating lymphocytes in samples of peripheral blood cells or cells from lymph nodes, stimulating the cells with antigen, and measuring cytokine production, cell proliferation and/or cell viability, such as by incorporation of tritiated thymidine or non-radioactive assays, such as MTT assays and the like.

In certain embodiments, a chimeric Tim receptor modified host cell has a phagocytic index of about 20 to about 1,500 for a target cell. A "phagocytic index" is a measure of phagocytic activity of the transduced host cell as determined by counting the number of target cells or particles ingested per chimeric Tim receptor modified host cell during a set period of incubation of a suspension of target cells or particles and chimeric Tim receptor modified host cells in media. Phagocytic index may be calculated by multiplying [total number of engulfed target cells/total number of counted chimeric Tim receptor modified cells (e.g., phagocytic frequency)]×[average area of target cell or particle staining per chimeric Tim receptor+host cell×100 (e.g., hybrid capture)] or [total number of engulfed particles/total number of counted chimeric Tim receptor modified host cells]×[number of chimeric Tim receptor modified host cells containing engulfed particles/total number of counted chimeric Tim receptor cells]×100. In certain embodiments, a chimeric Tim receptor modified cell has a phagocytic index of about 30 to about 1,500; about 40 to about 1,500; about 50 to about 1,500; about 75 to about 1,500; about 100 to about 1,500; about 200 to about 1,500; about 300 to about 1,500; about 400 to about 1,500; about 500 to about 1,500; about 20 to about 1,400; about 30 to about 1,400; about 40 to about 1,400; about 50 to about 1,400; about 100 to about 1,400; about 200 to about 1,400; about 300 to about 1,400; about 400 to about 1,400; about 500 to about 1,400; about 20 to about 1,300; about 30 to about 1,300; about 40 to about 1,300; about 50 to about 1,300; about 100 to about 1,300; about 200 to about 1,300; about 300 to about 1,300; about 400 to about 1,300; about 500 to about 1,300; about 20 to about 1,200; about 30 to about 1,200; about 40 to about 1,200; about 50 to about 1,200; about 100 to about 1,200; about 200 to about 1,200; about 300 to about 1,200; about 400 to about 1,200; about 500 to about 1,200; about 20 to about 1,100; about 30 to about 1,100; about 40 to about 1,100; about 50 to about 1,100; about 100 to about 1,100; about 200 to about 1,100; about 300 to about 1,100; about 400 to about 1,100; or about 500 to about 1,100; about 20 to about 1,000; about 30 to about 1,000; about 40 to about 1,000; about 50 to about 1,000; about 100 to about 1,000; about 200 to about 1,000; about 300 to about 1,000; about 400 to about 1,000; or about 500 to about 1,000; about 20 to about 750; about 30 to about 750; about 40 to about 750; about 50 to about 750; about 100 to about 750; about 200 to about 750; about 300 to about 750; about 400 to about 750; or about 500 to about 750; about 20 to about 500; about 30 to about 500; about 40 to about 500; about 50 to about 500; about 100 to about 500; about 200 to about 500; or about 300 to about 500. In further embodiments, the incubation time is from about 2 hours to about 4 hours, about 2 hours, about 3 hours, or about 4 hours. In yet further embodiments, a chimeric Tim receptor modified cell exhibits phagocytic index that is statistically significantly higher than a cell transduced with truncated EGFR control. Phagocytic index may be calculated using methods known in the art and as further described in the Examples and PCT Application No. PCT/US2017/053553 (incorporated herein by reference in its entirety), including quantification by flow cytometry or fluorescence microscopy.

Host cells may be from an animal, such as a human, primate, cow, horse, sheep, dog, cat, mouse, rat, rabbit, guinea pig, pig, or a combination thereof. In a preferred embodiment, the animal is a human. Host cells may be obtained from a healthy subject or a subject having a disease associated with expression or overexpression of an antigen.
Methods of Use In one aspect, the present disclosure provides methods for conferring or enhancing phosphatidylserine-specific cytotoxic activity of a cell comprising introducing into a host cell a nucleic acid molecule encoding at least one chimeric Tim receptor or a chimeric Tim receptor vector according to any of the embodiments described herein; and expressing the at least one chimeric Tim receptor in the host cell, wherein the at least one chimeric Tim receptor enhances the phosphatidylserine-specific cytotoxic activity of the host cell as compared to a the host cell prior to modification to express a chimeric Tim receptor. In certain embodiments, the cytotoxic activity of the host cell is increased at least about 10%, 15%, 20%, 25%, 30%, 35%, 40%, 50%, 55%, 60%, 65%, 70%, 75%, 80%, 85%, 90%, 95%, 100%, 110%, 120%, 130%, 140%, 150%, 160%, 170%, 180%, 190%, 200% or more as compared to the host cell prior to modification with a nucleic acid molecule encoding a chimeric Tim receptor or a chimeric Tim receptor vector. In some embodiments, the host cell is an immune cell. In some embodiments, the host cell is a T cell or an NK cell. Methods of measuring cytotoxic activity of host cells, particularly immune cells such as T cells and NK cells, include a chromium ($^{51}$Cr)-release assay, a β-gal or firefly luciferase release assay, flow cytometric methods of mediating target cell death and effector cell activity (see, e.g., Expert Rev. Vaccines, 2010, 9:601-616).

In certain embodiments, methods for conferring or enhancing phosphatidylserine-specific cytotoxic activity of a cell further comprise conferring or enhancing phosphatidylserine-specific engulfment activity of the host cell expressing the at least one chimeric Tim receptor. In certain such embodiments, the host cell does not naturally exhibit an engulfment phenotype prior to modification with the chimeric Tim receptor. For example in certain such embodiments, the engulfment activity of the host cell is increased at least about 10%, 15%, 20%, 25%, 30%, 35%, 40%, 50%, 55%, 60%, 65%, 70%, 75%, 80%, 85%, 90%, 95%, 100%, 110%, 120%, 130%, 140%, 150%, 160%, 170%, 180%, 190%, 200% or more as compared to the host cell prior to modification to express the chimeric Tim receptor vector. In certain embodiments, the host cell does not naturally possess engulfment activity. In some embodiments, the host cell is an immune cell. In some embodiments, the host cell is a T cell or an NK cell. Methods of measuring engulfment activity of host cells include methods as described in International Application Publication No. WO2018/064076 (incorporated herein by reference in its entirety).

In another aspect, a chimeric Tim receptor, a polynucleotide encoding a chimeric Tim receptor, a chimeric Tim receptor vector, or a host cell that expresses a chimeric Tim receptor according to any of the embodiments provided herein may be used in a method of enhancing effector function of the host cell. In certain embodiments, enhanced effector function comprises increased cytotoxic activity, increased antigen specific cytokine production (e.g., IFN-γ, IL-2, TNF-α, or any combination thereof), increased anti-apoptotic signaling, increased persistence, increased expansion, increased proliferation, or any combination thereof. In certain embodiments, the effector function of the host cell is enhanced at least about 10%, 15%, 20%, 25%, 30%, 35%, 40%, 50%, 55%, 60%, 65%, 70%, 75%, 80%, 85%, 90%, 95%, 100%, 110%, 120%, 130%, 140%, 150%, 160%, 170%, 180%, 190%, 200% or more as compared to a host cell that is not modified with a nucleic acid molecule encoding a chimeric Tim receptor or a chimeric Tim receptor vector. In some embodiments, the host cell is an immune cell. In certain embodiments, the host cell is a T cell or an NK cell.

In another aspect, host cells modified with chimeric Tim receptors of the present disclosure can be used in methods for inhibiting or reducing immune cell exhaustion. In some embodiments, the immune cell is a T cell or NK cell. In certain embodiments, reduced exhaustion in T cells comprises; (a) decreased expression of PD-1, TIGIT, LAG3, TIM3, or any combination thereof in T cells; (b) increased production of IFN-γ, IL-2, TNF-α, or any combination thereof in T cells; or both (a) and (b). In certain embodiments, reduced exhaustion in NK cells comprises; (a) decreased expression of PD-1, NKG2A, TIM3, or any combination thereof in NK cells; (b) increased production of IFN-γ, TNF-α, or both in NK cells; or both (a) and (b). In certain embodiments, the expression of an immune checkpoint molecule is decreased at least about 5%, 10%, 15%, 20%, 25%, 30%, 35%, 40%, 50%, 55%, 60%, 65%, 70%, 75%, 80%, 85%, 90%, 95%, or 100% in a host immune cell expressing the chimeric Tim receptor as compared to a host immune cell that is not modified with a nucleic acid molecule encoding a chimeric Tim receptor or a chimeric Tim receptor vector. In certain embodiments, the expression of the cytokine is increased at least about 5%, 10%, 15%, 20%, 25%, 30%, 35%, 40%, 50%, 55%, 60%, 65%, 70%, 75%, 80%, 85%, 90%, 95%, 100%, 110%, 120%, 130%, 140%, 150%, 160%, 170%, 180%, 190%, 200% or more in a host immune cell expressing the chimeric Tim receptor as compared to a host immune cell that is not modified with a nucleic acid molecule encoding a chimeric Tim receptor or a chimeric Tim receptor vector.

In another aspect, a chimeric Tim receptor, a polynucleotide encoding a chimeric Tim receptor, a chimeric Tim receptor vector, or a host cell that expresses a chimeric Tim receptor according to any of the embodiments provided herein may be used in a method of reducing an immunosuppressive response to phosphatidylserine in a host cell. In certain embodiments, the immunosuppressive response comprises secretion of anti-inflammatory cytokines (e.g., IL-10, TGF-β, or both), the decrease in secretion of inflammatory cytokines (e.g., TNF-α, IL-1β, and IL-12), or both. In certain embodiments, the immunosuppressive response of the host cell to phosphatidylserine is decreased at least about 5%, 10%, 15%, 20%, 25%, 30%, 35%, 40%, 50%, 55%, 60%, 65%, 70%, 75%, 80%, 85%, 90%, 95%, 100% as compared to a host cell that is not modified with a nucleic acid molecule encoding a chimeric Tim receptor or a chimeric Tim receptor vector. In some embodiments, the host cell is an immune cell. In certain embodiments, the host cell is a T cell or an NK cell.

In yet another aspect, a chimeric Tim receptor, a polynucleotide encoding a chimeric Tim receptor, a chimeric Tim receptor vector, or a host cell that expresses a chimeric Tim receptor according to any of the embodiments provided herein may be used in methods for eliminating target cells bearing surface exposed phosphatidylserine, e.g., for the elimination of cancer cells bearing surface presented phosphatidylserine. In certain embodiments, the target cells are damaged, stressed, apoptotic, necrotic cells (e.g., tumor cells) bearing surface exposed phosphatidylserine. In certain embodiments, host cells expressing chimeric Tim receptors clear damaged, stressed, apoptotic, or necrotic target cells bearing surface exposed phosphatidylserine via inducing apoptosis, or both inducing apoptosis and engulfment. Host cells expressing chimeric Tim receptors may be administered to a subject alone, or in combination with other therapeutic agents, including for example CAR-T cells, TCRs, antibodies, radiation therapy, chemotherapy, small molecules, oncolytic viruses, electropulse therapy, etc.

In another aspect, a chimeric Tim receptor, a polynucleotides encoding a chimeric Tim receptor, a chimeric Tim receptor vector, or a host cell that expresses a chimeric Tim receptor according to any of the embodiments provided herein may be used in methods to enhance the effect of a therapeutic agent that induces cellular stress, damage, necrosis, or apoptosis. Certain therapies, such as chemotherapy, radiation therapy, UV light therapy, electropulse therapy, adoptive cellular immunotherapy (e.g., CAR-T cells, TCRs) and oncolytic viral therapy, can induce cell damage or death to tumor cells, diseased cells, and cells in their surrounding environment. Cells expressing chimeric Tim receptors can be administered in combination with the cell damaging/cytotoxic therapy to bind to the phosphatidylserine moieties exposed on the outer leaflet of targeted cells and clear stressed, damaged, diseased, apoptotic, necrotic cells.

In another aspect, the present disclosure provides methods for conferring or enhancing antigen capture, antigen processing, and/or antigen presentation activity of a cell comprising introducing into a host cell a nucleic acid molecule encoding at least one chimeric Tim receptor or a chimeric Tim receptor vector according to any of the embodiments described herein; and expressing the at least one chimeric Tim receptor in the host cell, wherein the at least one chimeric Tim receptor enhances the antigen capture, antigen processing, and/or antigen presentation activity of the host cell as compared to a the host cell prior to modification to express a chimeric Tim receptor. In some embodiments, the chimeric Tim receptor comprises an ITAM containing intracellular signaling domain and/or a costimulatory domain; and a TLR2 or TLR8 intracellular signaling domain. In some embodiments, addition of a TLR signaling domain, e.g., TLR2 intracellular signaling domain or TLR8 intracellular signaling domain, to a chimeric Tim receptor design having traditional T cell signaling (e.g., CD28 and/or CD3ζ) enhances antigen capture, antigen processing, and/or antigen presentation by T cells.

In another aspect, a chimeric Tim receptor, a polynucleotides encoding a chimeric Tim receptor, a chimeric Tim receptor vector, or a host cell that expresses a chimeric Tim receptor according to any of the embodiments provided herein may be used in a method of treating a subject suffering from a disease, disorder or undesired condition. Embodiments of these methods include administering to a subject a therapeutically effective amount of a pharmaceutical composition including one or more chimeric Tim receptors, polynucleotides encoding one or more chimeric Tim receptors, vectors comprising polynucleotides encoding one or more chimeric Tim receptors, or a population of host cells genetically modified to express one or more chimeric Tim receptors according to the present description.

Diseases that may be treated with cells expressing a chimeric Tim receptor as described in the present disclosure include cancer and infectious diseases (viral, bacterial, fungal, protozoan infections). Adoptive immune and gene therapies are promising treatments for various types of cancer (Morgan et al., *Science* 314:126, 2006; Schmitt et al., *Hum. Gene Ther.* 20:1240, 2009; June, *J. Clin. Invest.* 117:1466, 2007) and infectious disease (Kitchen et al., *PLOS One* 4:38208, 2009; Rossi et al., *Nat. Biotechnol.* 25:1444, 2007; Zhang et al., *PLOS Pathog.* 6: e1001018, 2010; Luo et al., *J. Mol. Med.* 89:903, 2011).

A wide variety of cancers, including solid tumors and leukemias are amenable to the compositions and methods disclosed herein. Exemplary cancers that may be treated using the receptors, modified host cells, and composition described herein include adenocarcinoma of the breast, prostate, and colon; all forms of bronchogenic carcinoma of the lung; myeloid leukemia; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, Merkel cell, mucinous, non-small cell lung, oat cell, papillary, scirrhous, bronchiolar, bronchogenic, squamous cell, and transitional cell). Additional types of cancers that may be treated using the receptors, modified host cells, and composition described herein include histiocytic disorders; malignant histiocytosis; leukemia; Hodgkin's disease; immunoproliferative small; non-Hodgkin's lymphoma; plasmacytoma; multiple myeloma; chronic myeloid leukemia (CML); acute myeloid leukemia (AML); plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor. Further, the following types of cancers are also contemplated as amenable to treatment using the receptors, modified host cells, and composition described herein: adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin. The types of cancers that may be treated also include angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; cervical dysplasia, and peritoneal cancer.

Examples of hyperproliferative disorders amenable to therapy using the receptors, modified host cells, and composition described herein include B-cell cancers (B-cell malignancies), including B-cell lymphomas (such as various forms of Hodgkin's disease, non-Hodgkin's lymphoma (NHL) or central nervous system lymphomas), leukemias (such as acute lymphoblastic leukemia (ALL), chronic lymphocytic leukemia (CLL), Hairy cell leukemia, B cell blast transformation of chronic myeloid leukemia, acute myeloid leukemia (AML), chronic myeloid leukemia, and myelomas (such as multiple myeloma). Additional B cell cancers that may be treated using the receptors, modified host cells, and composition described herein include small lymphocytic lymphoma, B-cell prolymphocytic leukemia, lymphoplasmacytic lymphoma, splenic marginal zone lymphoma, plasma cell myeloma, solitary plasmacytoma of bone, extraosseous plasmacytoma, extra-nodal marginal zone B-cell lymphoma of mucosa-associated (MALT) lymphoid tissue, nodal marginal zone B-cell lymphoma, follicular lymphoma, mantle cell lymphoma, diffuse large B-cell lymphoma, mediastinal (thymic) large B-cell lymphoma, intravascular large B-cell lymphoma, primary effusion lymphoma, Burkitt's lymphoma/leukemia, B-cell proliferations of uncertain malignant potential, lymphomatoid granulomatosis, and post-transplant lymphoproliferative disorder.

Infectious diseases include those associated with infectious agents and include any of a variety of bacteria (e.g., pathogenic *E. coli, S. typhimurium, P. aeruginosa, B. anthracis, C. botulinum, C. difficile, C. perfringens, H. pylori, V. cholerae, Listeria* spp., *Rickettsia* spp., *Chlamydia* spp., and the like), mycobacteria, and parasites (including any known parasitic member of the Protozoa). Infectious viruses include eukaryotic viruses, such as adenovirus, bunyavirus, herpesvirus, papovavirus, papillomavirus (e.g., HPV), paramyxovirus, picornavirus, rhabdovirus (e.g., Rabies), orthomyxovirus (e.g., influenza), poxvirus (e.g., Vaccinia), reovirus, retrovirus, lentivirus (e.g., HIV), flavivirus (e.g., HCV, HBV) or the like. In certain embodiments, a composition comprising a chimeric Tim receptor according to the present disclosure is used for treating infection with a microbe capable of establishing a persistent infection in a subject.

A chimeric Tim receptor of the present disclosure may be administered to a subject in cell-bound form (e.g., gene therapy of target cell population). Thus, for example, a chimeric Tim receptor of the present disclosure may be administered to a subject expressed on the surface of T cells, Natural Killer Cells, Natural Killer T cells, B cells, lymphoid precursor cells, antigen presenting cells, dendritic cells, Langerhans cells, myeloid precursor cells, mature myeloid cells, including subsets thereof, or any combination thereof. In certain embodiments, methods of treating a subject comprise administering an effective amount of chimeric Tim receptor modified cells (i.e., recombinant cells that express one or more chimeric Tim receptors). The chimeric Tim receptor modified cells may be xenogeneic, syngeneic, allogeneic, or autologous to the subject.

Pharmaceutical compositions including chimeric Tim receptor modified cells may be administered in a manner appropriate to the disease or condition to be treated (or prevented) as determined by persons skilled in the medical art. An appropriate dose, suitable duration, and frequency of administration of the compositions will be determined by such factors as the condition of the patient, size, weight, body surface area, age, sex, type and severity of the disease, particular therapy to be administered, particular form of the active ingredient, time and the method of administration, and other drugs being administered concurrently. The present disclosure provides pharmaceutical compositions comprising chimeric Tim receptor modified cells and a pharmaceutically acceptable carrier, diluent, or excipient. Suitable excipients include water, saline, dextrose, glycerol, or the like and combinations thereof. Other suitable infusion medium can be any isotonic medium formulation, including saline, Normosol R (Abbott), Plasma-Lyte A (Baxter), 5% dextrose in water, or Ringer's lactate.

A treatment effective amount of cells in a pharmaceutical composition is at least one cell (for example, one chimeric Tim receptor modified T cell) or is more typically greater than $10^2$ cells, for example, up to $10^6$, up to $10^7$, up to $10^8$ cells, up to $10^9$ cells, up to $10^{10}$ cells, or up to $10^{11}$ cells or more. In certain embodiments, the cells are administered in a range from about $10^6$ to about $10^{10}$ cells/m$^2$, preferably in a range of about $10^7$ to about $10^9$ cells/m$^2$. The number of cells will depend upon the ultimate use for which the composition is intended as well as the type of cells included therein. For example, a composition comprising cells modified to contain a chimeric Tim receptor will comprise a cell population containing from about 5% to about 95% or more of such cells. In certain embodiments, a composition comprising chimeric Tim receptor modified cells comprises a cell population comprising at least 5%, 10%, 15%, 20%, 25%, 30%, 35%, 40%, 45%, 50%, 55%, 60%, 65%, 70%, 75%, 80%, 85%, 90%, 95% or more of such cells. For uses provided herein, the cells are generally in a volume of a liter or less, 500 mls or less, 250 mls or less, or 100 mls or less. Hence the density of the desired cells is typically greater than $10^4$ cells/ml and generally is greater than $10^7$ cells/ml, generally $10^8$ cells/ml or greater. The cells may be administered as a single infusion or in multiple infusions over a range of time. Repeated infusions of chimeric Tim receptor modified cells may be separated by days, weeks, months, or even years if relapses of disease or disease activity are present. A clinically relevant number of immune cells can be apportioned into multiple infusions that cumulatively equal or exceed $10^6$, $10^7$, $10^8$, $10^9$, $10^{10}$, or $10^{11}$ cells. A preferred dose for administration of a host cell comprising a recombinant expression vector as described herein is about $10^7$ cells/m$^2$, about $5 \times 10^7$ cells/m$^2$, about $10^8$ cells/m$^2$, about $5 \times 10^8$ cells/m$^2$, about $10^9$ cells/m$^2$, about $5 \times 10^9$ cells/m$^2$, about $10^{10}$ cells/m$^2$, about $5 \times 10^{10}$ cells/m$^2$, or about $10^{11}$ cells/m$^2$.

Chimeric Tim receptor compositions as described herein may be administered intravenously, intraperitoneally, intranasally, intratumorly, into the bone marrow, into the lymph node, and/or into cerebrospinal fluid.

Chimeric Tim receptor compositions may be administered to a subject in combination with one or more additional therapeutic agents. Examples of therapeutic agents that may be administered in combination with a chimeric Tim compositions according to the present description include radiation therapy, adoptive cellular immunotherapy agent (e.g., recombinant TCR, enhanced affinity TCR, CAR, TCR-CAR, scTCR fusion protein, dendritic cell vaccine), antibody therapy, immune checkpoint molecule inhibitor therapy, UV light therapy, electric pulse therapy, high intensity focused ultrasound therapy, oncolytic virus therapy, or a pharmaceutical therapy, such as a chemotherapeutic agent, a therapeutic peptide, a hormone, an aptamer, antibiotic, anti-viral agent, anti-fungal agent, anti-inflammatory agent, a small molecule therapy, or any combination thereof. In certain embodiments, the chimeric Tim receptor modified host cells may clear stressed, damaged, apoptotic, necrotic, infected, dead cells displaying surface phosphatidylserine induced by the one or more additional therapeutic agents.

In certain embodiments, the chimeric Tim receptor and adoptive cellular immunotherapy agent (e.g., a CAR, TCR-CAR, TCR, etc. described above) are administered to the subject in the same host cell or different host cells. In certain embodiments, the chimeric Tim receptor and adoptive cellular immunotherapy agent are expressed in the same host cell from the same vector or from separate vectors. In certain embodiments, the chimeric Tim receptor and adoptive cellular immunotherapy agent are expressed in the same host cell from a multicistronic vector. In certain embodiments, the chimeric Tim receptor is expressed in the same host cell type as the adoptive cellular immunotherapy agent (e.g., the chimeric Tim receptor is expressed CD4 T cells and the CAR/or TCR is expressed in CD4 T cells, or the chimeric Tim receptor is expressed CD8 T cells and the CAR/or TCR is expressed in CD8 T cells). In other embodiments, the chimeric Tim receptor is expressed in a different host cell type as the adoptive immunotherapy agent (e.g., the chimeric Tim receptor is expressed CD4 T cells and the CAR/or TCR is expressed in CD8 T cells). Cellular immunotherapy compositions comprising a combination of immune cells or cellular subsets engineered with chimeric Tim receptors and a cellular immunotherapy agent (e.g., CAR, TCR, etc.), methods of making, and methods of use are described in PCT International Publication No. WO2019/191340, which is incorporated herein by reference in its entirety.

Exemplary antigens that a recombinant TCR, enhanced affinity TCR, CAR, TCR-CAR, or scTCR fusion protein may target include WT-1, mesothelin, MART-1, NY-ESO-1, MAGE-A3, HPV E7, survivin, a Fetoprotein, and a tumor-specific neoantigen.

CARs of the present disclosure may target a variety of antigens, including a viral antigen, bacterial antigen, fungal antigen, parasitic antigen, tumor antigen, autoimmune disease antigen. Exemplary antigens that a CAR may target include CD138, CD38, CD33, CD123, CD72, CD79a, CD79b, mesothelin, PSMA, BCMA, ROR1, MUC-16, LICAM, CD22, CD19, CD20, CD23, CD24, CD37, CD30, CA125, CD56, c-Met, EGFR, GD-3, HPV E6, HPV E7, MUC-1, HER2, folate receptor α, CD97, CD171, CD179a, CD44v6, WT1, VEGF-α, VEGFR1, IL-13Rα1, IL-13Rα2, IL-11Rα, PSA, FcRH5, NKG2D ligand, NY-ESO-1, TAG-72, CEA, ephrin A2, ephrin B2, Lewis A antigen, Lewis Y antigen, MAGE, MAGE-A1, RAGE-1, folate receptor β, EGFRviii, VEGFR-2, LGR5, SSX2, AKAP-4, FLT3, fucosyl GM1, GM3, o-acetyl-GD2, and GD2.

Radiation therapy includes external beam radiation therapy (e.g., conventional external beam radiation therapy, stereotactic radiation, 3-dimensional conformal radiation therapy, intensity-modulated radiation therapy, volumetric modulated arc therapy, particle therapy, proton therapy, and auger therapy), brachytherapy, systemic radioisotope therapy, intraoperative radiotherapy, or any combination thereof.

Exemplary antibodies for use in conjunction with the chimeric Tim compositions described herein include rituxmab, pertuzumab, trastuzumab, alemtuzumab, Ibritumomab tiuxetan, Brentuximab vedotin, cetuximab, bevacizumab, abciximab, adalimumab, alefacept, basilizimab, belimumab, bezlotoxumab, canakinumab, certolizumab pegol, daclizumab, denosumab, efalizumab, golimumab, olaratumab, palivizumab, panitumumab, and tocilizumab.

Exemplary inhibitors of immune checkpoint molecules that may be for use in conjunction with the chimeric Tim compositions described herein include checkpoint inhibitors targeting PD-L1, PD-L2, CD80, CD86, B7-H3, B7-H4, HVEM, adenosine, GAL9, VISTA, CEACAM-1, CEACAM-3, CEACAM-5, PVRL2, PD-1, CTLA-4, BTLA, KIR, LAG3, TIM3, A2aR, CD244/2B4, CD160, TIGIT, LAIR-1, PVRIG/CD112R, or any combination thereof. In certain embodiments, an immune checkpoint inhibitor may be an antibody, a peptide, an RNAi agent, or a small molecule. An antibody specific for CTLA-4 may be ipilimumab or tremelimumab. An antibody specific for PD-1 may be pidilizumab, nivolumab, or pembrolizumab. An antibody specific for PD-L1 may be durvalumab, atezolizumab, or avelumab.

Exemplary chemotherapeutics for use in conjunction with the chimeric Tim receptor compositions described herein may include an alkylating agent, a platinum based agent, a cytotoxic agent, an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and a DNA repair inhibitor.

A chemotherapeutic includes non-specific cytotoxic agents that inhibit mitosis or cell division, as well as molecularly targeted therapy that blocks the growth and spread of cancer cells by targeting specific molecules that are involved in tumor growth, progression, and metastasis (e.g., oncogenes). Exemplary non-specific chemotherapeutics for use in conjunction with the expression cassette compositions described herein may include an alkylating agent, a platinum based agent, a cytotoxic agent, an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), hypomethylating agent, and a DNA repair inhibitor.

Examples of chemotherapeutic agents considered for use in combination therapies contemplated herein include vemurafenib, dabrafenib, trametinib, cobimetinib, anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), fdabra tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), ibrutinib, venetoclax, crizotinib, alectinib, brigatinib, ceritinib, and vinorelbine (Navelbine®).

Exemplary alkylating agents for use in combination therapies contemplated herein include nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents for use in combination therapies contemplated herein include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNUR); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Exemplary platinum-based agents for use in combination therapies contemplated herein include carboplatin, cisplatin, oxaliplatin, nedaplatin, picoplatin, satraplatin, phenanthriplatin, and triplatin tetranitrate.

Exemplary hypomethylating agents for use in combination therapies include azacitidine and decitabine.

Exemplary molecularly targeted inhibitors for use in conjunction with the chimeric Tim receptor compositions described herein include small molecules that target molecules involved in cancer cell growth and survival, including for example, receptor tyrosine kinase inhibitors, RAF inhibitors, BCL-2 inhibitors, ABL inhibitors, TRK inhibitors, c-KIT inhibitors, c-MET inhibitors, CDK4/6 inhibitors, FAK inhibitors, FGFR inhibitors, FLT3 inhibitors, IDH1 inhibitors, IDH2 inhibitors, PDGFRA inhibitors, and RET inhibitors Exemplary molecularly targeted therapy includes hormone antagonists, signal transduction inhibitors, gene expression inhibitors (e.g., translation inhibitors), apoptosis inducers, angiogenesis inhibitors (e.g., a VEGF pathway inhibitor), tyrosine kinase inhibitors (e.g., an EGF/EGFR pathway inhibitor), growth factor inhibitors, GTPase inhibitors, serine/threonine kinase inhibitors, transcription factor inhibitors, inhibitors of driver mutations associated with cancer, B-Raf inhibitors, RAF inhibitors, a MEK inhibitors, mTOR inhibitors, adenosine pathway inhibitors, EGFR inhibitors, PI3K inhibitors, BCL2 inhibitors, VEGFR inhibitors, MET inhibitors, MYC inhibitors, BCR-ABL inhibitors, ABL inhibitors, HER2 inhibitors, H-RAS inhibitors, K-RAS inhibitors, PDGFR inhibitors, ALK inhibitors, ROS1 inhibitors, BTK inhibitors, TRK inhibitors, c-KIT inhibitors, c-MET inhibitors, CDK4/6 inhibitors, FAK inhibitors, FGFR inhibitors, FLT3 inhibitors, IDH1 inhibitors, IDH2 inhibitors, PARP inhibitors, PDGFRA inhibitors, and RET inhibitors. In certain embodiments, use of molecularly targeted therapy comprises administering a molecularly targeted therapy specific for the molecular target to a subject identified as having a tumor that possesses the molecular target (e.g., driver oncogene). In certain embodiments, the molecular target has an activating mutation. In certain embodiments, use of chimeric Tim receptor modified cells in combination with a molecularly targeted inhibitor increases the magnitude of anti-tumor response, the durability of anti-tumor response, or both. In certain embodiments, a lower than typical dose of molecularly targeted therapy is used in combination with chimeric Tim receptor modified cells.

Exemplary angiogenesis inhibitors include, without limitation A6 (Angstrom Pharmaceuticals), ABT-510 (Abbott Laboratories), ABT-627 (Atrasentan) (Abbott Laboratories/Xinlay), ABT-869 (Abbott Laboratories), Actimid (CC4047, Pomalidomide) (Celgene Corporation), AdGVPEDF.11D (GenVec), ADH-1 (Exherin) (Adherex Technologies), AEE788 (Novartis), AG-013736 (Axitinib) (Pfizer), AG3340 (Prinomastat) (Agouron Pharmaceuticals), AGX1053 (AngioGenex), AGX51 (AngioGenex), ALN-VSP (ALN-VSP (2) (Alnylam Pharmaceuticals), AMG 386 (Amgen), AMG706 (Amgen), Apatinib (YN968D1) (Jiangsu Hengrui Medicine), AP23573 (Ridaforolimus/MK8669) (Ariad Pharmaceuticals), AQ4N (Novavea), ARQ 197 (ArQule), ASA404 (Novartis/Antisoma), Atiprimod (Callisto Pharmaceuticals), ATN-161 (Attenuon), AV-412 (Aveo Pharmaceuticals), AV-951 (Aveo Pharmaceuticals), Avastin (Bevacizumab) (Genentech), AZD2171 (Cediranib/Recentin) (AstraZeneca), BAY 57-9352 (Telatinib) (Bayer), BEZ235 (Novartis), BIBF1120 (Boehringer Ingelheim Pharmaceuticals), BIBW 2992 (Boehringer Ingelheim Pharmaceuticals), BMS-275291 (Bristol-Myers Squibb), BMS-582664 (Brivanib) (Bristol-Myers Squibb), BMS-690514 (Bristol-Myers Squibb), Calcitriol, CCI-779 (Torisel) (Wyeth), CDP-791 (ImClone Systems), Ceflatonin (Homoharringtonine/HHT) (ChemGenex Therapeutics), Celebrex (Celecoxib) (Pfizer), CEP-7055 (Cephalon/Sanofi), CHIR-265 (Chiron Corporation), NGR-TNF, COL-3 (Metastat) (Collagenex Pharmaceuticals), Combretastatin (Oxigene), CP-751,871 (Figitumumab) (Pfizer), CP-547,632 (Pfizer), CS-7017 (Daiichi Sankyo Pharma), CT-322 (Angiocept) (Adnexus), Curcumin, Dalteparin (Fragmin) (Pfizer), Disulfiram (Antabuse), E7820 (Eisai Limited), E7080 (Eisai Limited), EMD 121974 (Cilengitide) (EMD Pharmaceuticals), ENMD-1198 (EntreMed), ENMD-2076 (EntreMed), Endostar (Simcere), Erbitux (ImClone/Bristol-Myers Squibb), EZN-2208 (Enzon Pharmaceuticals), EZN-2968

(Enzon Pharmaceuticals), GC1008 (Genzyme), Genistein, GSK1363089 (Foretinib) (GlaxoSmithKline), GW786034 (Pazopanib) (GlaxoSmithKline), GT-111 (Vascular Biogenics Ltd.), IMC-1121B (Ramucirumab) (ImClone Systems), IMC-18F1 (ImClone Systems), IMC-3G3 (ImClone LLC), INCB007839 (Incyte Corporation), INGN 241 (Introgen Therapeutics), Iressa (ZD1839/Gefitinib), LBH589 (Faridak/Panobinostst) (Novartis), Lucentis (Ranibizumab) (Genentech/Novartis), LY317615 (Enzastaurin) (Eli Lilly and Company), Macugen (Pegaptanib) (Pfizer), MEDI522 (Abegrin) (MedImmune), MLN518 (Tandutinib) (Millennium), Neovastat (AE941/Benefin) (Aeterna Zentaris), Nexavar (Bayer/Onyx), NM-3 (Genzyme Corporation), Noscapine (Cougar Biotechnology), NPI-2358 (Nereus Pharmaceuticals), OSI-930 (OSI), Palomid 529 (Paloma Pharmaceuticals, Inc.), Panzem Capsules (2ME2) (EntreMed), Panzem NCD (2ME2) (EntreMed), PF-02341066 (Pfizer), PF-04554878 (Pfizer), PI-88 (Progen Industries/Medigen Biotechnology), PKC412 (Novartis), Polyphenon E (Green Tea Extract) (Polypheno E International, Inc.), PPI-2458 (Praecis Pharmaceuticals), PTC299 (PTC Therapeutics), PTK787 (Vatalanib) (Novartis), PXD101 (Belinostat) (CuraGen Corporation), RAD001 (Everolimus) (Novartis), RAF265 (Novartis), Regorafenib (BAY73-4506) (Bayer), Revlimid (Celgene), Retaane (Alcon Research), SN38 (Liposomal) (Neopharm), SNS-032 (BMS-387032) (Sunesis), SOM230 (Pasireotide) (Novartis), Squalamine (Genaera), Suramin, Sutent (Pfizer), Tarceva (Genentech), TB-403 (Thrombogenics), Tempostatin (Collard Biopharmaceuticals), Tetrathiomolybdate (Sigma-Aldrich), TG100801 (TargeGen), Thalidomide (Celgene Corporation), Tinzaparin Sodium, TKI258 (Novartis), TRC093 (Tracon Pharmaceuticals Inc.), VEGF Trap (Aflibercept) (Regeneron Pharmaceuticals), VEGF Trap-Eye (Regeneron Pharmaceuticals), Veglin (VasGene Therapeutics), Bortezomib (Millennium), XL184 (Exelixis), XL647 (Exelixis), XL784 (Exelixis), XL820 (Exelixis), XL999 (Exelixis), ZD6474 (AstraZeneca), Vorinostat (Merck), and ZSTK474.

Exemplary B-Raf inhibitors include vemurafenib, dabrafenib, and encorafenib.

Exemplary MEK inhibitors include binimetinib, cobimetinib, refametinib, selumetinib, and trametinib.

Exemplary BTK inhibitors include ibrutinib, pirtobrutinib (Loxo-305), tirabrutinib, tolebrutinib, evobrutinib, fenebrutinib (GDC-0853), acalabrutinib, vecabrutinib (SNS-062), ONO-4059, spebrutinib, zanubrutinib (BGB-3111), HM71224, and M7583.

Exemplary TRK inhibitors include entrectinib, larotrectinib, CH7057288, ONO-7579, LOXO-101, lestaurtinib, and LOXO-195.

Exemplary c-KIT inhibitors include imatinb, sunitinb, and ponatinib.

Exemplary c-MET inhibitors include capmatinib, crizotinib, tivantinib, onartuzumab, INCB28060, AMG-458, savolitinib, and tepotinib.

Exemplary CDK4/6 inhibitors include palbociclib, ribociclib, abemaciclib, and trilaciclib.

Exemplary FAK inhibitors include defactinib, GSK2256098, BI853520, and PF-00562271.

Exemplary FGFR inhibitors include erdafitinib, pemigatinib, infigratinib, rogaratinib, AZD4547, BGJ398, FP-1039, and ARQ 087.

Exemplary FLT-3 inhibitors include quizartinib, crenolanib, gilteritinib, midostaurin, and lestaurtinib.

Exemplary IDH1 inhibitors include ivosidenib, BAY-1436032, and AGI-5198.

An exemplary IDH2 inhibitor includes enasidenib.

Exemplary PARP inhibitors include talazoparib, niraparib, rucaparib, olaparib, veliparib, CEP 9722, and E7016.

Exemplary PDGFRA inhibitors include imatinib, regorafenib, crenolanib, and olaratumab.

Exemplary pan-RAF inhibitors include belvarafenib, LXH254, LY3009120, INU-152, and HM95573.

Exemplary RET inhibitors include lenvatinib, alectinib, vandetanib, cabozantinib, BLU-667, and LOXO-292.

Exemplary ROS1 inhibitors include ceritinib, lorlatinib, entrectinib, crizotinib, TPX-0005, and DS-6051b.

Exemplary Vascular Endothelial Growth Factor (VEGF) receptor inhibitors include, but are not limited to, Bevacizumab (Avastin®), axitinib (Inlyta®); Brivanib alaninate (BMS-582664, (S)-((R)-1-(4-(4-Fluoro-2-methyl-1H-indol-5-yloxy)-5-methylpyrrolo[2,1-f][1,2,4]triazin-6-yloxy) propan-2-yl) 2-aminopropanoate); Sorafenib (Nexavar®); Pazopanib (Votrient®); Sunitinib malate (Sutent®); Cediranib (AZD2171, CAS 288383-20-1); Vargatef (BIBF1120, CAS 928326-83-4); Foretinib (GSK1363089); Telatinib (BAY57-9352, CAS 332012-40-5); Apatinib (YN968D1, CAS 811803 May 1); Imatinib (Gleevec®); Ponatinib (AP24534, CAS 943319-70-8); Tivozanib (AV951, CAS 475108-18-0); Regorafenib (BAY73-4506, CAS 755037-03-7); Vatalanib dihydrochloride (PTK787, CAS 212141-51-0); Brivanib (BMS-540215, CAS 649735-46-6); Vandetanib (Caprelsa® or AZD6474); Motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470); Dovitinib dilactic acid (TKI258, CAS 852433-84-2); Linfanib (ABT869, CAS 796967-16-3); Cabozantinib (XL184, CAS 849217-68-1); Lestaurtinib (CAS 111358-88-4); N-[5-[[[5-(1,1-Dimethylethyl)-2-oxazolyl] methyl]thio]-2-thiazolyl]-4-piperidinecarboxamide (BMS38703, CAS 345627-80-7); (3R,4R)-4-Amino-1-((4-((3-methoxyphenyl)amino)pyrrolo[2,1-f][1,2,4]triazin-5-yl) methyl) piperidin-3-ol (BMS690514); N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8); 4-Methyl-3-[[1-methyl-6-(3-pyridinyl)-1H-pyrazolo[3,4-d]pyrimidin-4-yl]amino]-N-[3-(trifluoromethyl)phenyl]-benzamide (BHG712, CAS 940310-85-0); and Aflibercept (Eylea®).

Exemplary EGF pathway inhibitors include, without limitation tyrphostin 46, EKB-569, erlotinib (Tarceva®), gefitinib (Iressa®), erbitux, nimotuzumab, lapatinib (Tykerb®), cetuximab (anti-EGFR mAb), [188]Re-labeled nimotuzumab (anti-EGFR mAb), and those compounds that are generically and specifically disclosed in WO 97/02266, EP 0 564 409, WO 99/03854, EP 0 520 722, EP 0 566 226, EP 0 787 722, EP 0 837 063, U.S. Pat. No. 5,747,498, WO 98/10767, WO 97/30034, WO 97/49688, WO 97/38983 and WO 96/33980. Exemplary EGFR antibodies include, but are not limited to, Cetuximab (Erbitux®); Panitumumab (Vectibix®); Matuzumab (EMD-72000); Trastuzumab (Herceptin®); Nimotuzumab (hR3); Zalutumumab; TheraCIM h-R3; MDX0447 (CAS 339151-96-1); and ch806 (mAb-806, CAS 946414-09-1). Exemplary Epidermal growth factor receptor (EGFR) inhibitors include, but not limited to, Erlotinib hydrochloride (Tarceva®); ceritinib; brigatinib; osimeritinib; icotinib; Gefitnib (Iressa®); N-[4-[(3-Chloro-4-fluorophenyl)amino]-7-[[(3"S")-tetrahydro-3-furanyl] oxy]-6-quinazolinyl]-4 (dimethylamino)-2-butenamide, Tovok®); Vandetanib (Caprelsa®); Lapatinib (Tykerb®); (3R,4R)-4-Amino-1-((4-((3-methoxyphenyl)amino) pyrrolo [2,1-f][1,2,4]triazin-5-yl)methyl) piperidin-3-ol (BMS690514); Canertinib dihydrochloride (CI-1033); 6-[4-[(4-Ethyl-1-piperazinyl)methyl]phenyl]-N-[(1R)-1-phenylethyl]-7H-Pyrrolo[2,3-d]pyrimidin-4-amine (AEE788, CAS 497839-62-0); Mubritinib (TAK165); Pelitinib (EKB569); Afatinib (BIBW2992); Neratinib (HKI-272); N-[4-[[1-[(3-Fluorophenyl)methyl]-1H-indazol-5-yl]amino]-5-methylpyrrolo[2,1-f][1,2,4]triazin-6-yl]-carbamic acid, (3S)-3-morpholinylmethyl ester (BMS599626); N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8); 4-[4-[[(1R)-1-Phenylethyl]amino]-7H-pyrrolo[2,3-d]pyrimidin-6-yl]-phenol (PKI166, CAS 187724-61-4); rocelitinib.

Exemplary mTOR inhibitors include, without limitation, rapamycin (Rapamune®), and analogs and derivatives thereof; SDZ-RAD; Temsirolimus (Torisel®; also known as CCI-779); Ridaforolimus (formally known as deferolimus, (1R,2R,4S)-4-[(2R)-2[(1R,9S,12S,15R,16E,18R,19R,21R, 23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0^{4,9}]hexatriaconta-16,24,26,28-tetraen-12-yl]propyl]-2-methoxycyclohexyl dimethylphosphinate, also known as AP23573 and MK8669, and described in PCT Publication No. WO 03/064383); Everolimus (Afinitor® or RAD001); Rapamycin (AY22989, Sirolimus®); Simapimod (CAS 164301-51-3); (5-{2,4-Bis[(3S)-3-methylmorpholin-4-yl]pyrido[2,3-d] pyrimidin-7-yl}-2-methoxyphenyl) methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7 (8H)-one (PF04691502, CAS 1013101-36-4); and N2-[1,4-dioxo-[[4-(4-oxo-8-phenyl-4H-1-benzopyran-2-yl) morpholinium-4-yl]methoxy]butyl]-L-arginylglycyl-L-α-aspartyIL-serine-, inner salt (SF1126, CAS 936487-67-1).

Exemplary Phosphoinositide 3-kinase (PI3K) inhibitors include, but are not limited to, duvelisib, idelalisib, 4-[2-(1H-Indazol-4-yl)-6-[[4-(methylsulfonyl) piperazin-1-yl] methyl]thieno[3,2-d]pyrimidin-4-yl]morpholine (also known as GDC 0941 and described in PCT Publication Nos. WO 09/036082 and WO 09/055730); 2-Methyl-2-[4-[3-methyl-2-oxo-8-(quinolin-3-yl)-2,3-dihydroimidazo[4,5-c] quinolin-1-yl]phenyl]propionitrile (also known as BEZ 235 or NVP-BEZ 235, and described in PCT Publication No. WO 06/122806); 4-(trifluoromethyl)-5-(2,6-dimorpholino-pyrimidin-4-yl) pyridin-2-amine (also known as BKM120 or NVP-BKM120, and described in PCT Publication No. WO2007/084786); Tozasertib (VX680 or MK-0457, CAS 639089-54-6); (5Z)-5-[[4-(4-Pyridinyl)-6-quinolinyl]methylene]-2,4-thiazolidinedione (GSK1059615, CAS 958852-01-2); (1E,4S,4aR,5R,6aS,9aR)-5-(Acetyloxy)-1-[(di-2-propenylamino)methylene]-4,4a,5,6,6a,8,9,9a-octahydro-11-hydroxy-4-(methoxymethyl)-4a,6a-dimethyl-cyclopenta [5,6]naphtho[1,2-c]pyran-2,7,10(1H)-trione (PX866, CAS 502632-66-8); and 8-Phenyl-2-(morpholin-4-yl)-chromen-4-one (LY294002, CAS 154447-36-6). Exemplary Protein Kinase B (PKB) or AKT inhibitors include, but are not limited to. 8-[4-(1-Aminocyclobutyl)phenyl]-9-phenyl-1,2, 4-triazolo[3,4-f][1,6]naphthyridin-3 (2H)-one (MK-2206, CAS 1032349-93-1); Perifosine (KRX0401); 4-Dodecyl-N-1,3,4-thiadiazol-2-yl-benzenesulfonamide (PHT-427, CAS 1191951-57-1); 4-[2-(4-Amino-1,2,5-oxadiazol-3-yl)-1-ethyl-7-[(3S)-3-piperidinylmethoxy]-1H-imidazo[4,5-c] pyridin-4-yl]-2-methyl-3-butyn-2-ol (GSK690693, CAS 937174-76-0); 8-(1-Hydroxyethyl)-2-methoxy-3-[(4-methoxyphenyl) methoxy]-6H-dibenzo[b,d]pyran-6-one (palomid 529, P529, or SG-00529); Tricirbine (6-Amino-4-methyl-8-(β-D-ribofuranosyl)-4H,8H-pyrrolo[4,3,2-de]pyrimido[4,5-c]pyridazine); (αS)-α-[[[5-(3-Methyl-1H-indazol-5-yl)-3-pyridinyl]oxy]methyl]-benzeneethanamine (A674563, CAS 552325-73-2); 4-[(4-Chlorophenyl)

methyl]-1-(7H-pyrrolo[2,3-d]pyrimidin-4-yl)-4-piperidi-namine (CCT128930, CAS 885499-61-6); 4-(4-Chlorophe-nyl)-4-[4-(1H pyrazol-4-yl)phenyl]-piperidine (AT7867, CAS 857531-00-1); and Archexin (RX-0201, CAS 663232-27-7).

In certain embodiments, a tyrosine kinase inhibitor used in combination with chimeric Tim receptor modified cells is an anaplastic lymphoma kinase (ALK) inhibitor. Exemplary ALK inhibitors include crizotinib, ceritinib, alectinib, bri-gatinib, dalantercept, entrectinib, and lorlatinib.

In certain embodiments where chimeric Tim receptor modified cells are administered in combination with one or more additional therapies, the one or more additional thera-pies may be administered at a dose that might otherwise be considered subtherapeutic if administered as a monotherapy. In such embodiments, the chimeric Tim receptor composi-tion may provide an additive or synergistic effect such that the one or more additional therapies can be administered at a lower dose. Combination therapy includes administration of a chimeric Tim receptor compositions as described herein before an additional therapy (e.g., 1 day to 30 days or more before the additional therapy), concurrently with an addi-tional therapy (on the same day), or after an additional therapy (e.g., 1 day-30 days or more after the additional therapy). In certain embodiments, the chimeric Tim receptor modified cells are administered after administration of the one or more additional therapies. In further embodiments, the chimeric Tim receptor modified cells are administered 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days after administration of the one or more additional therapies. In still further embodiments, the chimeric Tim receptor modi-fied cells are administered within 4 weeks, within 3 weeks, within 2 weeks, or within 1 week after administration of the one or more additional therapies. Where the one or more additional therapies involves multiple doses, the chimeric Tim receptor modified cells may be administered after the initial dose of the one or more additional therapies, after the final dose of the one or more additional therapies, or in between multiple doses of the one or more additional therapies.

In certain embodiments, methods of the present disclosure include a depletion step. A depletion step to remove chimeric Tim receptors from the subject may occur after a sufficient amount of time for therapeutic benefit in order to mitigate toxicity to a subject. In such embodiments, the chimeric Tim receptor vector may include an inducible suicide gene, such as iCASP9, inducible Fas, or HSV-TK. Similarly, a chimeric Tim receptor vector may be designed for expression of a known cell surface antigen such as CD20 or truncated EGFR (SEQ ID NO:16) that facilitates depletion of transduced cells through infusion of an associated monoclonal antibody (mAb), for example, Rituximab for CD20 or Cetuximab for EGFR. Alemtuzumab, which targets CD52 present on the surface of mature lymphocytes, may also be used to deplete transduced B cells, T cells, or natural killer cells.

Subjects that can be treated by the compositions and methods of the present disclosure include animals, such as humans, primates, cows, horses, sheep, dogs, cats, mice, rats, rabbits, guinea pigs, or pigs. The subject may be male or female, and can be any suitable age, including infant, juvenile, adolescent, adult, and geriatric subjects.

EXAMPLES

Example 1: CER-T Cells Elicit Cytotoxic Effects on Primed-Ptd-Ser+ Tumor Cells

TLR-containing chimeric Tim4 receptor-T cells are engi-neered to target cells that display elevated levels of the cell membrane stress-signal, phosphatidylserine (Ptd-Ser). Ptd-Ser is a phospholipid normally found on the inner leaflet of the plasma cell membrane. Upon activation of certain down-stream signals (e.g., caspase 3/7 activation), Ptd-Ser is externalized to the outer cell membrane. Its engagement by Ptd-Ser specific receptors on professional phagocytes/anti-gen presenting cells (APCs) triggers multi-component sig-naling complexes that ultimately culminate in the reorgani-zation of the actin cytoskeleton. Tim-4 (T cell immunoglobulin mucin-4) is one of several receptors that specifically bind to Ptd-Ser. Its expression in resident and peritoneal macrophages is linked to clearance of apoptotic cells during normal tissue homeostasis. In dendritic cells (DCs), Tim-4-Ptd-Ser interactions mediate capture and engulfment of antigen for cross-priming of T cells.

Several strategies were developed to efficiently induce or prime Ptd-Ser on various tumor cell lines. This priming step uses standard of care therapeutics such as targeted small molecule inhibitors to induce cell stress and/or apoptosis. Once induced, Ptd-Ser serves as a target for chimeric Tim4 receptor-T cell engagement, activation and cytolytic func-tion. This two-step 'prime and kill' strategy is shown using a variety of small molecule inhibitor-chimeric Tim4 recep-tor-T cell product combinations, as well as combinations with engineered CAR T and TCR products.

In ovarian tumors, poly (ADP-ribose) polymerase (PARP) inhibitors, such as Niraparib, are clinically approved drugs which target DNA damage response pathways. Responses are rarely complete, with relapse common after treatment. To induce Ptd-Ser exposure, BRCA-2 mutated Kuramochi cell line was treated with therapeutic doses of the PARP inhibitor Niraparib. Brief exposure to Niraparib elicits changes in membrane phospholipid symmetry, in a dose dependent manner, and is effective in inhibiting growth of Kuramochi cells (FIG. 7A). The addition of chimeric Tim4 receptor pCTX133 (Tim4 binding domain-TLR2 signaling domain-CD3z signaling domain), at low effector:target ratios (1:1), enhanced the potency of Niraparib in vitro compared to transduced-controls, demonstrating the ability of pCTX133 to elicit direct cytotoxic effects on target cells (FIG. 7B).

In mantle cell lymphoma, Bruton's Tyrosine Kinase (BTK) inhibitors, such as ibrutinib, are clinically approved drugs that target a pro-survival kinase. Responses are rarely complete, and relapse is common after treatment. Treatment of JeKo-1 MCL with Ibrutinib exposes Ptd-Ser, as deter-mined by immunohistochemistry using a recombinant murine Tim4 protein (FIG. 8A). JeKo-1 mantle cell lym-phoma cell lines were treated with a 25 uM Ibrutinib for 24 h, followed by drug wash out and co-culture with 0.5 uM Ibrutinib with chimeric Tim4 receptor pCTX136 (Tim4 binding domain-CD28 signaling domain-CD3z signaling domain) or control cells at 3:1, 2:1, or 1:1 E:T ratios. Co-culture with chimeric Tim4 receptor cells induced near elimination of JeKo-1 target cells, as compared to Ibrutinib treatment or treatment with control T cells (FIG. 8B).

Chimeric Tim-4 receptors having TLR2 intracellular sig-naling domain or TLR8 intracellular signaling domain, and CD28 intracellular signaling domain or CD3zeta intracellu-lar signaling domain were tested for their capacity to pro-mote tumor cell acquisition and elicit cytotoxic and APC-like function. To assess antigen acquisition, target cells were co-cultured with chimeric Tim-4 receptor T cells and evalu-ated by transmission electron microscopy (TEM) or flow cytometry. Target cells were treated with a small molecule inhibitor to induce Ptd-Ser externalization and evaluated for lysosomal uptake using a pH indicator dye (pHrodo Red).

An alternative prime and kill therapeutic strategy combines TLR-containing chimeric Tim4 receptor-T cells with Chimeric Antigen Receptor-T (CAR)-T cells. This combinatorial approach utilizes the CAR to specifically target tumor cells, leading to upregulation of Ptd-Ser. A CD19 CAR-T cell product (anti-CD19 scFv-CD28 costimulatory signaling domain-CD3ζ signaling domain; "1928z CAR") rapidly induces Ptd-Ser on CD19+ Mantle Cell Lymphoma (MCL) cells in a dose dependent manner (FIG. 5A). In co-culture studies, measured by incucyte and by FACS, a combination of 1928z CAR-T cells (pCTX184) and pCTX131 (Tim4-TLR8-CD3z) showed enhanced potency. 1928z CAR T cells were combined at low effector:target ratios at multiple CAR:CER ratios using pCTX131 (Tim4-TLR8-CD3z) cells (FIG. 5B, FIG. 6A). pCTX156 is truncated EGFR (EGFRt) control. Increases in inflammatory cytokines such as IFN-γ were observed from supernatants, in line with the observed increase in cytolytic function (FIG. 5C). In addition, in co-culture studies, measured by incucyte, a combination of 1928z CAR-T cells and pCTX131 (Tim4-TLR8-CD3z) showed enhanced induction of cleaved caspase in target cells. 1928z CAR T cells were combined at low effector:target ratios at multiple CAR:CER ratio using pCTX131 (Tim4-TLR8-CD3z) cells (FIG. 6B).

Thus, this example highlights that pCTX133 and pCTX131 (TLR2 and TLR8)-containing chimeric Tim4 receptor-T cells can elicit cytolytic activity towards primed solid tumor and hematologic target cell lines expressing cell surface Ptd-Ser and augment small molecule and CAR-based therapeutic approaches.

Example 2: Chimeric Tim4 Receptor-T Cells Mediate Antigen Capture and Presentation Activated T cells have been shown to be capable of Ag processing and presentation, since they express class II molecules, display antigen on the cell surface, and can deliver costimulatory signals to other T cells[10]. Unlike professional APCs, though, T cells are limited by their inefficient capture of soluble antigens[9]. APCs, in contrast, utilize constitutively expressed Ag uptake receptors to capture and engulf antigen for subsequent degradation and MHC loading[12][13]. The capture of a soluble antigen can be up to 103 times more efficient in the presence of surface receptors that bind to Ag with high affinity[14].

In dendritic cells (DCs), Tim-4-Ptd-Ser interactions mediate capture, engulfment, and concentration of antigen, allowing DCs to present antigen to T cells with high efficiency. Indeed, Tim-4 receptor blockade in preclinical NSCLC models impairs activation of tumor specific CD8+ T cells and promotes tumor progression[12]. Furthermore, gene expression profiling shows downregulation of Tim-4 expression in advanced tumor cells, concordant with decreased antigen uptake, presentation, and T cell activation.

Experimental results presented here indicates that T cells can be re-directed as antigen-presenting T cells for immunotherapy by enhancing their antigen uptake, capture and co-stimulatory capabilities. The fusion of a human Tim-4 phagocytic uptake receptor to intracellular signaling sequences that drive antigen uptake as well as antigen processing and presentation adds enhanced APC capabilities to T cells. The modular design of chimeric Tim receptors incorporates intracellular domains that drive multicomponent signaling complexes, such as CD3ζ, CD28, 4-1BB, ITAM and TLR signaling, to induce cellular activation, cytolytic function, secretion of cytokines and chemokines, upregulation of adhesion and costimulatory molecules, and antigen degradation-processes required for mediating efficient T cell activation 15.

Chimeric Tim4 receptor-T cells were tested to determine whether they can capture and present soluble antigens and trigger activation and proliferation of recombinant E7-restricted T cell clones in a co-culture system. First expression of Tim4 was confirmed on transduced CER T cells by flow cytometry. Tim4 binding domain-CD28 transmembrane-CD28 signaling domain-CD3z signaling domain (CTX247) and Tim4 binding domain-CD28 signaling domain-CD3z signaling domain-TLR2 signaling domain (CTX1107) were stained for Tim4 and EGFR, a transduction marker encoded on each vector. Tim4 expression was observed on CTX247 or CTX1107 transduced cells, but not mock transduced controls (FIG. 4) E7-restricted TCRs target the E7 protein from HPV16 and have the TCRα chain and TCRβ chain sequence provided in SEQ ID NO:156. E7 TCRs proliferate in response to APCs pulsed with E7 peptide through MHC class I. For autologous APCs, CD4+ and CD8+ chimeric Tim4 receptor T cell products transduced with different Tim-4 chimeric receptors were pulsed with a pool of 15-mer peptides containing 11-mer overlaps derived from the E7 protein from HPV16 or vehicle. Chimeric Tim4 receptor T cells were pulsed at 37° C. for 4 hrs with E7 peptides and tested for their capacity to trigger E7-specific activation and proliferation. E7-TCR cell surface activation marker responses were evaluated by flow cytometry 24 hours following co-culture with chimeric Tim4 receptor-T cell products. After an additional 5 days of co-culture, proliferative responses were assessed by Cell Trace (CT) Violet dilution.

Figure 1A:
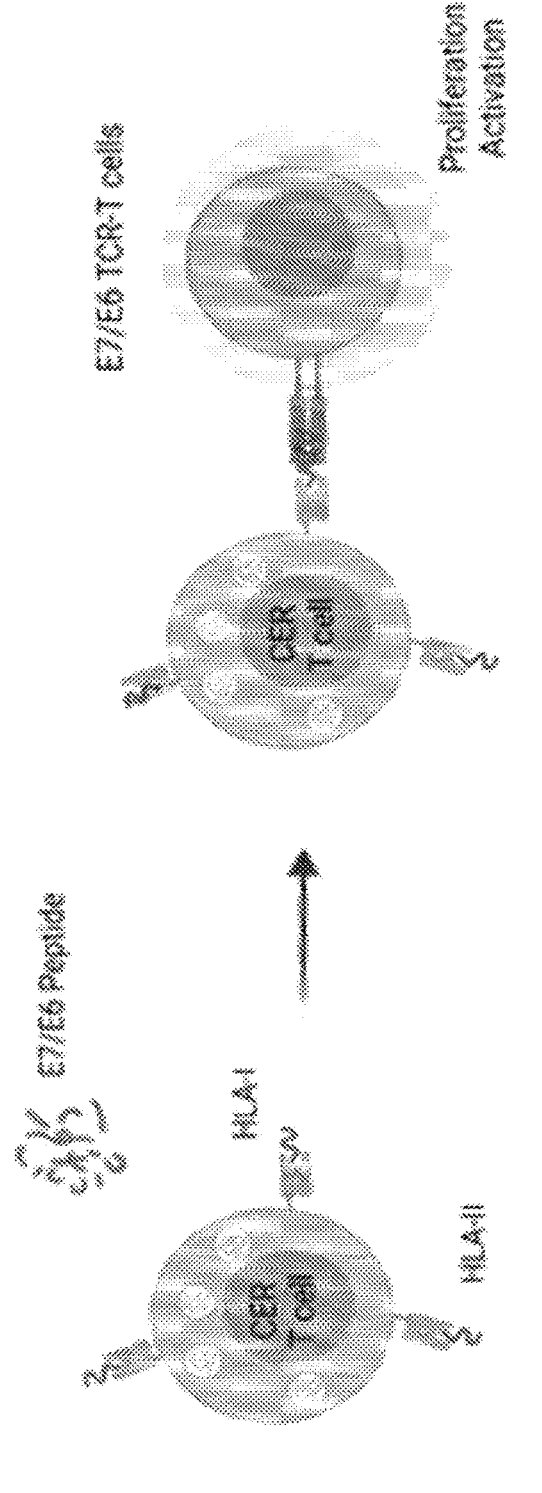
FIGS. 1A-1C: an in vitro co-culture system to evaluate T cell antigen presentation function shows that addition of T cells containing chimeric Tim4 receptors with a TLR intracellular signaling domain added to the CD3ζ signaling domain (and optionally a CD28 signaling domain) show enhanced capacity to serve as an antigen presenting cell (APC).
Figures 1B, 1C:
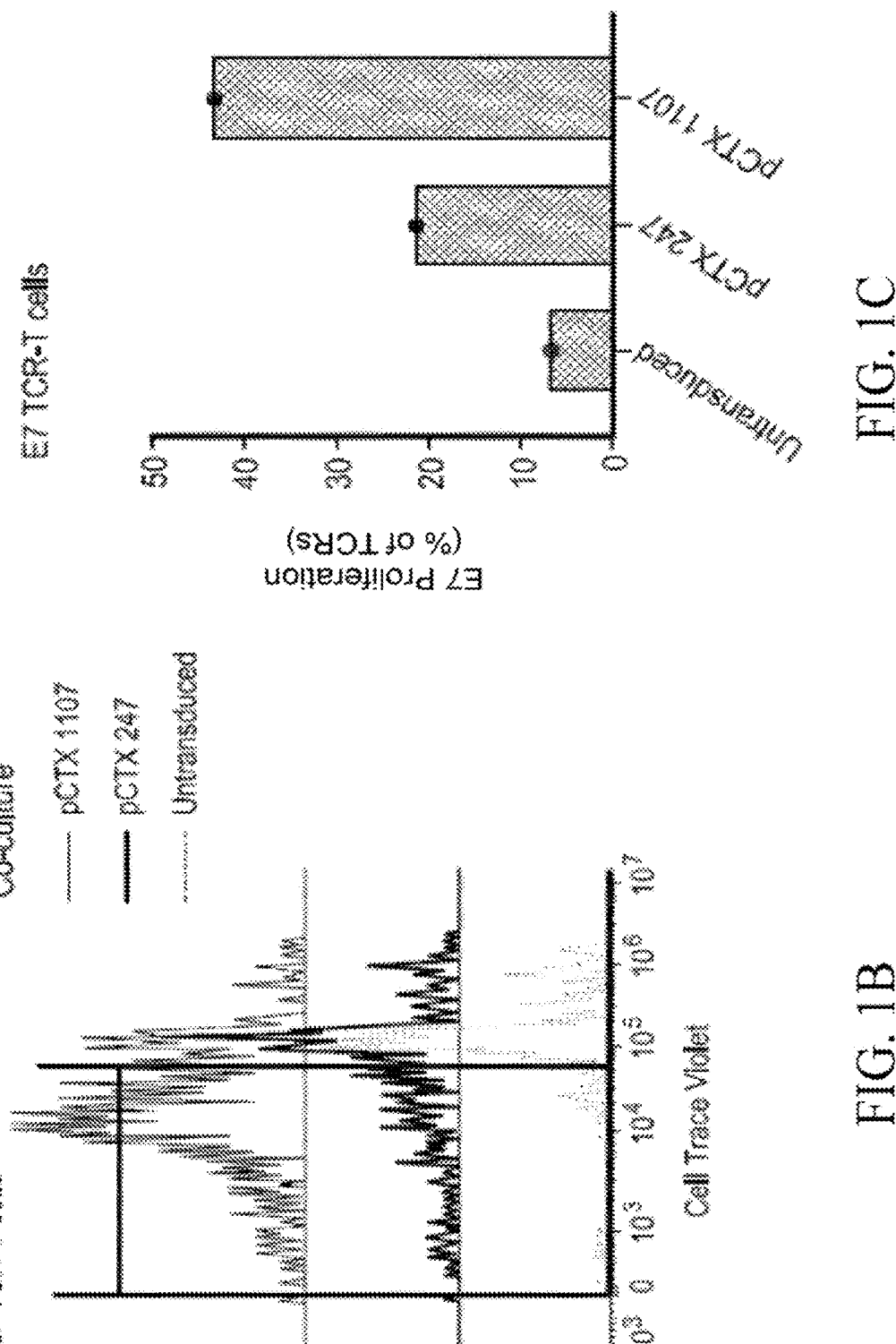
Figure 2:
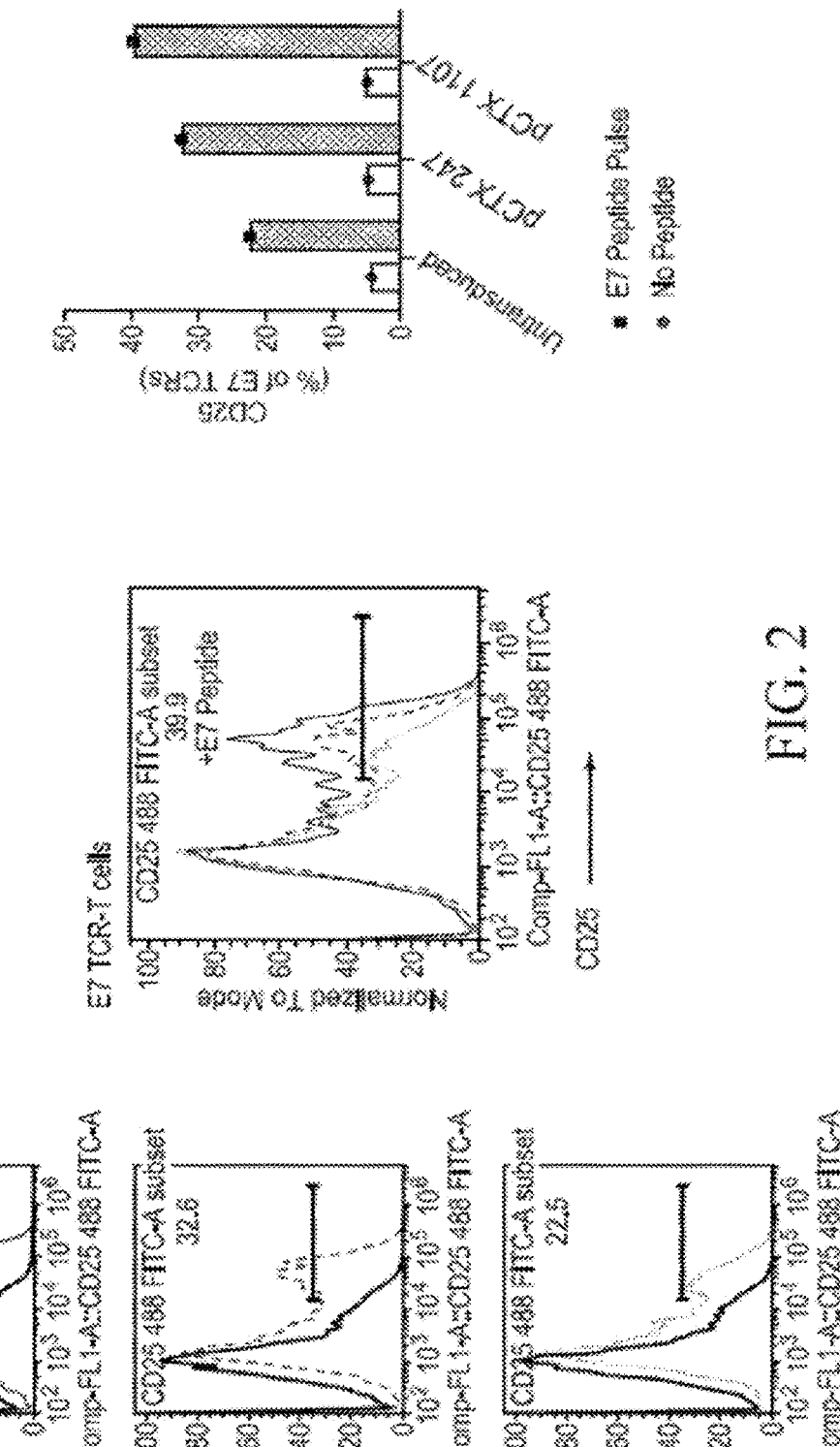
FIG. 2: T cells containing chimeric Tim4 receptors with a TLR intracellular signaling domain added to the CD3ζ signaling domain (and optionally a CD28 signaling domain) are strong stimulators of autologous E7-specific T cell responses. CER-T cells were pulsed with E7 peptide and tested for their capacity to trigger an autologous E7-specific T cell response. CD25, a T cell activation marker, was evaluated on E7 TCR-T cells, 24 hours after CER-T cells were pulsed with E7 peptides. CER-T pCTX1107 contains a TLR-2 ICD and is a strong stimulator of E7-specific activation.
Figure 3:
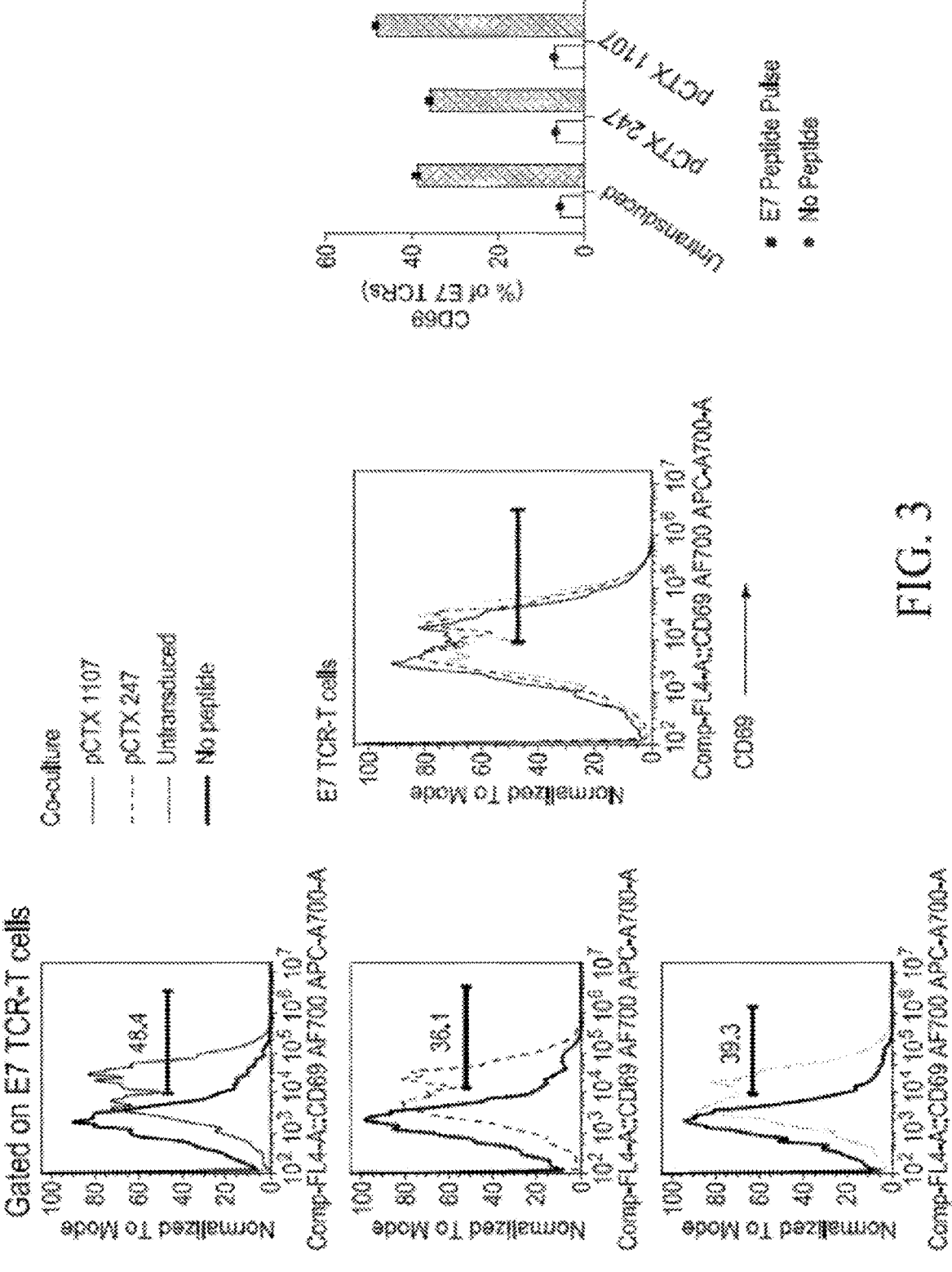
FIG. 3: T cells containing chimeric Tim4 receptors with a TLR intracellular signaling domain added to the CD3ζ signaling domain (and optionally a CD28 signaling domain) are strong stimulators of autologous E7-specific T cell responses. CER-T cells were pulsed with E7 peptide and tested for their capacity to trigger an autologous E7-specific T cell response. CD69, an early marker for T cell activation, was evaluated on E7 TCR-T cells, 24 hours after CER-T cells were pulsed with E7 peptides. CER-T pCTX1107 contains a TLR-2 ICD and is a strong stimulator of E7-specific activation.

FIGS. 1B-1C show that pCTX1107 (Tim4 binding domain-CD28 intracellular signaling domain-CD3ζ intracellular signaling domain-TLR2 intracellular signaling domain) CER T cells were indeed stimulatory for E7-specific T cells, whereas pCTX247 (Tim4 binding domain-CD28 intracellular signaling domain-CD3ζ intracellular signaling domain) or untransduced T cells were not stimulatory, even when pulsed with high concentrations of E7 peptide. In these experiments, the only difference in construct design between pCTX247 and pCTX1107 was the addition of a TLR-2 intracellular sequence (FIG. 1A), implicating TLR signaling in amplifying T cell presentation of soluble antigen and triggering of E7 TCRs Evidence for pCTX1107 being a strong stimulatory of E7-specific activation was also seen in CD25 and CD69 upregulation measured by flow cytometry (FIG. 2). A higher frequency of E7-TCR containing T cells expressed both activation markers 24 hours after co-culture (FIG. 2). The E7 TCR-T cell surface activation markers CD25 and CD69 were upregulated 41.2% vs. 23.1% relative to controls 24 hrs. following co-culture with chimeric Tim4 receptor-T and the percentage of dividing E7-TCR-T cells by 6 days was 44% for TIM4/CD28/CD3z/TLR2 chimeric Tim4 receptor T cells vs 8% relative to controls.

Cell Trace Violet labeled E7-specific TCR T cells were cultured for 4 days with untransduced T cells (UT), T cells transduced with a Tim4-CD28-CD3z construct (CTX247) or a Tim4-CD28-CD3z-TLR2 construct (CTX1107) and JeKo-1 cells at a 1:2:2 ratio in the presence of a pool of 15 mer peptides with 11aa overlap (100 ng each peptide) derived from the HPV16 E7 protein. Duplicate cultures were incubated with HLA A, B, C blocking antibodies (clone W6/32) or matched mouse IgG2a antibodies for the duration of the culture. FIG. 10 shows percent E7 TCR cells in culture among live cells as determined by flow cytometry based on staining of mouse TCRb+ cells. Activation of E7-specific TCR T cells mediated by chimeric Tim4 receptor antigen presentation is blocked by anti-HLA-I antibodies.

Example 3: Transfection of T Cells with Chimeric Tim4 Receptors

Chimeric Tim4 receptors pCTX1183, pCTX1161, pCTX1189, pCTX1184, pCTX1163, pCTX1162, pCTX1190, pCTX1186, pCTX1187, pCTX1164, pCTX1185, and pCTX1165 (see, Table 8) were transfected into Jurkat T lymphocyte cell line (FIGS. 9A-9B).

REFERENCES

1. Aderem, A. & Underhill, D. M. Mechanisms of phagocytosis in macrophages. *Annu. Rev. Immunol.* 17, 593-623 (1999).
2. Fu, C. & Jiang, A. Dendritic Cells and CD8 T Cell Immunity in Tumor Microenvironment. *Front. Immunol.* 9, 3059 (2018).
3. Steinhagen, F., Kinjo, T., Bode, C. & Klinman, D. M. TLR-based immune adjuvants. *Vaccine* 29, 3341-3355 (2011).
4. Meås, H. Z. et al. Sensing of HIV-1 by TLR8 activates human T cells and reverses latency. *Nat. Commun.* 11, 147 (2020).
5. Wille-Reece, U. et al. HIV Gag protein conjugated to a Toll-like receptor 7/8 agonist improves the magnitude and quality of Th1 and CD8+ T cell responses in nonhuman primates. *Proc. Natl. Acad. Sci. U.S.A* 102, 15190-15194 (2005).
6. Deres, K., Schild, H., Wiesmüller, K. H., Jung, G. & Rammensee, H. G. In vivo priming of virus-specific cytotoxic T lymphocytes with synthetic lipopeptide vaccine. *Nature* 342, 561-564 (1989).
7. Jackson, D. C. et al. A totally synthetic vaccine of generic structure that targets Toll-like receptor 2 on dendritic cells and promotes antibody or cytotoxic T cell responses. *Proc. Natl. Acad. Sci. U.S.A* 101, 15440-15445 (2004).
8. Zhu, X., Ramos, T. V., Gras-Masse, H., Kaplan, B. E. & BenMohamed, L. Lipopeptide epitopes extended by an Nepsilon-palmitoyl-lysine moiety increase uptake and maturation of dendritic cells through a Toll-like receptor-2 pathway and trigger a Th1-dependent protective immunity. *Eur. J. Immunol.* 34, 3102-3114 (2004).
9. Lanzavecchia, A., Roosnek, E., Gregory, T., Berman, P. & Abrignani, S. T cells can present antigens such as HIV gp120 targeted to their own surface molecules. *Nature* 334, 530-532 (1988).
10. Barnaba, V., Watts, C., de Boer, M., Lane, P. & Lanzavecchia, A. Professional presentation of antigen by activated human T cells. *Eur. J. Immunol.* 24, 71-75 (1994).
11. Bandola-Simon, J. & Roche, P. A. Dysfunction of antigen processing and presentation by dendritic cells in cancer. *Mol. Immunol.* 113, 31-37 (2019).
12. Caronni, N. et al. TIM4 expression by dendritic cells mediates uptake of tumor-associated antigens and anti-tumor responses. *Nat. Commun.* 12, 2237 (2021).
13. Engering, A. et al. The dendritic cell-specific adhesion receptor DC-SIGN internalizes antigen for presentation to T cells. *J. Immunol. Baltim. Md* 1950 168, 2118-2126 (2002).
14. Lanzavecchia, A. Antigen-specific interaction between T and B cells. *Nature* 314, 537-539 (1985).
15. Boross, P. et al. FcRγ-chain ITAM signaling is critically required for cross-presentation of soluble antibody-antigen complexes by dendritic cells. *J. Immunol.* Baltim. Md 1950 193, 5506-5514 (2014).
16. Greenberg, S., Chang, P., Wang, D. C., Xavier, R. & Seed, B. Clustered syk tyrosine kinase domains trigger phagocytosis. *Proc. Natl. Acad. Sci. U.S.A.* 93, 1103-1107 (1996).
17. Lennartz, M. & Drake, J. Molecular mechanisms of macrophage Toll-like receptor-Fc receptor synergy. *F1000Research* 7, 21 (2018).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet including but not limited to, U.S. Provisional Patent Application No. 63/066,085, filed on Aug. 14, 2020 and U.S. Provisional Patent Application No. 63/226,643, filed on Jul. 28, 2021, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

---

What is claimed:

1. A chimeric engulfment receptor comprising a single chain chimeric protein, the single chain chimeric protein comprising:

(a) an extracellular domain comprising a binding domain comprising: a Tim4 IgG V domain and a Tim4 mucin domain;

(b) an intracellular signaling domain, wherein the intracellular signaling domain comprises a CD28 signaling domain, a CD3ζ signaling domain, and a TLR2 signaling domain; and (c) a CD28 transmembrane domain positioned between and connecting the extracellular domain and the intracellular signaling domain.

2. The chimeric engulfment receptor of claim 1, wherein the binding domain comprises the amino acid sequence of SEQ ID NO:2.

3. The chimeric engulfment receptor of claim 1, wherein the binding domain comprises the amino acid sequence of SEQ ID NO:2.

4. The chimeric engulfment receptor of claim 1, wherein the CD28 transmembrane domain comprises the amino acid sequence of SEQ ID NO:7.

5. The chimeric engulfment receptor of claim 1, wherein the CD28 signaling domain comprises the amino acid sequence of SEQ ID NO:4 or SEQ ID NO:26.

6. The chimeric engulfment receptor of claim 1, wherein the CD3ζ signaling domain comprises the amino acid sequence of SEQ ID NO:5 or SEQ ID NO:27.

7. The chimeric engulfment receptor of claim 1, wherein the TLR2 signaling domain comprises the amino acid sequence of SEQ ID NO: 122.

8. The chimeric engulfment receptor of claim 1, wherein the chimeric engulfment receptor comprises from N-terminus to C-terminus: a Tim4 signal peptide comprising the amino acid sequence of SEQ ID NO:118; a Tim4 binding domain comprising the amino acid sequence of SEQ ID NO:42; a CD28 transmembrane domain comprising the amino acid sequence of SEQ ID NO: 7; a CD28 signaling domain comprising the amino acid sequence of SEQ ID NO:4; a CD3ζ signaling domain comprising the amino acid sequence of SEQ ID NO:27; and a TLR2 signaling domain comprising the amino acid sequence of SEQ ID NO:122.

9. The chimeric engulfment receptor of claim 1, wherein the chimeric engulfment receptor comprises the amino acid sequence of SEQ ID NO:128 or SEQ ID NO: 129.

10. A polynucleotide encoding the chimeric engulfment receptor of claim 1.

11. A vector comprising the polynucleotide of claim 10.

12. An engineered immune cell comprising the vector of claim 11.

13. The engineered immune cell of claim 12, wherein the immune cell is a T cell.

14. The engineered immune cell of claim 13, wherein the T cell is a CD4+T cell, a CD8+T cell, or a CD4+/CD8+T cell.

15. The engineered immune cell of claim 12, wherein the immune cell is a human immune cell.

16. A pharmaceutical composition comprising the engineered immune cell of claim 12 and a pharmaceutically acceptable excipient.

17. A method of treating cancer in a subject, comprising administering an effective amount of the engineered immune cell of claim 12 to the subject.

18. The method of claim 17, wherein the cancer is breast cancer; prostate cancer; ovarian cancer; cervical cancer; skin cancer; pancreatic cancer; colorectal cancer; renal cancer;

liver cancer; brain cancer; lymphoma; leukemia; lung cancer; adenocarcinoma of the breast; adenocarcinoma of the prostate; and adenocarcinoma of the colon; a form of bronchogenic carcinoma of the lung; myeloid leukemia; melanoma; hepatoma; neuroblastoma; papilloma; apudoma; choristoma; branchioma; malignant carcinoid syndrome; carcinoid heart disease; Walker carcinoma; basal cell carcinoma; basosquamous carcinoma; Brown-Pearce carcinoma; ductal carcinoma; Ehrlich tumor carcinoma; Krebs 2 carcinoma; Merkel cell carcinoma; mucinous carcinoma; nonsmall cell lung carcinoma; oat cell carcinoma; papillary carcinoma; scirrhous carcinoma; bronchiolar carcinoma; squamous cell carcinoma; transitional cell carcinoma; a histiocytic disorders; malignant histiocytosis; Hodgkin's disease; non-Hodgkin's lymphoma; plasmacytoma; multiple myeloma; chronic myeloid leukemia (CML); reticuloendotheliosis; chondroblastoma; chondroma; chondrosarcoma; fibroma; fibrosarcoma; giant cell tumor; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor; adenoma; cholangioma; cholesteatoma; cyclindroma; cystadenocarcinoma; cystadenoma; granulosa cell tumor; gynandroblastoma; hidradenoma; islet cell tumor; Leydig cell tumor; sertoli cell tumor; theca cell tumor; leimyoma; leiomyosarcoma; myoblastoma; myomma; rhabdomyoma; rhabdomyosarcoma; ependymoma; ganglioneuroma; glioma; medulloblastoma; meningioma; neurilemmoma; neuroepithelioma; neurofibroma; neuroma; paraganglioma; paraganglioma nonchromaffin; angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; leukosarcoma; sarcoma; neoplasms; neurofibromatosis; cervical dysplasia; peritoneal cancer; B-cell cancers; B-cell lymphoma central nervous system lymphoma; acute lymphoblastic leukemia (ALL); chronic lymphocytic leukemia (CLL); acute myeloid leukemia (AML); Hairy cell leukemia; B cell blast transformation of chronic myeloid leukemia; myeloma; small lymphocytic lymphoma; B-cell prolymphocytic leukemia; lymphoplasmacytic lymphoma; splenic marginal zone lymphoma; plasma cell myeloma; solitary plasmacytoma of bone; extraosseous plasmacytoma; extra-nodal marginal zone B-cell lymphoma of mucosaassociated (MALT) lymphoid tissue; nodal marginal zone B-cell lymphoma; follicular lymphoma; mantle cell lymphoma; diffuse large B-cell lymphoma, mediastinal (thymic) large B-cell lymphoma; intravascular large B-cell lymphoma; primary effusion lymphoma; Burkitt's lymphoma/leukemia; B-cell proliferations of uncertain malignant potential; lymphomatoid granulomatosis; or post-transplant lymphoproliferative disorder.

19. The method of claim 17, wherein the method further comprises administering an additional therapeutic agent to the subject.

20. The method of claim 19, wherein the additional therapeutic agent comprises radiation, cellular immunotherapy, antibody, immune checkpoint molecule inhibitor, chemotherapy, hormone therapy, peptide, antibiotic, antiviral agent, anti-fungal agent, anti-inflammatory agent, UV light therapy, electric pulse therapy, high intensity focused ultrasound therapy, oncolytic virus therapy, a small molecule therapy, or any combination thereof.

21. The method of claim 19, wherein the additional therapeutic agent comprises an angiogenesis inhibitor, a VEGF pathway inhibitor, tyrosine kinase inhibitor, an EGF pathway inhibitor, receptor tyrosine kinase inhibitor, growth factor inhibitor, GTPase inhibitor, serine/threonine kinase inhibitor, transcription factor inhibitor, B-Raf inhibitor, RAF inhibitor, MEK inhibitor, mTOR inhibitor, EGFR inhibitor, ALK inhibitor, ROS1 inhibitor, BCL-2 inhibitor, PI3K inhibitor, VEGFR inhibitor, BCR-ABL inhibitor, MET inhibitor, MYC inhibitor, ABL inhibitor, HER2 inhibitor, BTK inhibitor, H-RAS inhibitor, K-RAS inhibitor, PDGFR inhibitor, TRK inhibitor, c-KIT inhibitor, c-MET inhibitor, CDK4/6 inhibitor, FAK inhibitor, FGFR inhibitor, FLT3 inhibitor, IDH1 inhibitor, IDH2 inhibitor, PDGFRA inhibitor, or RET inhibitor.

22. The method of claim 21, wherein the BTK inhibitor is ibrutinib, pirtobrutinib (Loxo-305), tirabrutinib (ONO-4059), tolebrutinib, evobrutinib, fenebrutinib (GDC-0853), acalabrutinib, spebrutinib, zanubrutinib (BGB-3111), HM71224, or M7583.

\* \* \* \* \*